US007928077B2

(12) United States Patent
Wong et al.

(10) Patent No.: US 7,928,077 B2
(45) Date of Patent: Apr. 19, 2011

(54) ALPHA-GALACTOSYL CERAMIDE ANALOGS AND THEIR USE AS IMMUNOTHERAPIES

(75) Inventors: Chi-Huey Wong, La Jolla, CA (US); Alice Yu, Taipei (TW); Ya-Jen Chang, Taipei (TW); Kun-Hsien Lin, Taipei (TW); Jung-Tung Hung, Taipei (TW)

(73) Assignee: Academia Sinica, Taipei (TW)

( * ) Notice: Subject to any disclaimer, the term of this patent is extended or adjusted under 35 U.S.C. 154(b) by 259 days.

(21) Appl. No.: 12/218,082

(22) Filed: Jul. 11, 2008

(65) Prior Publication Data
US 2010/0008954 A1  Jan. 14, 2010

(51) Int. Cl.
A61K 31/7032 (2006.01)
C07H 15/18 (2006.01)
(52) U.S. Cl. ......................................... 514/25; 536/17.9
(58) Field of Classification Search .................. None
See application file for complete search history.

(56) References Cited

U.S. PATENT DOCUMENTS

| 5,290,551 | A  | * | 3/1994 | Berd ........................ 424/193.1 |
| 6,344,354 | B1 | * | 2/2002 | Webster et al. ............ 435/235.1 |
| 2007/0238871 | A1 | | 10/2007 | Tsuji et al. |
| 2008/0260774 | A1 | | 10/2008 | Wong et al. |
| 2009/0117089 | A1 | | 5/2009 | Steinman et al. |
| 2009/0233875 | A1 | | 9/2009 | Tsuji et al. |

FOREIGN PATENT DOCUMENTS

| WO | 2006/071848 A1 | 6/2006 |
| WO | 2007/035717 A1 | 3/2007 |
| WO | 2008/128207 A1 | 10/2008 |

OTHER PUBLICATIONS

Lin K-H et al. In vivo protection of bacterial and viral infections in murine models using a synthetic new α-GalCer analog, Antimicrobial Agents and Chemotherapy, 54(10):4129-36, (2010).
Li, X et al., Design of a Potent CD1d-binding NKT Cell Ligand as a Vaccine Adjuvant, Proc. Nat. Acad. Sci. U.S.A., 107(29):13010-5, (2010).
Li, X et al., Identification of C-glycoside nalogues that display a potent biological activity against murine and human invariant atural killer T cells, Immunology 127:216-225. (2009).
Schiefner, A et al., Structural Evaluation of potent NKT Cell Agonists: Implications for Design of Novel Stimulatory Ligands, J Mol Biol 394:71-82. (2009).
Wu D., et al. Glycolipids as Immunostimulating agents, Bioorg Med Chem 16:1073-83. (2008).
Trappeniers M., et al. Synthesis and in vitro evaluation of alpha-GalCer epimers, Chem Med Chem 3:1061-70. (2008).
Kinjo Y., et al. Natural Sphingomonas Glycolipids Vary Greatly in their Ability to Activate Natural Killer T Cells, Chem. Biol., 15(7):654-664, (2008).
Liang, P-H., et al. Quantitative microarray analysis of intact lycolipid-CD1d interaction and correlation with cell-based cytokine roduction, J Am Chem Soc 130:12348-54. (2008).
Huang Y., et al., Enhancement of HIV DNA vaccine immunogenicity by the NKT cell ligand, alpha-galactosylceramide, Vaccine 26:1807-1816. (2008).
Chang Y-J., et al. Potent immune-modulating and anticancer effects of NKT cell stimulatory glycolipids. Proc Natl Acad Sci U S A 104:10299-304. (2007.
Tsuji M. Glycolipids and phospholipids as natural CD1d-binding NKT cell ligands, Cell Mol Life Sci 63:1889-1898. (2006).
Fujio M., et al. Structure-based discovery of glycolipids for CD1d-mediated NKT cell activation: tuning the adjuvant versus immunosuppression activity, J Am Chem Soc 128:9022-3. (2006).
Wu D., et al. Design of natural killer T cell activators: structure and function of a microbial glycosphingolipid bound to mouse CD1d, Proc Natl Acad Sci U S A 103:3972-7. (2006).
Kinjo Y., et al. Recognition of bacterial glycosphingolipids by natural killer T cells, Nature 434:520-5. (2005).
Wu D., et al. Bacterial glycolipids and analogs as antigens for CD1d-restricted NKT cells, Proc. Natl. Acad. Sci. U.S.A., 102:1351-1356 (2005).
Fan G-T et al. Synthesis of α-galactosyl ceramide and the related glycolipids for evaluation of their activities on mouse splenocytes, Tetrahedron 61:1855-1862. (2005).
Plettenburg O., et al. Rapid preparation of glycolipid libraries by cross metathesis, Adv. Synth. Catal. 344,622-626 (2002).
Gonzalez-Aseguinolaza G., et al. Natural killer T cell ligand alpha-galactosylceramide enhances protective immunity induced by malaria vaccines, J Exp Med 195:617-24. (2002).
Plettenburg O., et al. Synthesis of α-galactosyl ceramide, a potent immunostimulatory agent, J. Org Chem. 67, 4559-4564 (2002).

* cited by examiner

*Primary Examiner* — Eric S Olson
(74) *Attorney, Agent, or Firm* — Eckman Basu LLP

(57) ABSTRACT

The present disclosure relates to synthetic alpha-galactosyl ceramide (α-GalCer) analogs, and their use as immunotherapies. In one aspect, a method of activating a cytokine response in a subject includes administering an effective amount of a compound to a subject, wherein the subject has an adaptive immune system that includes a population of cells, the population including at least one lymphocyte and at least one antigen-presenting cell, and wherein the compound is represented by the structure of formula 1:

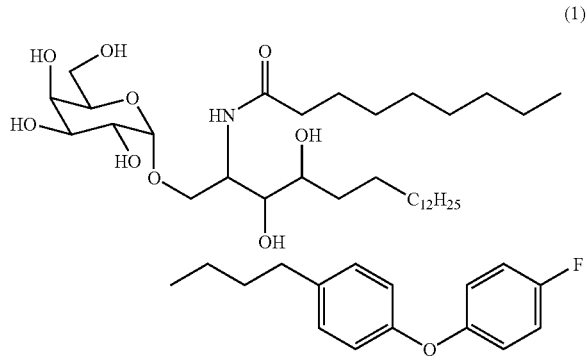

(1)

or a pharmaceutically acceptable salt thereof; forming a complex between the compound and the antigen-presenting cell, wherein the formation of the complex results in the activation of a receptor on the lymphocyte; and activating the lymphocyte to produce the cytokine response.

47 Claims, 113 Drawing Sheets

FIG. 7

| Human | basal | C1 | C2 | C3 | C4 | C5 | C6 | C7 | C8 | C9 | C10 | C11 | C12 | C13 | C14 | C15 | C16 | C17 |
|---|---|---|---|---|---|---|---|---|---|---|---|---|---|---|---|---|---|---|
| TH1 bias | pg/ml | fold | fold | fold | fold | fold | fold | fold | fold | fold | fold | fold | fold | fold | fold | fold | fold | fold |
| IFN-γ | 4613 | 3.4 | 2.7 | 2.4 | 1.3 | 2.2 | 2.1 | 2.8 | 1.9 | 3.3 | 4.6 | 6.4 | 3.9 | 6.6 | 3.4 | 4.2 | 5.2 | 1.9 |
| IL-2 | 20.5 | 2.3 | 1.8 | 1.3 | 1.2 | 1.6 | 1.4 | 1.5 | 1.3 | 2.4 | 5.9 | 6.1 | 1.9 | 2.8 | 2.3 | 3.4 | 3.9 | 1.5 |
| IL-12 p70 | 22 | 1.8 | 1.6 | 1.7 | 1 | 1.6 | 1.2 | 1.7 | 1.8 | 2.8 | 3.3 | 4.7 | 2.1 | 3.2 | 2.7 | 2.3 | 3 | 1 |
| IL-12 p40 | 396 | 1.4 | 1.7 | 1.9 | 1.7 | 1.8 | 1.4 | 1.9 | 1.8 | 2 | 2.4 | 2.3 | 1.8 | 1.8 | 1.8 | 1.4 | 2.1 | 1.4 |
| RANTES | 6413 | 1.6 | 2 | 2.4 | 1.5 | 1.5 | 1.5 | 1.7 | 1.3 | 1.6 | 1.8 | 1.7 | 2 | 2.5 | 1.6 | 2.1 | 1.6 | 1.8 |
| MIP-α | 13365 | 2.9 | 3.5 | 3.5 | 1.5 | 3.2 | 3.2 | 3.4 | 2.8 | 3.4 | 3 | 3.3 | 3.5 | 3.6 | 3.3 | 3.4 | 3.4 | 2.7 |
| MCP-1 | 10768 | 0.9 | 1.4 | 1.7 | 1.4 | 1.5 | 1 | 1.4 | 0.9 | 1.4 | 1.3 | 1 | 1.8 | 2 | 1.2 | 1.5 | 0.6 | 1.3 |
| IL-8 | 4325 | 1.7 | 2.2 | 2.3 | 1.9 | 1.9 | 1.6 | 2.4 | 1.9 | 2.2 | 2.2 | 1.8 | 2.3 | 3 | 1.4 | 2.2 | 1.8 | 1.6 |
| TNF-α | 193.5 | 7.7 | 3 | 5.5 | 2.5 | 3.7 | 3.3 | 3.3 | 5.5 | 8.4 | 8.7 | 8.1 | 3.4 | 7.6 | 1.7 | 5.6 | 7.4 | 2.2 |
| IL-3 | 57 | 1.9 | 1.7 | 1.7 | 1.1 | 2.3 | 1.8 | 1.6 | 1.9 | 3.3 | 4.1 | 4.2 | 2.6 | 1.7 | 1.3 | 1.8 | 2.5 | 1.4 |
| GM-CSF | 511 | 3.5 | 3 | 2.9 | 1.6 | 4.1 | 2.8 | 3.5 | 3.8 | 6.6 | 5.6 | 6.7 | 5.8 | 4.3 | 2 | 3.4 | 5.4 | 4.7 |
| IL-15 | 150 | 2.6 | 2.4 | 2 | 1.8 | 2.2 | 2.2 | 2.1 | 2.2 | 2.3 | 2.6 | 2.8 | 2.3 | 2.3 | 1.7 | 2.3 | 2.7 | 2.1 |
| TH2 bias | | | | | | | | | | | | | | | | | | |
| IL-4 | 825 | 3.9 | 2.8 | 2.9 | 2.1 | 2.9 | 1.9 | 2.4 | 2.2 | 2.7 | 3 | 2.6 | 2.8 | 2.7 | 1.5 | 3.2 | 1.9 | 2.7 |
| IL-6 | 630 | 1.8 | 1.9 | 2.3 | 1.5 | 1.9 | 1.6 | 2.3 | 2.1 | 2.7 | 2.7 | 2.2 | 1.9 | 2.8 | 1 | 1.6 | 2.1 | 1.8 |
| IL-10 | 1530 | 1.2 | 1.9 | 1.7 | 0.6 | 1.8 | 1.3 | 1.7 | 2.2 | 2.5 | 2.4 | 2.3 | 2 | 1.2 | 0.7 | 1.4 | 1.8 | 1.5 |
| IL-13 | 803 | 1.8 | 1.9 | 2 | 1.6 | 2.4 | 1.6 | 2.1 | 1.4 | 1.6 | 2.6 | 1.7 | 1.8 | 2.3 | 1.1 | 1.6 | 1.6 | 1.6 |

25 cytokine/chemokine

| human iNKT/DC | D | C1 | C23 | 7DW8-5 | C34 | C17 |
|---|---|---|---|---|---|---|
| TH1 bias | pg/mL | pg/mL | pg/mL | pg/mL | pg/mL | pg/mL |
| IFN-gamma | 57 | 1886 | 4349 | 4358 | 4103 | 1073 |
| IL-1 alpha | 47 | 46 | 61 | 47 | 48 | 40 |
| IL-1 beta | 46 | 35 | 76 | 33 | 28 | 26 |
| IL-2 | 33 | 119 | 430 | 506 | 517 | 71 |
| IL-12 p40 | 473 | 460 | 902 | 759 | 665 | 403 |
| IL-12 p70 | 158 | 353 | 691 | 582 | 510 | 134 |
| IL-15 | 26 | 25 | 29 | 30 | 28 | 25 |
| IL-8 | 5000 | 7241 | 14664 | 2609715 | 50209792 | 5463133 |
| MCP-1 | 297 | 5284 | 9394 | 72354 | 60707 | 8268 |
| MIP-1 beta | 2413 | 1583 | 2935 | 2843 | 2211 | 2118 |
| RANTES | 16447 | 23491 | 36440 | 285864050 | 1325045972 | 31159 |
| TH2 bias | | | | | | |
| IL-4 | 110 | 320 | 264 | 279 | 286 | 184 |
| IL-6 | 600 | 1887 | 4091 | 647732 | 77590 | 13803 |
| IL-10 | 1717 | 2046 | 3739 | 2236 | 2032 | 1580 |
| IL-13 | 139 | 204 | 4499 | 2688 | 1852 | 142 |
| TH17 | | | | | | |
| IL-17 | 64 | 894 | 376 | 66 | 49 | 12 |
| other | | | | | | |
| TNF-alpha | 151 | 218 | 2963 | 1787 | 1687 | 89 |
| Eotaxin | 53 | 51 | 74 | 67 | 52 | 48 |
| GM-CSF | 50 | 42 | 591 | 661 | 487 | 55 |
| IL-3 | 4 | 6 | 30 | 25 | 33 | 5 |
| IL-5 | 17 | 11 | 31 | 26 | 22 | 14 |
| IL-7 | 35 | 32 | 36 | 35 | 33 | 30 |
| IP-10 | 14930 | 1434559 | 163782 | 146750 | 1634841 | 21224 |
| IL-1RA | 14103 | 62820 | 50335 | 61420 | 49656 | 16564 |
| IL-18 | 7 | 29 | 73 | 19 | 16 | 3 |
| IL-21 | NA | NA | NA | NA | NA | NA |

| Mouse TH1 bias | basal pg/mL | C1 fold | C2 fold | C3 fold | C9 fold | C11 fold | C13 fold | C14 fold | C16 fold |
|---|---|---|---|---|---|---|---|---|---|
| IFN-γ * | 20.4 | 300 | 43.8 | 3.1 | 160.8 | 48.3 | 122.5 | 27.5 | 166.1 |
| IL-1β | 85.3 | 7.8 | 2.4 | 2 | 3.2 | 4.7 | 3.4 | 4.8 | 3.4 |
| IL-2 | 14.8 | 58.9 | 14 | 17.2 | 22 | 70.3 | 75.3 | 21.5 | 50.5 |
| IL12 p70* | 109 | 3.2 | 3.5 | 1.2 | 1.4 | 2.6 | 6.6 | 1.4 | 1.6 |
| IL-12 p40* | 69.4 | 2.8 | 0.9 | 1.9 | 2.1 | 3.8 | 3.5 | 4.4 | 2.4 |
| RANTES | 278 | 2.6 | 0.9 | 0.9 | 1.6 | 2.3 | 2.1 | 2.8 | 2.2 |
| MIP-β | 291 | 3.6 | 1.5 | 1.4 | 2.5 | 3.8 | 5.3 | 1.8 | 5.1 |
| MCP-1 | 122 | 18.7 | 2.6 | 5.6 | 14.8 | 19.4 | 32.9 | 8 | 23.6 |
| KC | 180 | 30.5 | 3.9 | 7.6 | 16.4 | 11 | 19.2 | 16.1 | 6.9 |
| TNF α * | 8 | 51 | 2 | 6 | 36.3 | 22.4 | 38.8 | 8.7 | 45.6 |
| IL-3 | 8.35 | 3 | 1.5 | 2.8 | 1.8 | 2.4 | 2.3 | 10.4 | 1.9 |
| GM-CSF | 82.8 | 13.1 | 1.6 | 4.9 | 7.3 | 2.9 | 7.9 | 37.6 | 2.7 |
| TH2 bias | | | | | | | | | |
| IL-4 | 7.46 | 240 | 26.2 | 26.8 | 42.9 | 53.1 | 115 | 21.2 | 49.6 |
| IL-6 | 33.1 | 5.5 | 1.5 | 1.7 | 2.2 | 2.8 | 6.3 | 4.9 | 5.8 |
| IL-10* | 81.2 | 3.6 | 5.4 | 1.1 | 2.4 | 1.3 | 2.2 | 1.5 | 1.3 |
| IL-13 | 75.8 | 15.1 | 0.9 | 2.3 | 2.4 | 10.9 | 12.6 | 1.7 | 7.7 |

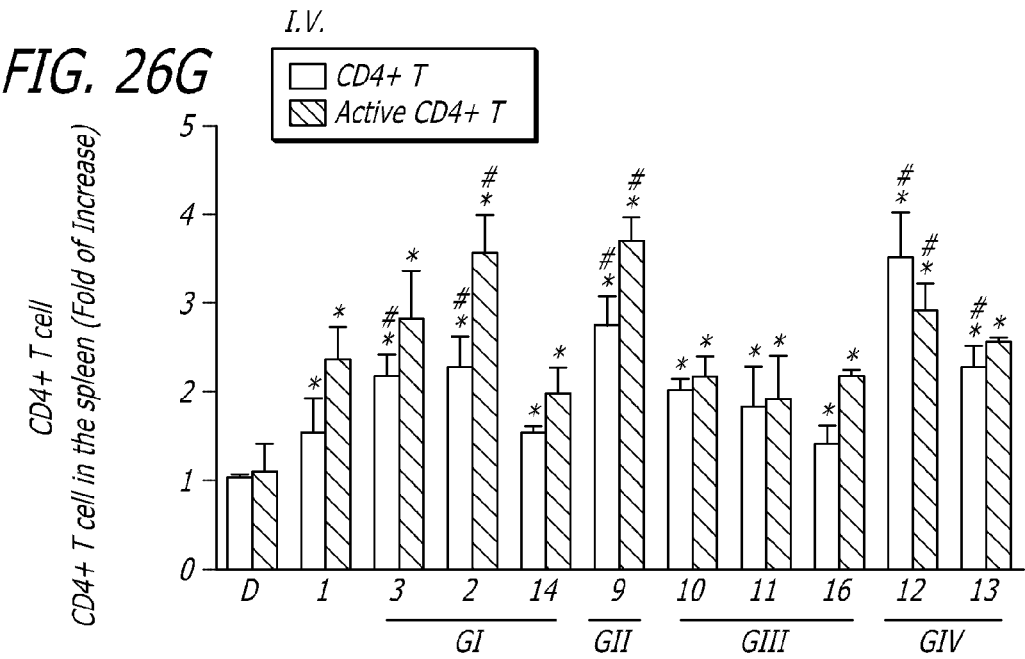
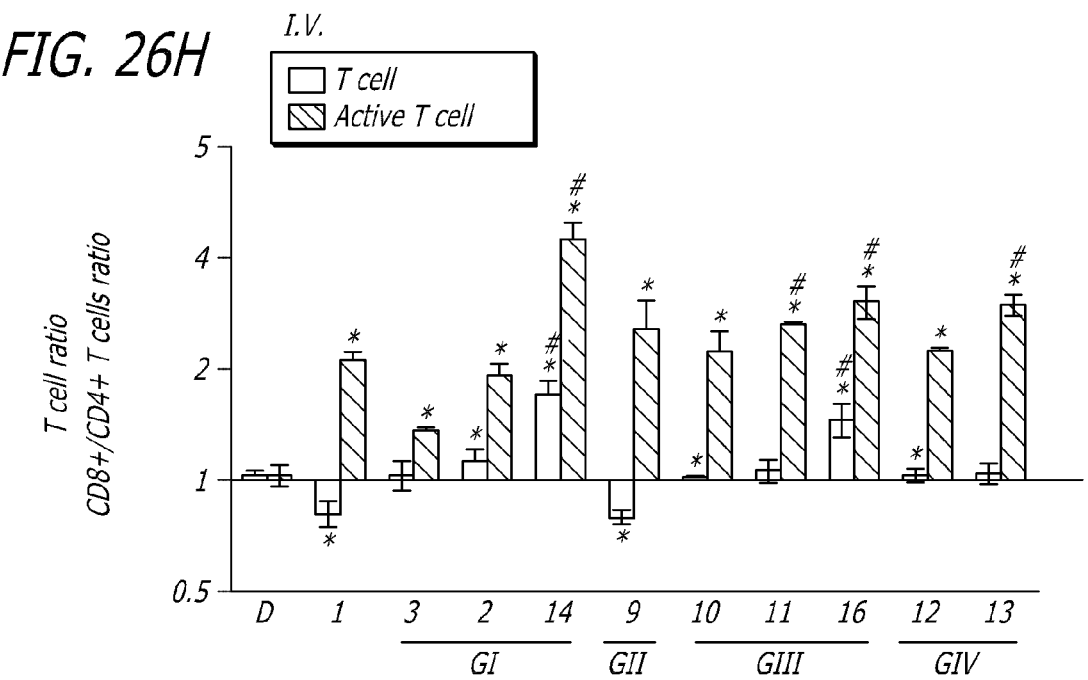

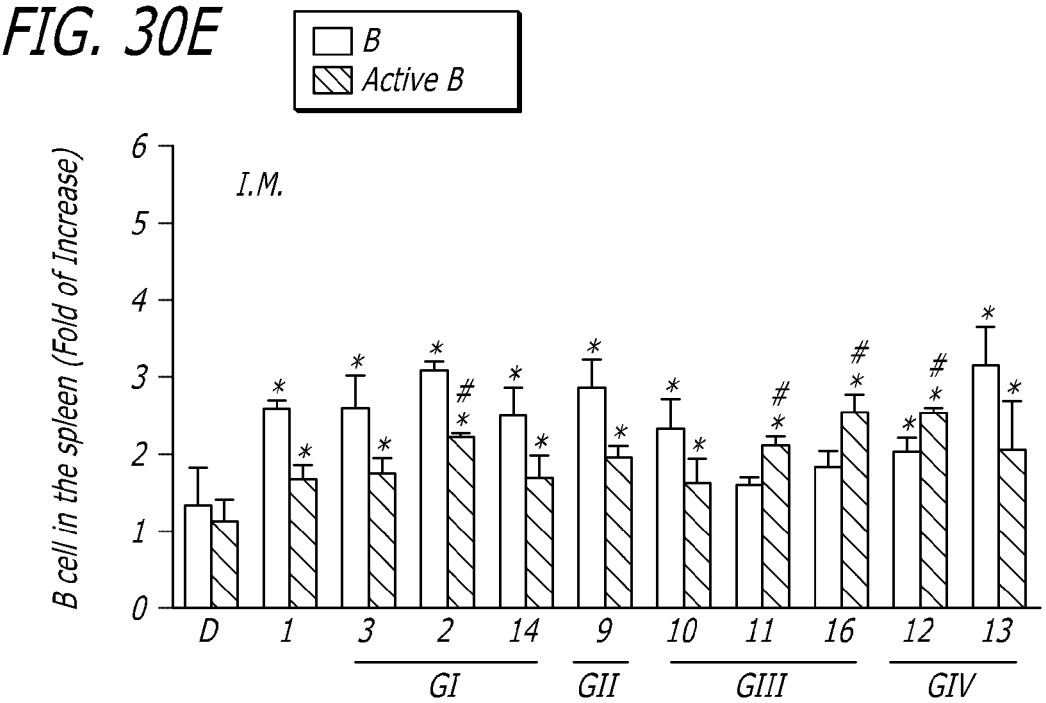
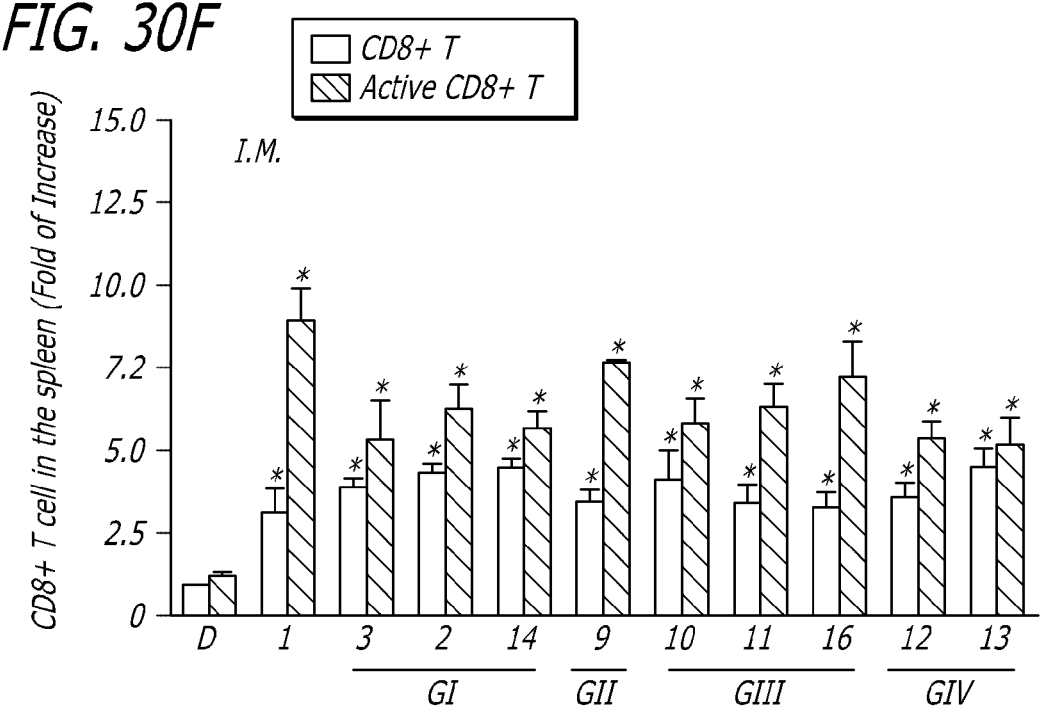

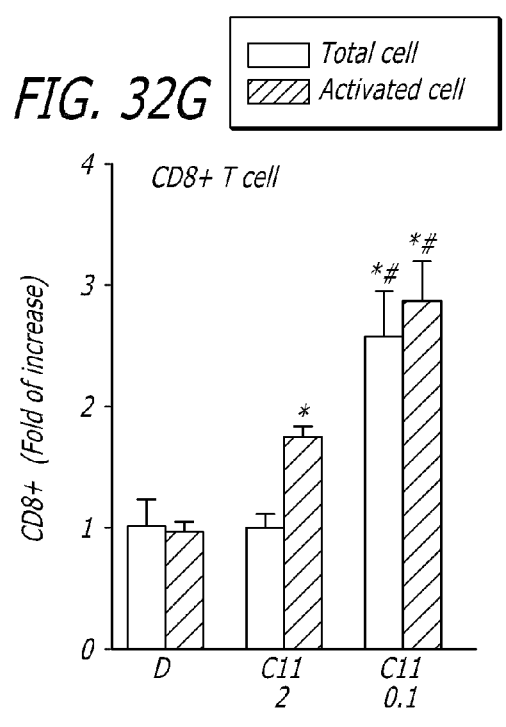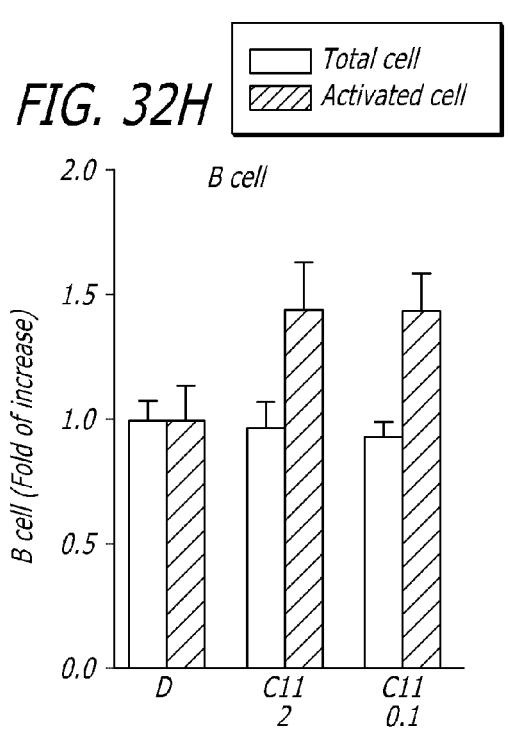

FIG. 34

| 24 cytokine/chemokine | D 2h pg/mL | C1 2h pg/mL | C23 2h pg/mL | C26 2h pg/mL | C8-5 2h pg/mL | C30 2h pg/mL | C17 2h pg/mL | D18 2h pg/mL | C1 18h pg/mL | C23 18h pg/mL | C26 18h pg/mL | C8-5 18h pg/mL | C30 18h pg/mL | C17 18h pg/mL |
|---|---|---|---|---|---|---|---|---|---|---|---|---|---|---|
| TH1 bias | | | | | | | | | | | | | | |
| IFN-gamma | 23 | 106 | 63 | 66 | 19 | 99 | 77 | 20 | 1270 | 706 | 341 | 713 | 890 | 110 |
| IL-1 alpha | 78 | 171 | 62 | 119 | 65 | 153 | 75 | 53 | 50 | 92 | 94 | 145 | 110 | 67 |
| IL-1 beta | 59 | 110 | 224 | 62 | 69 | 152 | 111 | 75 | 49 | 298 | 86 | 60 | 103 | 73 |
| IL-2 | 25 | 323 | 26 | 28 | 75 | 413 | 82 | 27 | 19 | 45 | 32 | 37 | 31 | 51 |
| IL-12 p40 | 109 | 120 | 133 | 164 | 62 | 93 | 374 | 81 | 72 | 617 | 284 | 131 | 119 | 181 |
| IL-12 p70 | 172 | 279 | 1062 | 553 | 156 | 417 | 912 | 110 | 1690 | 2105 | 783 | 1065 | 2393 | 260 |
| KC | 216 | 2027 | 303 | 223 | 1567 | 2450 | 455 | 225 | 494 | 275 | 256 | 318 | 352 | 231 |
| MCP-1 | 477 | 1270 | 573 | 583 | 1510 | 2780 | 631 | 467 | 837 | 1263 | 837 | 580 | 588 | 392 |
| MIP-1 beta | 78 | 322 | 85 | 77 | 385 | 345 | 155 | 52 | 107 | 124 | 113 | 238 | 174 | 115 |
| RANTES | 191 | 279 | 322 | 298 | 233 | 336 | 370 | 206 | 178 | 769 | 327 | 266 | 223 | 108 |
| TH2 bias | | | | | | | | | | | | | | |
| IL-4 | 19 | 455 | 185 | 213 | 214 | 263 | 322 | 8 | 21 | 29 | 24 | 19 | 18 | 19 |
| IL-6 | 20 | 49 | 90 | 24 | 26 | 39 | 53 | 47 | 24 | 220 | 57 | 50 | 41 | 23 |
| IL-10 | 69 | 296 | 452 | 84 | 66 | 243 | 331 | 138 | 237 | 858 | 141 | 185 | 227 | 145 |
| IL-13 | 47 | 101 | 56 | 39 | 38 | 174 | 112 | 51 | 79 | 136 | 39 | 92 | 114 | 91 |
| TH17 | | | | | | | | | | | | | | |
| IL-17 | 247 | 253 | 579 | 582 | 341 | 314 | 639 | 277 | 128 | 1245 | 632 | 321 | 230 | 129 |
| other | | | | | | | | | | | | | | |
| TNF-alpha | 20 | 195 | 22 | 19 | 59 | 140 | 35 | 23 | 40 | 30 | 31 | 37 | 43 | 17 |
| VEGP | 56 | 59 | 60 | 67 | 45 | 66 | 74 | 65 | 133 | 123 | 115 | 109 | 135 | 55 |
| GM-CSF | 27 | 347 | 28 | 74 | 54 | 202 | 89 | 15 | 14 | 114 | 64 | 16 | 24 | 11 |
| IL-3 | 38 | 42 | 68 | 107 | 23 | 25 | 82 | 23 | 27 | 339 | 138 | 85 | 58 | 16 |
| IL-5 | 97 | 114 | 163 | 103 | 124 | 195 | 148 | 74 | 118 | 193 | 192 | 89 | 137 | 108 |
| IL-9 | 74 | 178 | 37 | 61 | 67 | 102 | 196 | 70 | 64 | 215 | 81 | 106 | 61 | 168 |
| IL-IRA | 467 | 595 | 517 | 327 | 518 | 898 | 1102 | 325 | 617 | 722 | 547 | 611 | 935 | 578 |
| IL-18 | 165 | 143 | 180 | 192 | 110 | 113 | 155 | 158 | 114 | 152 | 161 | 107 | 66 | 122 |
| IL-21 | 38 | 546 | 29 | NA | 31 | 204 | 264 | NA | NA | NA | 26 | 200 | 928 | NA |

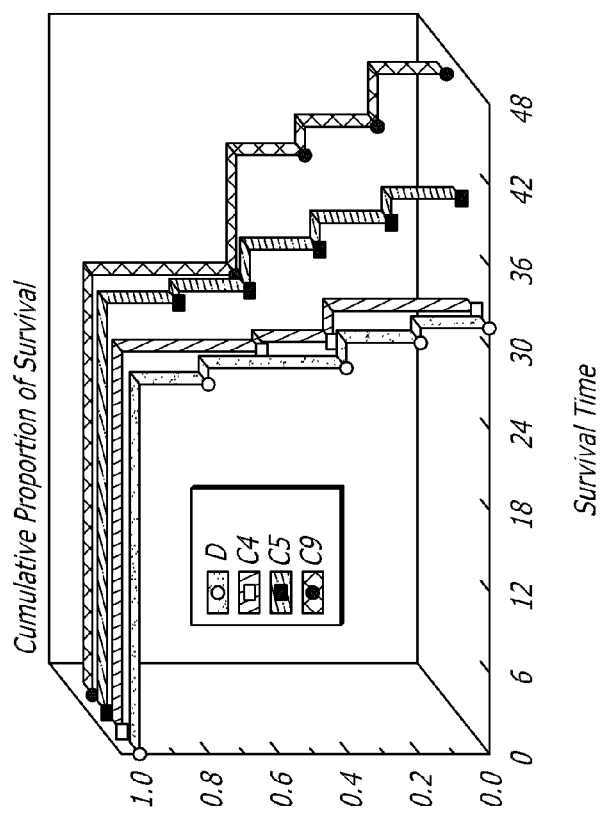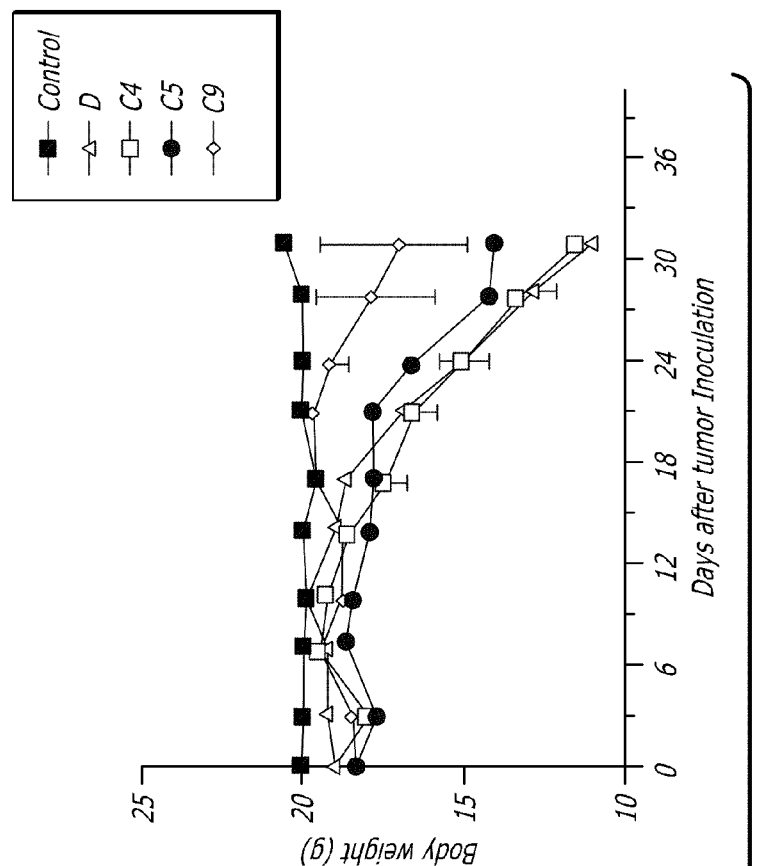
FIG. 37B

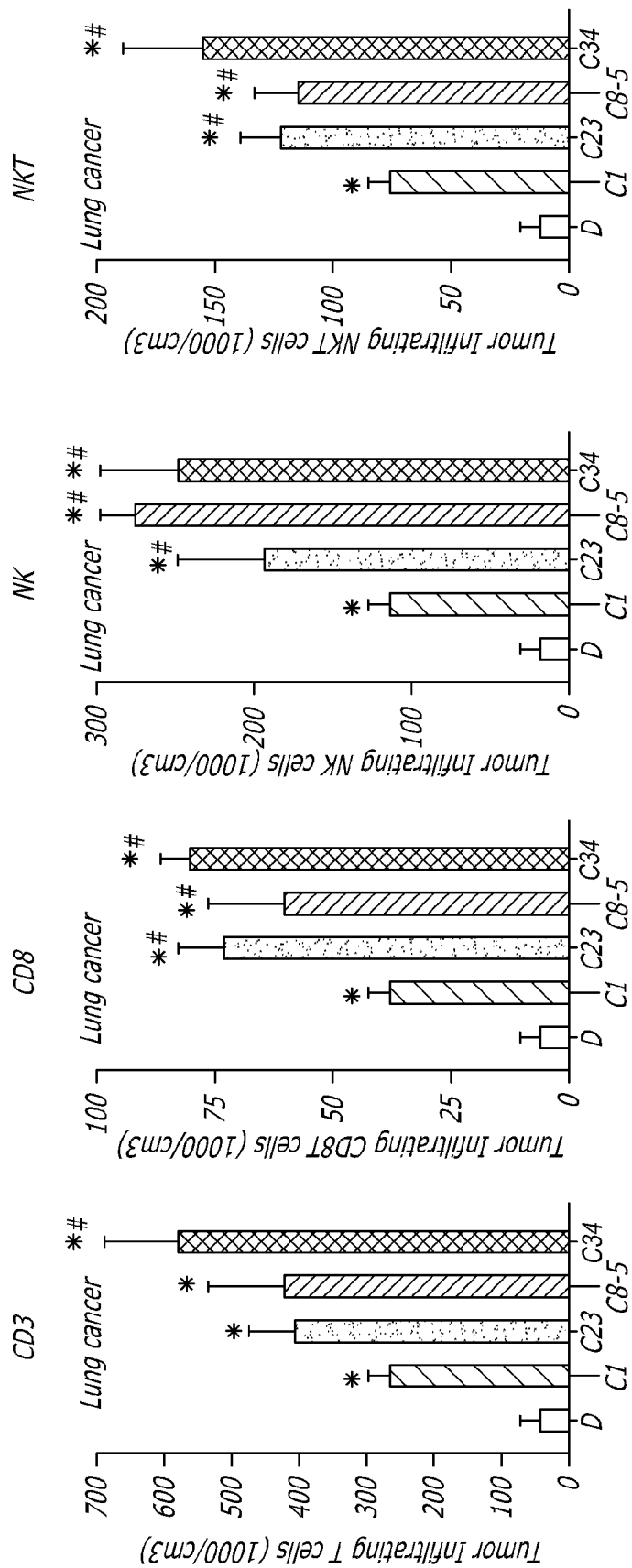

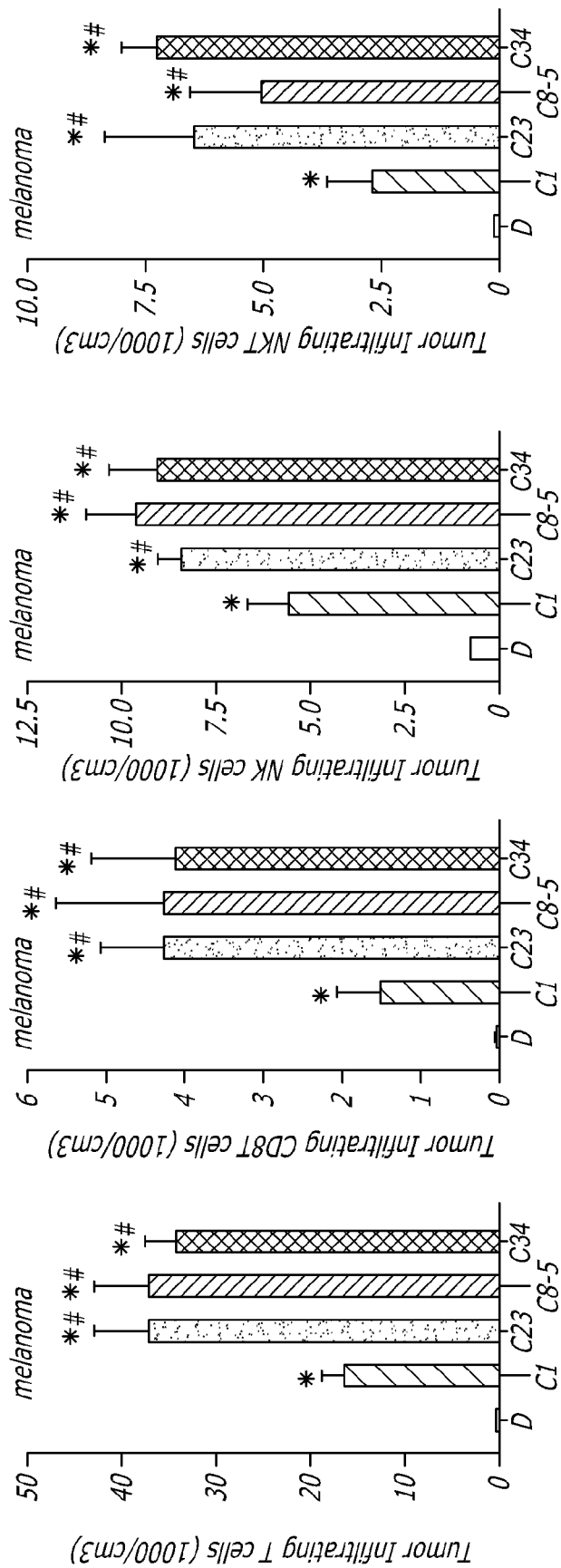

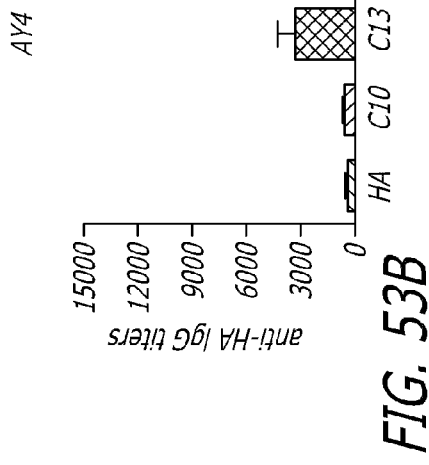
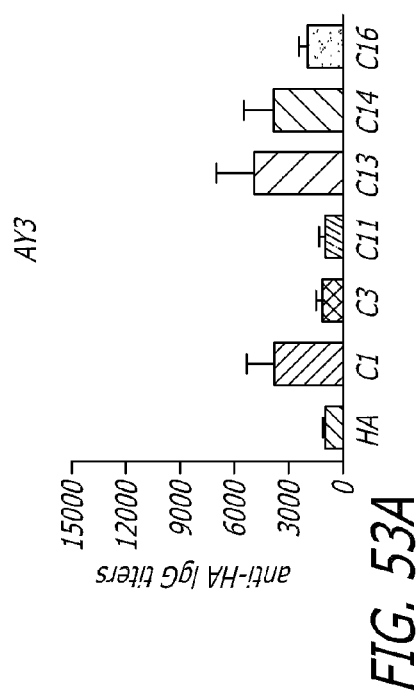
FIG. 53A / FIG. 53B / FIG. 53C / FIG. 53D

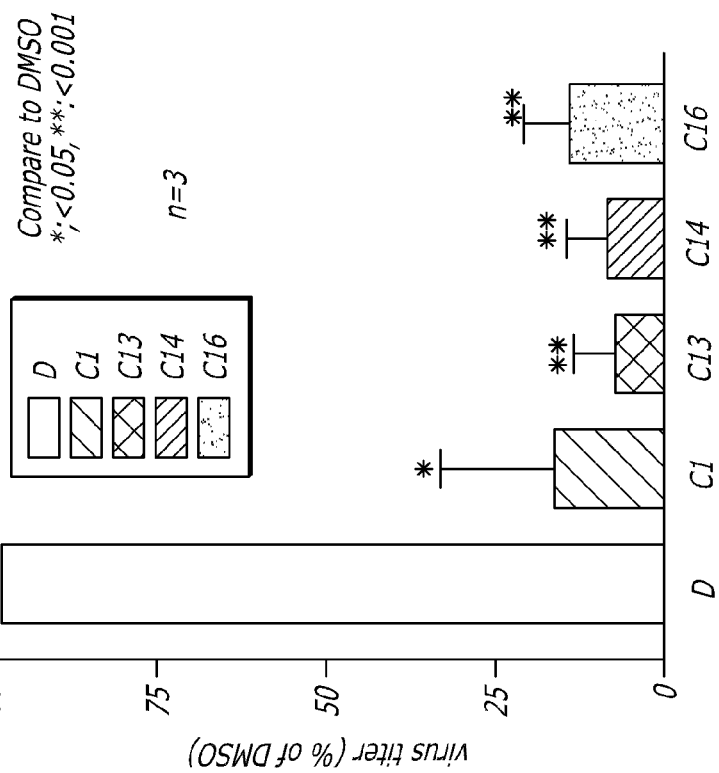
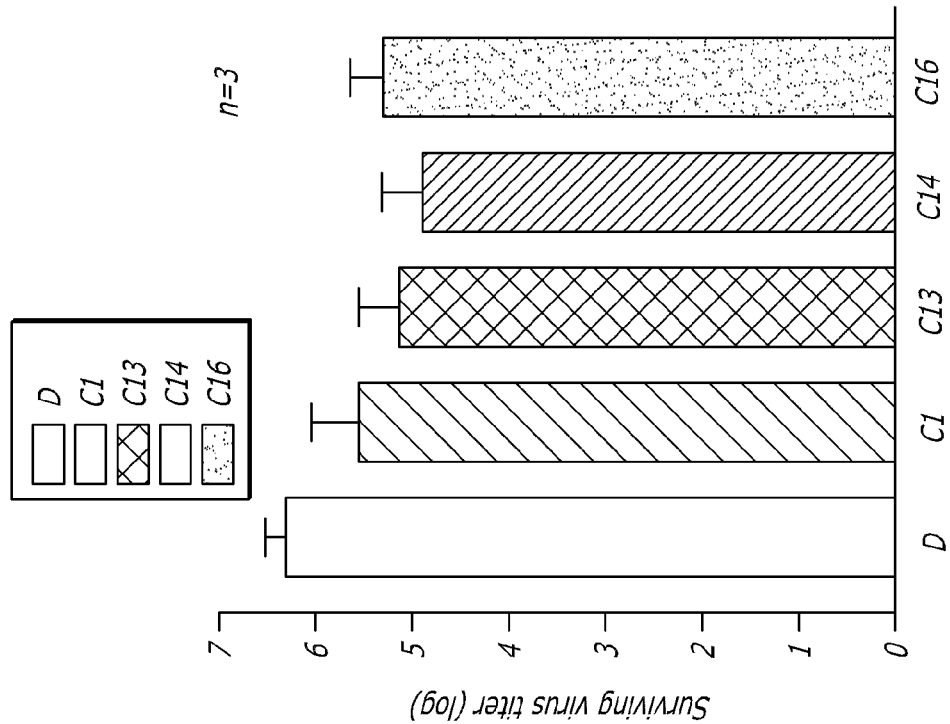
FIG. 60A
FIG. 60B

US 7,928,077 B2

ALPHA-GALACTOSYL CERAMIDE ANALOGS AND THEIR USE AS IMMUNOTHERAPIES

RELATED APPLICATION

None.

FIELD OF THE DISCLOSURE

The present disclosure relates to alpha-galactosyl ceramide (α-GalCer) analogs, and their use as immunotherapies.

BACKGROUND

Natural killer T cells (NKTs) represent a subset of T lymphocytes with unique properties, including reactivity for natural or synthetic glycolipids presented by CD1d and expression of an invariant T cell antigen receptor (TCR) alpha chain. NKTs are different from functionally differentiated conventional αβ T cells in that they share properties of both natural killer cells and T cells are can rapidly produce both $T_H1$-type and $T_H2$-type responses upon stimulation with their ligands (innate immunity). The activation of NKTs paradoxically can lead either to suppression or stimulation of immune responses. For example, the production of $T_H1$ cytokines is thought to promote cellular immunity with antitumor, antiviral/antibacterial, and adjuvant activities, whereas $T_H2$ cytokine production is thought to subdue autoimmune diseases and promote antibody production. Because NKTs play a regulatory role in the immune system, they are attractive targets for immunotherapy.

SUMMARY OF THE DISCLOSURE

In one exemplary implementation, DC development may be stimulated via the use of granulocyte-macrophage colony-stimulating-factor (GM-CSF), or in another exemplary implementation, interleukin (IL)-3, which may, in another exemplary implementation, enhance DC survival.

In one exemplary implementation, the DCs utilized in the methods of this disclosure may express myeloid markers, such as, for example, CD11c or, in another exemplary implementation, an IL-3 receptor-α (IL-3Rα) chain (CD123). In another exemplary implementation, the DCs may produce type I interferons (IFNs). In one exemplary implementation, the DCs utilized in the methods of this disclosure express costimulatory molecules. In another exemplary implementation, the DCs utilized in the methods of this disclosure may express additional adhesion molecules, which may, in one implementation, serve as additional costimulatory molecules, or in another implementation, serve to target the DCs to particular sites in vivo, when delivered via the methods of this disclosure, as described further hereinbelow.

In one exemplary implementation, the dendritic cells used in the methods of this disclosure may express CD83, an endocytic receptor to increase uptake of the autoantigen such as DEC-205/CD205 in one implementation, or DC-LAMP (CD208) cell surface markers, or, in another implementation, varying levels of the antigen presenting MHC class I and II products, or in another implementation, accessory (adhesion and co-stimulatory) molecules including CD40, CD54, CD58 or CD86, or any combination thereof. In another implementation, the dendritic cells may express varying levels of CD115, CD14, CD68 or CD32.

In one exemplary implementation, mature dendritic cells are used for the methods of this disclosure. In one implementation, the term "mature dendritic cells" refers to a population of dendritic cells with diminished CD115, CD14, CD68 or CD32 expression, or in another implementation, a population of cells with enhanced CD86 expression, or a combination thereof. In another implementation, mature dendritic cells will exhibit increased expression of one or more of p55, CD83, CD40 or CD86 or a combination thereof. In another implementation, the dendritic cells used in the methods of this disclosure will express the DEC-205 receptor on their surface. In another implementation, maturation of the DCs may be accomplished via, for example, CD40 ligation, CpG oligodeoxyribonucleotide addition, ligation of the IL-1, TNFα or TOLL like receptor ligand, bacterial lipoglycan or polysaccharide addition or activation of an intracellular pathway such as TRAF-6 or NF-κB.

In one exemplary implementation, inducing DC maturation may be in combination with endocytic receptor delivery of a preselected antigen. In one implementation, endocytic receptor delivery of antigen may be via the use of the DEC-205 receptor.

In one exemplary implementation, the maturation status of the dendritic may be confirmed, for example, by detecting either one or more of 1) an increase expression of one or more of p55, CD83, CD40 or CD86 antigens; 2) loss of CD115, CD14, CD32 or CD68 antigen; or 3) reversion to a macrophage phenotype characterized by increased adhesion and loss of veils following the removal of cytokines which promote maturation of PBMCs to the immature dendritic cells, by methods well known in the art, such as, for example, immunohistochemistry, FACS analysis, and others.

NKT expansion, in one implementation, varies in response to a presenting antigen. In one implementation, an α-GalCer analog of this disclosure is supplied in the culture simultaneously with dendritic cell contact with the NKTs. In another implementation, dendritic cells, which have already processed antigen are contacted with the NKTs.

In one exemplary implementation, the term "contacting a target cell" refers herein to both direct and indirect exposure of cell to the indicated item. In one implementation, contact of NKTs with an α-GalCer analog of this disclosure, a cytokine, growth factor, dendritic cell, or combination thereof, is direct or indirect. In one implementation, contacting a cell may comprise direct injection of the cell through any means well known in the art, such as microinjection. It is also envisioned, in another implementation, that supply to the cell is indirect, such as via provision in a culture medium that surrounds the cell, or administration to a subject, via any route well known in the art, and as described hereinbelow.

Methods for priming dendritic cells with antigen are well known to one skilled in the art, and may be effected, as described for example Hsu et al., Nature Med. 2:52-58 (1996); or Steinman et al. International application PCT/US93/03141.

In one implementation, the α-GalCer analog is administered to a subject, and, in another implementation, is targeted to the dendritic cell, wherein uptake occurs in vivo, for methods as described hereinbelow.

α-GalCer analog uptake and processing, in one implementation, can occur within 24 hours, or in another implementation, longer periods of time may be necessary, such as, for example, up to and including 4 days or, in another implementation, shorter periods of time may be necessary, such as, for example, about 1-2 hour periods.

In another implementation, the NKTs expanded by the dendritic cells in the methods of this disclosure are autologous, syngeneic or allogeneic, with respect to the dendritic cells.

In one implementation, the NKTs can be used to modulate an immune response, in a disease-specific manner. It is to be understood that any immune response, wherein it is desired to enhance cytokine production, or elicit a particular cytokine profile, including interferon-γ, interleukin-2 and/or interleukin-4, the NK T cells of this disclosure may be thus utilized, and represents an implementation of this disclosure.

In another implementation, the methods of this disclosure may further comprise the step of culturing previously isolated, NKTs with additional dendritic cells, and an α-GalCer analog of the present disclosure, for a period of time resulting in further NKT expansion, cytokine production, or a combination thereof.

In another implementation, this disclosure provides a method for delaying onset, reducing incidence or suppressing a disease in a subject, comprising the steps of contacting in a culture NKTs with dendritic cells and an α-GalCer analog of the present disclosure, for a period of time resulting in NKT expansion, cytokine production or a combination thereof, and administering NKTs thus obtained to the subject, wherein the NKTs delay onset, reduce incidence or suppress a disease in the subject, thereby delaying onset, reducing incidence or suppressing a disease in the subject.

In one exemplary implementation, cells for administration to a subject in this disclosure may be provided in a composition. These compositions may, in one implementation, be administered parenterally or intravenously. The compositions for administration may be, in one implementation, sterile solutions, or in other implementations, aqueous or non-aqueous, suspensions or emulsions. In one implementation, the compositions may comprise propylene glycol, polyethylene glycol, injectable organic esters, for example ethyl oleate, or cyclodextrins. In another implementation, compositions may also comprise wetting, emulsifying and/or dispersing agents. In another implementation, the compositions may also comprise sterile water or any other sterile injectable medium. In another implementation, the compositions may comprise adjuvants, which are well known to a person skilled in the art (for example, vitamin C, antioxidant agents, etc.) for some of the methods as described herein, wherein stimulation of an immune response is desired, as described further hereinbelow.

In one exemplary implementation, the disclosure provides a compound represented by the structure of formula 1:

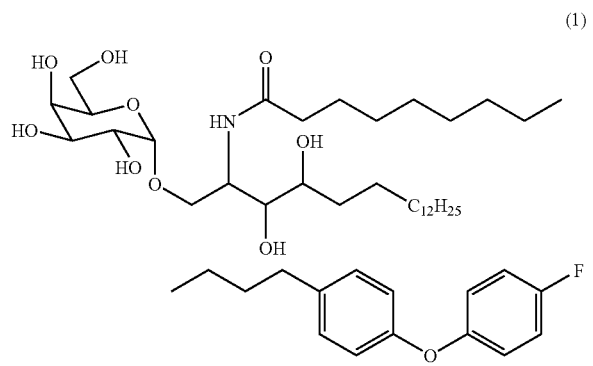

(1)

In one implementation, the α-GalCer analogs, cells, vaccines or compositions of this disclosure may be administered to a subject via injection. In one implementation, injection may be via any means known in the art, and may include, for example, intra-lymphoidal, or SubQ injection.

In one implementation, the α-GalCer analogs of the present disclosure are delivered to dendritic cells in vivo in the steady state, which, in another implementation, leads to expansion of disease ameliorating NKTs. Analog delivery in the steady state can be accomplished, in one implementation, as described in Bonifaz, et al. (2002) Journal of Experimental Medicine 196: 1627-1638; Manavalan et al. (2003) Transpl Immunol. 11: 245-58.

In another exemplary implementation, select types of dendritic cells in vivo function to prime the NKTs.

In another exemplary implementation, this disclosure provides a method for modulating an immune response, which is an inappropriate or undesirable response. In one implementation, the immune response is marked by a cytokine profile which is deleterious to the host.

In one exemplary implementation, the NKTs of this disclosure may be administered to a recipient contemporaneously with treatment for a particular disease, such as, for example, contemporaneous with standard anti-cancer therapy, to serve as adjunct treatment for a given cancer. In another implementation, the NKTs of this disclosure may be administered prior to the administration of the other treatment.

In another exemplary implementation, this disclosure provides a method for modulating an immune response, which is directed to infection with a pathogen, and the immune response is not protective to the subject.

In another exemplary implementation, the immune response results in a cytokine profile, which is not beneficial to the host. In one implementation, the cytokine profile exacerbates disease. In one implementation, a $T_H2$ response is initiated when a $T_H1$ response is beneficial to the host, such as for example, in lepromatous leprosy. In another implementation, a $T_H1$ response is initiated, and persists in the subject, such as for example, responses to the egg antigen is schistosomiasis.

In another exemplary implementation, the disclosure provides a method of activating a cytokine response in a subject whereby an effective amount of a compound or a salt or a mixture is administered, wherein the subject has an adaptive immune system that includes a population of cells, the population including at least one lymphocyte and at least one antigen-presenting cell, and wherein the compound is represented by the structure of formula 1:

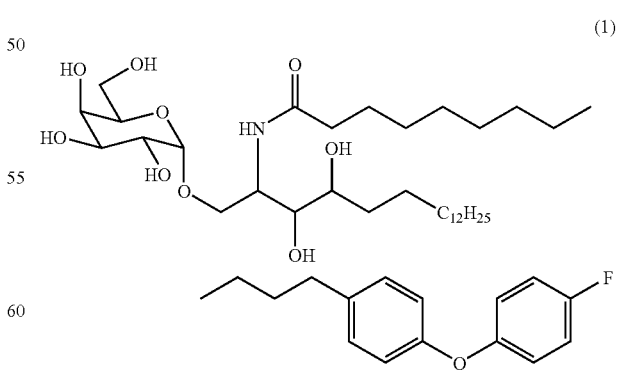

(1)

or a pharmaceutically acceptable salt thereof;

forming a complex between the compound and the antigen-presenting cell, wherein the formation of the com plex results in the activation of a receptor on the lymphocyte; and activating the lymphocyte to produce the cytokine response.

In some aspects of the method at least one lymphocyte is a T lymphocyte and in some cases the T lymphocyte is a Natural Killer T cell. In some instances the Natural Killer T cell is an invariant Natural Killer T cell. In some aspects In some aspects the at least one antigen-presenting cell is a dendritic cell. In some instances the dendritic cell is an immature or a mature dendritic cell.

In some aspects of the method administering the compound is accomplished by subcutaneous administration, intravenous administration, intranasal administration or intramuscular administration.

In some aspects of the method, the compound forms a complex with a CD1 molecule on the antigen-presenting cell. In some instances the CD1 molecule is a CD1d molecule. In some instances the receptor on the T lymphocyte is a T cell receptor. In some instances stimulating at least one other lymphocyte to produce the cytokine response, in some instances the at least one other lymphocyte is a T helper cell.

In some aspects of the method the cytokine response is a $T_H1$-type cytokine response which produces $T_H1$ cytokines which may also be selected from the group consisting of IFN-γ, IL-1β, IL-2, IL-3, IL-8, IL-12, IL-15, TNF-α, GM-CSF, RANTES, MIP-1α and MCP-1.

In some aspects of the method of claim 1 wherein the cytokine response is a $T_H2$-type cytokine response which produces $T_H2$ cytokines which may also be selected from the group consisting of IL-4, IL-6, IL-8, IL-10, IL-13, RANTES, MIP-1α and MCP-1

In some exemplary implementations the disclosure provides a vaccine comprising an effective amount of a compound represented by the structure of formula 1:

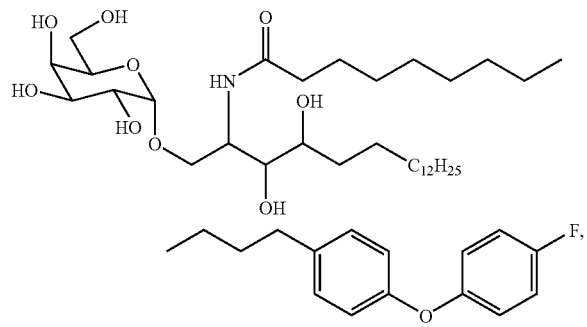

(1)

or a pharmaceutically acceptable salt thereof; and a vaccine agent.

In some instances the vaccine agent is selected from the group consisting of a killed microorganism, a live attenuated virus microorganism, a toxoid and a fragment of an inactivated or attenuated microorganism. In some instances the microorganism is a bacteria or a fungi. In some instances the toxoid is a tetanus or a diphtheria. In some instances the vaccine agent is capable of eliciting an immune response in a subject that is administered the vaccine. In some instances the compound acts as an immunologic adjuvant and is capable of modifying or augmenting the immune response elicited by the vaccine agent by stimulating the immune system which results in the subject responding to the vaccine more vigorously than without the compound.

In some exemplary implementations the disclosure provides an anti-tumor immunotherapy comprising administering an effective amount of a compound represented by the structure of formula 1:

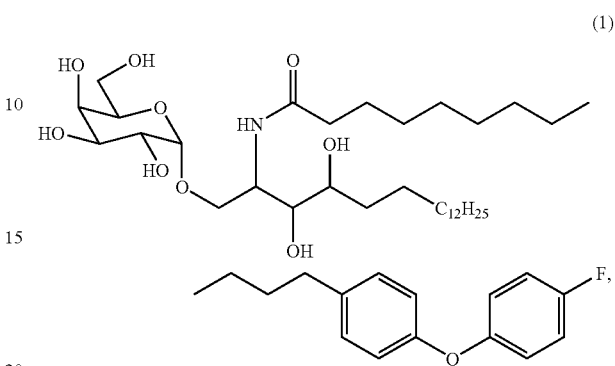

(1)

or a pharmaceutically acceptable salt thereof.

In some aspects of the method, the administration is based on at least one of cancer, an elevated risk for cancer or precancerous precursors. In some aspects of the method the administration of the compound elicits a response in at least one of tumor and cancer cells. In some aspects of the method the response elicited is a slowing down in a growth of the tumor. In some aspects of the method the response elicited is a reduction in a size of the tumor.

In some exemplary implementations the method includes the administration of the compound is to effect an adaptive immune system that includes a population of cells, the population including at least one lymphocyte and wherein the response elicited is an expansion of the population of cells in the adaptive immune system.

In some aspects of the method the expansion of the population of cells in the adaptive immune system includes an expansion in a number of T cells, CD8 Tcells, NK cells or NKT cells. In some aspects of the method includes providing a cancer vaccine to which the compound is added to. In some aspects of the method of the cancer is selected from the group consisting of lung cancer, breast cancer, hepatoma, leukemia, solid tumor and carcinoma.

In some aspects of the method the administration is based on an infectious disease resulting from the presence of pathogenic microbial agents. In some aspects of the method the pathogenic microbial agents are selected from the group consisting of viruses, bacteria, fungi, protozoa, multicellular parasites and aberrant proteins. In some aspects of the method the pathogenic microbial agent is a virus. In some aspects of the method the virus is selected from the group consisting of Retroviridae, Picornaviridae, Calciviridae, Togaviridae, Flaviridae, Coronaviridae, Rhabdoviridae, Filoviridae, Paramyxoviridae, Orthomyxoviridae, Bungaviridae, Arenaviridae, Reoviridae, Birnaviridae, Hepadnaviridae, Parvoviridae, Papovaviridae, Adenoviridae, Herpesviridae, Poxyiridae and Iridoviridae. In some aspects of the method the pathogenic microbial agent is a bacteria. In some aspects of the method the bacteria is selected from the group consisting of *Helicobacter pylori, Borellia burgdorferi, Legionella pneumophilia, Klebsiella Pneumoniae, Mycobacteria* sps, *Staphylococcus aureus, Neisseria gonorrhoeae, Neisseria meningitidis, Listeria monocytogenes, Streptococcus pyogenes, Streptococcus agalactiae, Streptococcus, Streptococcus faecalis, Streptococcus bovis, Streptococcus pneumoniae*, pathogenic *Campylobacter* sp., *Enterococcus* sp.,

*Chlamidia* sp., *Haemophilus influenzae*, *Bacillus antracis*, *corynebacterium diphtheriae*, *corynebacterium* sp., *Erysipelothrix rhusiopathiae*, *Clostridium perfringers*, *Clostridium tetani*, *Enterobacter aerogenes*, *Klebsiella pneumoniae*, *Pasturella multocida*, *Bacteroides* sp., *Fusobacterium nucleatum*, *Streptobacillus moniliformis*, *Treponema pallidium*, *Treponema pertenue*, *Leptospira*, *Actinomyces israelli*, *Sphingomonas capsulata* and *Francisella tularensis*. In some aspects of the method wherein the administration of the compound to a subject results in an enhanced bacterial clearance as compared to a subject not administered the compound. In some aspects of the method the administration of the compound results in the killing of the microbial agent. In some aspects of the method the administration of the compound results in the microbial agent not being able to grow.

BRIEF DESCRIPTION OF THE FIGURES

The patent or application contains at least one drawing executed in color. Copies of this patent or patent application publication with color drawings will be provided by the Office upon request and payment of the necessary fee.

FIG. 7 is a table showing the folds of increase over basal cytokine concentration in the supernatants of human NKTs from FIGS. 5 and 6 treated with α-GalCer or the indicated α-GalCer analogs of the present disclosure.

FIG. 12 is a table indicating the folds of increase over basal serum concentrations in the supernatants of human NKTs from FIG. 10 treated with α-GalCer or the indicated α-GalCer analogs of the present disclosure.

FIG. 25 is a table with the results (in folds of increase over basal cytokine concentration) in the supernatants of BALB/c mice injected IV with α-GalCer or the indicated α-GalCer analogs of the present disclosure. All cytokines/chemokines peaked at 2 hours after injection, except those marked with a * peaked at 18 hours.

FIG. 34 is a table with the results (in folds of increase over basal cytokine concentration) in the supernatants of BALB/c mice injected IV with α-GalCer or the indicated α-GalCer analogs of the present disclosure from FIG. 33. All cytokines/chemokines peaked at 2 hours after injection, except those marked with a * peaked at 18 hours.

FIG. 45(A-H) show $T_H1$-biased α-GalCer analogs of the present disclosure elicit more tumor infiltrating lymphocytes in lung and melanoma tumors. (A-D) show tumor infiltrating lymphocytes in lung cancer cells (TC-1). C57BL/6 mice were treated with vehicle, α-GalCer or α-GalCer analogs C23, C8-5 or C34 at 0.1 μg/mouse once per week for three weeks. (A) shows the population of CD3+ cells. (B) shows the population of CD8 T cells. (C) shows the population of NK cells. (D) shows the population of NKTs. All analysis was performed by normalizing to vehicle. (E-H) show tumor infiltrating lymphocytes in melanoma cells. C57BL/6 mice were treated with vehicle, α-GalCer or α-GalCer analogs C23, C8-5 or C34 at 0.1 μg/mouse once per week for three weeks. (E) shows the population of CD3+ cells. (F) shows the population of CD8 T cells. (G) shows the population of NKs. (H) shows the population of NKTs. All analysis was performed by normalizing to vehicle.

FIG. 53 (A-D) show the induction of anti-HA-specific IgG antibody by α-GalCer or the indicated α-GalCer analogs of the present disclosure. BALB/c mice were vaccinated by electrotransfer in muscle with α-GalCer or the indicated α-GalCer analogs with pHAc and boosted once with the same formulation 4 weeks later. Blood samples were collected at 2 weeks after the second vaccination and tested for anti-HAc-specific IgG antibody titers by ELISA. (A) shows titers of anti-HA specific IgG antibody (AY3). (B) shows titers of anti-HA specific IgG antibody (AY4). (C) titers of anti-HA specific IgG antibody (AY5). (D) shows titers of anti-HA specific IgG antibody (AY16).

FIG. 60(A-B) show the cytopathetic effect (CPE) of Madin-Darby canine kidney (MDCK) cells in vitro. MDCK cells were pretreated with vehicle, α-GalCer or one of the α-GalCer analogs C13, C14 or C16 at 10 µg/ml for four hours, followed by infection with FLU-A virus serotype H1N1 (WSN) at 10TCID50. (A) shows the survival virus titer (log 10) after treatment of glycolipids in vitro and (B) shows the virus titer in MDCK cells at 48 hours post-infection.

DETAILED DESCRIPTION OF THE DISCLOSURE

Figure 1A:
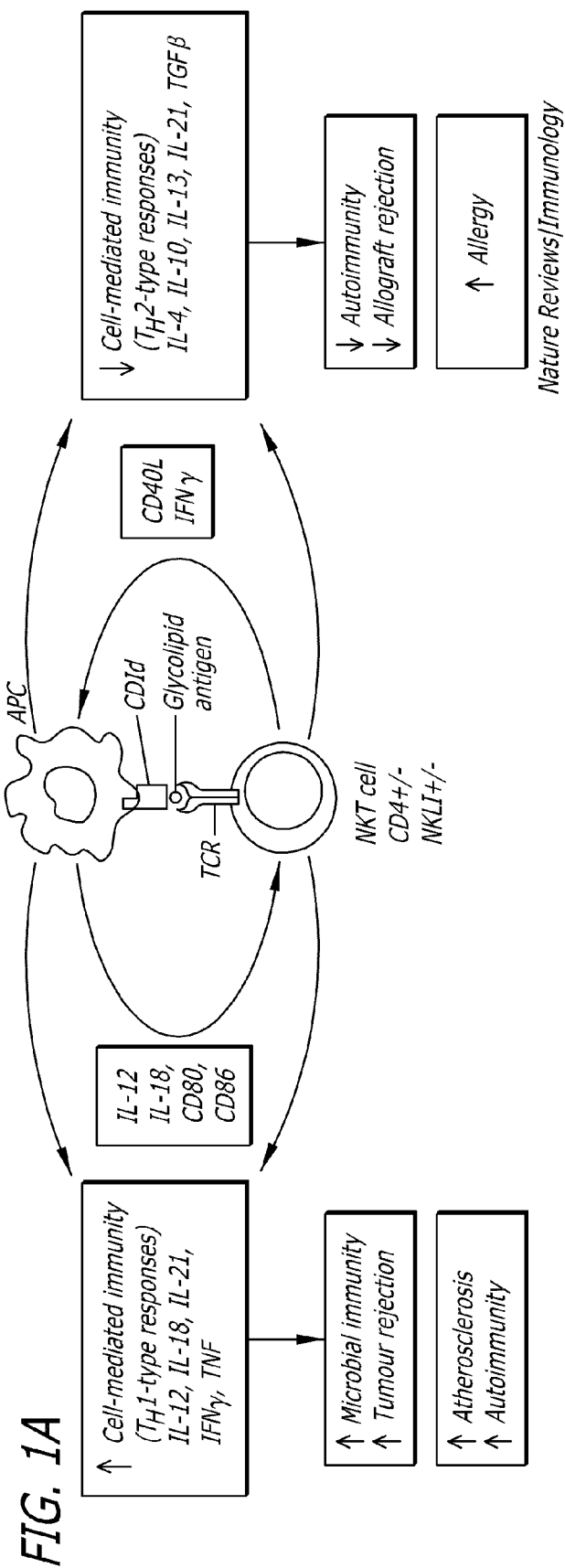
FIG. 1A shows a general scheme.

All scientific terms are to be given their ordinary meanings as understood by those of skill in the art, unless an alternate meaning is set forth below. In case of conflict, the definitions set forth in this specification shall control.

As used herein, the term "lipid" refers to any fat-soluble (lipophilic) molecule that participates in cell signaling pathways.

As used herein, the term "glycolipid" refers to a carbohydrate-attached lipid that serves as a marker for cellular recognition.

As used herein, the term "alpha-galactosyl ceramide" and "α-GalCer" refers to a glycolipid that stimulates natural killer T cells to produce both T helper ($T_H$)1 and $T_H$2 cytokines.

As used herein, the term "glycan" refers to a polysaccharide, or oligosaccharide. Glycan is also used herein to refer to the carbohydrate portion of a glycoconjugate, such as a glycoprotein, glycolipid, glycopeptide, glycoproteome, peptidoglycan, lipopolysaccharide or a proteoglycan. Glycans usually consist solely of O-glycosidic linkages between monosaccharides. For example, cellulose is a glycan (or more specifically a glucan) composed of beta-1,4-linked D-glucose, and chitin is a glycan composed of beta-1,4-linked N-acetyl-D-glucosamine. Glycans can be homo or heteropolymers of monosaccharide residues, and can be linear or branched. Glycans can be found attached to proteins as in glycoproteins and proteoglycans. They are generally found on the exterior surface of cells. O- and N-linked glycans are very common in eukaryotes but may also be found, although less commonly, in prokaryotes. N-Linked glycans are found attached to the R-group nitrogen (N) of asparagine in the sequon. The sequon is a Asn-X-Ser or Asn-X-Thr sequence, where X is any amino acid except proline As used herein, the term "glycoprotein" refers to a protein covalently modified with glycan(s). There are four types of glycoproteins: 1) N-linked glycoproteins, 2) O-linked glycoproteins (mucins), 3) glucosaminoglycans (GAGs, which are also called proteoglycans), 4) GPI-anchored. Most glycoproteins have structural micro-heterogeneity (multiple different glycan structures attached within the same glycosylation site), and structural macro-heterogeneity (multiple sites and types of glycan attachment).

As used herein, the term "analog" refers to a compound, e.g., a drug, whose structure is related to that of another compound but whose chemical and biological properties may be quite different.

As used herein, the term "antigen" is defined as any substance capable of eliciting an immune response.

As used herein, the term "pathogen" is a biological agent that causes disease or illness to it's host. The body contains many natural defenses against some of the common pathogens (such as Pneumocystis) in the form of the human immune system.

As used herein, the term "immunogen" refers to an antigen or a substance capable of inducing production of an antigen, such as a DNA vaccine.

As used herein, the term "immunogenicity" refers to the ability of an immunogen, antigen, or vaccine to stimulate an immune response.

As used herein, the term "immunotherapy" refers to an array of treatment strategies based upon the concept of modulating the immune system to achieve a prophylactic and/or therapeutic goal.

As used herein, the term "CD1d" refers to a member of the CD1 (cluster of differentiation 1) family of glycoproteins expressed on the surface of various human antigen-presenting cells. CD1d presented lipid antigens activate natural killer T cells. CD1d has a deep antigen-binding groove into which glycolipid antigens bind. CD1d molecules expressed on dendritic cells can bind and present glycolipids.

As used herein, the term "adaptive immune system" refers to highly specialized, systemic cells and processes that eliminate pathogenic challenges. The cells of the adaptive immune system are a type of leukocyte, called a lymphocyte. B cells and T cells are the major types of lymphocytes.

As used herein, the term "T cells" and "Ts" refer to a group of white blood cells known as lymphocytes, that play a central role in cell-mediated immunity. T cells can be distinguished from other lymphocyte types, such as B cells and NKs by the presence of a special receptor on their cell surface called the T cell receptor (TCR). Several different subsets of T cells have been described, each with a distinct function. Helper T ($T_H$) Cells are the "middlemen" of the adaptive immune system. Once activated, they divide rapidly and secrete small proteins called cytokines that regulate or "help" the immune response. Depending on the cytokine signals received, these cells differentiate into $T_H1$, $T_H2$, $T_H17$, or one of other subsets, which secrete different cytokines.

As used herein, the term "antigen-presenting cell" (APC) refers to a cell that displays foreign antigen complexed with major histocompatibility complex (MHC) on its surface. T-cells may recognize this complex using their TCR. APCs fall into two categories: professional or non-professional. Dendritic cells (DCs) fall under the professional category and are capable of presenting antigen to T cells, in the context of CD1. In an exemplary implementation, the DCs utilized in the methods of this disclosure may be of any of several DC subsets, which differentiate from, in one implementation, lymphoid or, in another implementation, myeloid bone marrow progenitors.

As used herein, the term "naïve cell" refers to an undifferentiated immune system cell, for example a CD4 T-cell, that has not yet specialized to recognize a specific pathogen.

As used herein, the term "natural killer cells" and "NKs" refers to a class of lymphoid cells which are activated by interferons to contribute to innate host defense against viruses and other intracellular pathogens.

As used herein, the term "natural killer T cells" (NKTs) refers to a subset of T cells that share characteristics/receptors with both conventional Ts and NKs. Many of these cells recognize the non-polymorphic CD1d molecule, an antigen-presenting molecule that binds self- and foreign lipids and glycolipids. The TCR of the NKTs are able to recognize glycolipid antigens presented (chaperoned) by a CD1d molecule. A major response of NKTs is rapid secretion of cytokines, including IL-4, IFN-γ and IL-10 after stimulation and thus influence diverse immune responses and pathogenic processes. The NKTs may be a homogenous population or a heterogeneous population. In one exemplary implementation, the population may be "non-invariant NKTs", which may comprise human and mouse bone marrow and human liver T cell populations that are, for example, CD1d-reactive noninvariant T cells which express diverse TCRs, and which can also produce a large amount of IL-4 and IFN-γ. The best known subset of CD1d-dependent NKTs expresses an invariant TCR-alpha (TCR-α) chain. These are referred to as type I or invariant NKTs (iNKTs). These cells are conserved between humans (Vα24i NKTs) and mice (Vα14i NKTs) and are implicated in many immunological processes.

As used herein, the term "cytokine" refers to any of numerous small, secreted proteins that regulate the intensity and duration of the immune response by affecting immune cells differentiation process usually involving changes in gene expression by which a precursor cell becomes a distinct specialized cell type. Cytokines have been variously named as lymphokines, interleukins, and chemokines, based on their presumed function, cell of secretion, or target of action. For example, some common interleukins include, but are not limited to, IL-12, IL-18, IL-2, IFN-γ, TNF, IL-4, IL-10, IL-13, IL-21 and TGF-β.

As used herein, the term "chemokine" refers to any of various small chemotactic cytokines released at the site of infection that provide a means for mobilization and activation of lymphocytes. Chemokines attract leukocytes to infection sites. Chemokines have conserved cysteine residues that allow them to be assigned to four groups. The groups, with representative chemokines, are C—C chemokines (RANTES, MCP-1, MIP-1α, and MIP-1β), C—X—C chemokines (IL-8), C chemokines (Lymphotactin), and CXXXC chemokines (Fractalkine).

As used herein, the term "$T_H2$-type response" refers to a pattern of cytokine expression such that certain types of cytokines, interferons, chemokines are produced. Typical $T_H2$ cytokines include, but are not limited to, IL-4, IL-5, IL-6 and IL-10.

As used herein, the term "$T_H1$-type response" refers to a pattern of cytokine expression such that certain types of cytokines, interferons, chemokines are produced. Typical $T_H1$ cytokines include, but are not limited to, IL-2, IFN-γ, GM-CSF and TNF-β.

As used herein, the term "$T_H1$ biased" refers to am immunogenic response in which production of $T_H1$ cytokines and/or chemokines is increased to a greater extent than production of $T_H2$ cytokines and/or chemokines.

As used herein, the term "epitope" is defined as the parts of an antigen molecule which contact the antigen binding site of an antibody or a T cell receptor.

As used herein, the term "vaccine" refers to a preparation that contains an antigen, consisting of whole disease-causing organisms (killed or weakened) or components of such organisms, such as proteins, peptides, or polysaccharides, that is used to confer immunity against the disease that the organisms cause. Vaccine preparations can be natural, synthetic or derived by recombinant DNA technology.

As used herein, the term "antimicrobial" refers to a substance that kills or inhibits the growth of microbes such as bacteria, fungi, or viruses.

As used herein, the term "toxoid" refers to a bacterial toxin whose toxicity has been weakened or suppressed either by chemical (formalin) or heat treatment, while other properties, typically immunogenicity, are maintained. Toxoids are used in vaccines as they induce an immune response to the original toxin or increase the response to another antigen. For example, the tetanus toxoid is derived from the tetanospasmin produced by *Clostridium tetani* and causing tetanus. The tetanus toxoid is used by many plasma centers in the United States for the development of plasma rich vaccines.

As used herein, the term "DNA vaccine" refers to a DNA construct that is introduced into cells and subsequently translated into specific antigenic proteins.

As used herein, the term "plasmid" refers to an extrachromosomal circular DNA capable of replicating, which may be used as a cloning vector.

As used herein, the term "microorganism" and "microbe" refers to an organism that is microscopic (too small to be seen by the naked human eye). Microorganisms are incredibly diverse and include, but are not limited to, bacteria and fungi.

As used herein, the term "immunologic adjuvant" refers to a substance used in conjunction with an immunogen which enhances or modifies the immune response to the immunogen. In an exemplary implementation, the α-GalCer analogs of the present disclosure are used as immunologic adjuvants to modify or augment the effects of a vaccine by stimulating the immune system of a patient who is administered the vaccine to respond to the vaccine more vigorously.

As used herein, the term "alum adjuvant" refers to an aluminum salt with immune adjuvant activity. This agent adsorbs and precipitates protein antigens in solution; the resulting precipitate improves vaccine immunogenicity by facilitating the slow release of antigen from the vaccine depot formed at the site of inoculation.

As used herein, the term "anti-tumor immunotherapy active agent" refers to an α-GalCer analog of the present disclosure that inhibits, reduces and/or eliminates tumors.

As used herein, the term "granulocyte-macrophage colony-stimulating factor" (GM-CSF) refers to a cytokine which serves as a colony-stimulating factor that stimulates production of white blood cells, particularly granulocytes (neutrophils, basophils, and eosinophils), macrophages, and cells in the bone marrow that are precursors of platelets.

As used herein, the term "antigen specific" refers to a property of a cell population such that supply of a particular antigen, or a fragment of the antigen, results in specific cell proliferation.

As used herein, the term "Flow cytometry" or "FACS" means a technique for examining the physical and chemical properties of particles or cells suspended in a stream of fluid, through optical and electronic detection devices.

As used herein α-GalCer analogs or synthetic α-GalCer analogs, unless otherwise noted, refer to structure-based synthetic glycolipid analogs based on alpha-galactosyl ceramide.

Amino acid residues in peptides shall hereinafter be abbreviated as follows: P Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. For further description of amino acids, please refer to Proteins: Structure and Molecular Properties by Creighton, T. E., W. H. Freeman & Co., New York 1983.

Mammalian and mycobacterial lipids are known to be presented by human CD1a, CD1b, CD1c, and CD1d. α-Galactosyl ceramide, a lipid found in the marine sponge *Agelas mauritianus*, has been the most extensively studied ligand for CD1d. It has been shown that in vitro stimulation of mouse spleen cells by α-GalCer led to the proliferation of NKTs and production of both IFN-☐ and IL-4, a $T_H1$-type and $T_H2$-type response, respectively. Murine studies have shown that cells can be rapidly activated by immature dendritic cells (iDCs) bearing α-GalCer and that the activated iNKTs can in turn induce full maturation of DCs.

In one aspect, the present disclosure provides a series of novel lipid portions of the α-GalCer analogs are capable of binding with a binding-groove on a CD1 molecule to form CD1-analog complexes. These CD1-analog complexes are presented to CD1-restricted T cells (NKTs) by means of T cell receptor recognition, and are capable of TCR activation, $T_H1$ and $T_H2$ cytokine release, and NKT expansion. In an exemplary implementation, an α-GalCer analog of the present disclosure is designed such that it has a strong binding affinity with the binding-groove on the CD1 molecule, correlating with a $T_H1$-biased immunogenic response. In another exemplary implementation, an α-GalCer analog of the present disclosure is designed such that it has a strong binding affinity with the binding-groove on the CD1 molecule, correlating with a $T_H2$-biased immunogenic response.

In another aspect of the present disclosure, the α-GalCer analogs may be used as immunotherapies. In an exemplary implementation, the α-GalCer analogs may be used for cancer immunotherapy. In an exemplary implementation, the α-GalCer analogs may be used for adjuvant immunotherapy. In another exemplary implementation, the α-GalCer analogs may be used for anti-microbial immunotherapy, which includes vaccination. In still another exemplary implementation, the α-GalCer analogs may be used for immunosuppression for the treatment of autoimmune diseases.

Figure 1B:
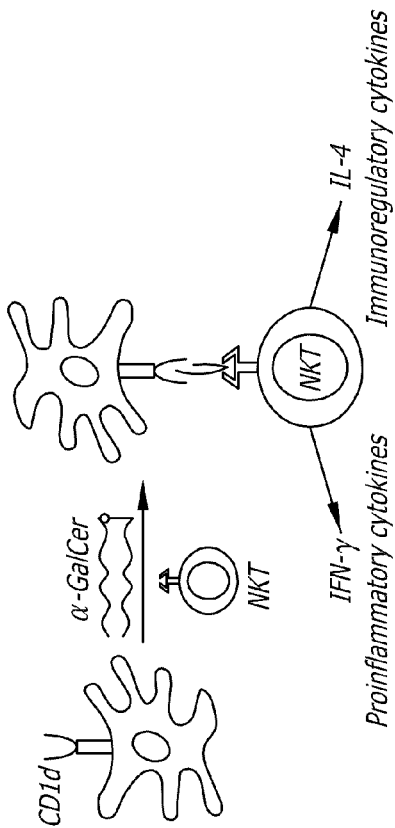
FIG. 1B shows how alpha-galactosyl ceramide (α-GalCer) and α-GalCer analogs of the present disclosure are capable of binding to CD1d and stimulating a rapid $T_H1$ and $T_H2$ cytokine response.

T Cell Receptor Recognition and Activation Via the α-GalCer Analogs of the Present Disclosure and the Resultant Immune Response FIG. 1A is a schematic illustration showing how invariant NKT cell recognition of glycolipid antigens presented by CD1d leads to a cascade of events. The lipid portions of the glycolipid antigens become inserted into a hydrophobic binding groove of the CD1 molecule to form CD1-antigen complexes, which are able to contact T-cell receptors (TCRs) on the NKTs, which leads to the cascade of events involving cytokines, chemokines and co-stimulatory molecules. The diversity and extent of cytokine production can have a broad range of effects, ranging from enhanced cell-mediated immunity ($T_H1$-type responses) to suppressed cell-mediated immunity ($T_H2$-type responses). FIG. 1B is a schematic illustration showing how NKT cell recognition of α-GalCer or an α-GalCer analog of the present disclosure presented by CD1d stimulates a rapid $T_H1$ and $T_H2$ cytokine response. In an exemplary implementation, a $T_H1$ cytokine response is initiated. In another exemplary implementation, a $T_H2$ cytokine response is initiated. In yet another exemplary implementation, both a $T_H1$ and $T_H2$ cytokine response is initiated.

Figures 1, 2:
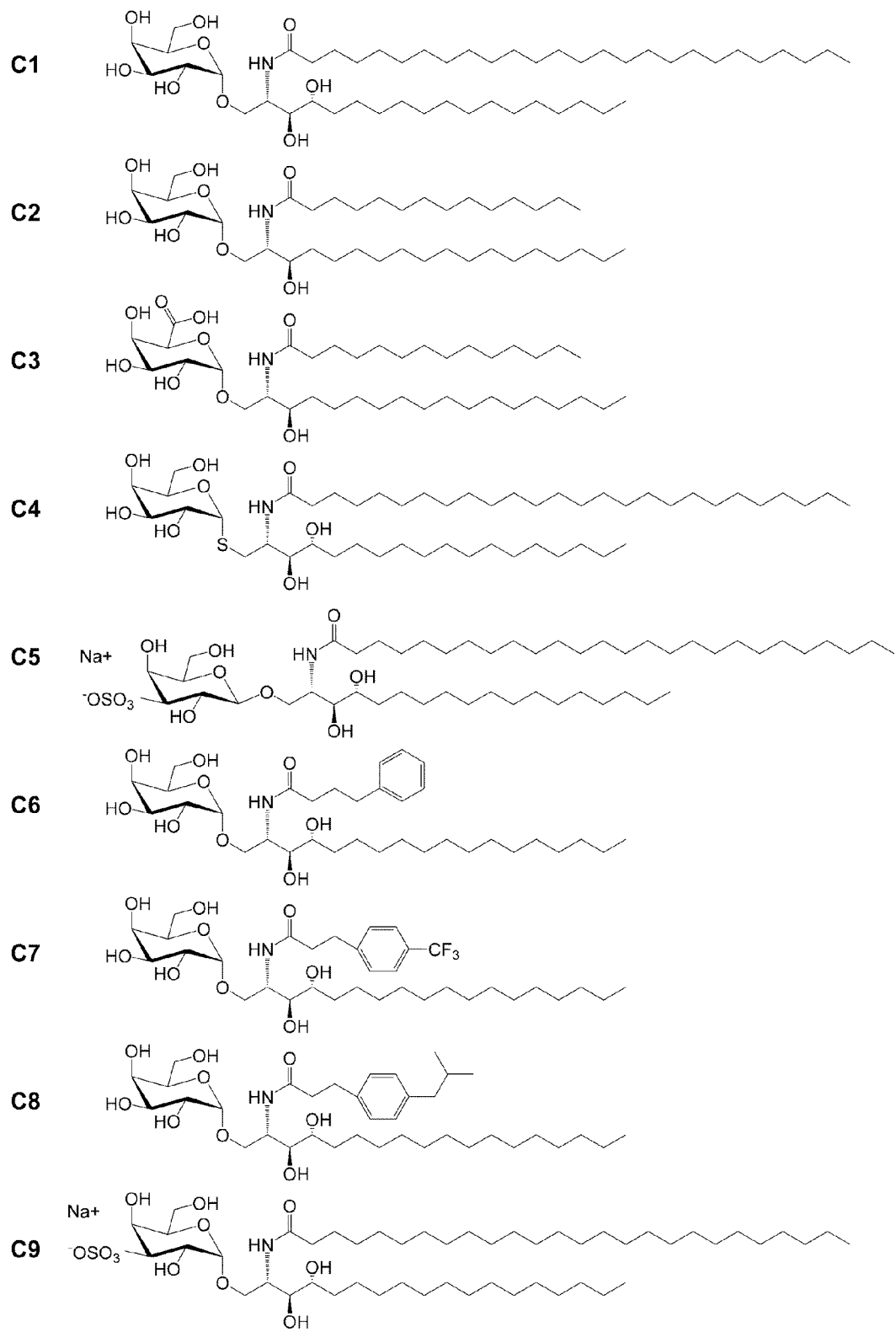
FIG. 1(A-B) are schematic illustrations showing Natural Killer T cell (NKT) function.
FIG. 2 shows the chemical structures of α-GalCer (C1) and various α-GalCer glycolipids (also referred to as analogs) of the present disclosure including: glycolipids of bacterial origin (C3, C3 and C14), glycolipids modified with sulfonation (C4, C5 and C9), phenyl-alkyl chain glycolipids (C6-C8, C10-C11, C15-C16, C18-C34, 7DW8-5 (aka, C8-5) and 7DW8-6 (aka, C8-6)) and phytosphingosine truncated glycolipids (C12, C13 and C17).
Figure 2:
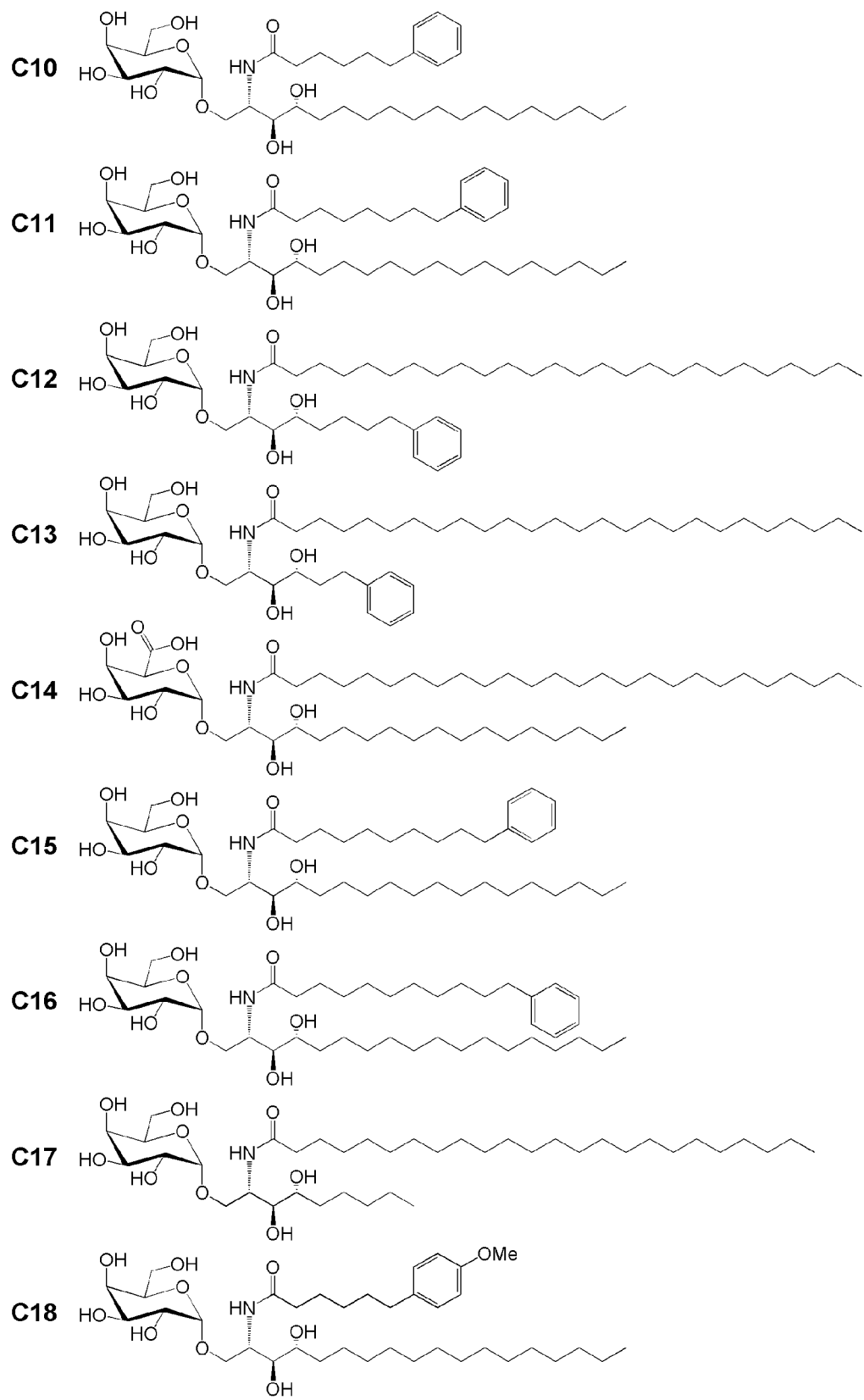
Figures 2, 3:
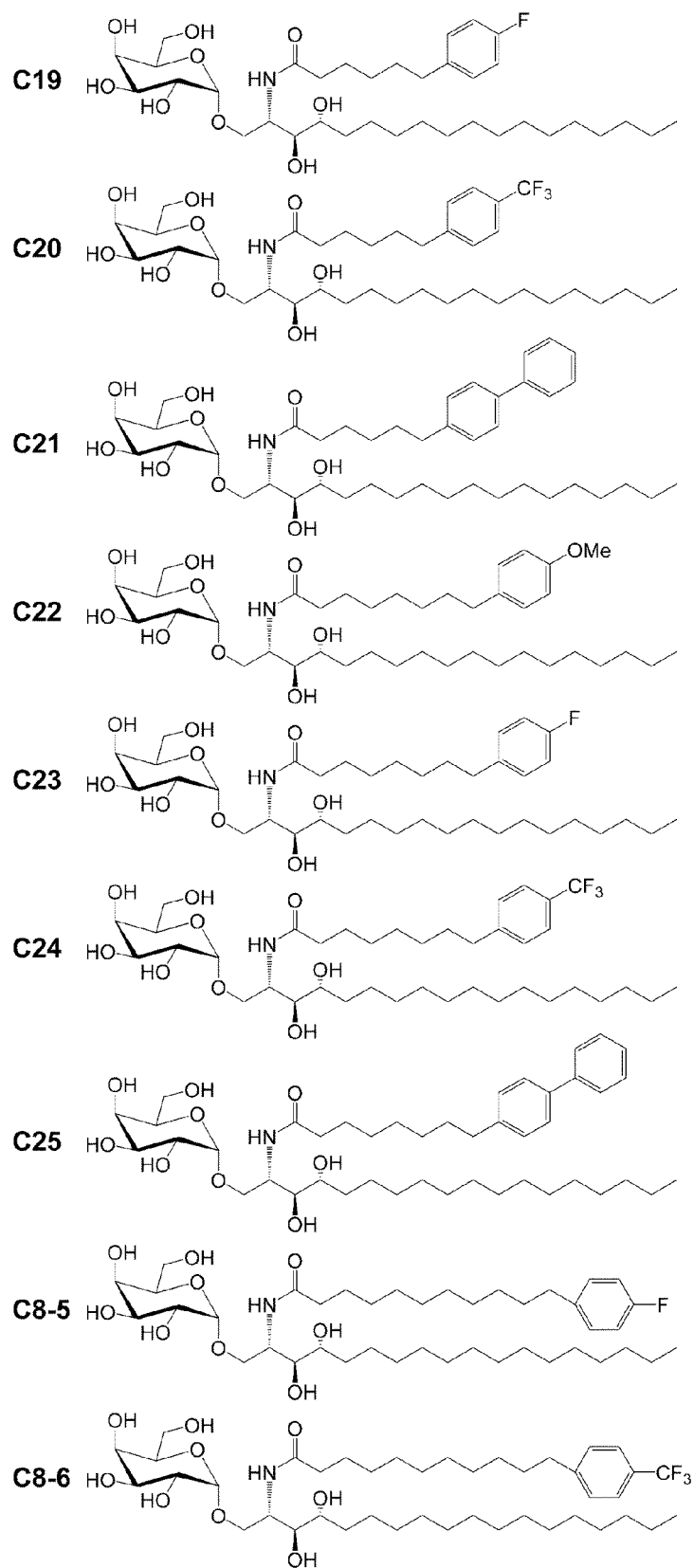
FIG. 3 shows synthetic schemes for C12 and C13 α-GalCer analogs of the present disclosure.

The chemical structures of α-GalCer, as well as the synthetic α-GalCer analogs of the present disclosure are shown in FIG. 2. The α-GalCer analogs of the present disclosure include α-GalCer analogs of bacterial origin (Group I: C2, C3 and C14), α-GalCer analogs modified with sulfonation (Group II: C4, C5 and C9), phenyl-alkyl chain α-GalCer analogs (Group III: C6-C8, C10-C11, C15-C16, C18-C34, C8-5 and C8-6) and phytosphingosine truncated α-GalCer analogs (Group IV: C12, C13 and C17). FIG. 3 shows an example of the synthesis of glycosphingolipid α-GalCer analogs C12 and C13.

In one aspect, the synthetic α-GalCer analogs of the present disclosure are capable of forming complexes with a CD1d molecule. In another aspect, the synthetic (α-GalCer analogs of the present disclosure are capable of being recognized by NKTs T-cell receptors. In yet another aspect, the synthetic α-GalCer analogs of the present disclosure are capable of eliciting a $T_H1$-type, a $T_H2$-type or a $T_H1$-type and a $T_H2$-type response. In an exemplary implementation, the α-GalCer analogs of the present disclosure are capable of activating NKTs in vitro. In another exemplary implementation, the α-GalCer analogs of the present disclosure are capable of activating NKTs in vivo.

A method is provided for stimulating or enhancing cytokine production in tissue, cells and/or in a subject, the method including: administering to the subject any one of the synthetic α-GalCer analogs of the present disclosure, wherein a NKT in the subject is activated following contact with the α-GalCer analog and a cytokine response is initiated. The cytokine may be, for example, interferon-γ (IFN-g) or interleukin-4 (IL-4).

In an exemplary implementation, the disclosure provides a method of activating a cytokine response in tissue, cells and/or a subject whereby an effective amount of a compound or a salt or a mixture is administered, the compound is selected from the group consisting of C2-C8, C85, C8-6 and C9-C34, and wherein the subject has an adaptive immune system that includes a population of cells, the population including at least one lymphocyte and at least one antigen-presenting cell; forming a complex between the compound and the antigen-presenting cell, wherein the formation of the complex results in the activation of a receptor on the lymphocyte; and activating the lymphocyte to produce the cytokine response.

Figures 2, 3, 4:
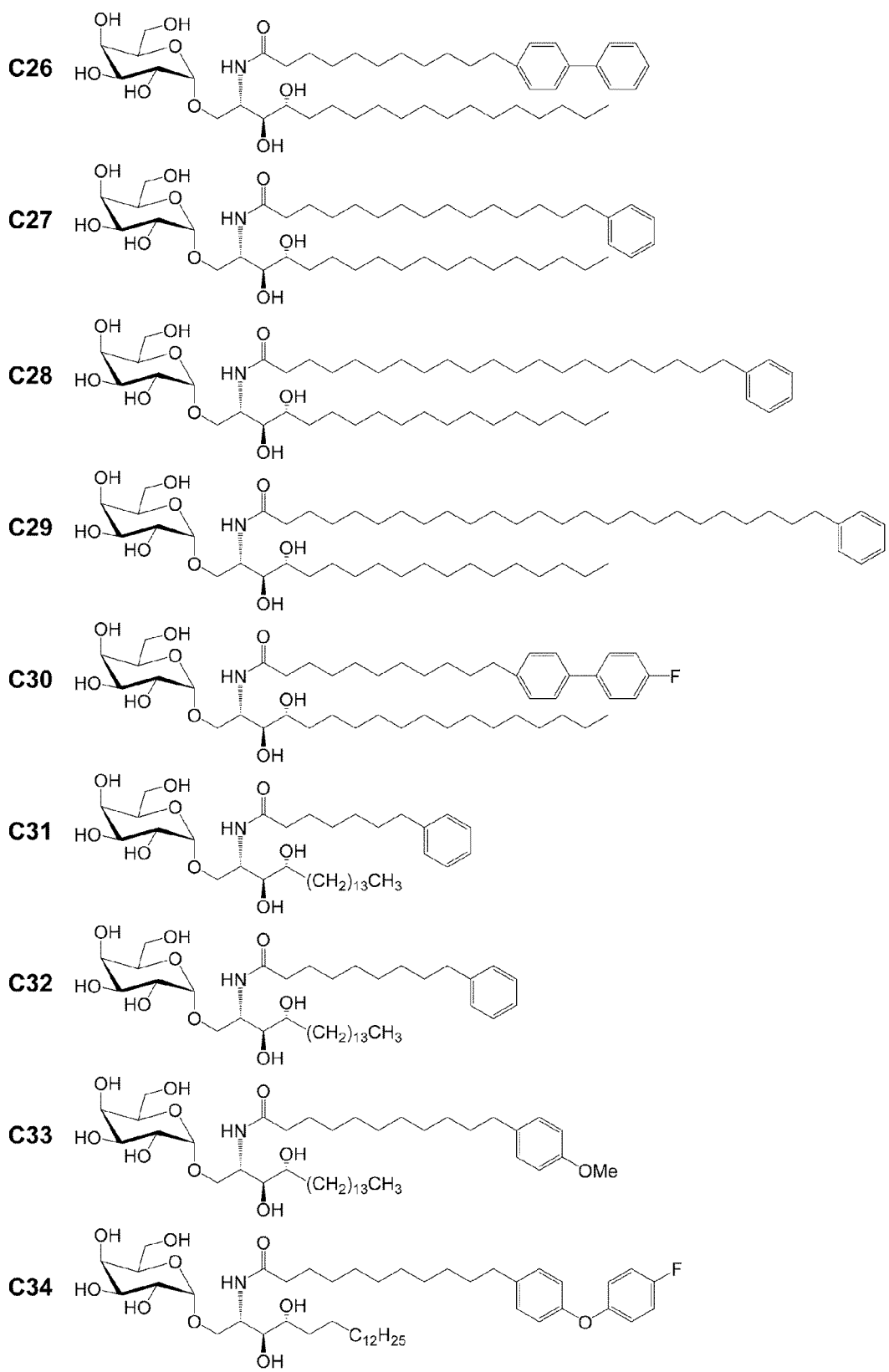
FIG. 4 shows IL-2 cytokine secretion levels (pg/ml) by murine 1.2 hybridomas treated with α-GalCer or the indicated α-GalCer analogs of the present disclosure.
Figure 3:
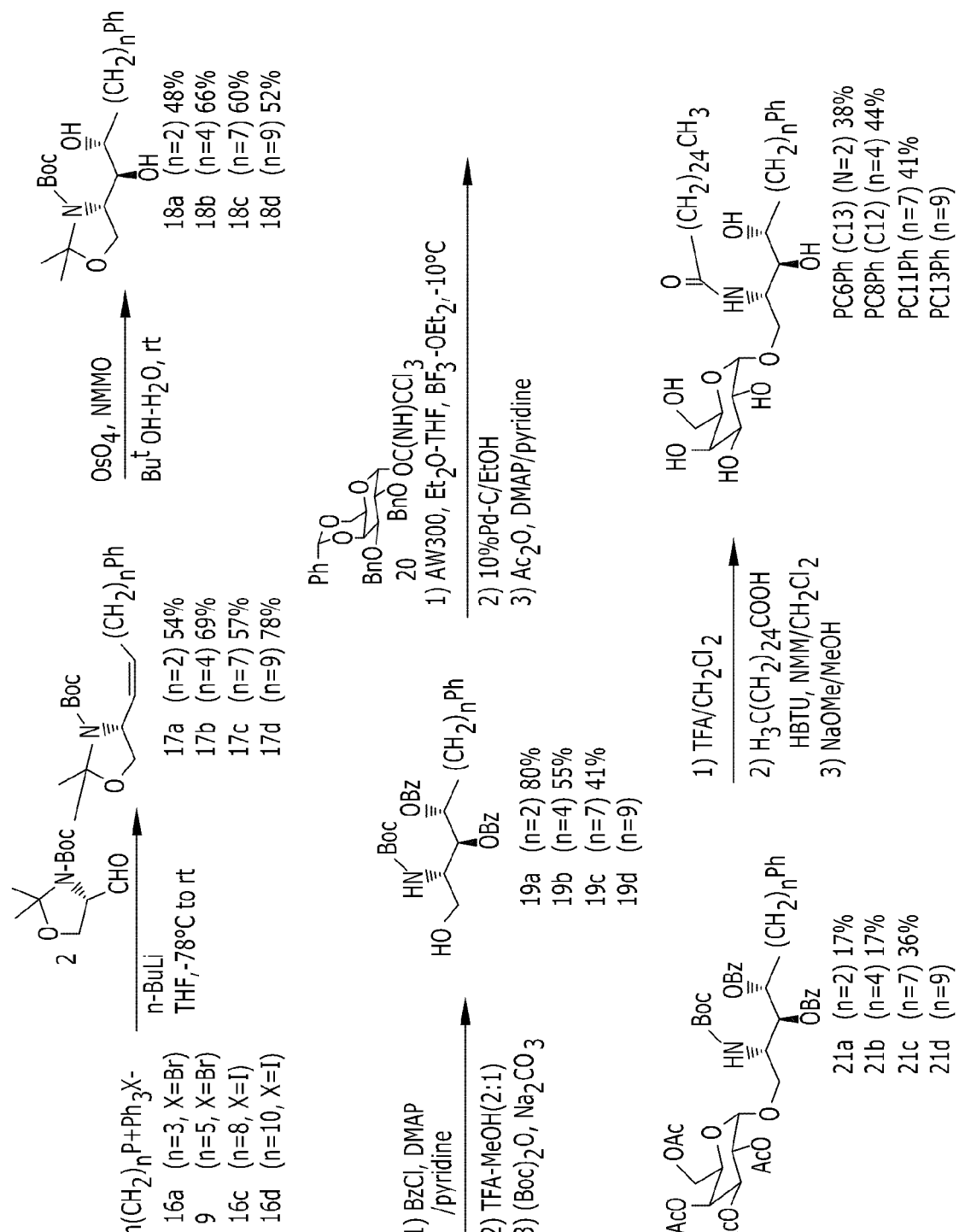
Figure 4:
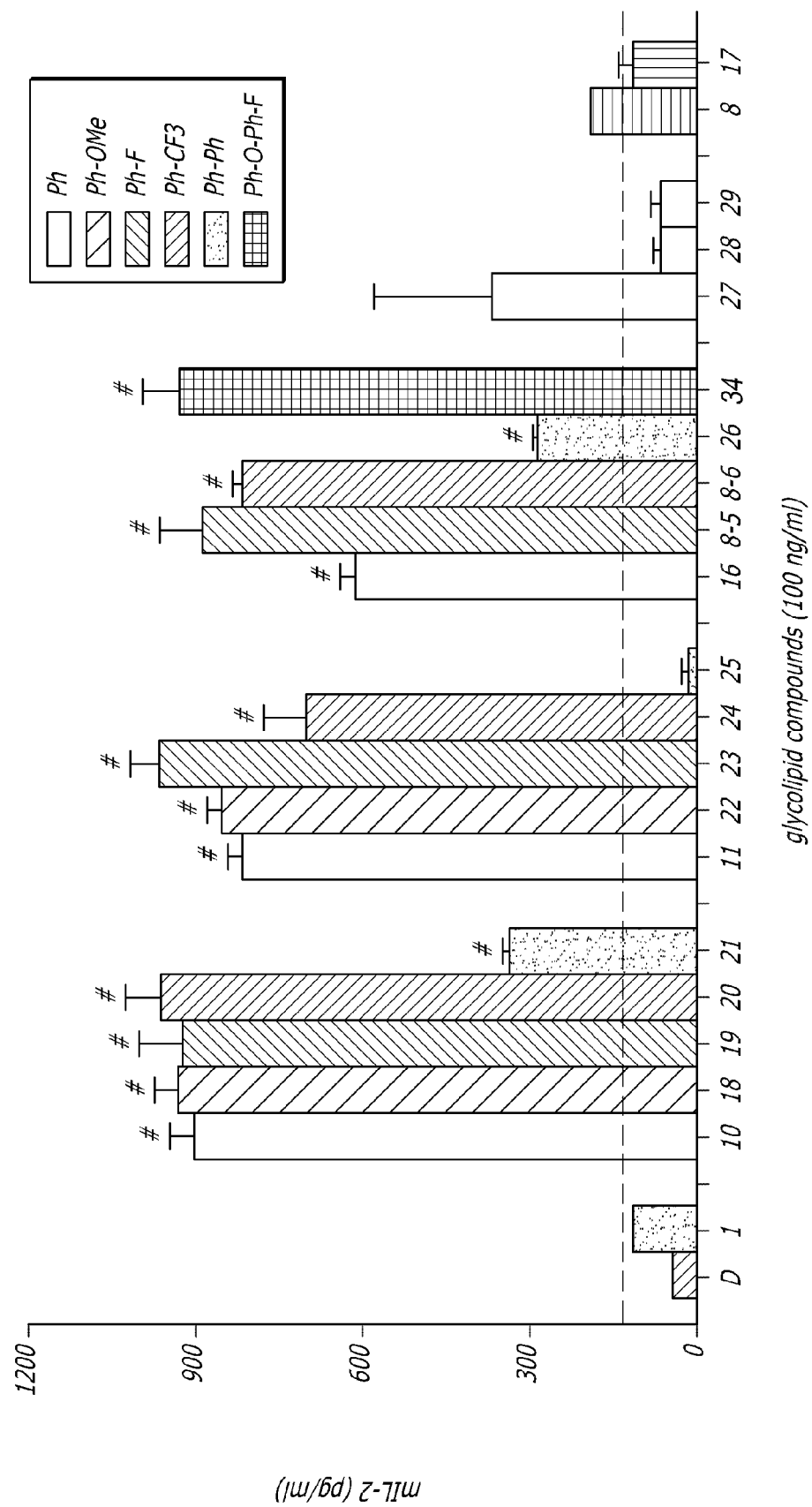
Figure 5A:
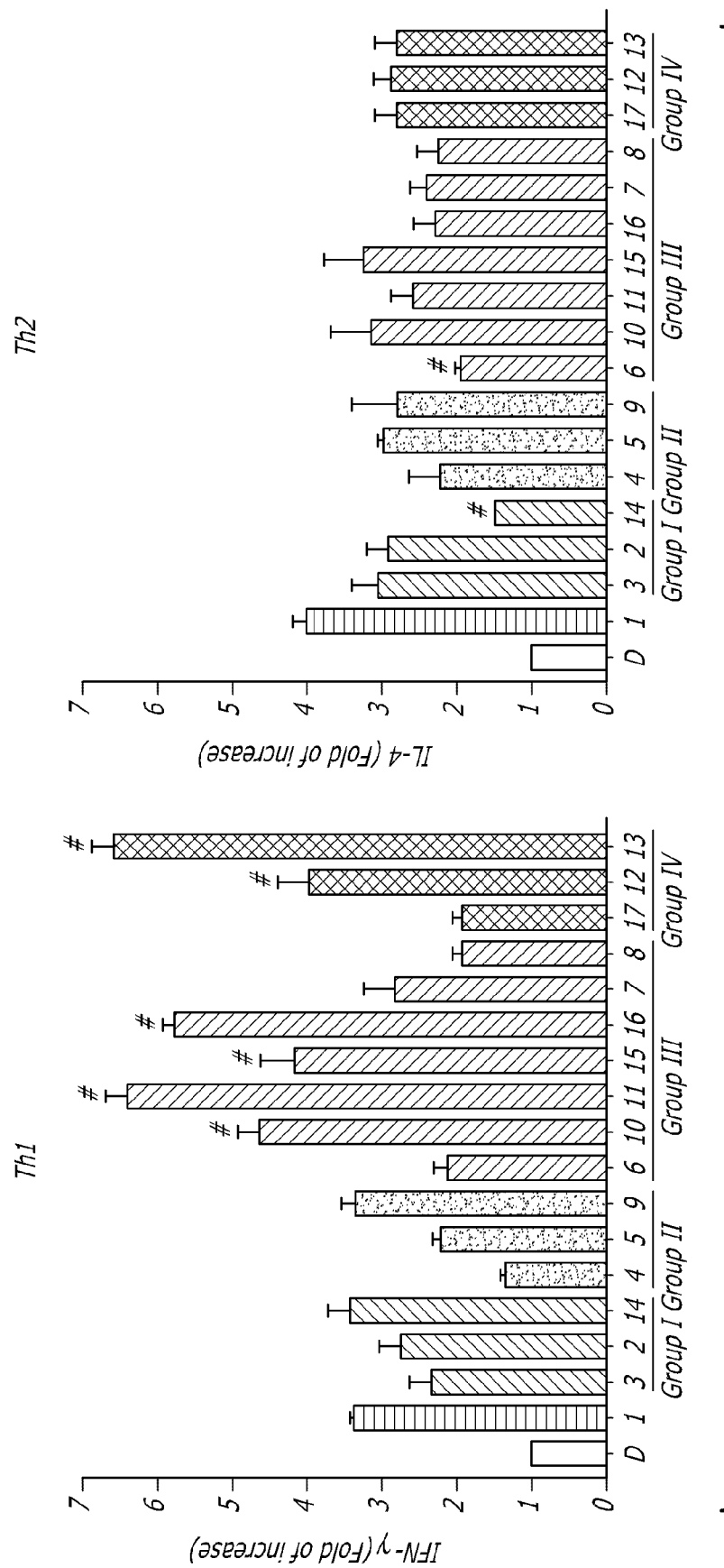
FIG. 5(A-C) show the "fold of increase" of (A) IFN-γ and IL-4, (B) IL-2 and IL-6, and (C) IL-12 and IL-10 cytokine production, normalized to DMSO control, by human CD161$^+$/CD3$^+$ NKTs treated with α-GalCer or the indicated α-GalCer analogs of the present disclosure and co-cultured with autologous immature CD14$^+$ DCs. Left side panels indicate a $T_H1$-type response and right side panels indicate a $T_H2$-type response.
Figure 5B:
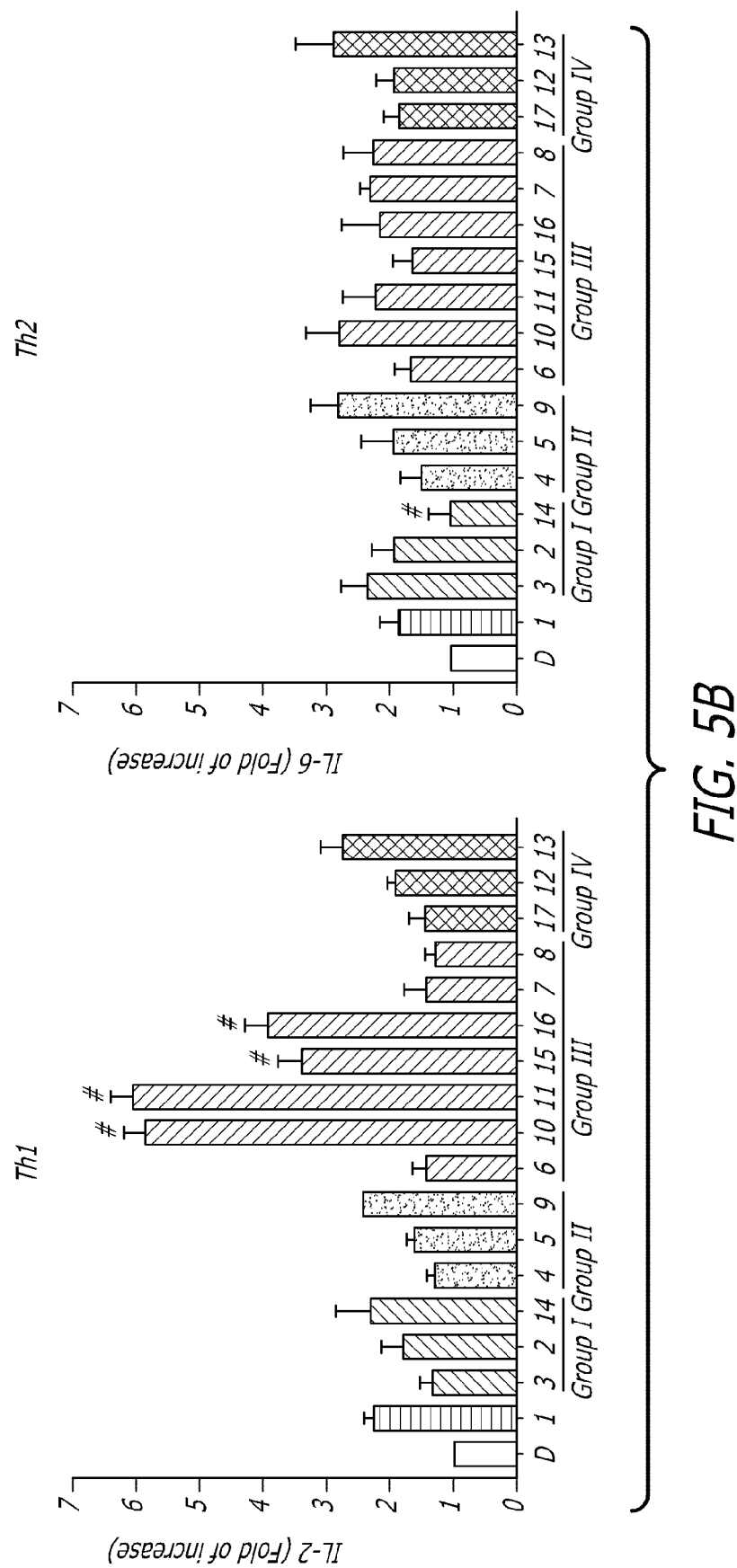
Figure 5C:
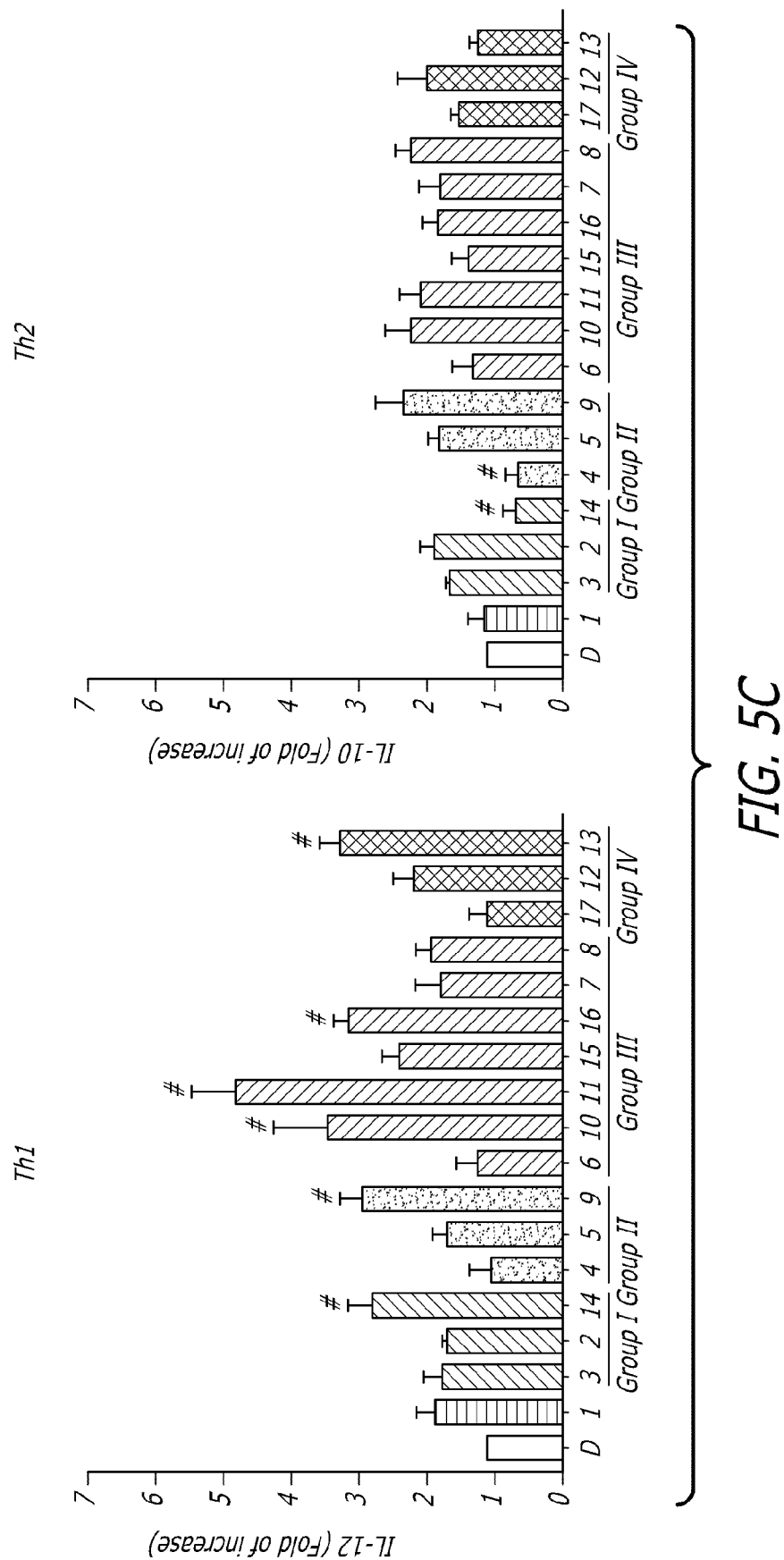
Figure 6A:
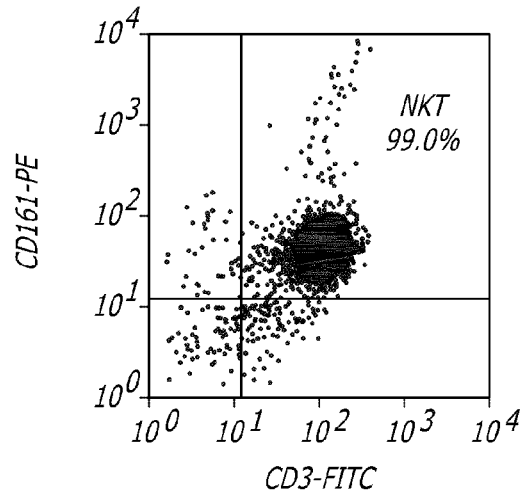
FIG. 6(A-B) show the (A) purity of human CD161$^+$CD3$^+$ NKTs and (B) the "fold of increase" of the ratio of IFN-γ/IL-4 cytokine production, normalized to control (DMSO), derived from the data shown in FIG. 5.
Figure 6B:
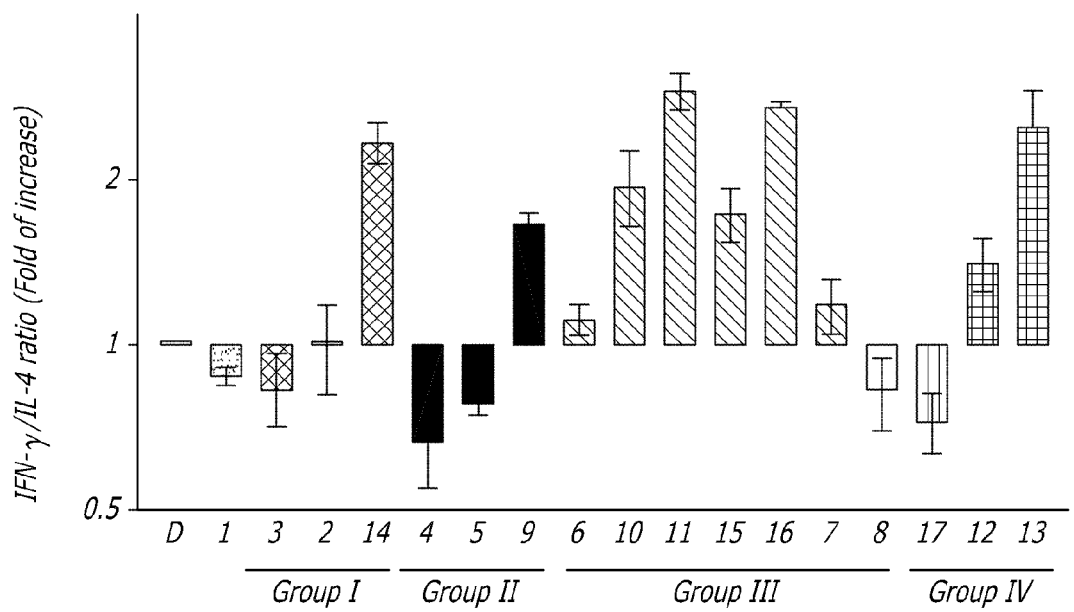
Figure 8A:
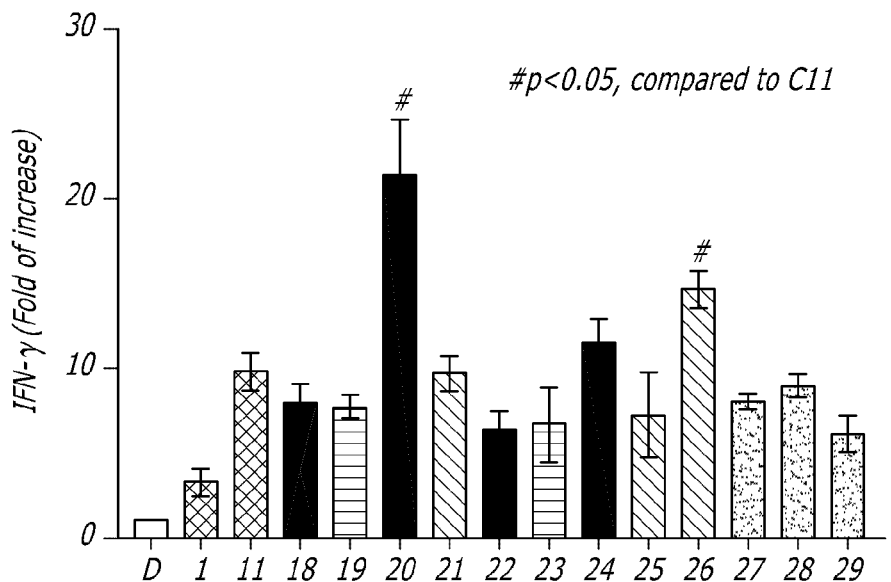
FIG. 8(A-F) shows the "fold of increase" of (A) IFN-γ, (B) IL-4, (C) the ratio of IFN-γ/IL-4, (D) IL-2, (E) IL-12 and (F) IL-6 cytokine production, normalized to control (DMSO), by naïve human NKTs treated with α-GalCer or the indicated α-GalCer analogs of the present disclosure and co-cultured with autologous immature DCs.
Figure 8B:
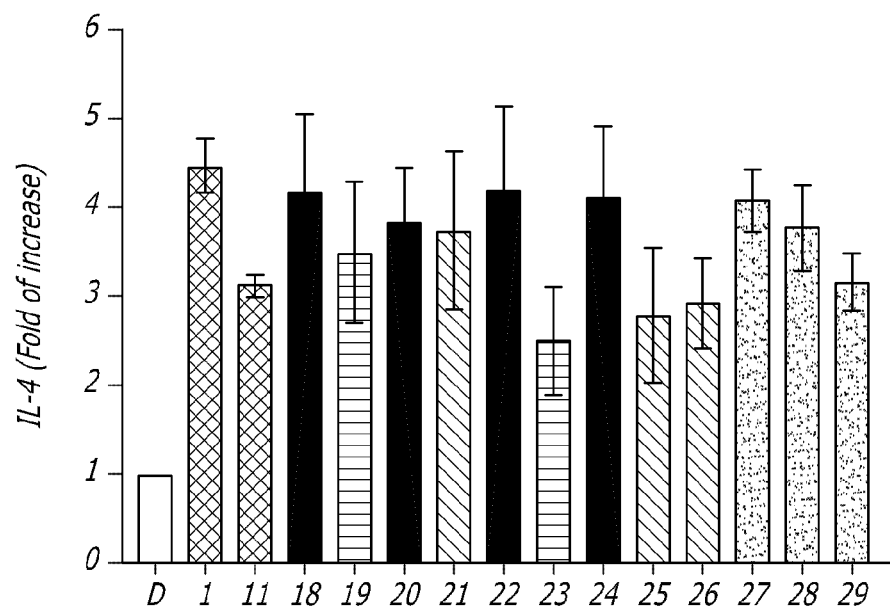
Figure 8C:
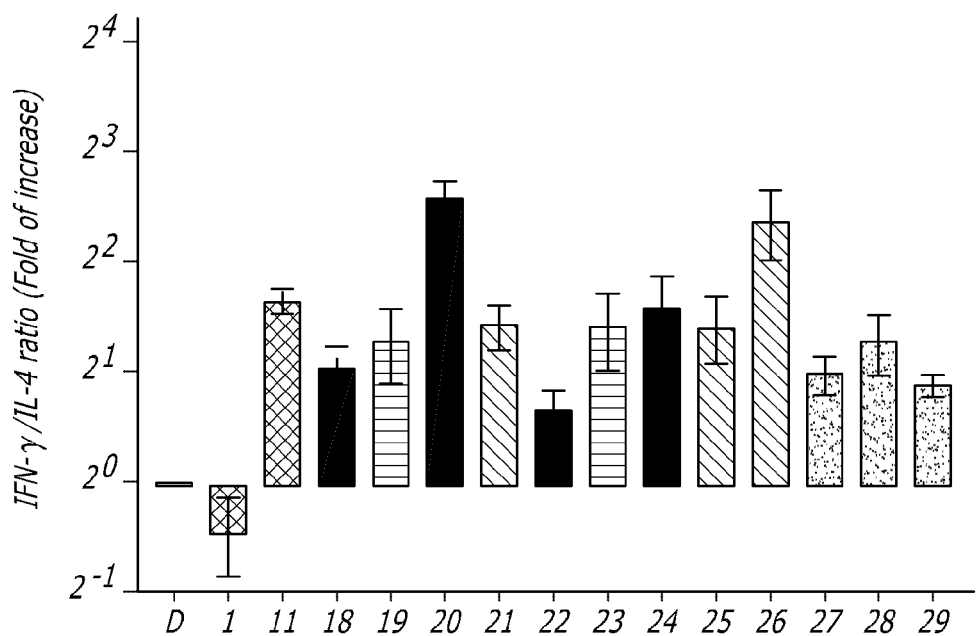
Figure 8D:
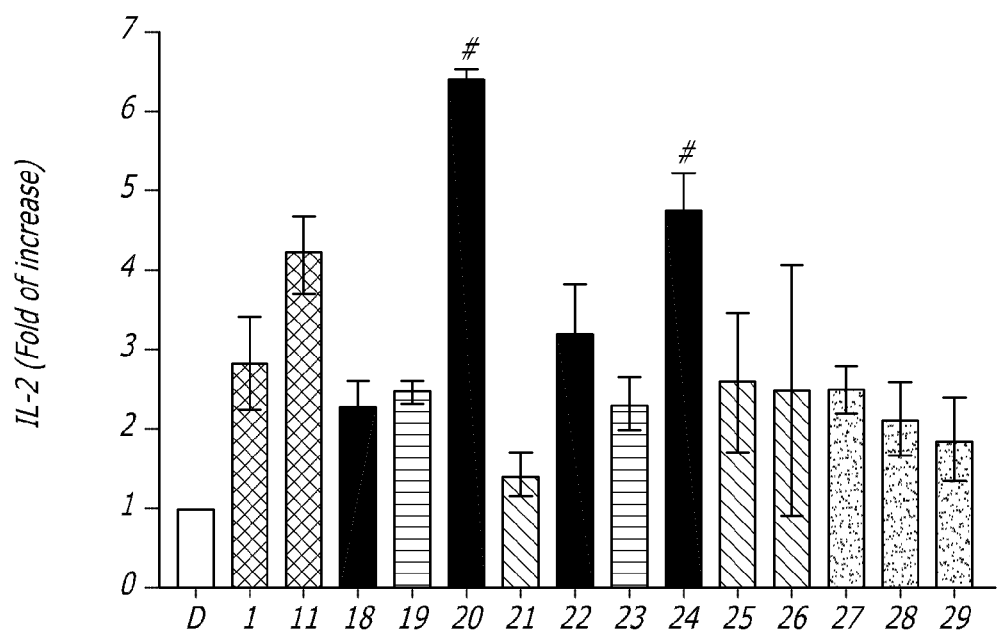
Figure 8E:
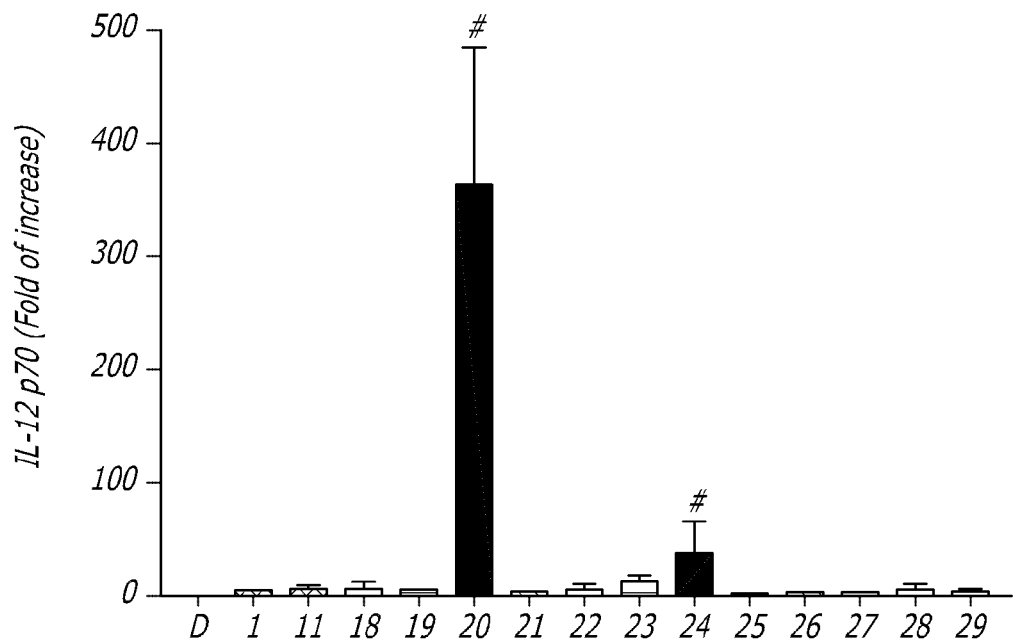
Figure 8F:
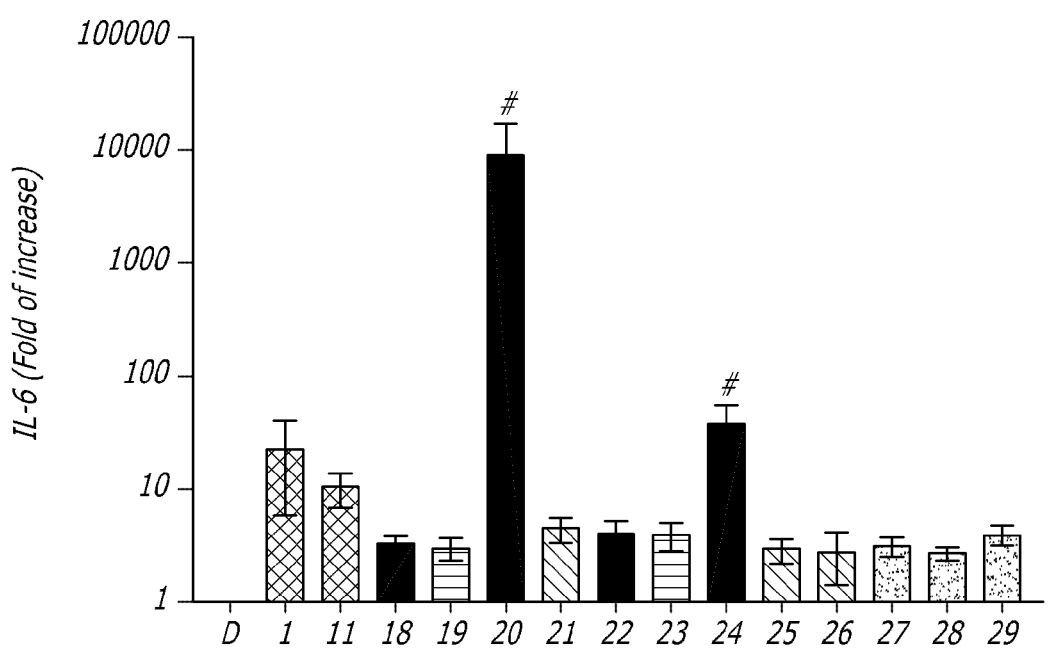

In an exemplary implementation, murine 1.2 hybridomas (CD1d-reactive Vα14i T cell hybridomas) were cultured in mCD1d-coated 96 well plate and pulsed with control DMSO, α-GalCer (C1) or the indicated α-GalCer analogs of the present disclosure at 100 ng/ml. IL-2 release into the tissue culture medium was measured after an 18 hour culture, as seen in FIG. 4. Most of the α-GalCer analogs of the present disclosure induced greater IL-2 production than α-GalCer. When the α-GalCer analogs of the present disclosure were examined for their capacity to elicit cytokine/chemokine production in human naïve NKTs (CD161$^+$CD3$^+$) in vitro, similar results were found. Human naïve CD161$^+$CD3$^+$ NKTs were cultured with autologous immature dendritic cells (CD14$^+$ DCs) and pulsed with control DMSO, α-GalCer or the indicated α-GalCer analogs of the present disclosure at 10 µg/ml. Cytokines released into the tissue culture medium was measured after an 18 hour culture, as seen in FIG. 5. The α-GalCer analogs were potent inducers of $T_H1$ and $T_H2$ cytokine secretion. FIG. 5A shows induction of IFN-γ and IL-4, FIG. 5B shows induction of IL-2 and IL-6 and FIG. 5C shows induction of IL-12 and IL-10. Aromatic compounds from Group III and IV, especially C11, C16 and C13, induced a significantly greater secretion of IFN-γ than α-GalCer, whereas, all α-GalCer analogs elicited slightly less IL-4 than α-GalCer. FIG. 6 shows the purity of human CD161$^+$CD3$^+$ NKTs (top) and the ratio of IFN-γ/IL-4, normalized to DMSO control (bottom). When expressed as IFN/IL-4 ratio, C9, C12, C13, C14 and all Group III compounds were more $T_H1$-biased; whereas C1, C3, C4, C5, C8 and C17 were more $T_H2$-biased. The induction of the cytokines and chemokines from the human CD161$^+$CD3$^+$ NKTs are listed in FIG. 7. The top five values for each cytokine are marked in bold. Some of the α-GalCer analogs tested showed a greater induction in chemokines than did α-GalCer; for example, C13 elicited a striking increase in chemokines such as MIP-1α, MCP-1, and IL-8. Aromatic compounds C10, C1, and C16 displayed a greater induction of IL-3, granulocyte/macrophage colony-stimulating factor (GM-CSF), and IL-15.

Figure 9:
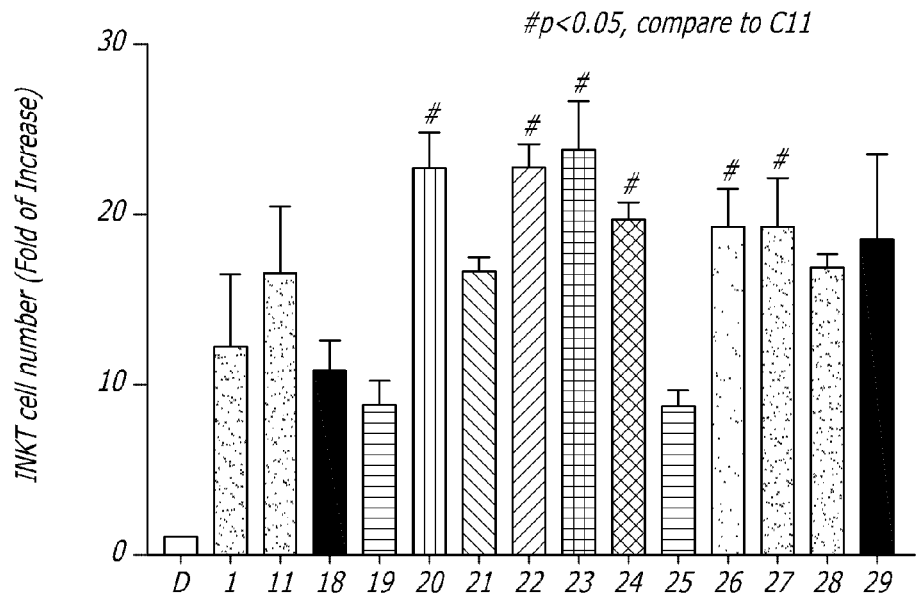
FIG. 9 shows the fold changes in the total number of iNKTs in response to the indicated α-GalCer analogs of the present disclosure.
Figure 10A:
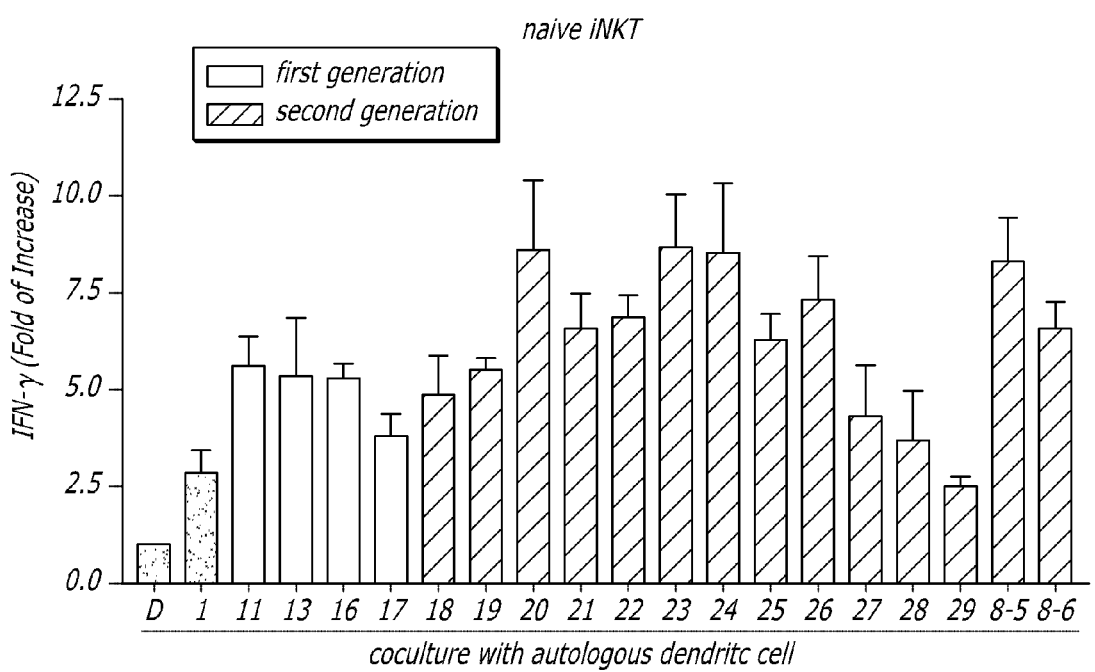
FIG. 10(A-E) shows IFN-γ cytokine production by (A) naïve iNKTs co-cultured with autologous dendritic cells, (B) naïve iNKTs co-cultured with HeLa-CD1d cells, (C) α-GalCer-pulsed iNKTs co-cultured with HeLa-CD1d cells and (D) α-GalCer analog C11-pulsed iNKTs co-cultured with HeLa-CD1d cells, normalized to vehicle control (DMSO), treated with α-GalCer or the indicated α-GalCer analogs of the present disclosure. (E) shows different basal levels of IFN-γ cytokine production in human naïve iNKTs, α-GalCer-pulsed iNKTs and α-GalCer analog C11-pulsed iNKTs.
Figure 10B:
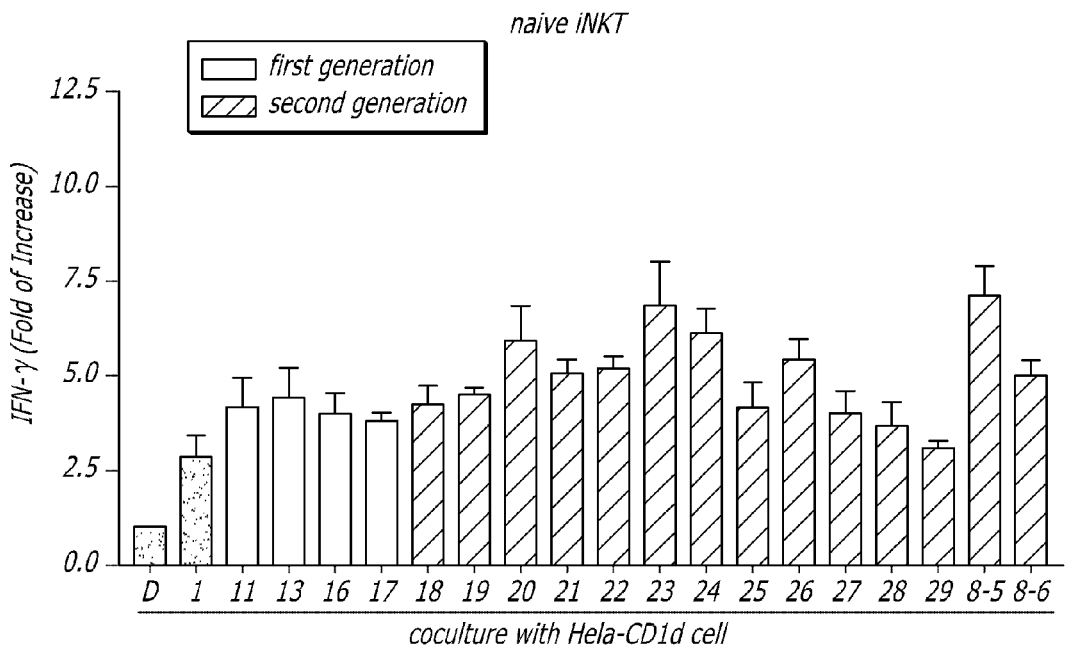
Figure 10C:
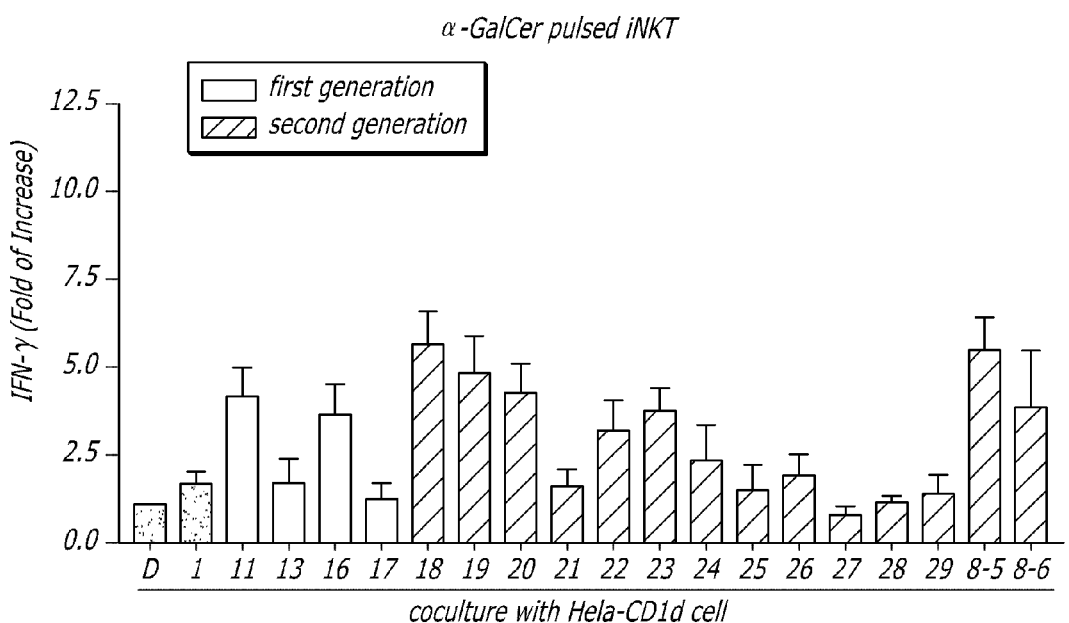
Figure 10D:
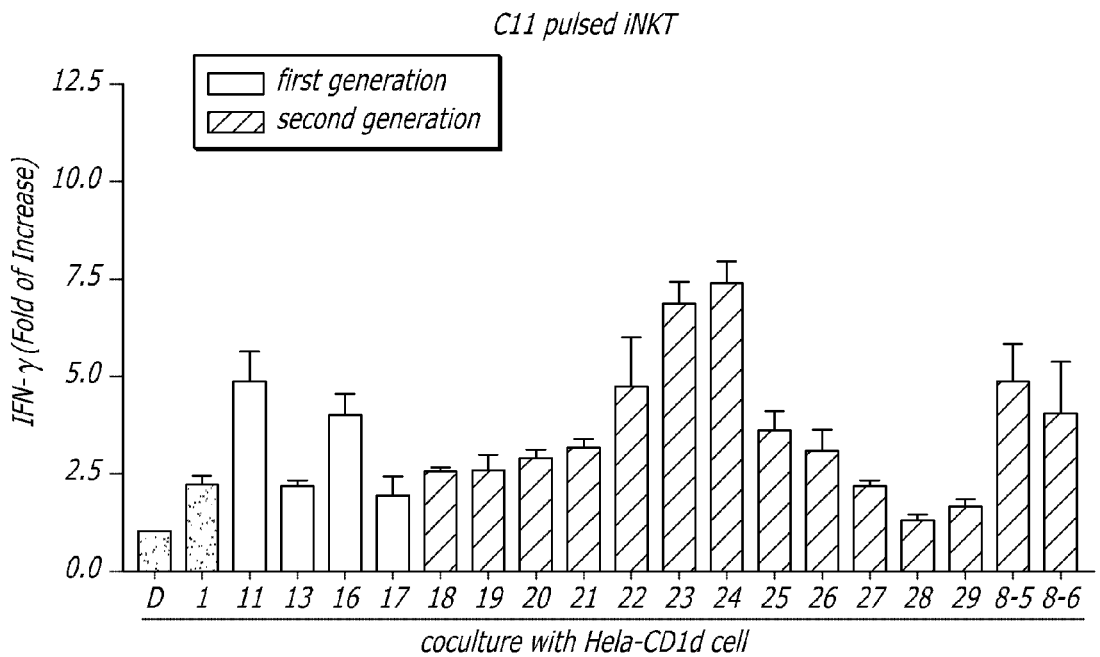
Figure 10E:
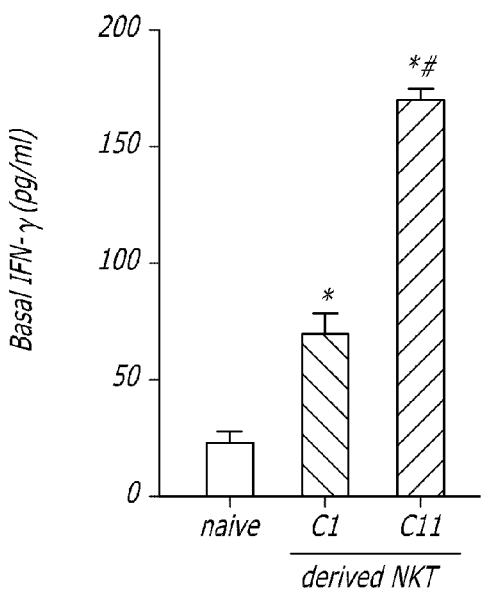

FIG. 8 shows more in vitro results for the capacity of the α-GalCer analogs of the present disclosure to elicit cytokine/chemokine production in primary naïve human iNKTs. Primary naïve human iNKTs were cultured with autologous immature DCs and pulsed with control DMSO, α-GalCer or the indicated α-GalCer analogs (C11 and C18-C29). As shown in FIG. 8A, all of the tested α-GalCer analogs of the present disclosure induced higher levels of INF-γ secretion than C1. α-GalCer analogs induced comparable levels of IL-4 (see FIG. 8B). α-GalCer analogs induced higher IFN-γ/IL-4 ratios, i.e., the $T_H1/T_H2$ bias than C1 (See FIG. 8C). α-GalCer analogs C20, C24 and C26 were significantly more potent in eliciting IFN-γ production, higher IFN-γ/IL-4 ratio, and higher levels of IL-2 (See FIG. 8D) than α-GalCer analog C11. α-GalCer analogs C20 and C24 induced IL-12 production and also elicited more IL-6 release than the other α-GalCer analogs tested (see FIGS. 8E and 8F). FIG. 9 shows the expansion of human iNKTs by α-GalCer analogs C11 and C18-C29. α-GalCer analogs C20, C22-C24 and C26-C27 induced significant greater expansion of CD1d-restricted human iNKT cells than C1 and C11.

FIG. 10 shows different IFN-γ secretion levels between naïve and various α-GalCer analog-pulsed human NKTs. FIG. 10A shows the IFN-γ secretion from human naïve iNKTs (Vα24$^+$) cultured with immature CD14$^+$ DCs, and pulsed with control DMSO, α-GalCer or the indicated α-GalCer analogs of the present disclosure. FIG. 10B-D show IFN-γ secretion in response to the α-GalCer analogs in three different sources of iNKTs: (B) Human naïve iNKTs, (C) α-GalCer pulsed iNKTs and (D) C11 pulsed iNKTs. The iNKTs were cultured with HeLa-CD1d cells, and pulsed with control DMSO, α-GalCer or the indicated α-GalCer analogs for 18 hours. FIG. 10E shows different basal levels of IFN-γ in human naïve iNKTs, α-GalCer pulsed iNKTs and C11 pulsed iNKTs.

Figure 11A:
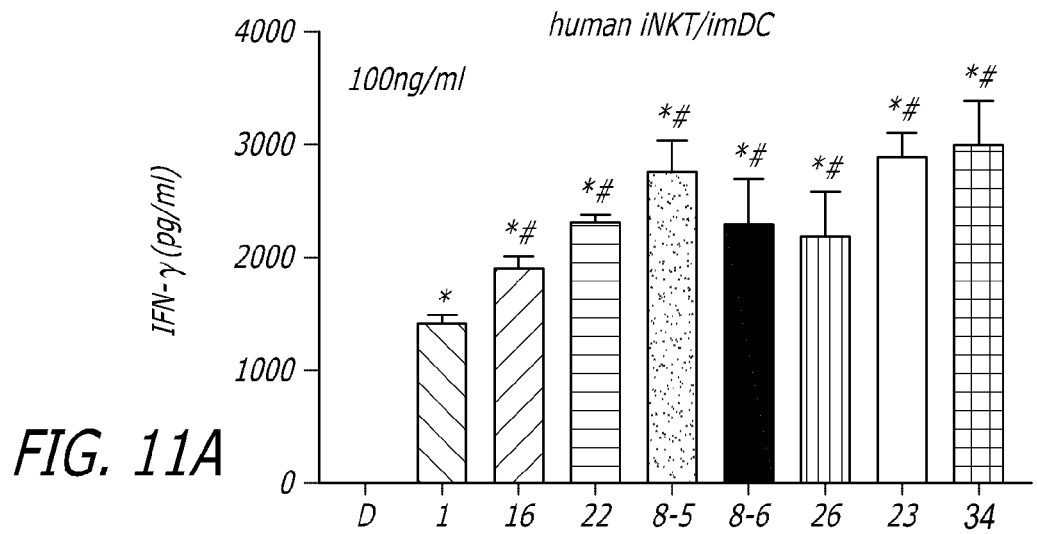
FIG. 11(A-C) shows (A) IFN-γ cytokine secretion levels (pg/ml), (B) IL-4 cytokine secretion levels (pg/ml) and (C) ratio of IFN-γ/IL-4 by human naïve iNKTs treated with α-GalCer or the indicated α-GalCer analogs of the present disclosure.
Figure 11B:
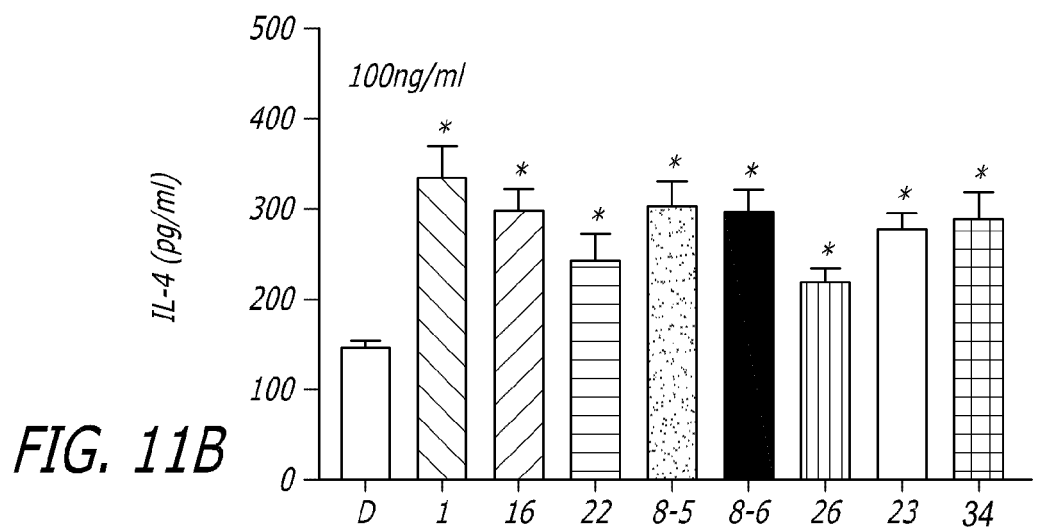
Figure 11C:
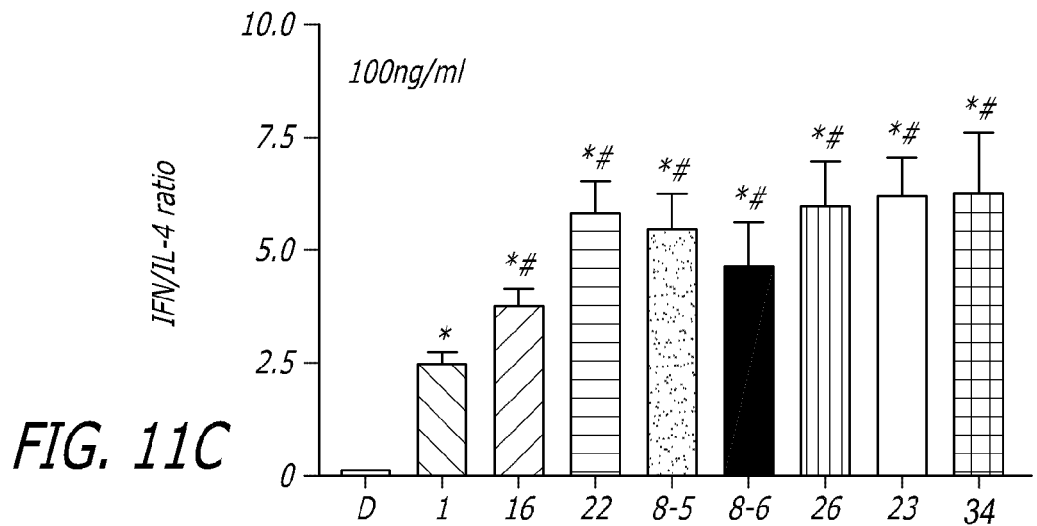

FIG. 11 shows $T_H1/T_H2$ cytokine production by invariant human naïve NKTs in response to the α-GalCer analogs of the present disclosure. Human Vα24+iNKTs were cultured with autologous immature CD14$^+$ DCs pulsed with control DMSO, α-GalCer or the indicated α-GalCer analogs for 18 hours. FIG. 11(A) shows the induction of IFN-γ, (B) shows the induction of IL-4 and (C) shows the ratio of IFN-γ over IL-4, normalized to DMSO control. The induction of cytokines and chemokines from the naïve human Vα24+iNKTs are listed in FIG. 12.

Expansion and Activation of NKTs Using α-GalCer Analogs

In one aspect, the synthetic α-GalCer analogs of the present disclosure are capable of expanding and activating NKs and iNKTs. Because decreased numbers of iNKTs in human peripheral blood mononuclear cells has been documented in patients with malignancies, expansion and activation of such patients' iNKTs with the α-GalCer analogs of the present disclosure may be therapeutically beneficial. In an exemplary implementation, the α-GalCer analogs of the present disclosure are capable of expanding human iNKTs in vitro.

A method is provided for producing an isolated, culture-expanded NKT population, comprising contacting Vα14i, or Vα24i T cells with dendritic cells and an (α-GalCer analog of the present disclosure, for a period of time resulting in analog-specific T cell expansion and isolating the expanded T cells thus obtained, thereby producing an isolated, culture-expanded NKT population. In an exemplary implementation, the method for producing an isolated culture-expanded NKT population further comprises the step of adding a cytokine or growth factor to the dendritic cell, NKT cell culture.

Figure 13:
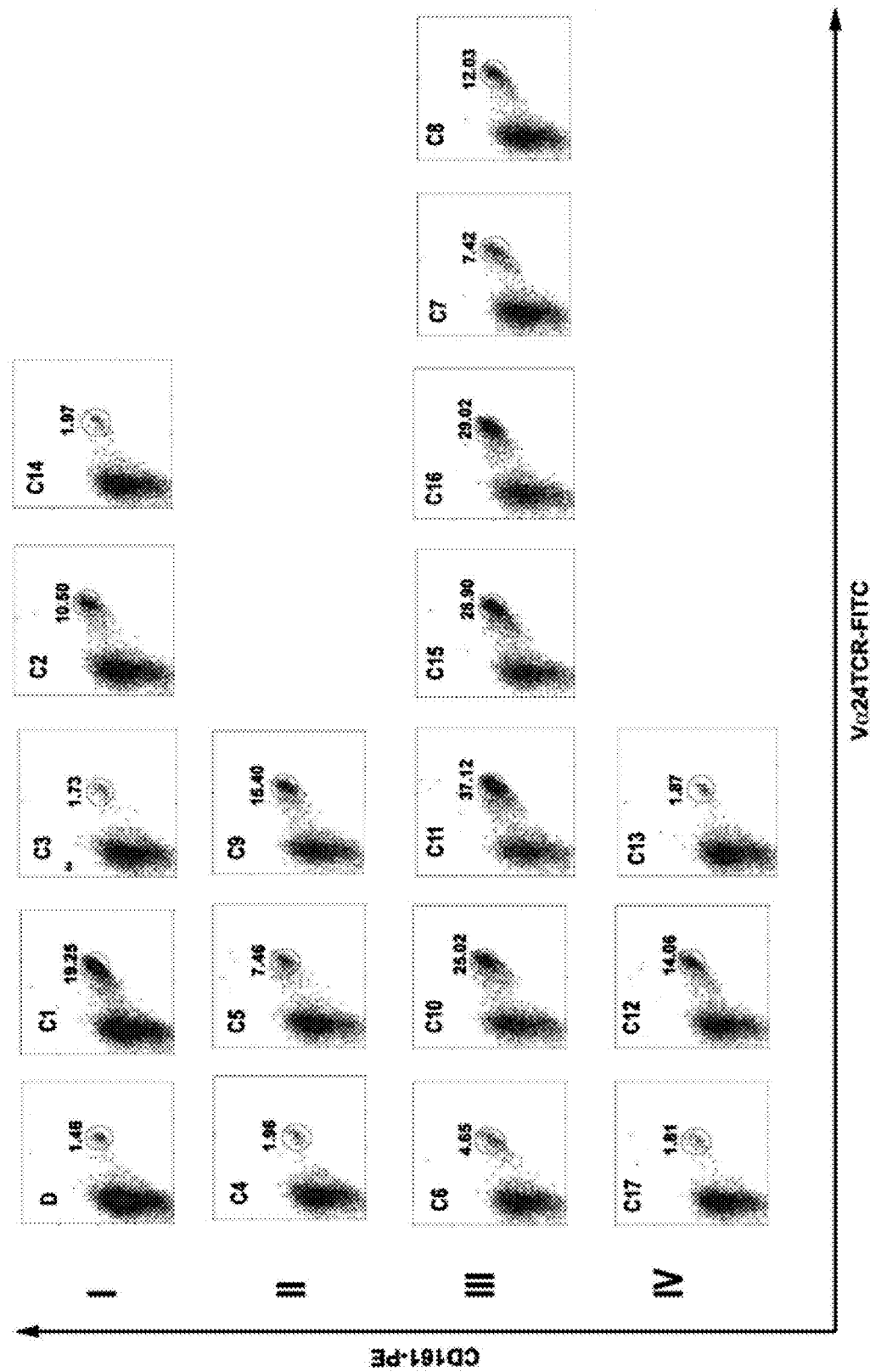
FIG. 13 shows representative flow cytometry data for the expansion of human CD56$^+$ cells (NK/NKT mixtures) cultured with autologous immature CD14$^+$ dendritic cells and pulsed with α-GalCer or the indicated α-GalCer analogs of the present disclosure. The percentage of CD161$^+$/Vα24TCR$^+$ cells in the NK/NKT mixtures is shown.
Figure 14:
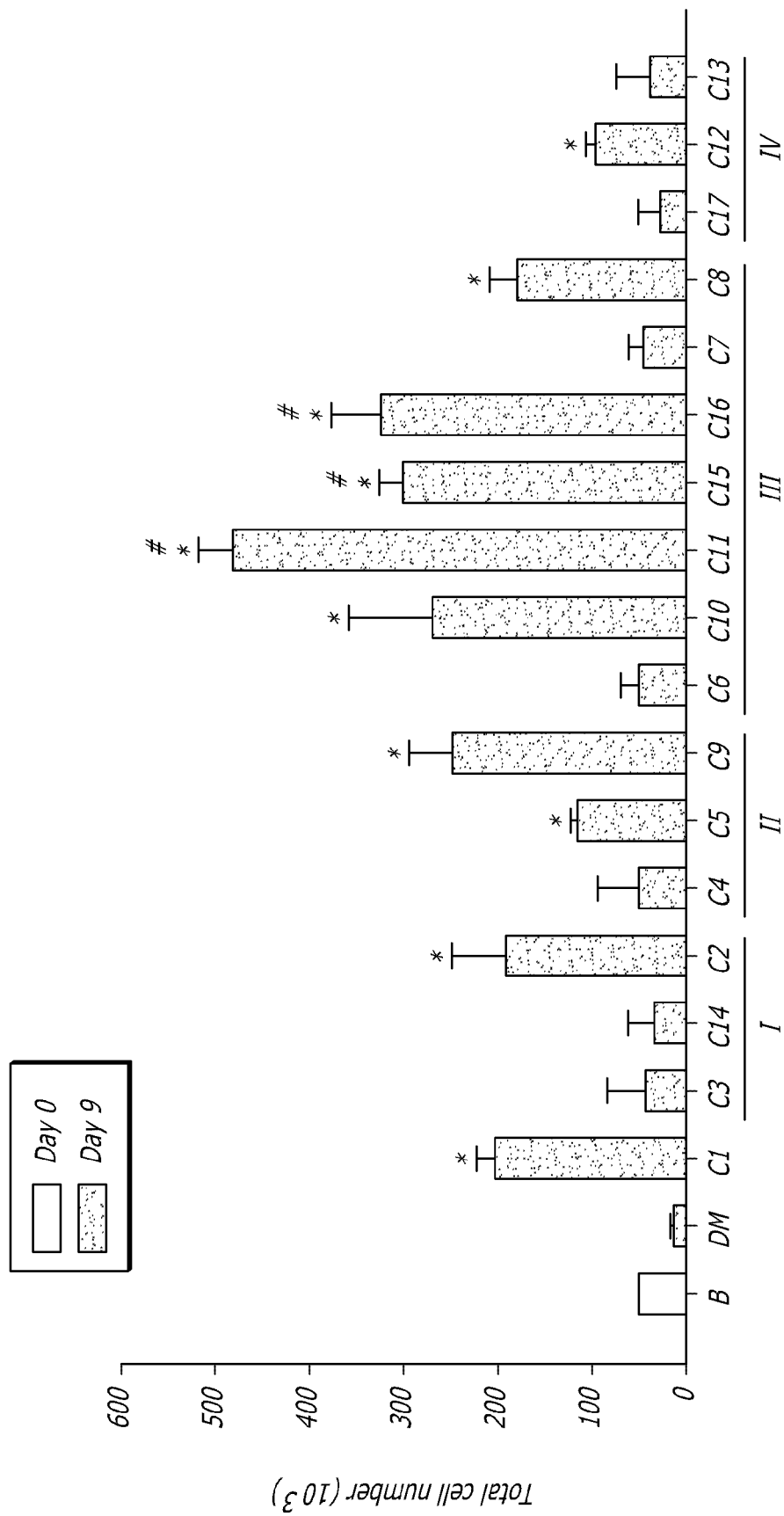
FIG. 14 shows the total number of iNKTs ($10^3$) found in the NK/NKT mixtures from FIG. 13.

Human CD56$^+$ cells (NK/NKT cell mixtures) were cultured with autologous immature CD14$^+$ DCs and pulsed with DMSO, α-GalCer or various α-GalCer analogs of the present disclosure. On day 9 after exposure, the expansion/survival of NKs and NKTs and of a subpopulation of NKTs, iNKTs (CD161$^+$/Vα24$^+$/CD56$^+$/CD3$^+$), was determined by flow cytometry. As shown in FIGS. 13 and 14, a significant increase in iNKTs over control was noted upon stimulation with C2, C8-C12 and C15-C16. Among the α-GalCer analogs tested, several of the aromatic compounds from Group III, especially C11, C15 and C16, were more effective than C1.

Figure 15A:
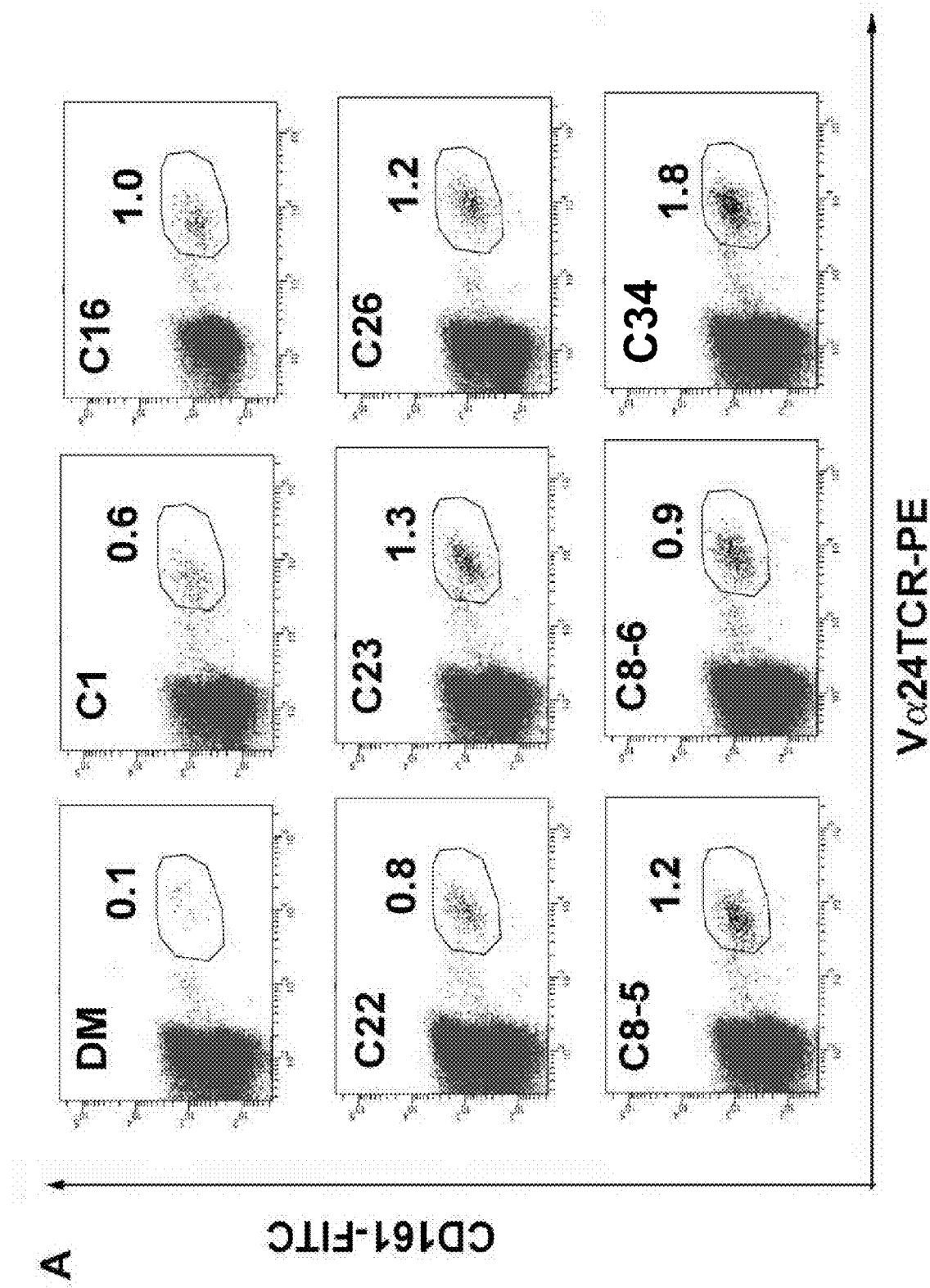
FIG. 15(A-B) show representative flow cytometry data for the expansion of human CD56$^+$ cells (NK/NKT mixtures) cultured with autologous immature CD14$^+$ dendritic cells pulsed with α-GalCer or the indicated α-GalCer analogs of the present disclosure. (A) shows representative flow cytometry data of the percentage of CD161$^+$/Vα24TCR$^+$ cells in the NK/NKT mixtures and (B) shows the fold of increase in the total number of iNKTs found in the NK/NKT mixtures.
Figure 15B:
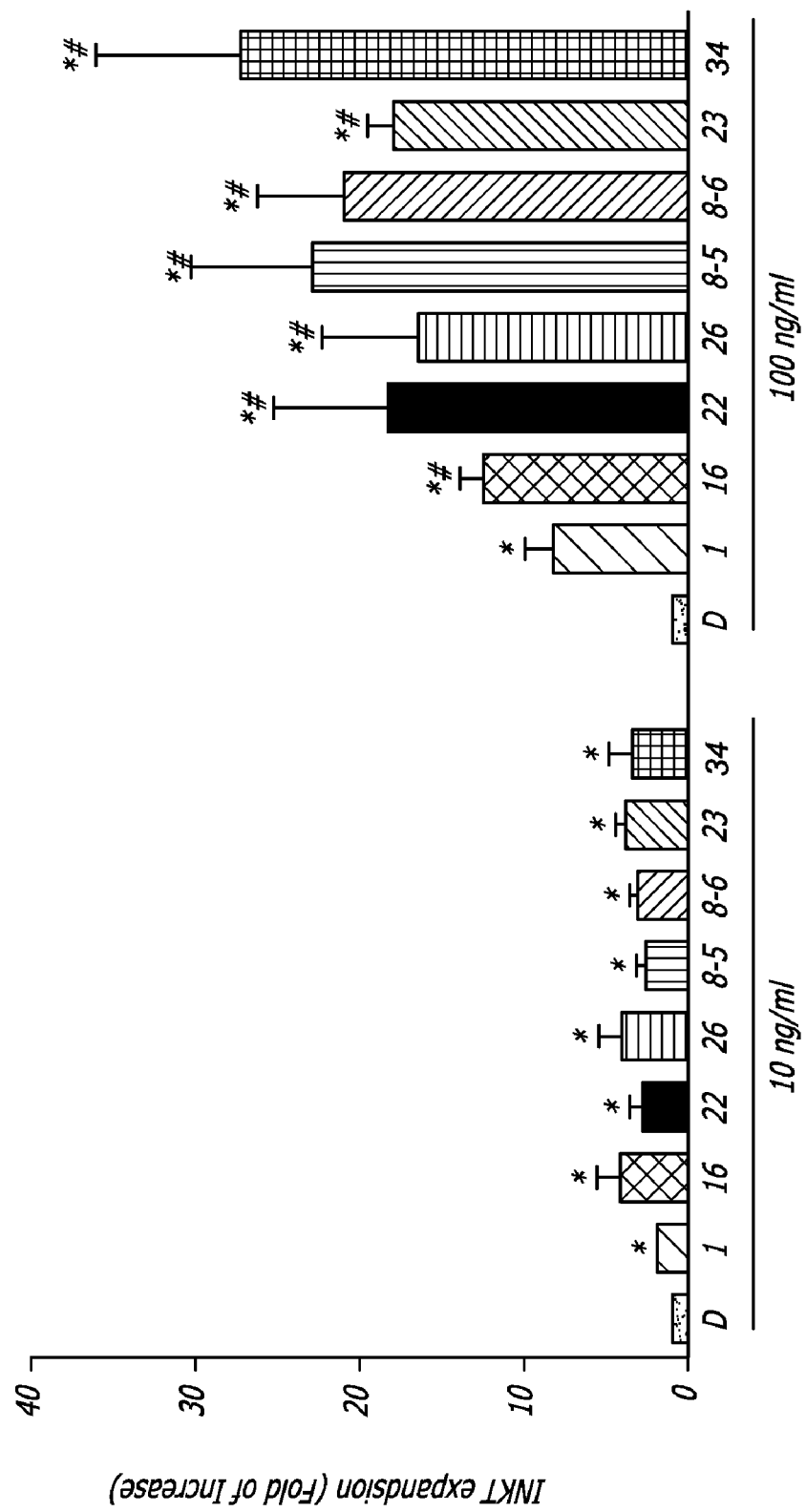

As shown in FIG. 15, human CD56$^+$ cells (NK/NKT mixtures) were cultured with autologous immature CD14$^+$ DCs and pulsed with DMSO, α-GalCer or various α-GalCer analogs of the present disclosure at 10 or 100 ng/ml on day 2 for 18 hours. The percentage of CD161$^+$/Vα24 TCR$^+$ cells in the NK/NKT mixtures were gated by flow cytometry on day 9. FIG. 15A shows the percentage of Vα24i NKTs in response to 100 ng/ml. FIG. 15B shows the fold changes in total number of Vα24i NKTs in response to different doses. *, $p<0.05$, compared with DMSO; #, $p<0.05$, compared with C1.

Maturation and Elongation of Dendritic Cells Using α-GalCer Analogs

The most efficient antigen-presenting cells (APCs) are mature, immunologically competent dendritic cells (DCs). DCs are capable of evolving from immature, antigen-capturing cells to mature, antigen-presenting, T cell-priming cells; converting antigens into immunogens and expressing molecules such as cytokines, chemokines, costimulatory molecules and proteases to initiate an immune response. The types of T cell-mediated immune responses (tolerance vs. immunity, $T_H1$ vs. $T_H2$) induced can vary, however, depending on the specific DC lineage and maturation stage in addition to the activation signals received from the surrounding microenvironment.

The ability of DCs to regulate immunity is dependent on DC maturation. Consequently, maturation of DCs is critical to the initiation of the immune response. A variety of factors can induce maturation following antigen uptake and processing within DCs. During their conversion from immature to mature cells, DCs undergo a number of phenotypical and functional changes. The process of DC maturation, in general, involves a redistribution of major histocompatibility complex (MHC) molecules from intracellular endocytic compartments to the DC surface, down-regulation of antigen internalization, an increase in the surface expression of costimulatory molecules, morphological changes (e.g. formation of dendrites), cytoskeleton re-organization, secretion of chemokines, cytokines and proteases, and surface expression of adhesion molecules and chemokine receptors.

In one aspect, the synthetic α-GalCer analogs of the present disclosure are capable of promoting the maturation of human DCs. Dendritic cell maturation may lead to enhanced adaptive immune responses. A method is disclosed for the maturation of dendritic cells that includes: providing immature dendritic cells; and incubating the immature dendritic cells with a concentration of α-GalCer analogs of the present disclosure for a period of time such that the immature dendritic cells become mature. In an exemplary implementation, these mature dendritic cells may then be used as immunotherapies, such as for example, cancer immunotherapies and adjuvant immunotherapies. In another exemplary implementation, the α-GalCer analogs of the present disclosure may be combined with immature denritic cells or mature denritic cells and then used as immunotherapies, such as for example, cancer immunotherapies and adjuvant immunotherapies.

Figure 16:
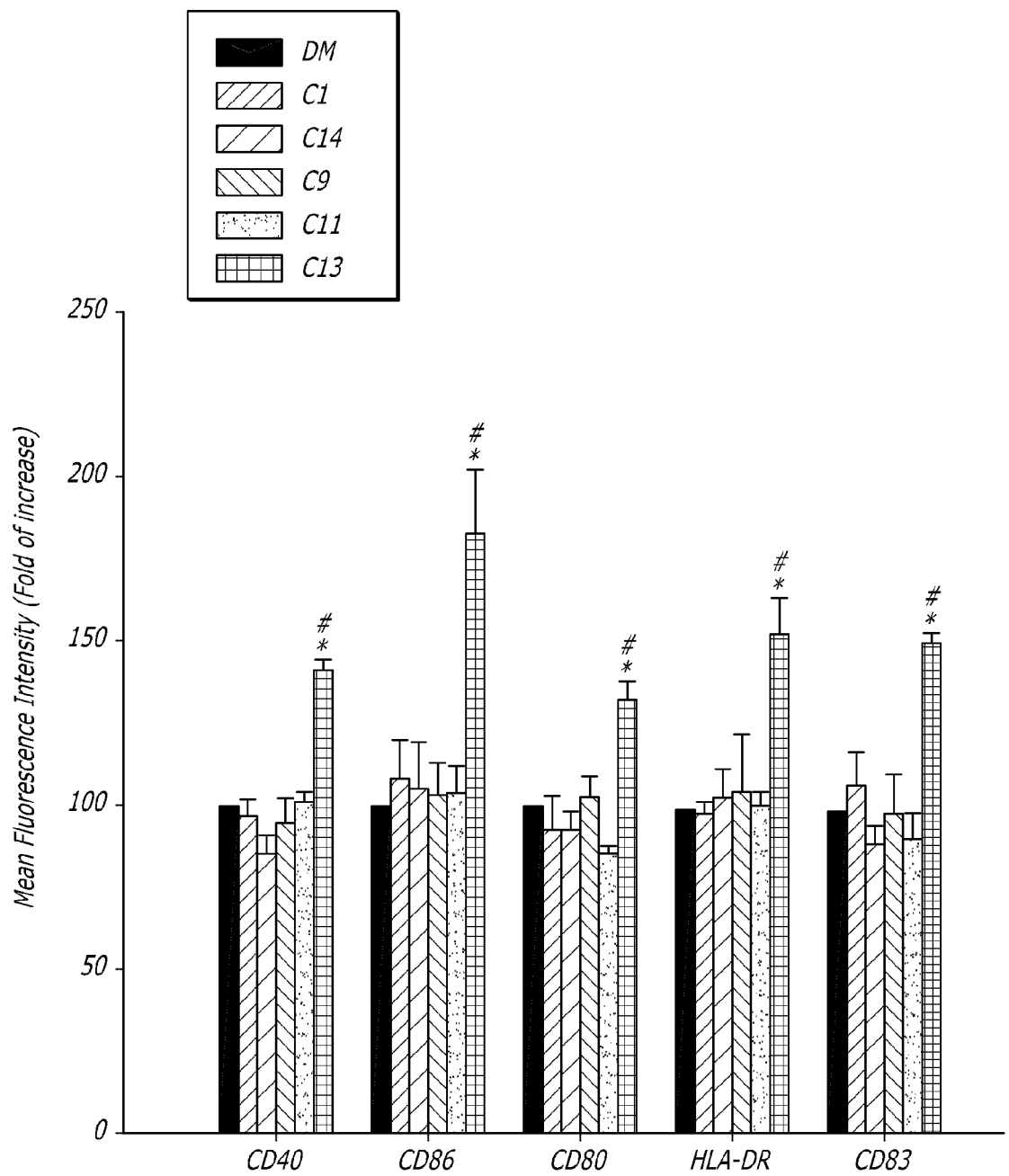
FIG. 16 shows the expression levels, as Mean Fluorescence Intensity (MFI), of surface proteins CD40, CD80, CD86, and CD83, as well as the MHC class II cell surface receptor HLA-DR, on dendritic cells (DCs) after immature human DCs were incubated with α-GalCer or the indicated α-GalCer analogs of the present disclosure.
Figure 17A:
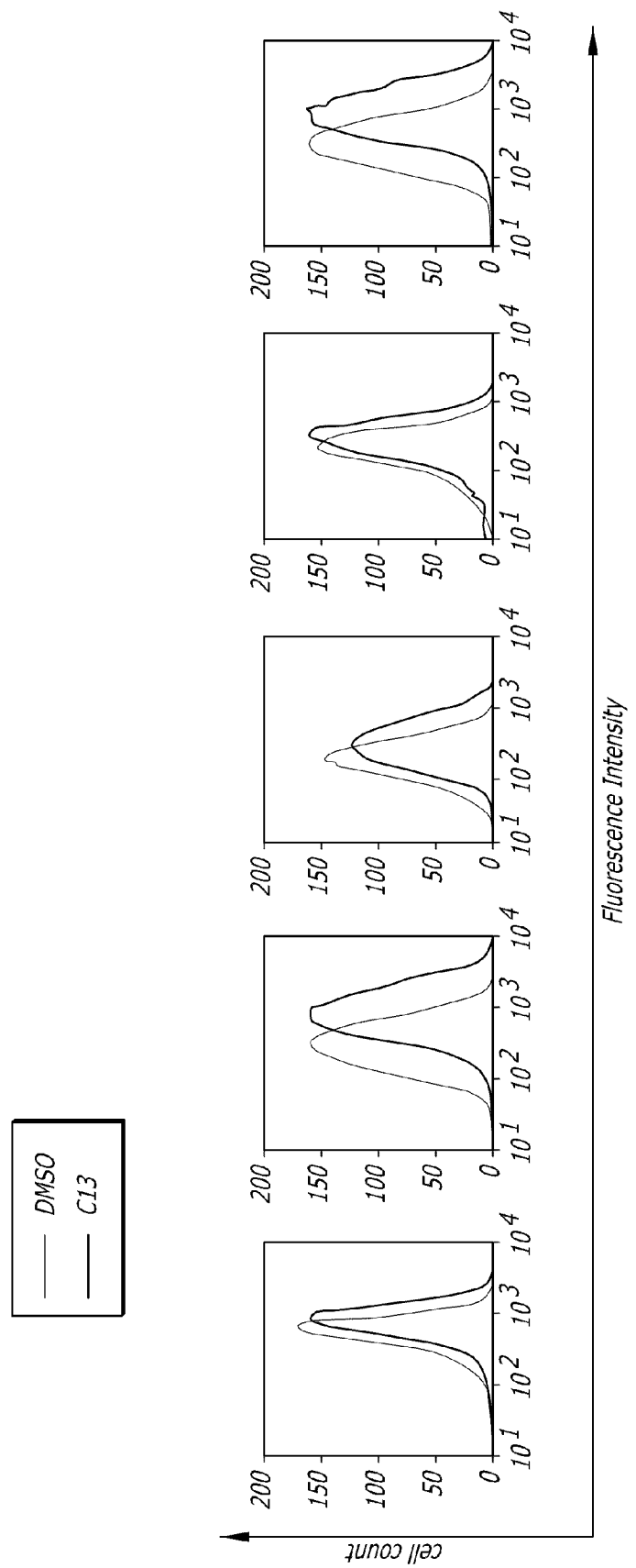
FIG. 17(A-B) shows how the α-GalCer analog C13 of the present disclosure promotes maturation of human monocyte-derived DCs. (A) shows histograms for CD40, CD80, CD83, CD86, and HLA-DR expression in DCs in response to C13. (B) shows the morphology of DCs incubated with C13 for 48 hours.
Figure 17B:
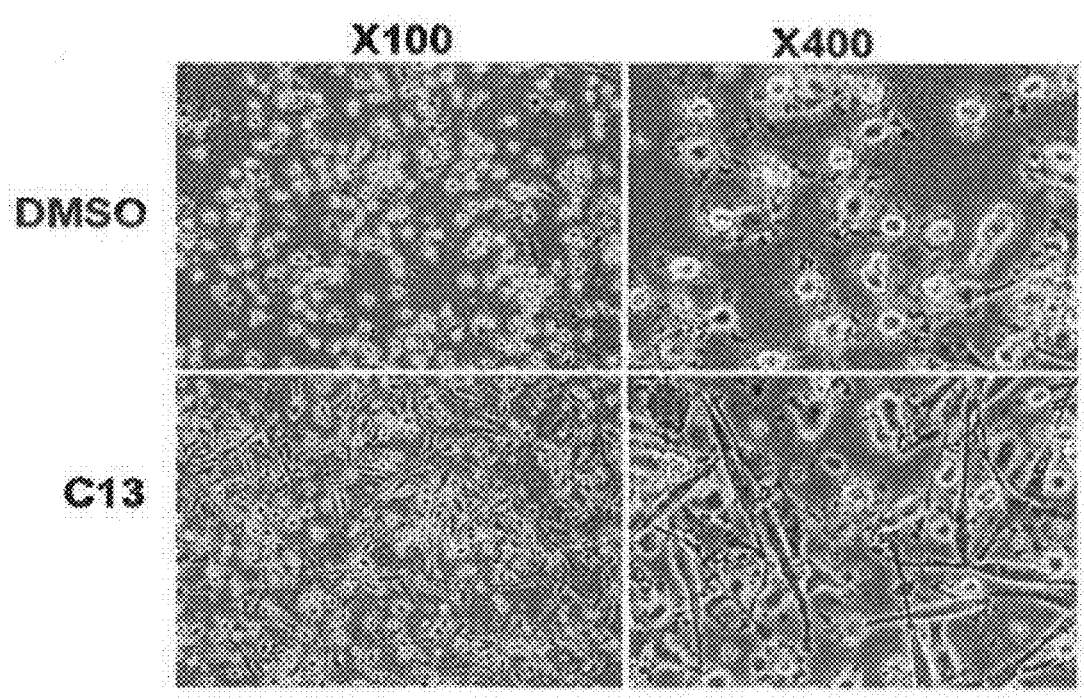

The α-GalCer analogs of the present disclosure are capable of inducing mouse splenic DC maturation. In vitro, the α-GalCer analogs of the present disclosure were able to directly augment the expression levels of various surface maturation markers, including CD40, CD54, CD80, CD83, CD86, CD209, and HLA-DR (MHC II molecule) on human DCs, along with dendritic elongation. As shown in FIG. 16, C13 showed a significant increase in the expression levels of CD40, CD80, CD83, CD86 and HLA-DR and promotes maturation of human monocyte-derived DCs. FIG. 17A shows histograms for CD40, CD80, CD83, CD86 and HLA-DR expression in DCs in response to C13. FIG. 17B shows the morphology of DCs incubated with C13 for 48 hours.

CD1d-Dependent TCR Activation of NKTs Using α-GalCer Analogs

Figure 18:
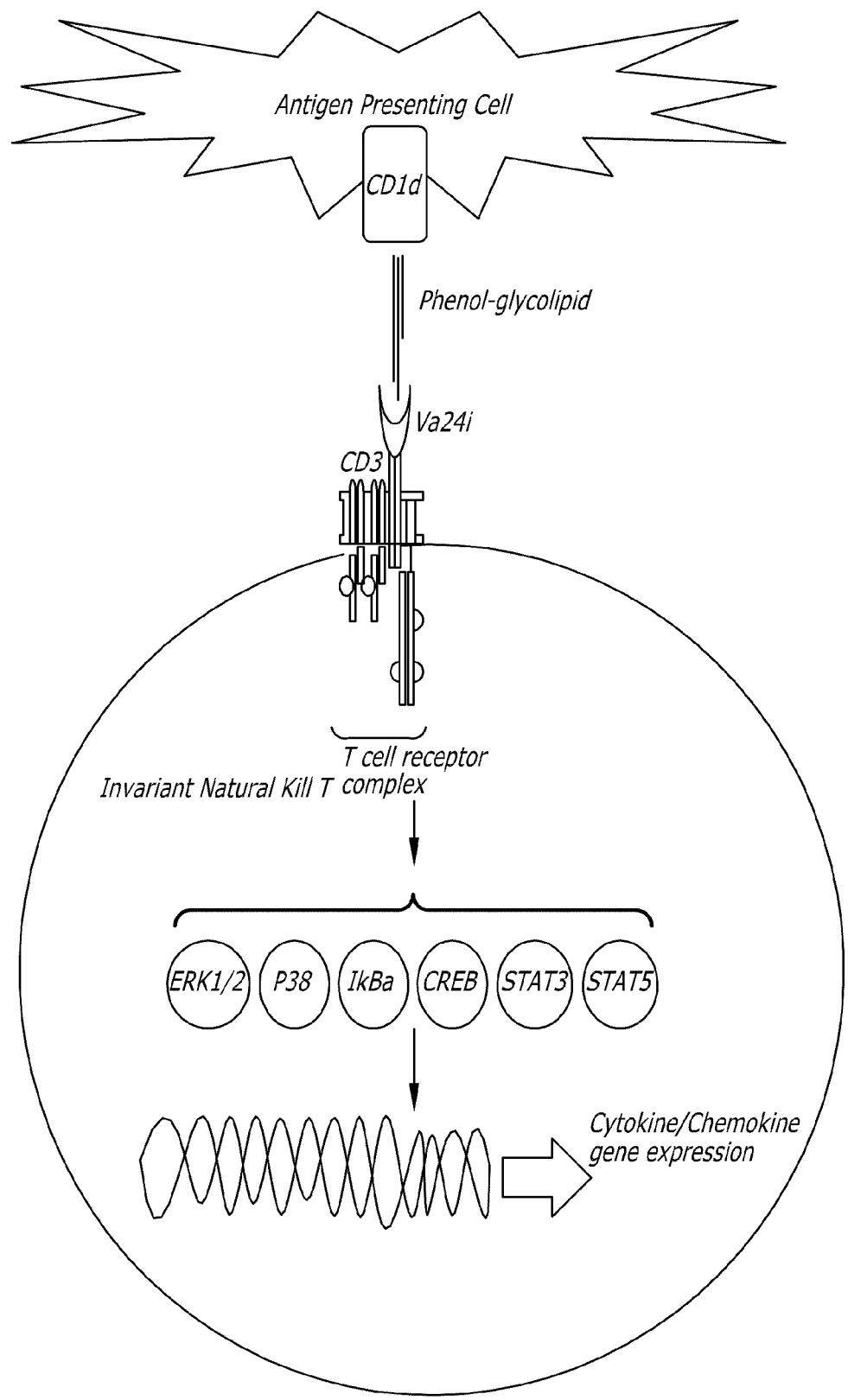
FIG. 18 shows a schematic illustration of the iNKT cell receptor signaling pathways.
Figure 19A:
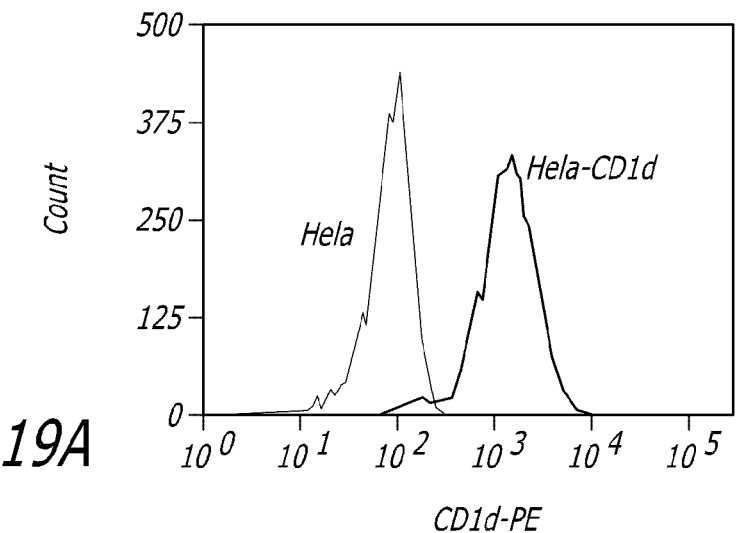
FIG. 19(A-E) demonstrates how α-GalCer analogs of the present disclosure promote CD1d-dependent T cell receptor (TCR) activation of human NKTs. (A) shows expression of CD1d in HeLa cells transfected with CD1d (HeLa-CD1d). (B) shows the intracellular levels of phospho-CD3ε. (C) shows the intracellular levels of phospho-ERK1/2. (D) shows the intracellular levels of phospho-Syk. (E) shows the intracellular levels of phospho-CREB.
Figure 19B:
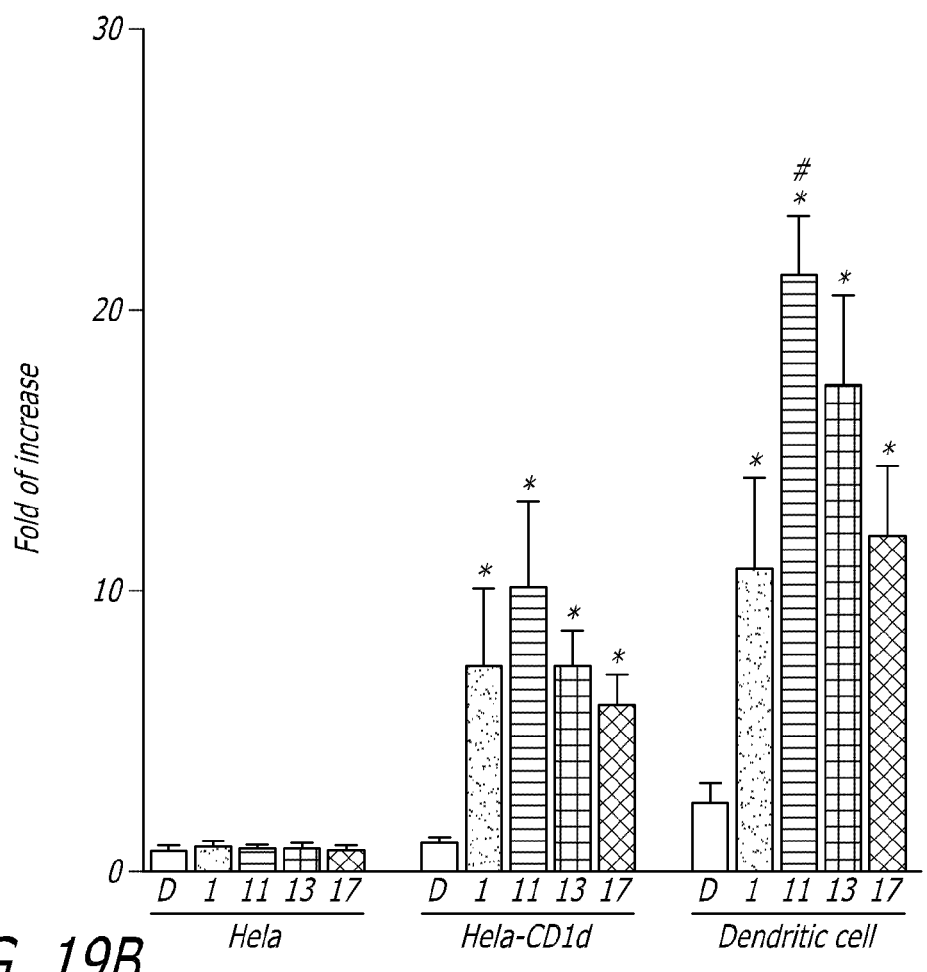
Figure 19C:
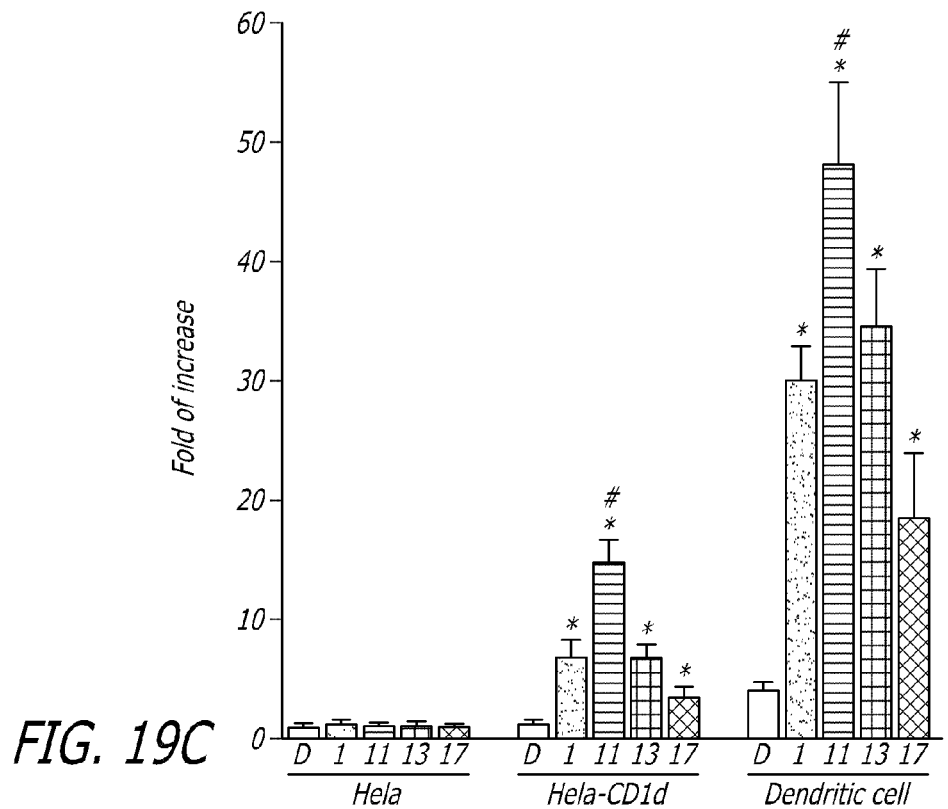
Figure 19D:
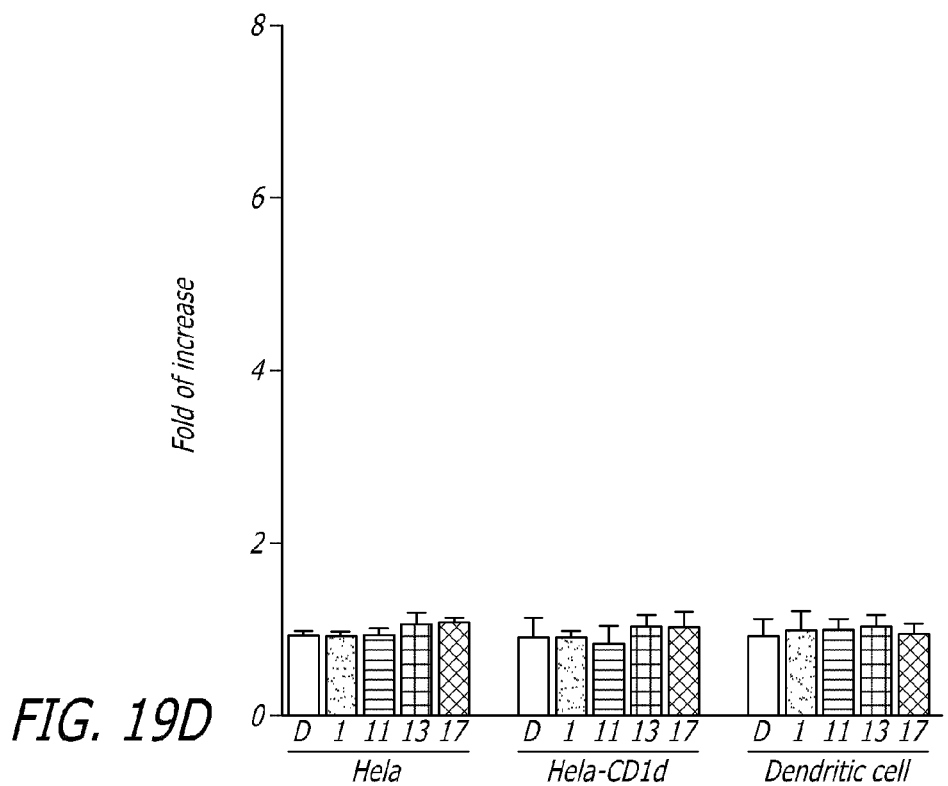
Figure 19E:
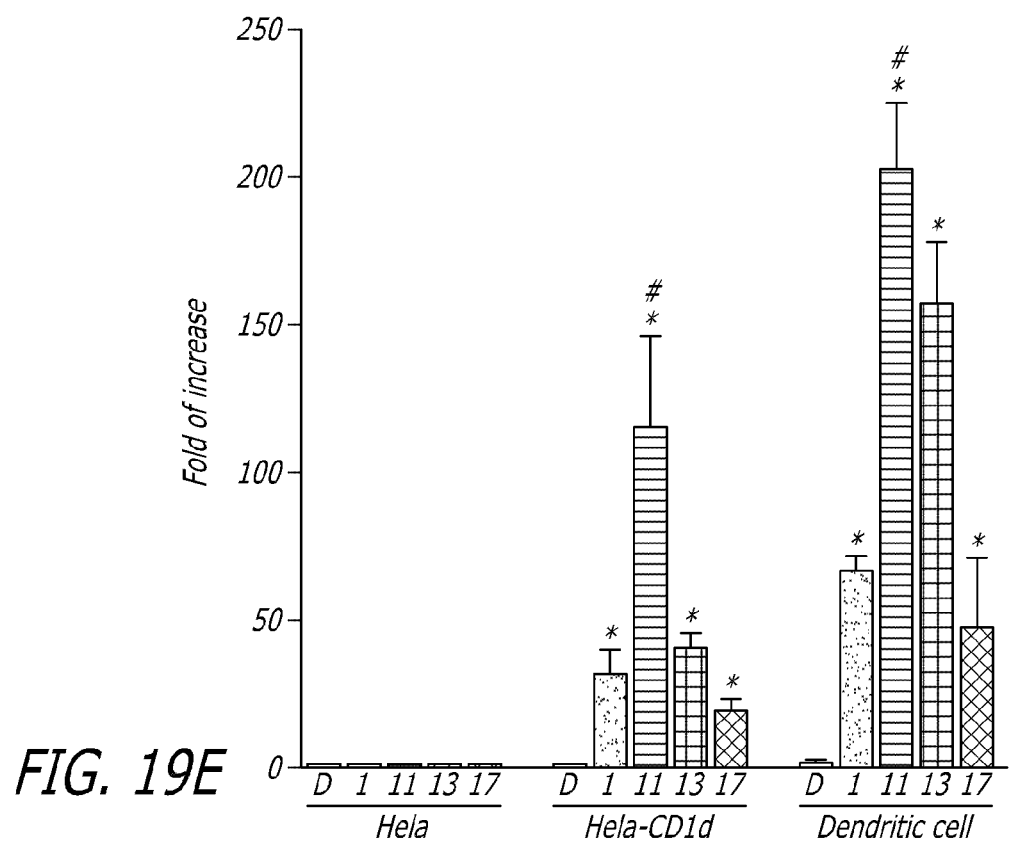
Figure 20A:
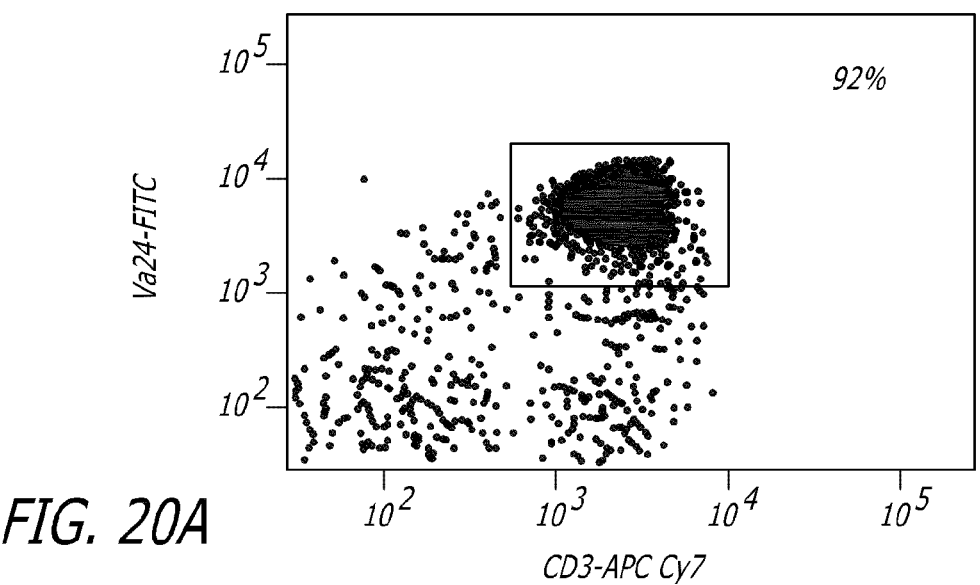
FIG. 20(A-L) demonstrates how α-GalCer analogs of the present disclosure promote CD1d-dependent T cell receptor (TCR) activation of naïve human iNKTs (Vα24$^+$). (A) shows the determination of isolated naïve human Vα24$^+$ T cells by flow cytometry. (B-L) shows activation of TCR on iNKTs. HeLa or HeLa-CD1d cells were loaded with α-GalCer or α-GalCer analogs C16, C23, 7DW8-5, 7DW8-6 or C26, and then added to naïve Vα24$^+$ T cells. The intracellular levels of the following phosphorylated proteins were measured and expressed as Median Fluorescence Intensity, and normalized to the amount of total input protein: (B) phospho-CD3ε (phosphotyrosine), (C) phospho-CREB (Ser-133), (D) phospho-ERK1/2 (Thr-185/Tyr-187), (E) phospho-p38 (Thr-180/Tyr-182), (F) phospho-IκBα (Ser32), (G) phospho-Lck, (H) phospho-Lat, (I) phospho-STAT3 (Ser727), (J) phospho-STAT5 A/B (Tyr 694/699), (K) phospho-Syk (Phospho-tyrosine) and (L) phospho-Zap-70 (Phospho-tyrosine). *, $p<0.05$, compared with DMSO control and #, $p<0.05$, compared with α-GalCer.
Figure 20B:
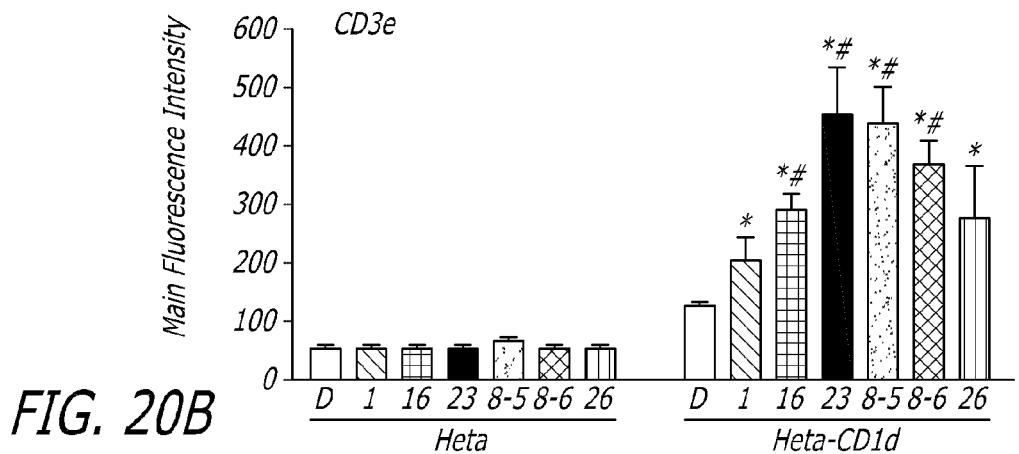
Figure 20C:
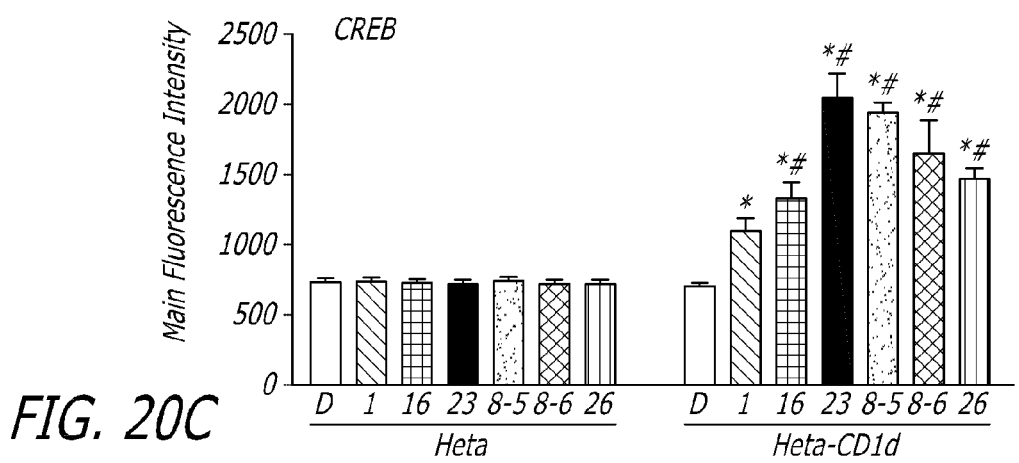
Figure 20D:
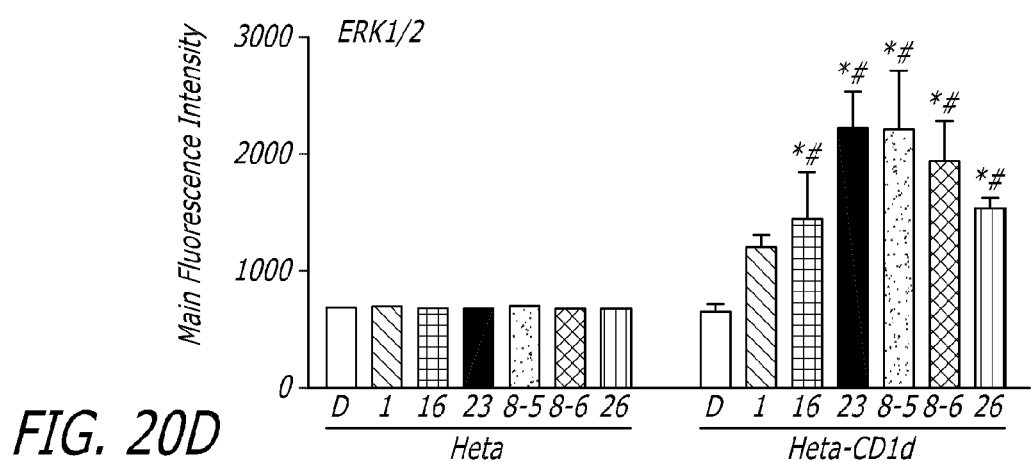
Figure 20E:
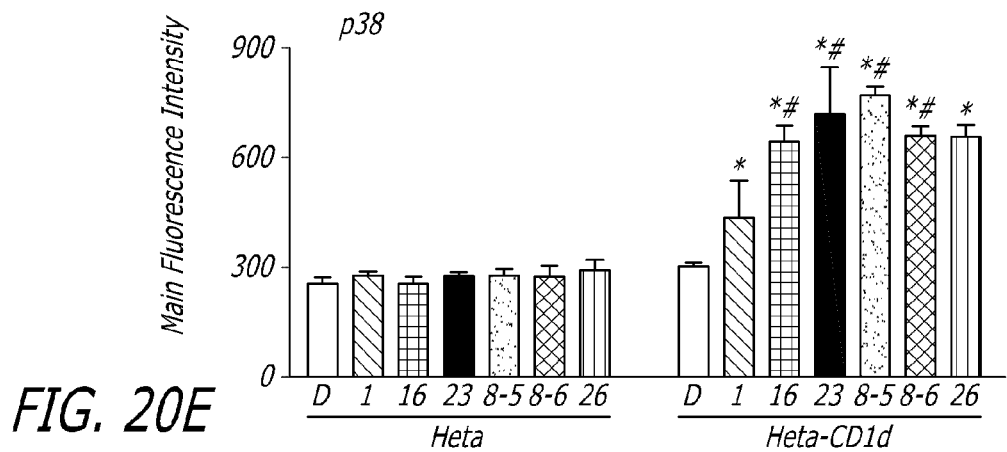
Figure 20F:
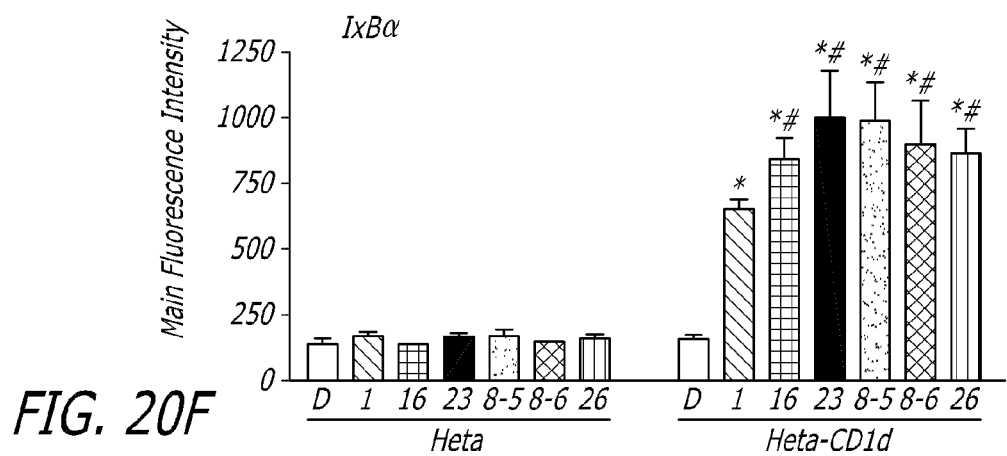
Figure 20G:
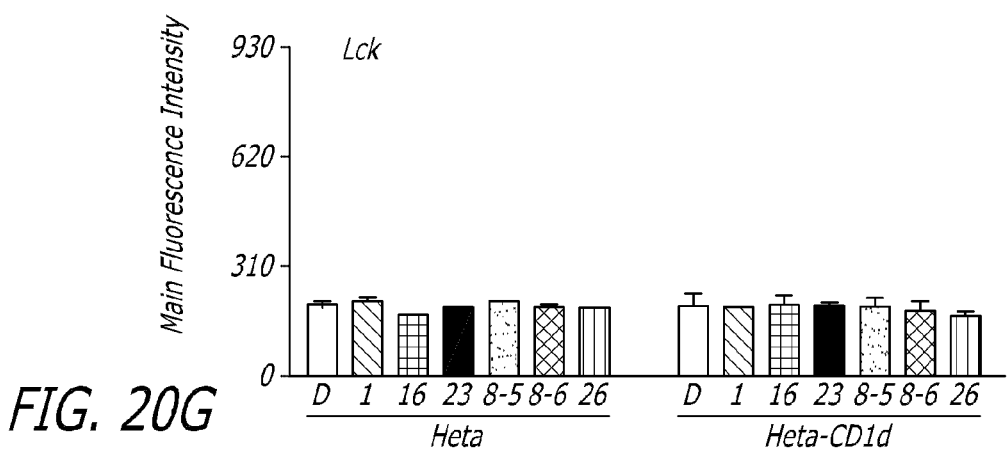
Figure 20H:
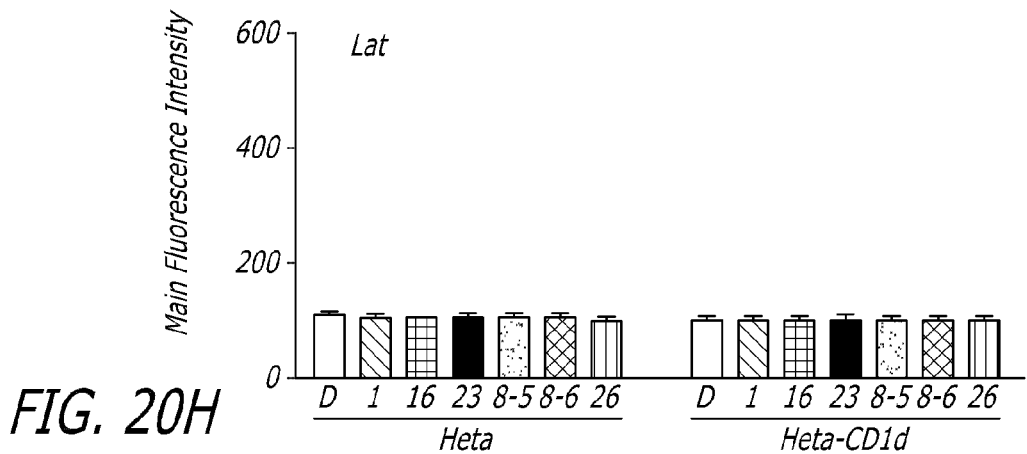
Figure 20I:
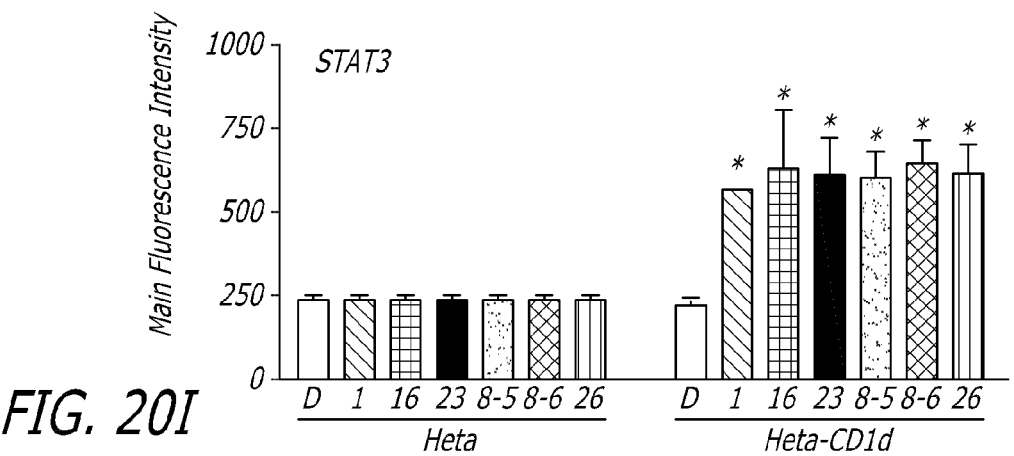
Figure 20J:
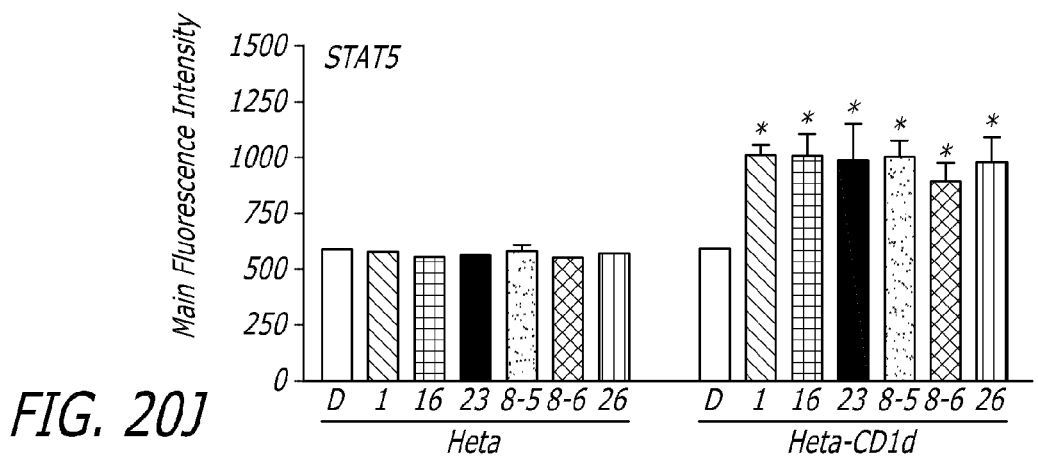
Figure 20K:
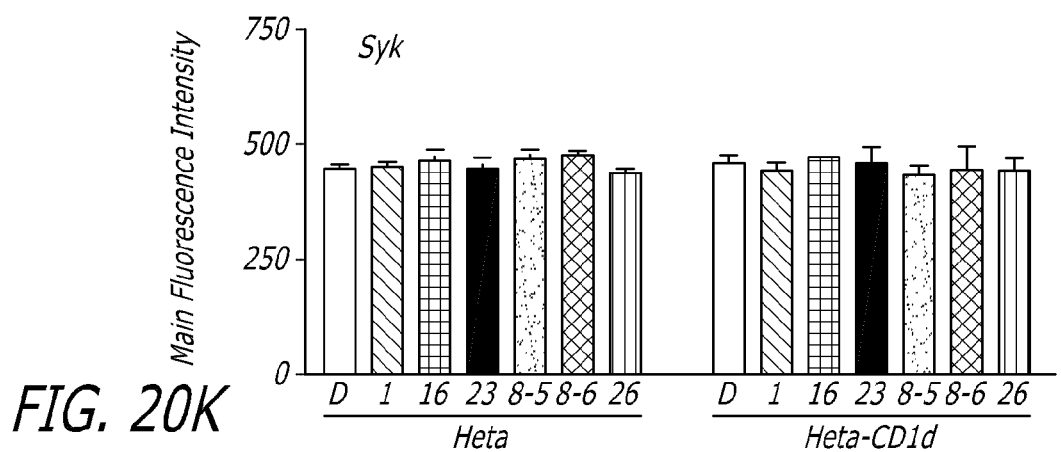
Figure 20L:
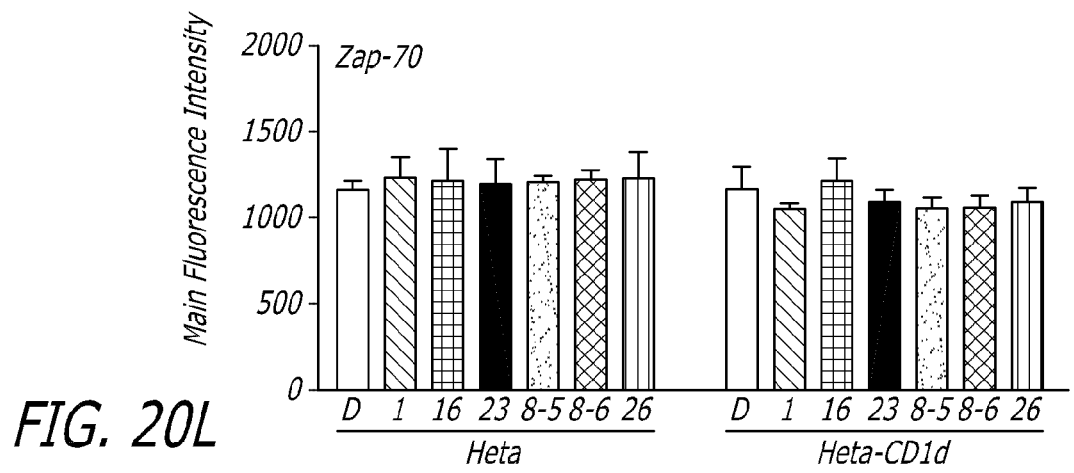

In yet another aspect, the synthetic α-GalCer analogs of the present disclosure are capable of inducing CD1d-dependent TCR activation. FIG. 18 shows a schematic illustration summarizing TCR signaling pathways in NKTs. iNKTs recognize glycolipid antigens presented in the context of CD1d on the surface of antigen presenting cells (APCs) via T cell receptor complexes. The binding of glycolipid antigens activates cytosolic kinases in iNKTs, including phosphorylation of ERK1/2, p38, IκBα, CREB, STAT3 and STAT5. These signaling cascades lead to iNKT proliferation and cytokine/chemokine production.

In an exemplary implementation, the α-GalCer analogs of the present disclosure are capable of inducing CD1d-dependent TCR activation of naïve human NKTs. To discern whether TCR activation is CD1d-dependent, the effects of various α-GalCer analogs of the present disclosure presented by HeLa-CD1d, overexpressing human CD1d, and control HeLa cells was determined. Also, the capacity of HeLa-CD1d (nonprofessional APCs) were compared with immature DCs (professional APCs) in presenting the various α-GalCer analogs to NKTs. As shown in FIG. 19, C1 and the α-GalCer analogs C11, C13 and C17 increased intracellular values of phospho-CD3ε by 7.3, 10, 7.3 and 5.9 folds of control, respectively, when presented by HeLa-CD1d cells and 10.8, 21.3, 17.3 and 12 folds respectively, when presented by DCs. For phospho-ERK1/2, C1 and the α-GalCer analogs C11, C13 and C17 induced 6.6, 14.6, 6.6 and 3.3 folds increase respectively, with HeLa-CD1d cells and 30, 48.3, 35 and 18.6 folds respectively, with DCs. The induction of phospho-CREB is even more surprising; C1 and the α-GalCer analogs C11, C13 and C17 induced 2, 117, 41 and 20 folds expression respectively, when presented by HeLa-CD1d cells and 68, 204, 158 and 49 folds increase respectively, when presented by DCs. None of the α-GalCer analogs tested had any effect on the phosphorylation of Syk, a protein kinase, known to play a role in B cell receptor signaling but not in the TCR pathway. These findings suggest that aromatic α-GalCer analogs of the present disclosure induced a strong TCR activation in a CD1d-dependent manner, and the extent of activation is greatly enhanced when presented by professional APCs as compared to non-professional APCs. None of the α-GalCer analogs of the present disclosure showed any effect on phosphorylation of CD3ε, ERK1/2 or CREB in NKT cells when co-cultured with control HeLa cells. Overall, compounds C11 and C13 appeared to be stronger in TCR activation than compounds C1 and C17, which were consistent with their greater induction of $T_H1$-biased cytokine profile triggered by C11 as compared with C1, because ERK1/2 and CREB activations have been reported to play a role in the induction of many $T_H1$ cytokines, such as IL-12 and IFN-γ. C13 also triggered significant activation of TCR, presumably as a consequence of the unique ability of C13 to enhance expression of co-stimulatory molecules on DCs. For the four α-GalCer analogs examined, the TCR was activated more potently when presented by DCs than by HeLa-CD1d cells, especially with C13. Higher levels of phosphorylated CD36, ERK1/2 and CREB induced by the α-GalCer analog C11 than by C1 is consistent with the notion that stronger binding of glycolipid to CD1d induces a greater stimulation of TCR on NKTs.

FIG. 20 shows another exemplary implementation of how α-GalCer analogs of the present disclosure are capable of inducing CD1d-dependent TCR activation. Various α-GalCer analogs of the present disclosure (specifically C16, C23, C26, C8-5 and C8-6) are capable of activating TCR signaling pathways in human iNKTs (Vα24⁺ T cells) with phosphorylation of ERK1/2, p38, IκBα, CREB, STAT3 and STAT5. To discern whether TCR activation is CD1d-dependent, the effects of various α-GalCer analogs of the present disclosure presented by HeLa-CD1d, overexpressing human CD1d, and control HeLa cells was determined. FIG. 20A shows the determination of isolated Vα24⁺ T cells by flow cytometry which contained 92% naïve Vα24⁺/CD3⁺ T cells. C1 and the α-GalCer analogs, specifically C16, C23, C26, C8-5 and C8-6, increased intracellular values of (B) phospho-CD3ε (Phospho-tyrosine), (C) phospho-CREB (Ser133), (D) phospho-ERK1/2 (Thr185/Tyr187), (E) phospho-p38 (Thr180/Tyr182), (F) phospho-IκBα (Ser32), (G) phospho-Lck, (H) phospho-Lat, (I) phospho-STAT3 (Ser727), (J) phospho-STAT5 A/B (Tyr 694/699), (K) phospho-Syk (Phospho-tyrosine) and (L) phospho-Zap-70 (Phospho-tyrosine). *, p<0.05, compared with DMSO; #, p<0.05, compared with C1.

Figure 21:
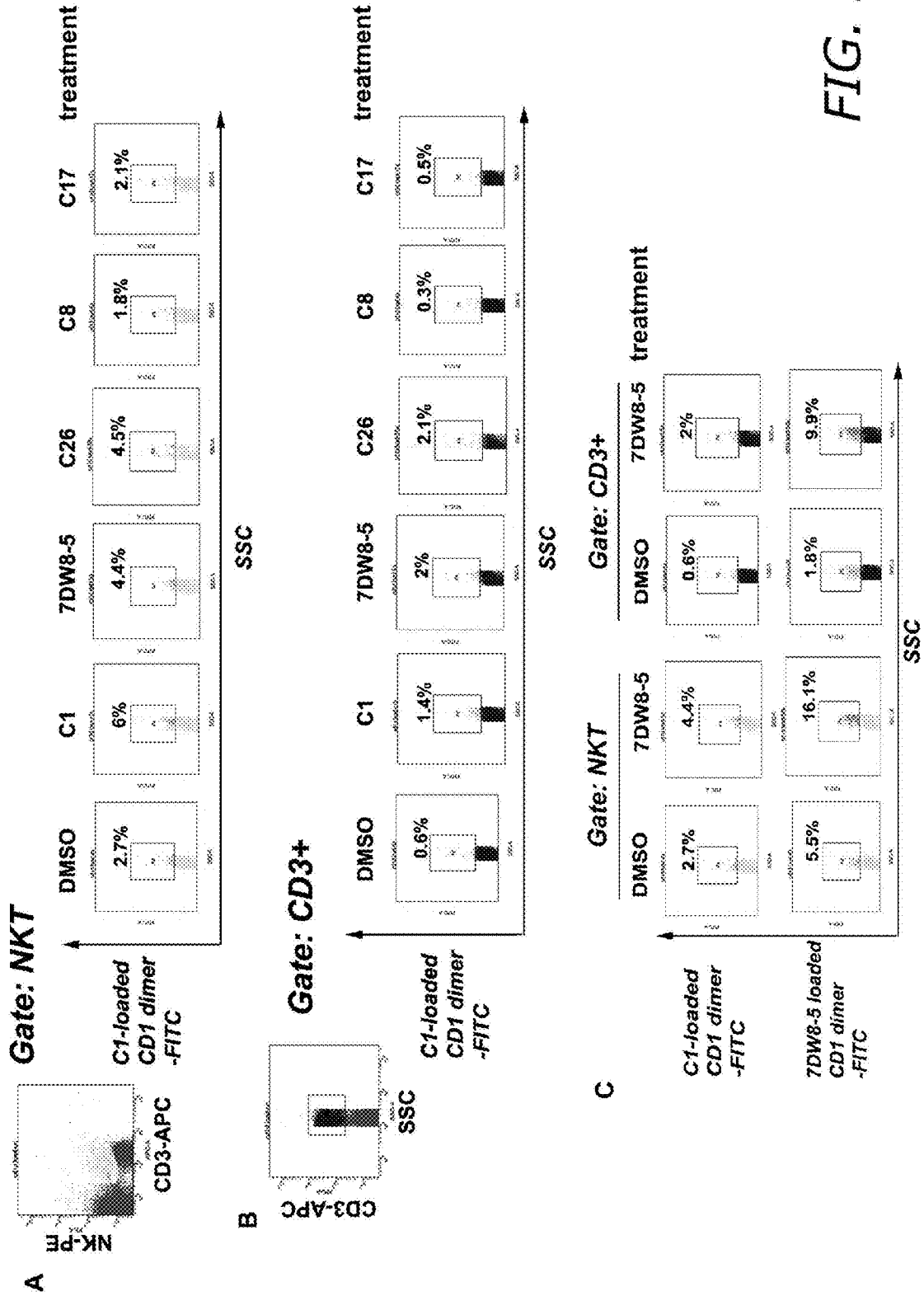
FIG. 21(A-C) shows how the α-GalCer analogs of the present disclosure induced greater cell expansion and display higher capacity to bind CD1d-restricted NKTs and T cells. Spleens from BALB/c mice were harvested 72 hour after intraveneous (IV) injection of 0.1 μg/mouse of vehicle, α-GalCer or the indicated α-GalCer analogs. (A) percentage of mouse NKTs or (B) T cells were determined. (C) shows different binding affinities of α-GalCer and the indicated α-GalCer analogs to CD1d-restricted NKTs and T cells.
Figure 22A:
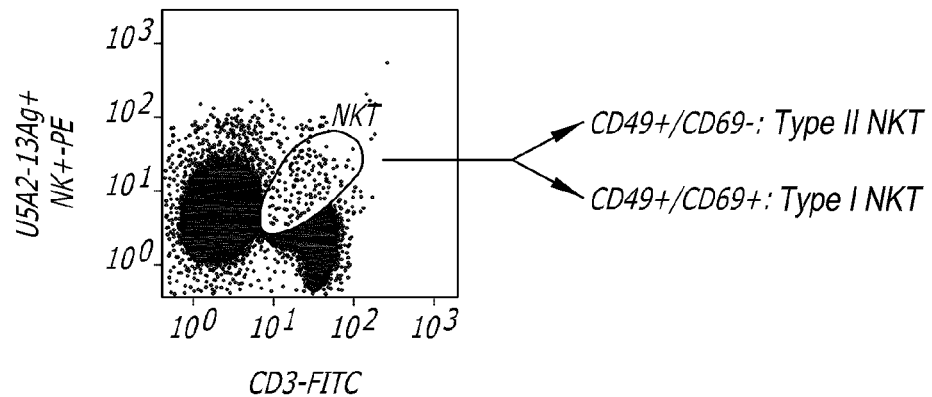
FIG. 22(A-D) show the CD1d-dependent expansion of two NKTs subsets and NK activation in response to the α-GalCer analogs of the present disclosure. (A-C) show the CD1d-dependent expansion of two NKTs subsets. Spleens from BALB/c wild type (WT) or CD1 KO mice were harvested 72 hours post-injection of α-GalCer or the indicated α-GalCer analogs of the present disclosure. Total numbers of NKTs, and its two subtypes, designated as Type I NKT and Type II NKT in (B) WT or (C) CD1 KO mice in response were assessed by FACS. (D) CD1d dependent-activation of NKs. The expansion of total number of NKs in WT (left panel) or CD1 KO (right panel) mice in response were assessed by FACS.
Figure 22B:
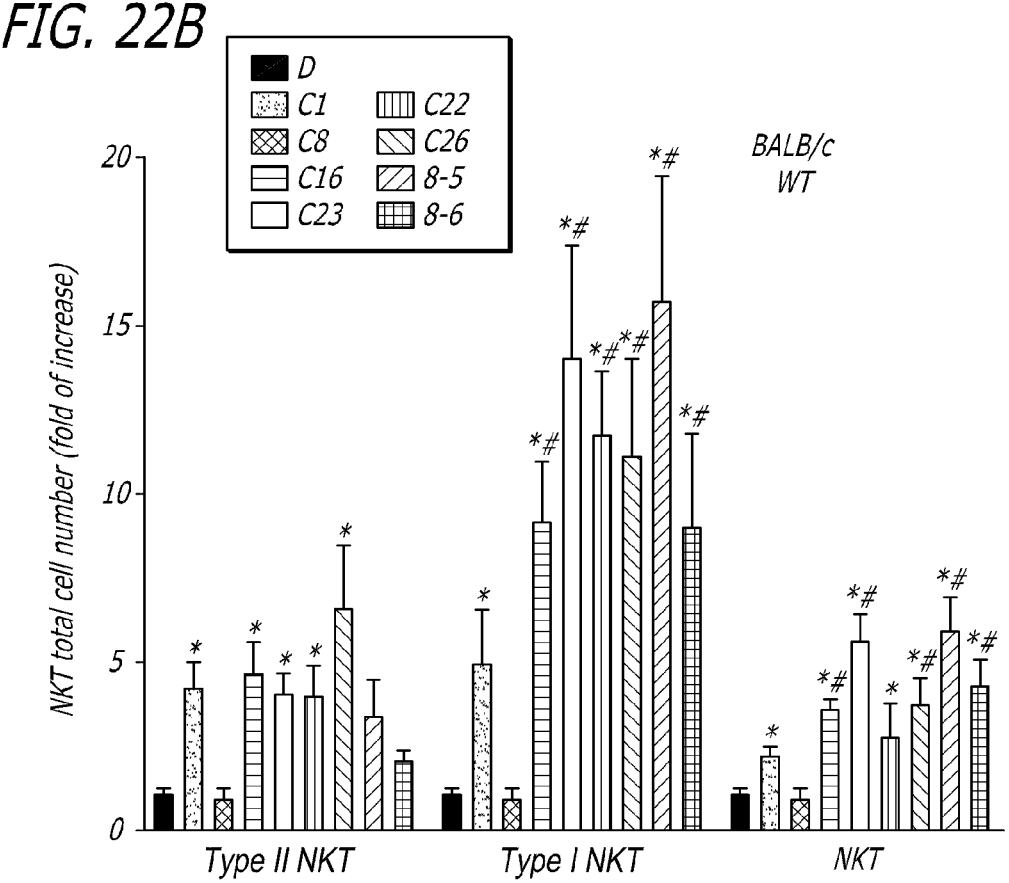
Figure 22C:
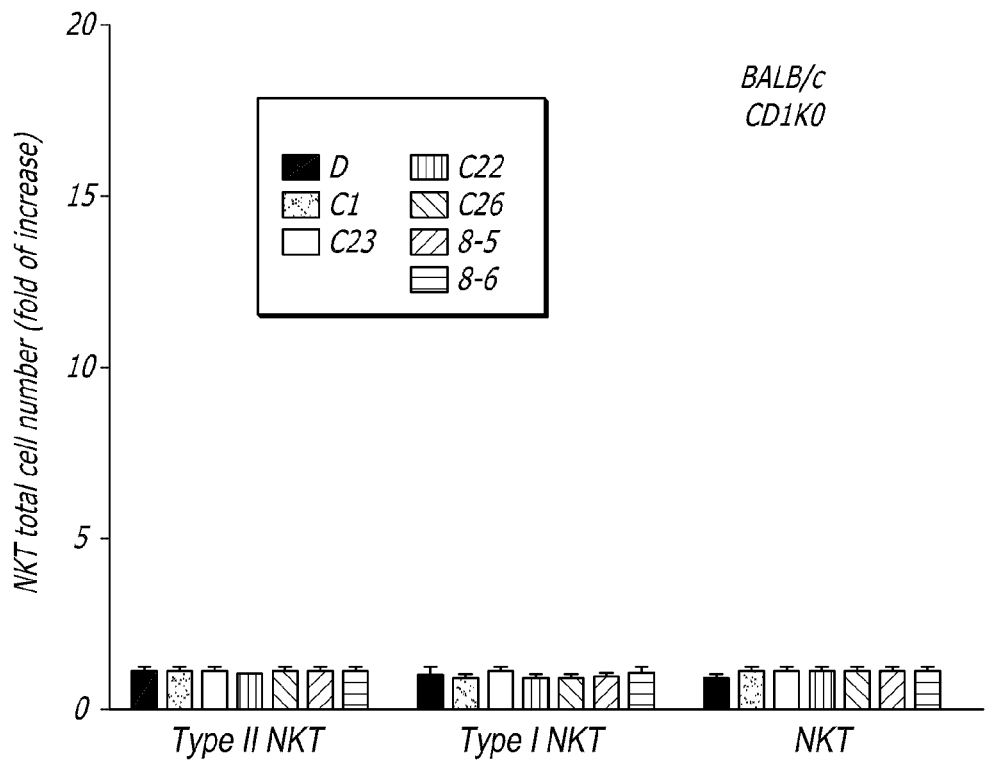
Figure 22D:
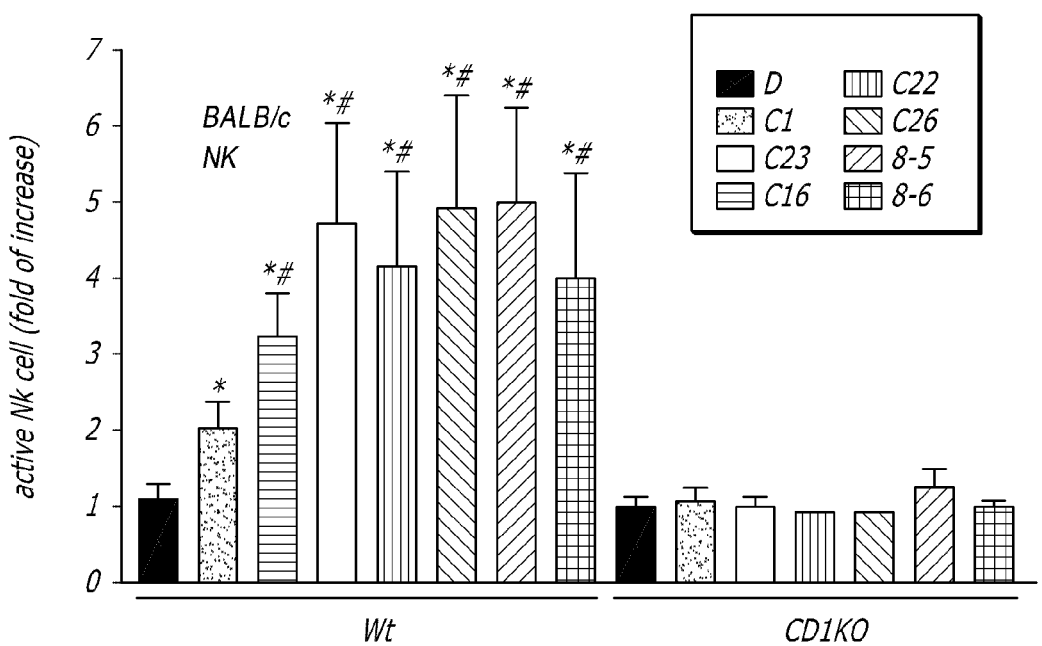

The α-GalCer analogs of the present disclosure also exhibit higher binding affinity to CD1d-restricted mouse NKT/Ts in vitro (FIG. 21) and CD1d-dependent activation of two subset NKTs and NKs in vivo (FIG. 22). As shown in FIG. 21, spleens from BALB/c mice were harvested 72 hours after intravenous (IV) injection of 0.1 μg/mouse of the indicated α-GalCer analogs (C1, 7DW8-5, C26, C8, C17) or vehicle. Percentage of mouse NKTs cells (FIG. 21A) or T cells (FIG. 21B) were stained with mCD1d tetramer loaded with α-GalCer (10 mole per μg). FIG. 21 C shows different binding affinity of α-GalCer and phenol α-GalCer analog 7DW8-5 to CD1d-restricted NKTs and T cells. FIG. 22 shows CD1-dependent expansion of two NKTs subsets. Spleens from BALB/c wild type (WT) or CD1 Knock out (KO) mice were harvested 72 h post-injection of DMSO control, α-GalCer or the indicated α-GalCer analogs C8, C16, C22, C23, C26, 7DW8-5 and 7DW8-6 IV. Total numbers of NKTs, and its two subtypes, designated as Type II NKT (CD3⁺/NK⁺/CD49⁺/CD69_) and Type I NKT (CD3⁺/NK⁺/CD49_/CD69⁺) in (B) wild type or (C) CD1 knockout mice in response to the indicated α-GalCer analogs were assessed by FACS. (D) shows CD1d-dependent activation of NKs. The expansion of total number of active NKs (CD3⁻/NK⁺/CD69⁺) in WT or CD1KO mice in response to the indicated α-GalCer analogs was assessed by FACS. *, p<0.05, compared with DMSO; #, p<0.05, compared with C1.

Figure 23A:
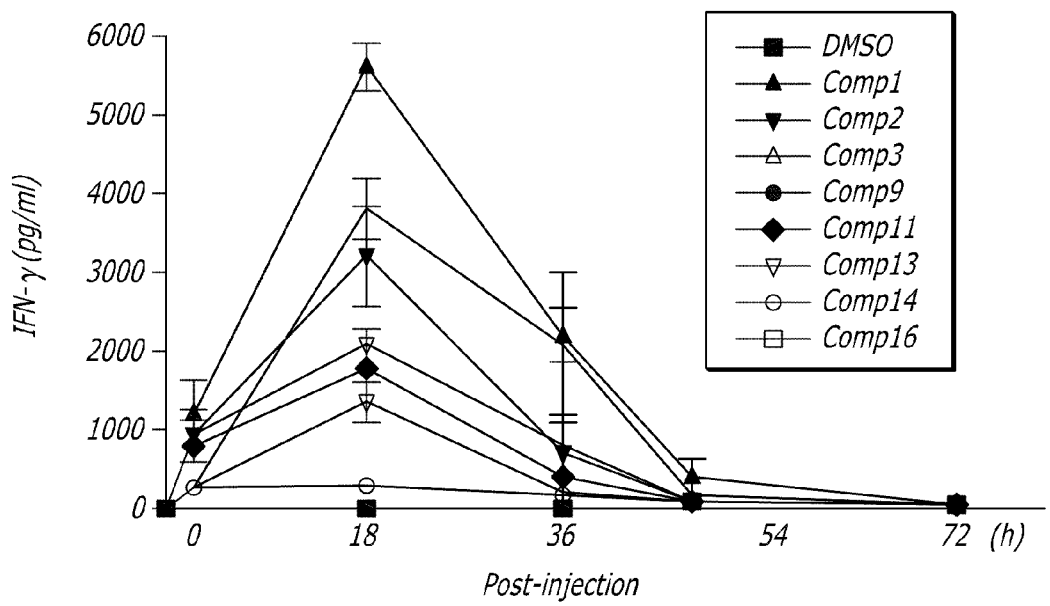
FIG. 23(A-C) show mouse serum levels (pg/ml) of various cytokines (A) IFN-γ, (B) IL-4, and (C) the ratio of IFN-γ/IL-4 after intraveneous (IV) injection with vehicle, α-GalCer or the indicated α-GalCer analogs of the present disclosure at 0, 2, 18, 36, 48, 72 h post-injection and normalized to DMSO control.
Figure 23B:
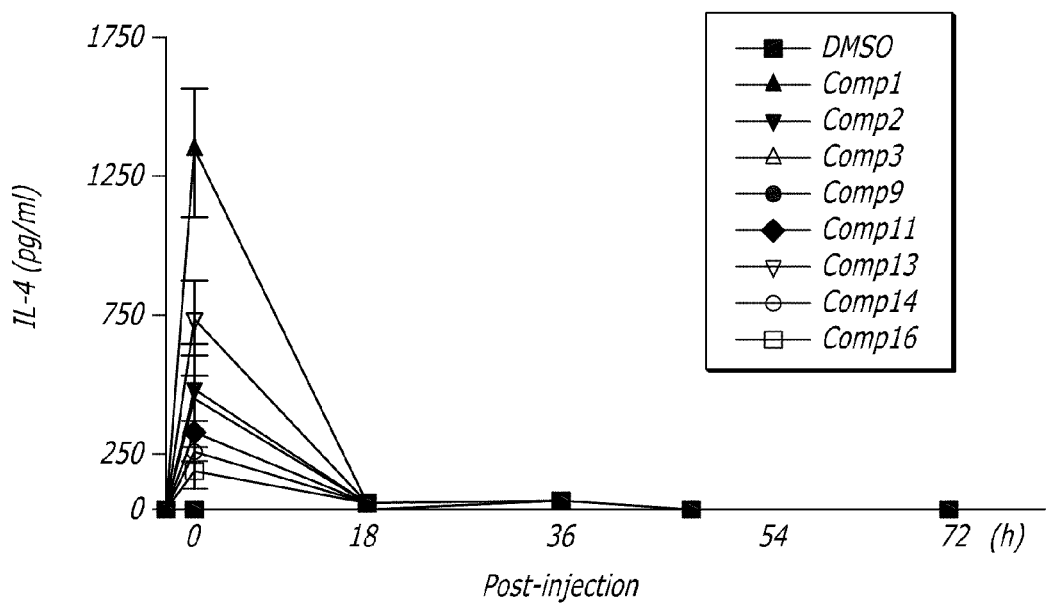
Figure 23C:
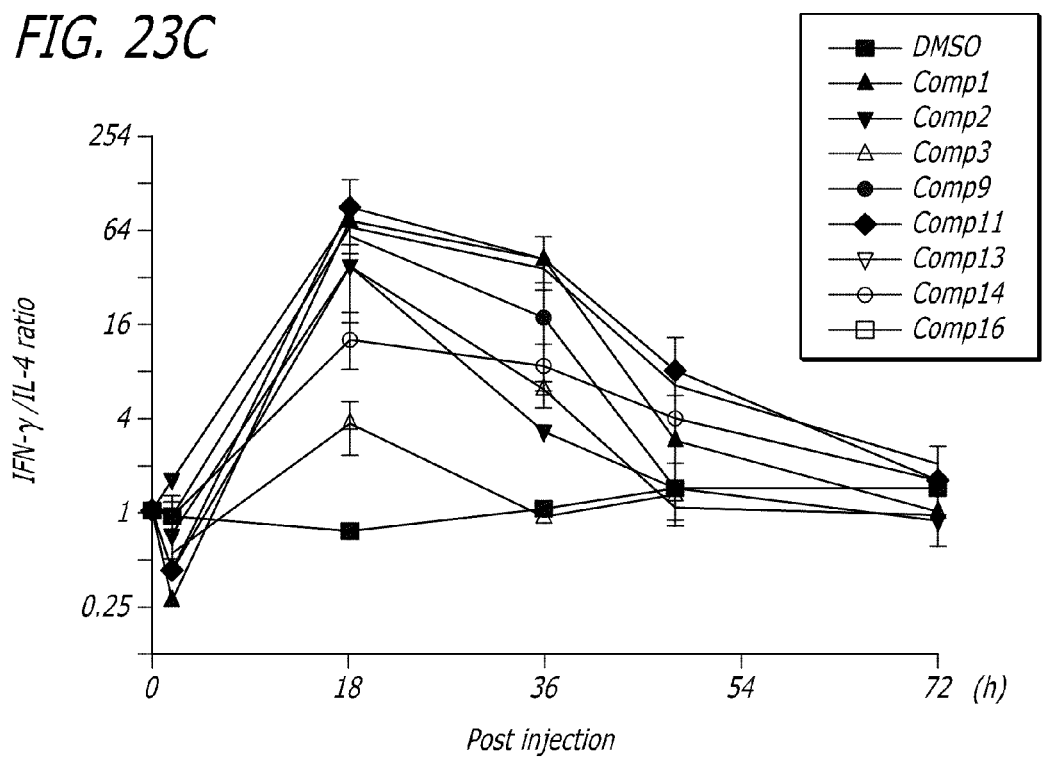
Figure 24A:
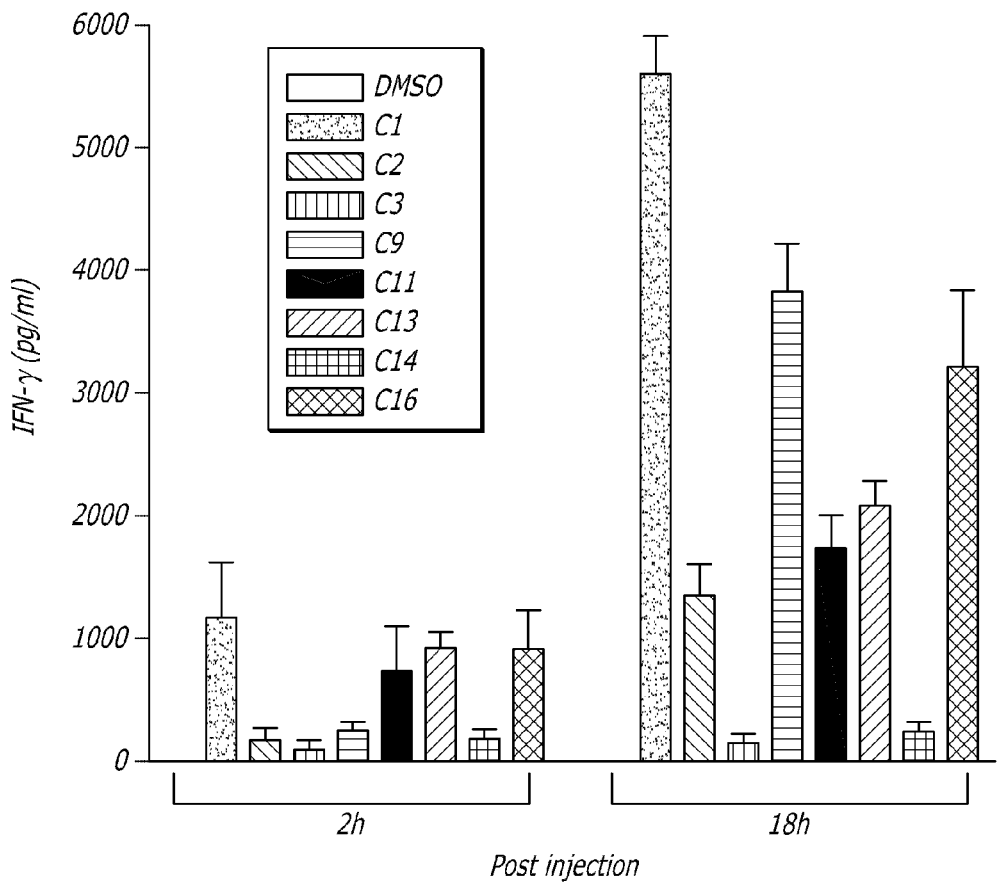
FIG. 24(A-C) show mouse serum levels (pg/ml) of various cytokines/chemokines A) IFN-γ, (B) IL-4, and (C) the ratio of IFN-γ/IL-4 at 2 and 18 h after IV injection with vehicle, α-GalCer or the indicated α-GalCer analogs of the present disclosure.
Figure 24B:
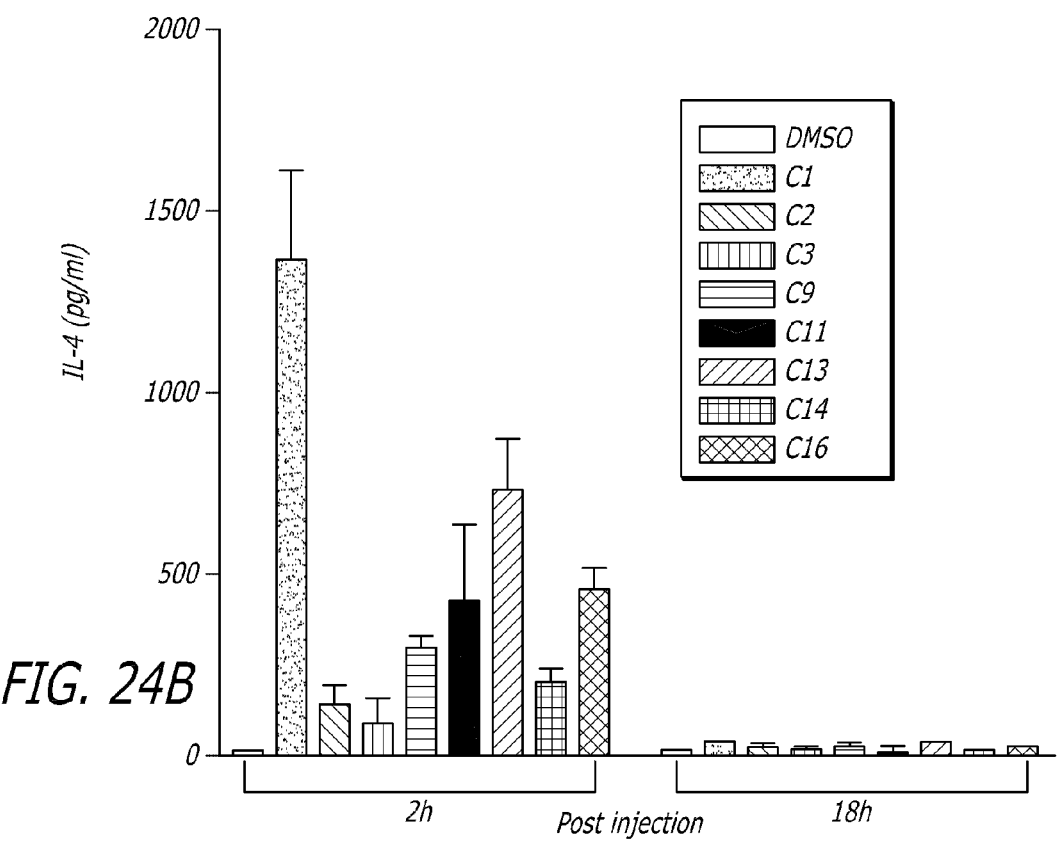
Figure 24C:
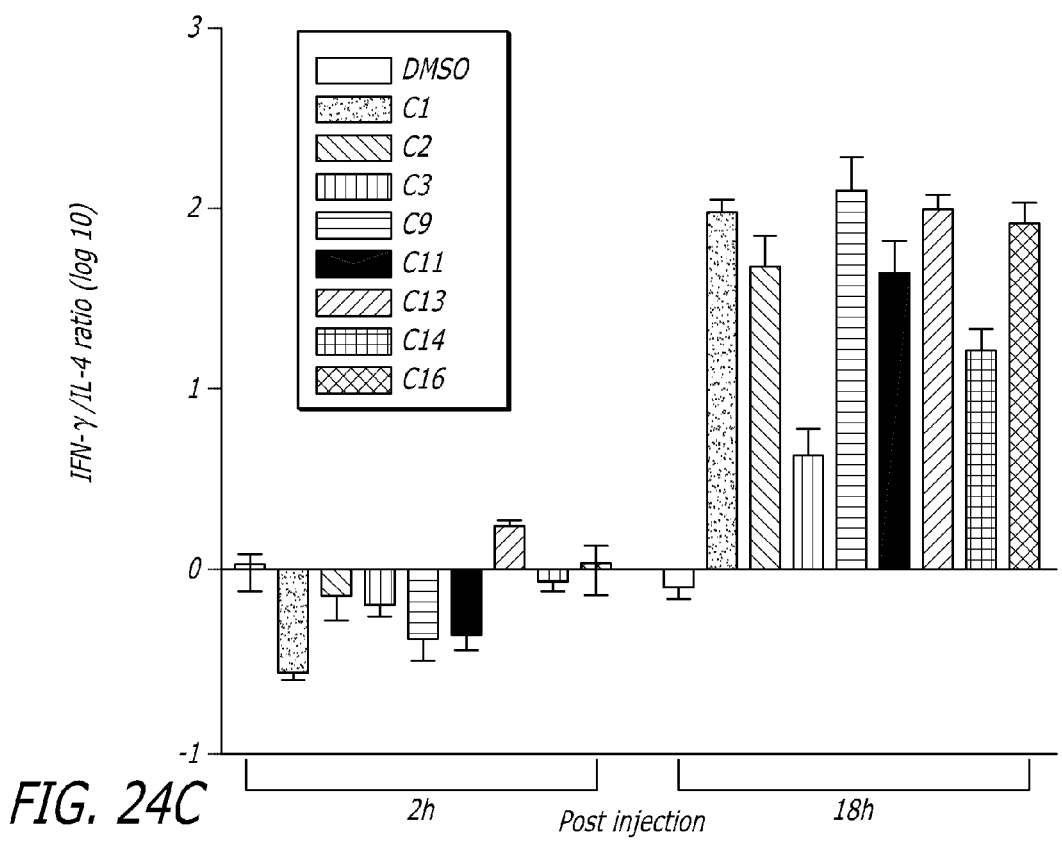
Figure 27A:
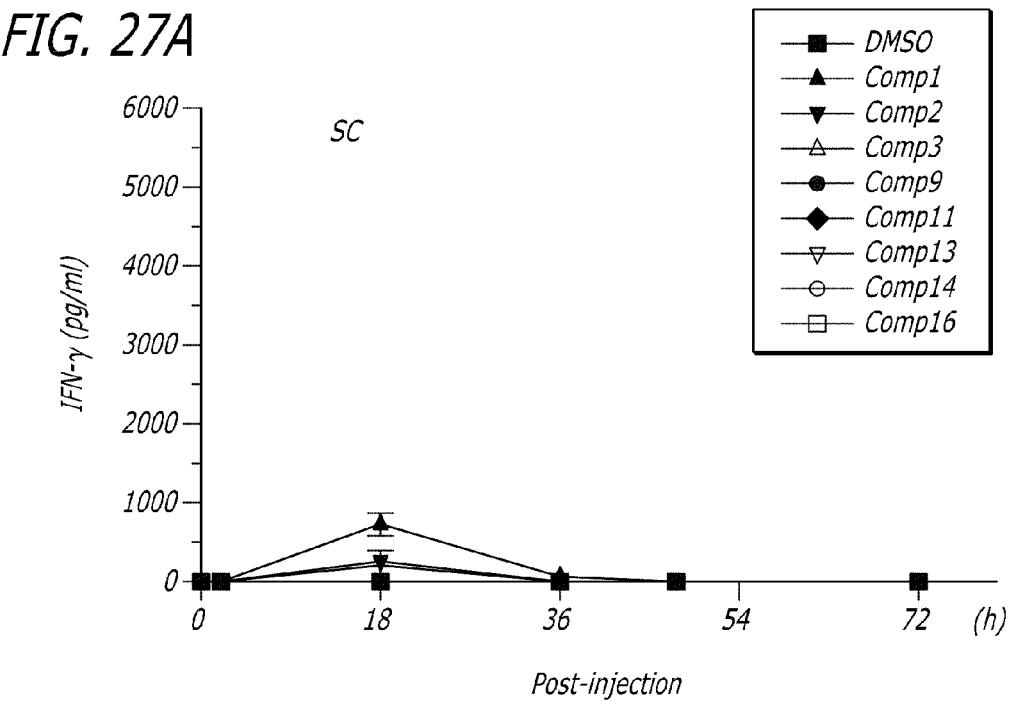
FIG. 27 (A-C) show mouse serum levels of various cytokines (A) IFN-γ, (B) IL-4, and (C) the ratio of IFN-γ/IL-4 after subcutaneous (SubQ) injection with vehicle, α-GalCer or the indicated α-GalCer analogs of the present disclosure at 0, 2, 18, 36, 48, 72 h post-injection and normalized to DMSO control.
Figure 27B:
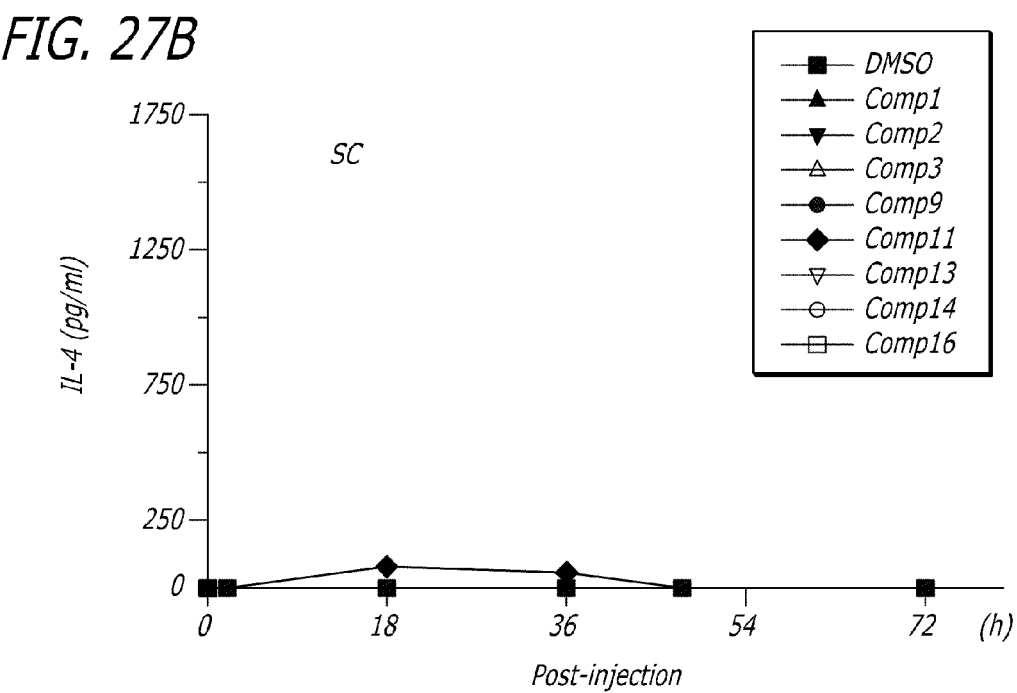
Figure 27C:
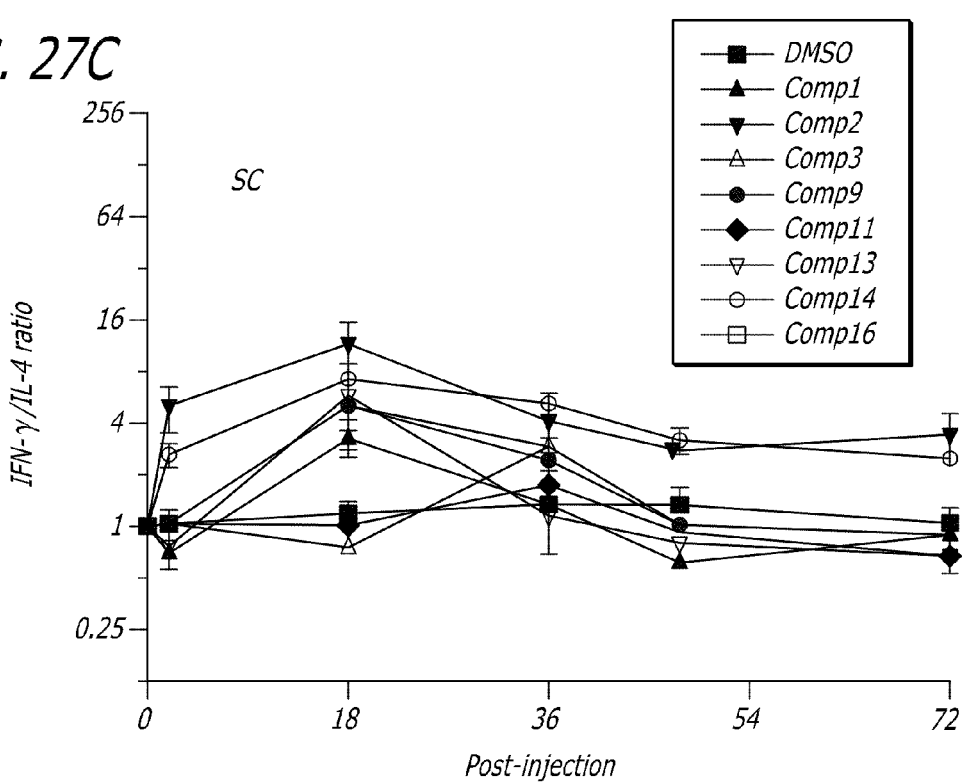
Figure 29A:
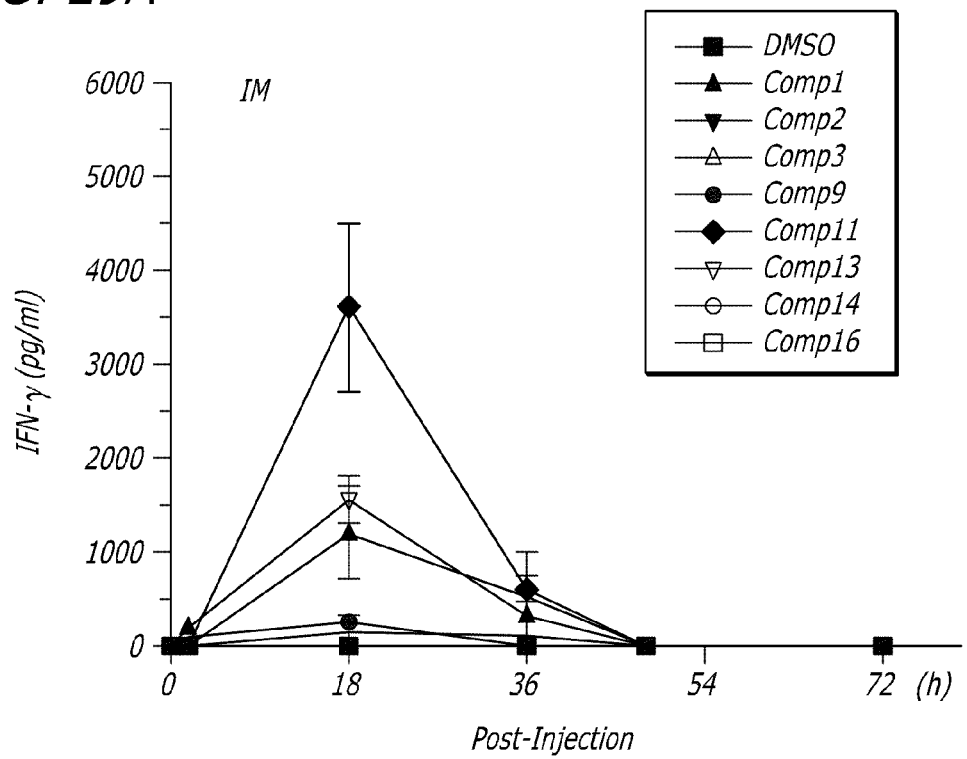
FIG. 29(A-C) show mouse serum levels of various cytokines (A) IFN-γ, (B) IL-4, and (C) the ratio of IFN-γ/IL-4 after intramuscular (IM) injection with vehicle, α-GalCer or the indicated α-GalCer analogs of the present disclosure at 0, 2, 18, 36, 48, 72 h post-injection and normalized to DMSO control.
Figure 29B:
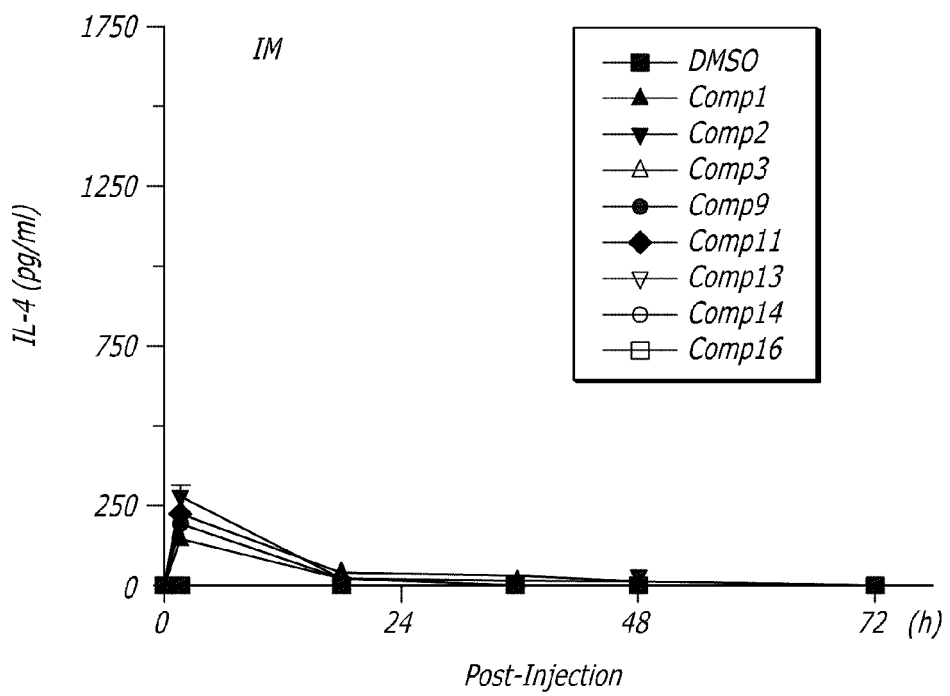
Figure 29C:
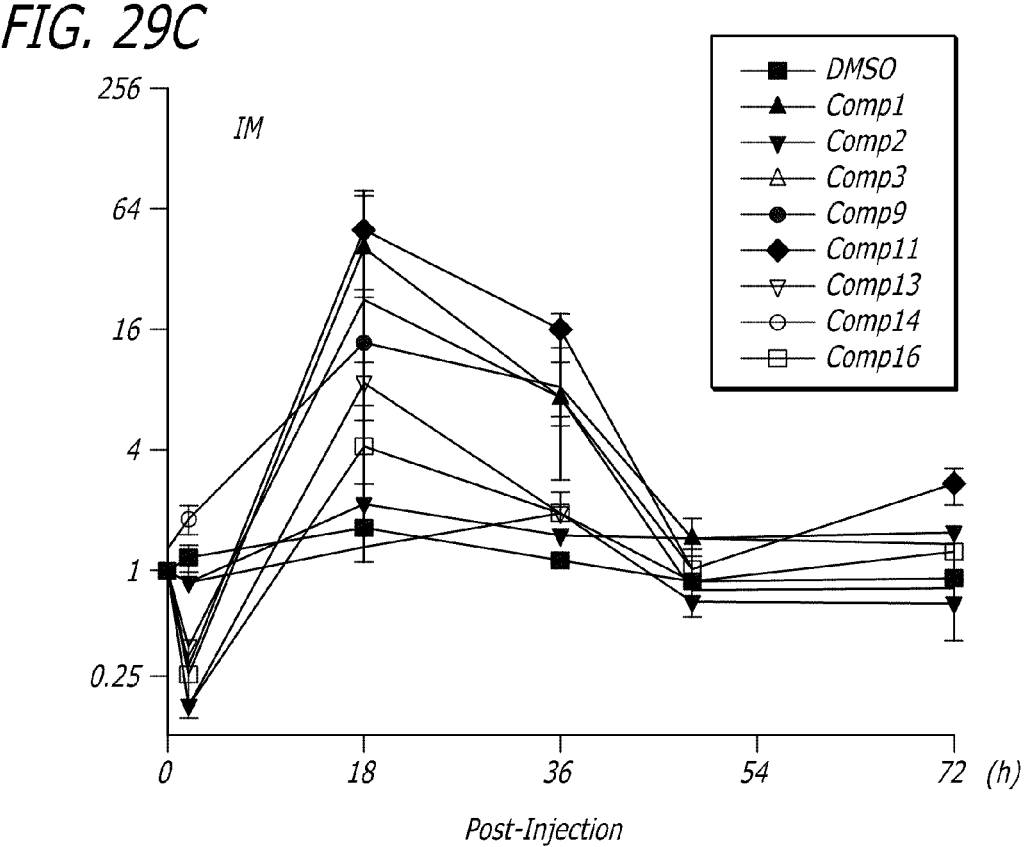

In Vivo $T_H$ Cell Activation, Expansion/Activation of Splenocytes and CD1d-Dependent TCR Activation of NKTs Using α-GalCer Analogs In still another aspect, the α-GalCer analogs of the present disclosure are capable of activating $T_H$ cells in vivo. To evaluate the impact of administration route on cytokine secretion, α-GalCer and seven α-GalCer analogs of the present disclosure were injected into BALB/c mice by either intravenous (IV), subcutaneous (SubQ) or intramuscular (IM) routes and the impact on cytokine production was determined. FIGS. 23A, 27A and 29A show the serum level of IFN-γ over a period of 72 hours after injection of various α-GalCer analogs through different routes. In general, an increase in cytokine production was detectable as early as 2 hours, peaked at 18 hours and gradually dropped down to the baseline level by 48 hours. When introduced through the IV route (FIG. 23A), the α-GalCer analog C9 and the α-GalCer analog C16 showed a level of activity close to that of C1, followed by the α-GalCer analogs C13, C11, C2, C14 and C3. Notably, the level of IFN-γ induced by SubQ administration (FIG. 27A) of the same α-GalCer analogs was much lower than that of the IV route, whereas the level of IM route (FIG. 29A) was intermediate. Although C1 induced the highest level of IFN-γ when given IV, the α-GalCer analog C9 surpassed C1 when given by SubQ and IM routes. FIGS. 23B, 27B, and 29B, show the levels of IL-4 after injections of the α-GalCer analogs through the different routes. All the α-GalCer analogs tested, as well as α-GalCer, showed little induction of IL-4 when introduced through the SubQ route, whereas intermediate levels of IL-4 were induced by all α-GalCer analogs when given by IM administration. When the data are expressed as IFN-γ/IL-4 ratio (FIGS. 23C, 27C and 29C) to reflect the $T_H1/T_H2$ bias, the aromatic α-GalCer analogs C1, C13, C16 and C14 of bacterial origin elicited less $T_H2$ responses than C1 at 2 hours via the IV route, and all α-GalCer analogs induced $T_H1$ bias responses during the period of 18-72 hours, as shown in FIGS. 23C, 27C and 29C. Furthermore, when administered by the SubQ route, all the tested α-GalCer analogs of the present disclosure showed a higher $T_H1/T_H2$ ratio than C1 during the entire period of 2-72 hours except α-GalCer analogs C2 and C3. On the other hand, when given by IM injection, all the α-GalCer analogs of the present disclosure showed a $T_H2$ biased response at 2 hours and again shifted to a more $T_H1$ biased response during the period of 18-72 hours except for C14. The latter showed a more $T_H1$ biased response at 2 hours and remaining $T_H1$ bias during the entire period of 2-72 hours. In another view, FIG. 24 shows mouse serum levels of secreted (A) IFN-γ, (B) IL-4 and (C) ratio of IFN-γ/IL-4 at 2 and 18 h following IV administration of indicated α-GalCer analogs.

Along with IFN-γ and IL-4, other cytokines and chemokines also increased significantly in sera in response to these novel α-GalCer analogs. These included IL-2, IL-6, KC, IL-10, IL-12, IL-13, GM-CSF, TNFα, RANTES, MCP-1, and MIP-1, which are listed in the Table in FIG. 25. In IV administration, these novel α-GalCer analogs elicit a greater $T_H1$ biased cytokine and chemokine response than C1. For example, aromatic α-GalCer analogs C11, C13 and C16 induce striking rises in IL-2, IL-12, MIP-1 and MCP-1, and C14 showed greater inductions of IL-3, GM-CSF and IL-12.

Figure 26A:
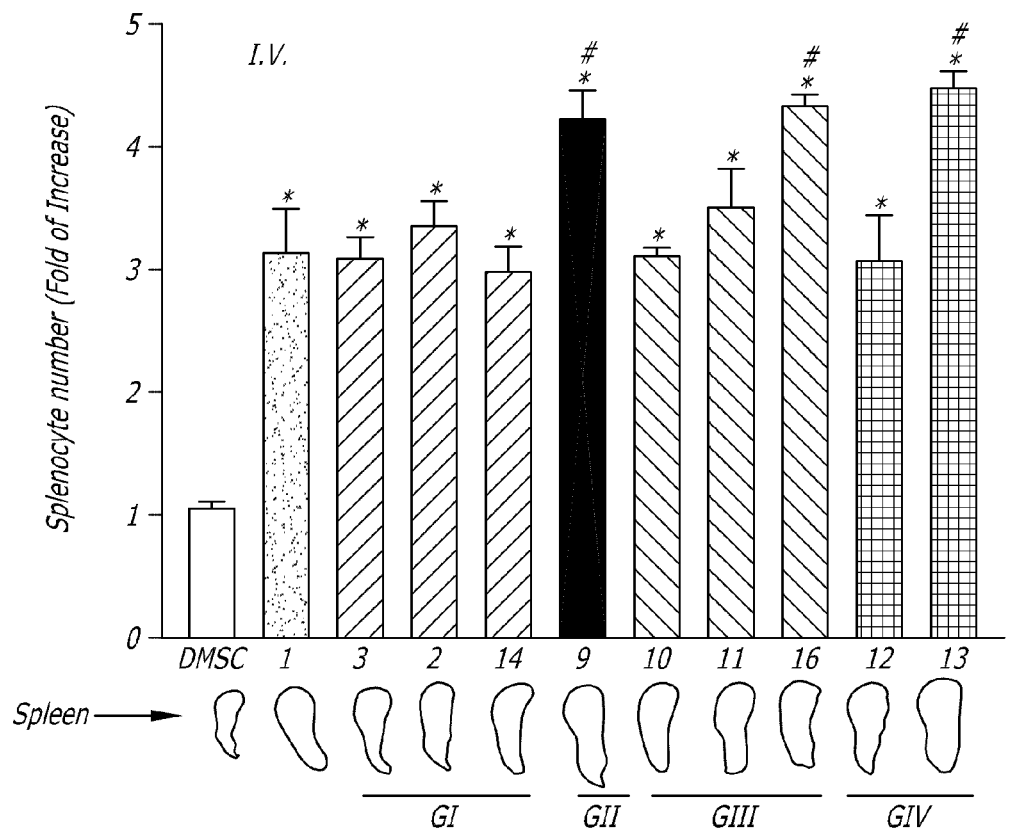
FIG. 26(A-H) show (A) the total number of nucleated cells and the spleen size, (B) the population of innate immune cells, including mature dendritic cells, (C) activated NKs, (D) activated NKTs, (E) active B cells, (F) active CD8$^+$ T cells, (G) active CD4$^+$ T cells and (H) the ratio of CD8$^+$/CD4$^+$ T cells, all normalized with DMSO, in response to the IV injection of vehicle, α-GalCer or the α-GalCer analogs from FIG. 23.
Figure 26B:
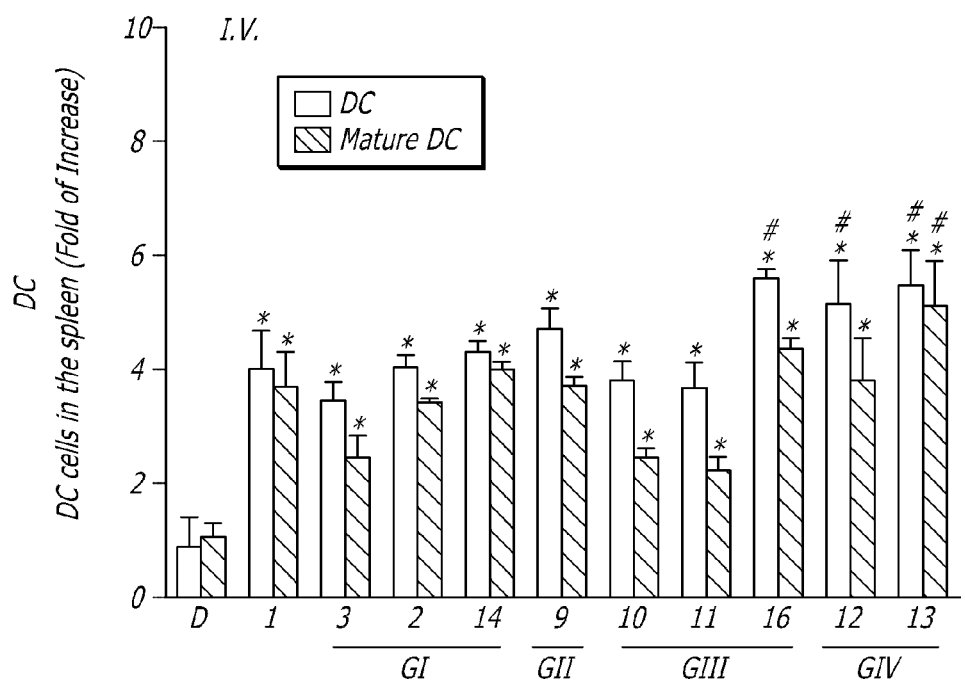
Figure 26C:
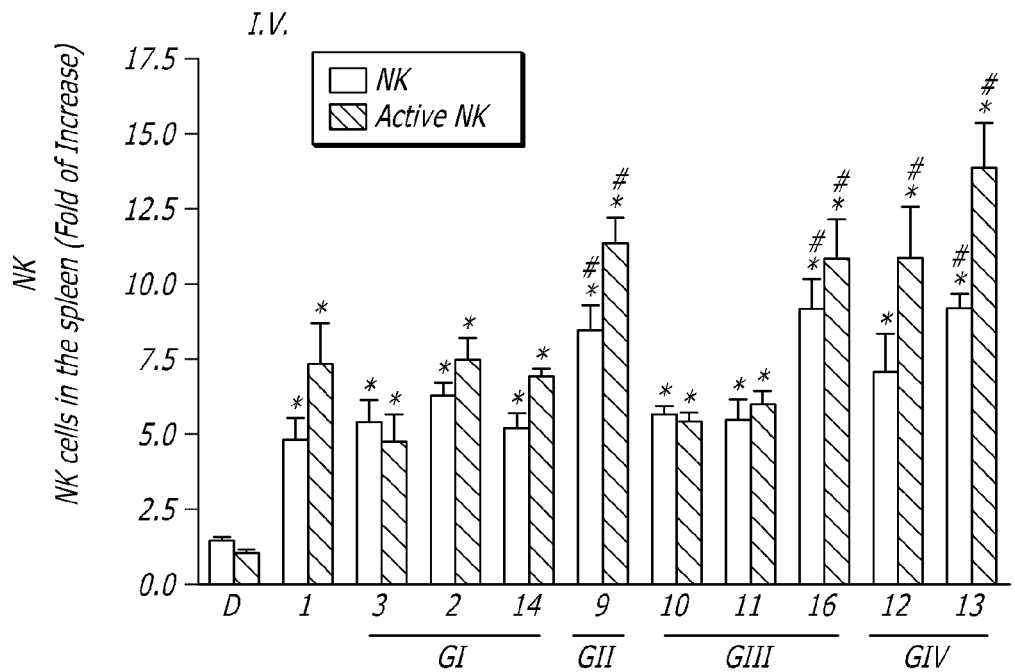
Figure 26D:
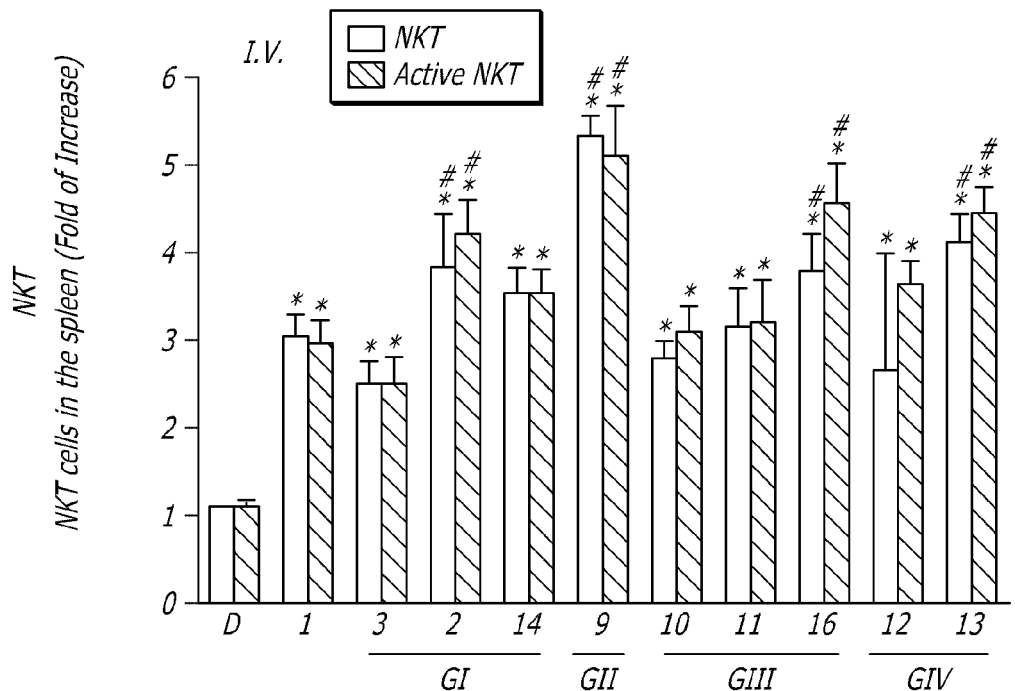
Figure 26E:
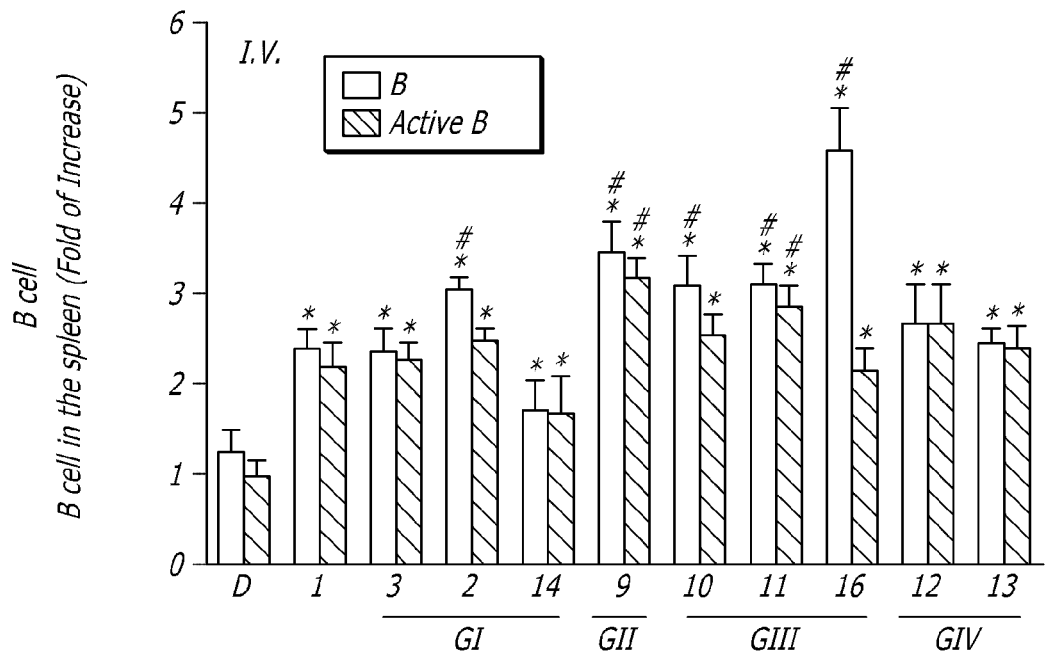
Figure 26F:
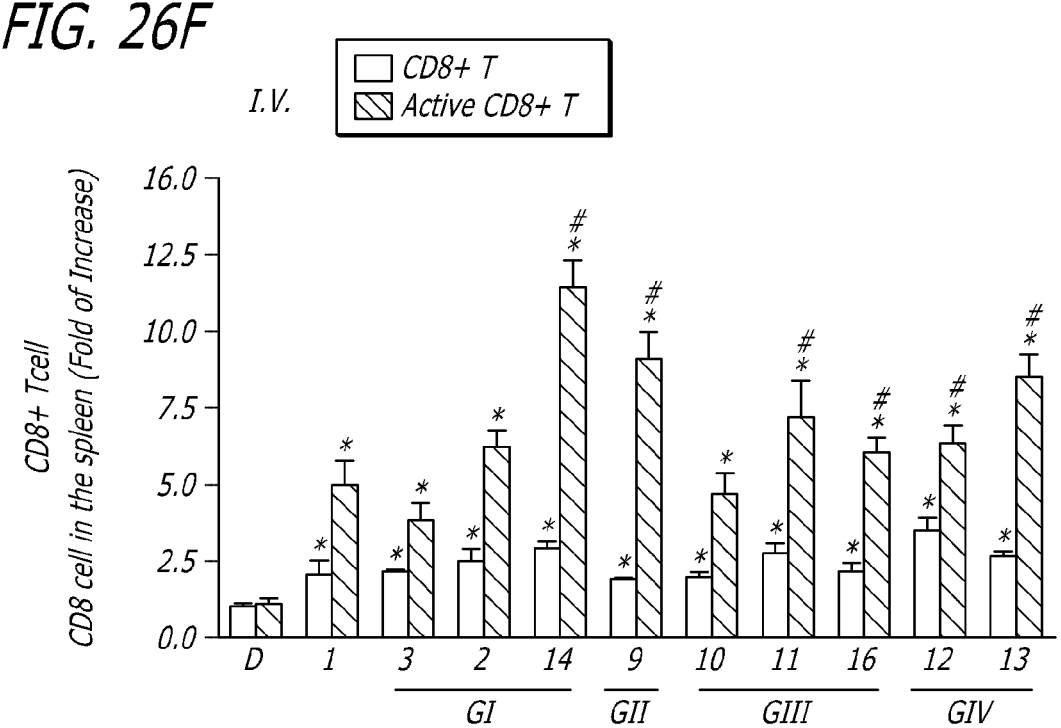
Figure 28A:
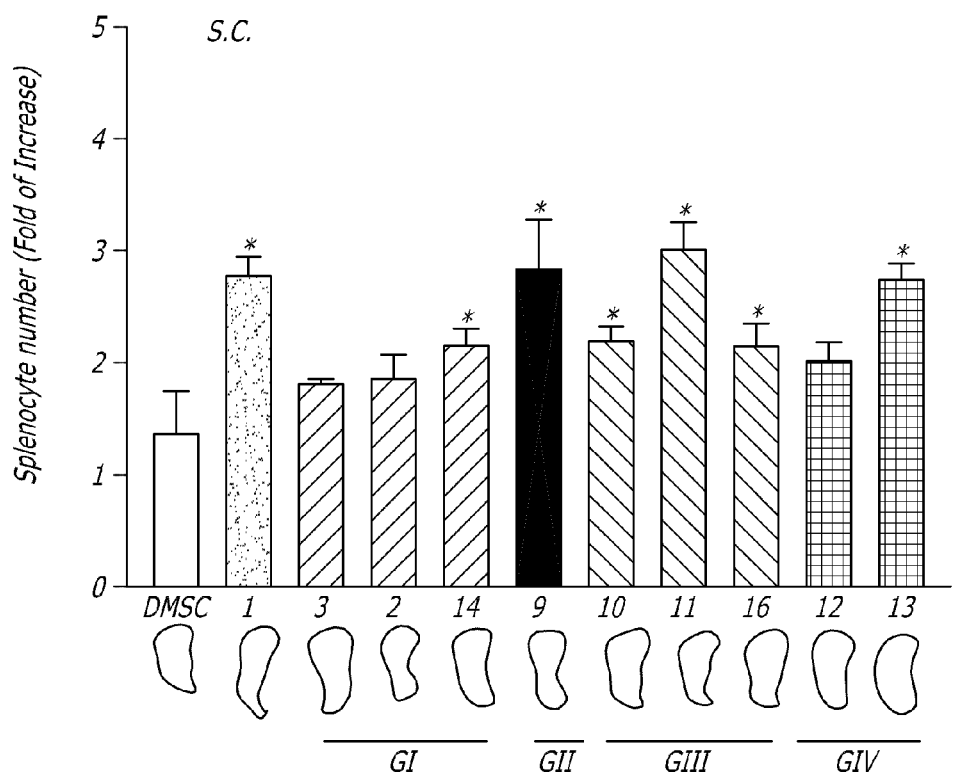
FIG. 28(A-H) show (A) the total number of nucleated cells and the spleen size, (B) the population of innate immune cells, including mature dendritic cells, (C) activated NKs, (D) activated NKTs, (E) active B cells, (F) active CD8$^+$ T cells, (G) active CD4$^+$ T cells and (H) the ratio of CD8$^+$/CD4$^+$ T cells, all normalized with DMSO, in response to the SubQ injection of vehicle, α-GalCer or the α-GalCer analogs from FIG. 27.
Figure 28B:
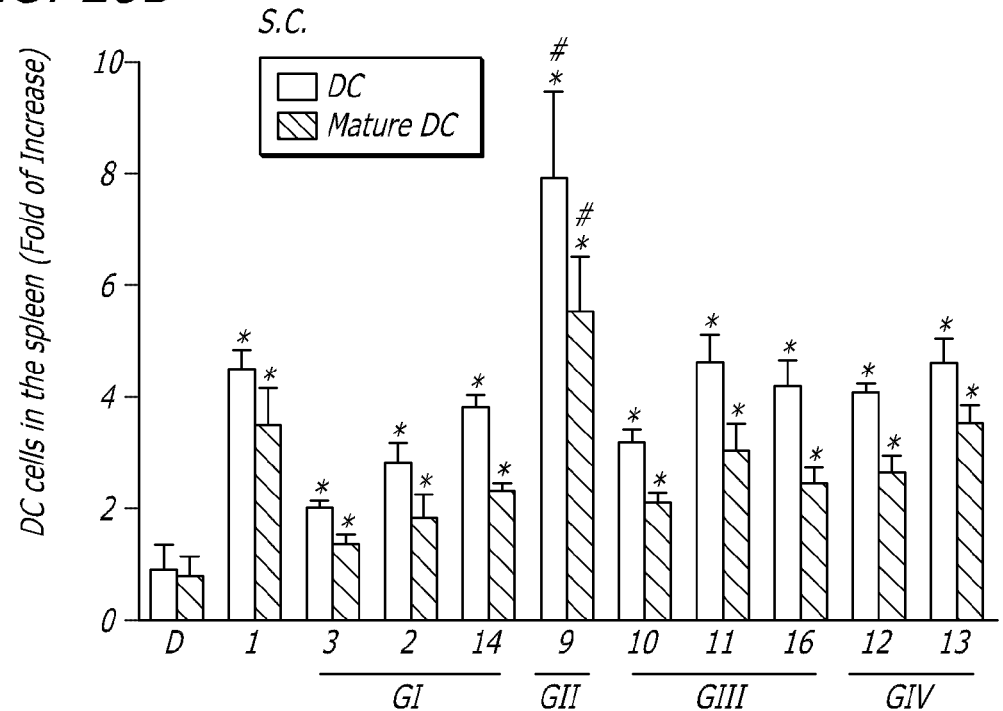
Figure 28C:
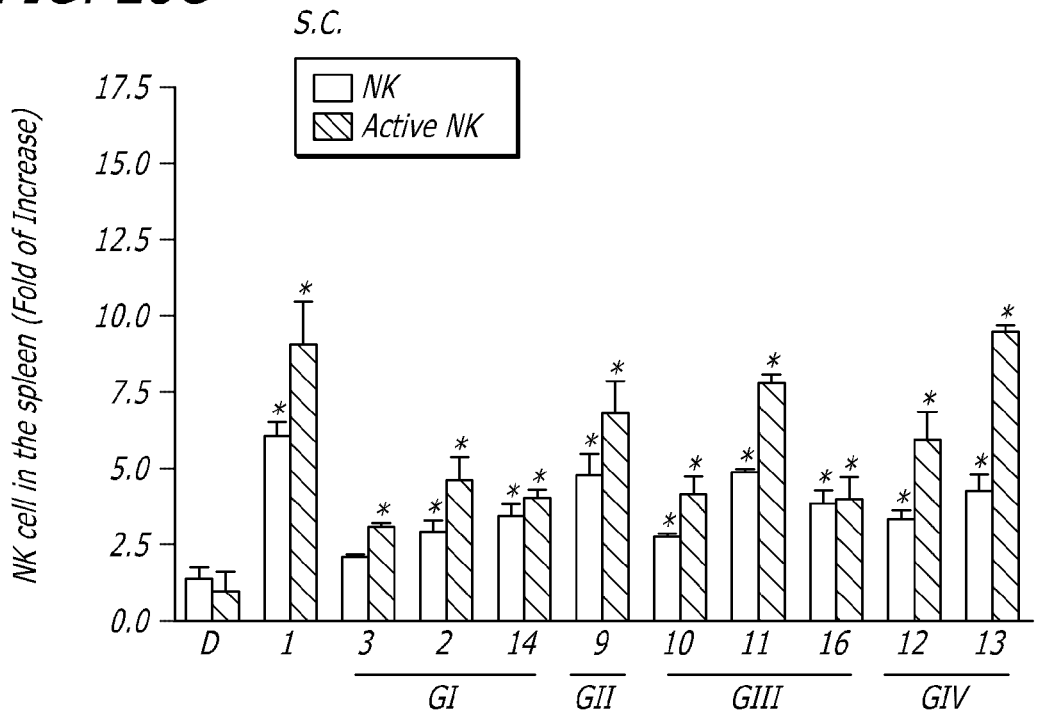
Figure 28D:
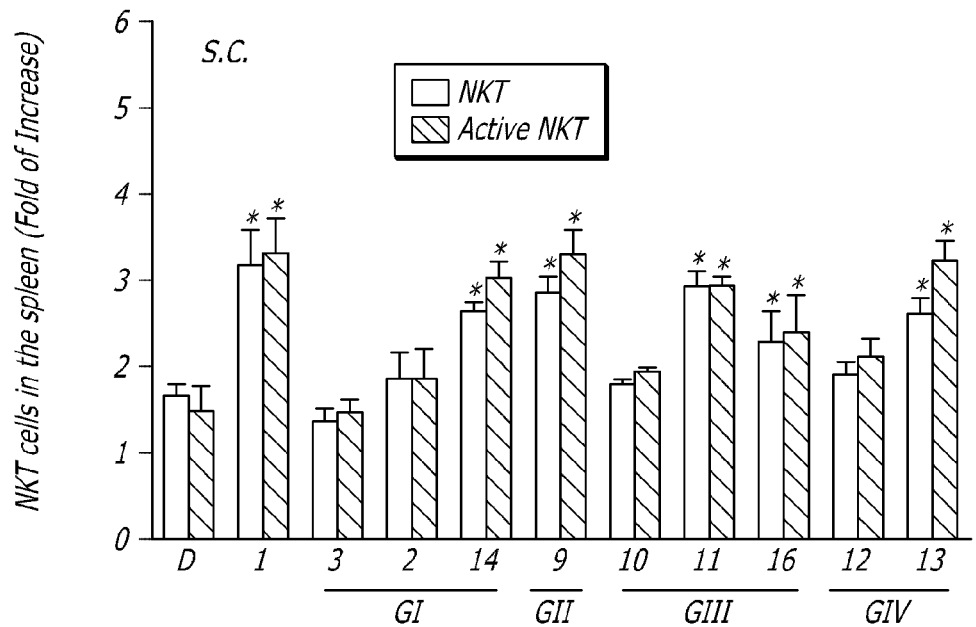
Figure 28E:
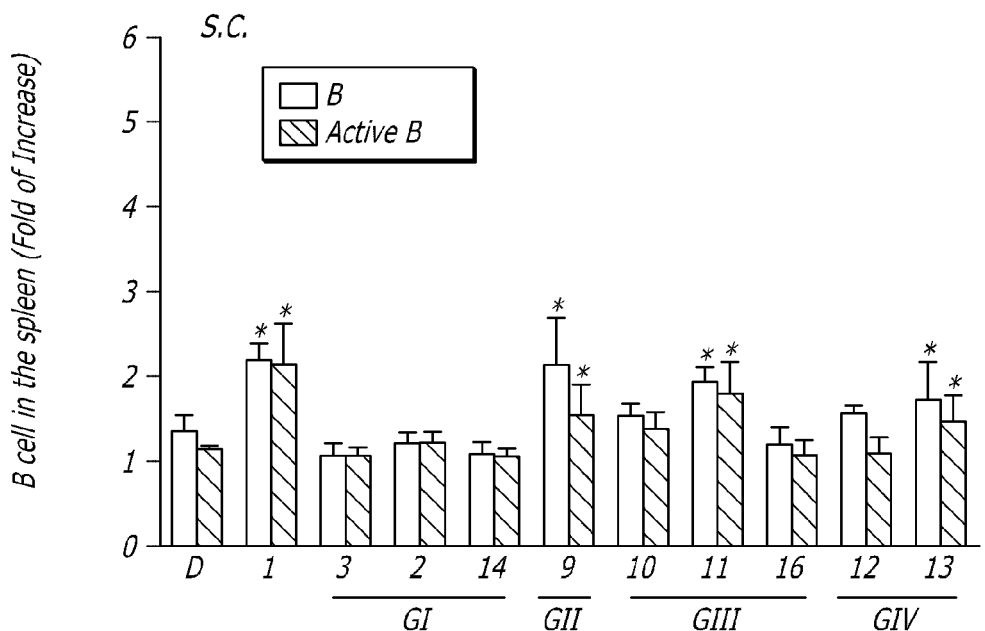
Figure 28F:
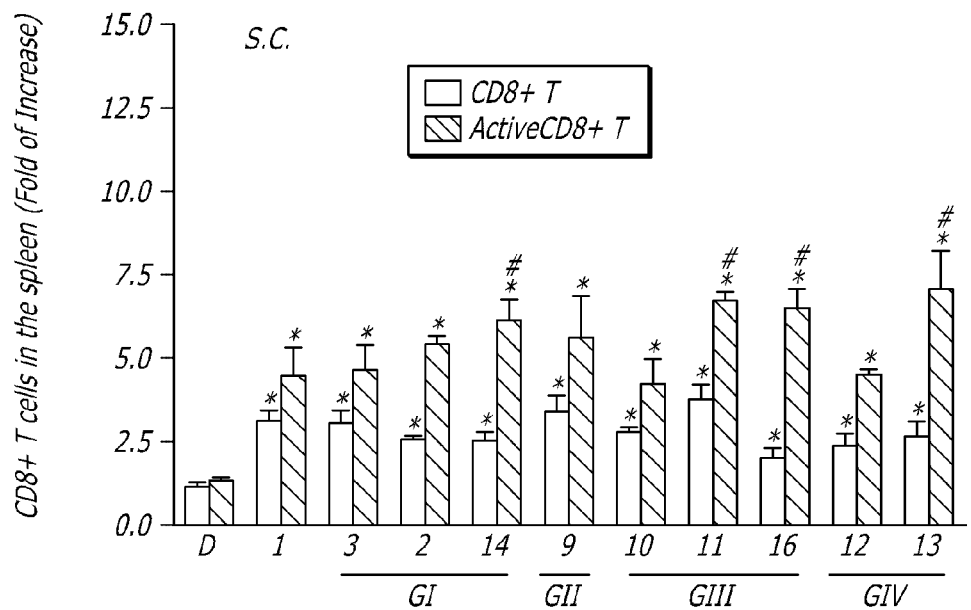
Figure 28G:
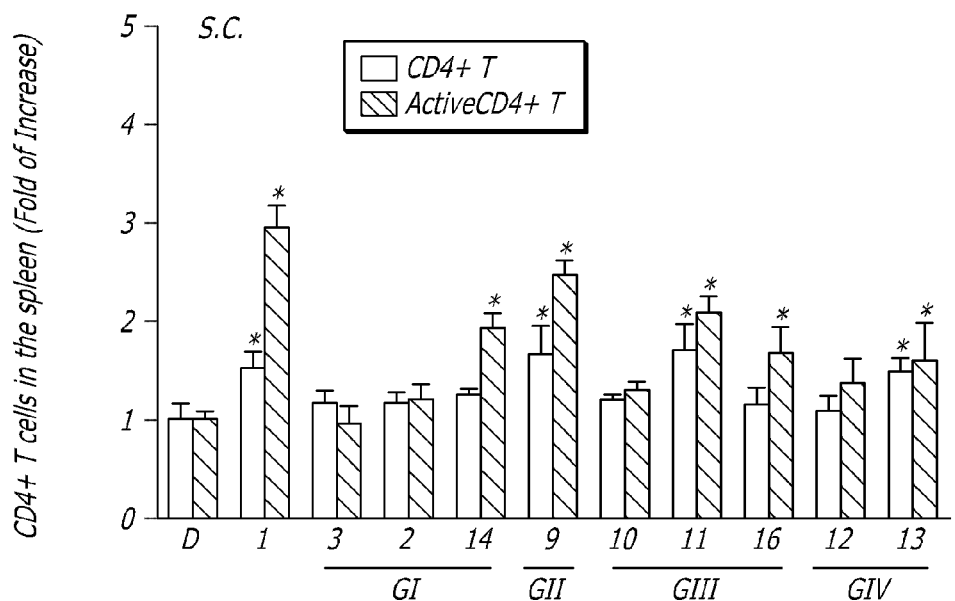
Figure 28H:
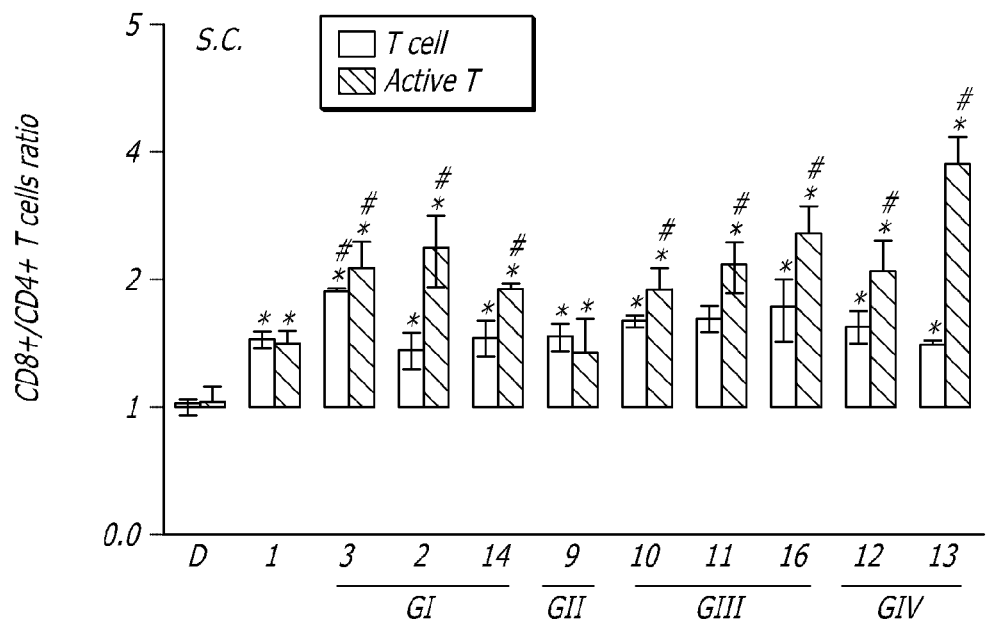
Figure 30A:
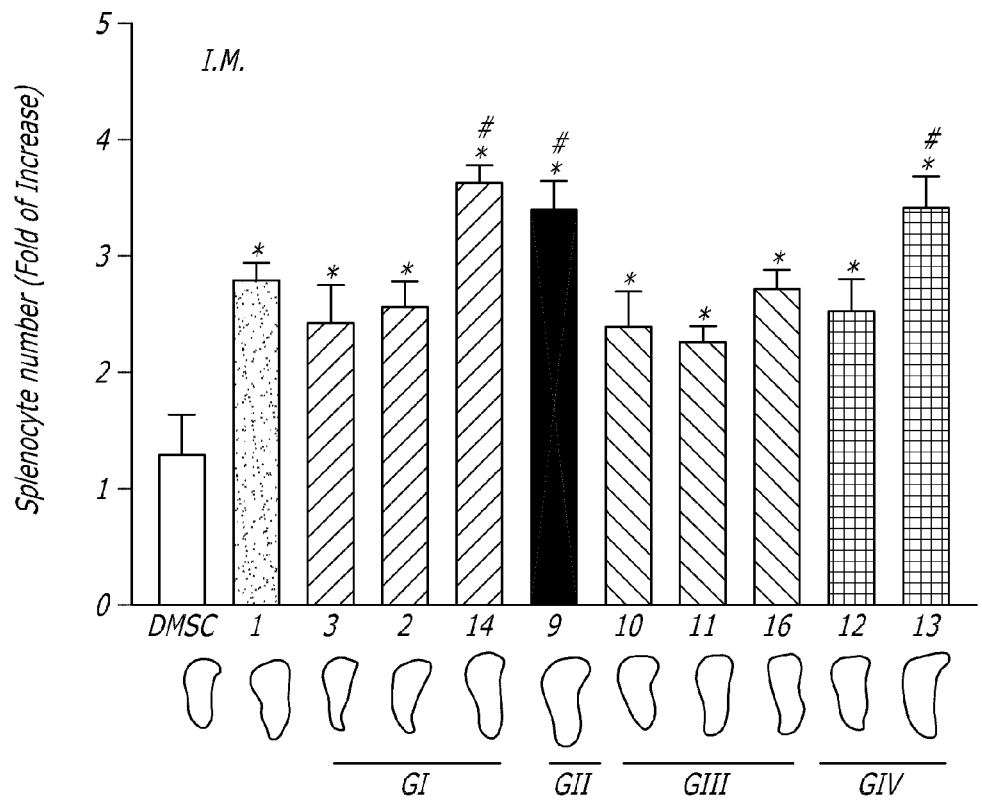
FIG. 30(A-H) show (A) the total number of nucleated cells and the spleen size, (B) the population of innate immune cells, including mature dendritic cells, (C) activated NKs, (D) activated NKTs, (E) active B cells, (F) active CD8$^+$ T cells, (G) active CD4$^+$ T cells and (H) the ratio of CD8$^+$/CD4$^+$ T cells, all normalized with DMSO, in response to the IM injection of vehicle, α-GalCer or the α-GalCer analogs from FIG. 29.
Figure 30B:
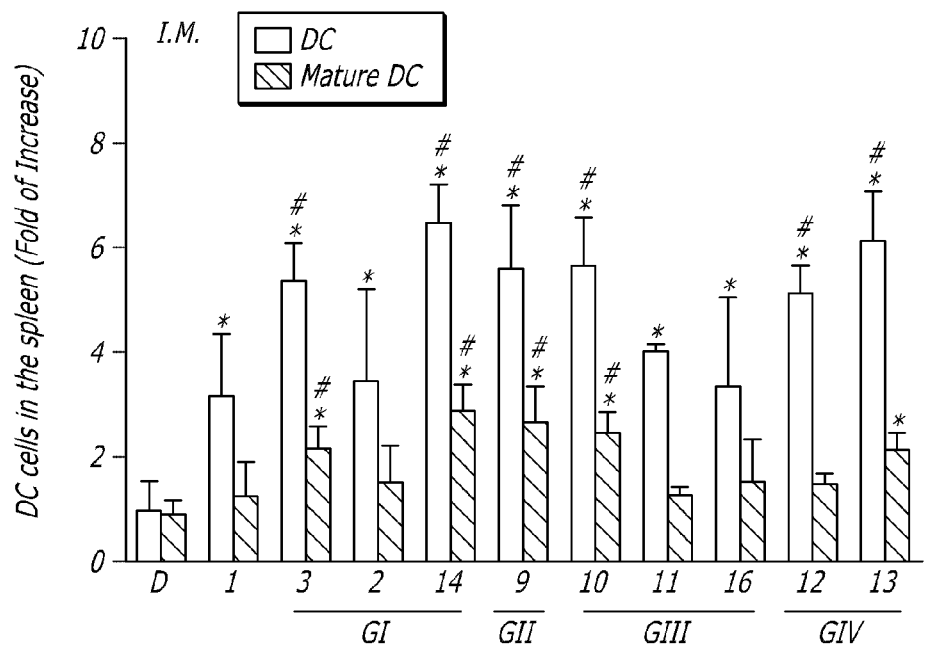
Figure 30C:
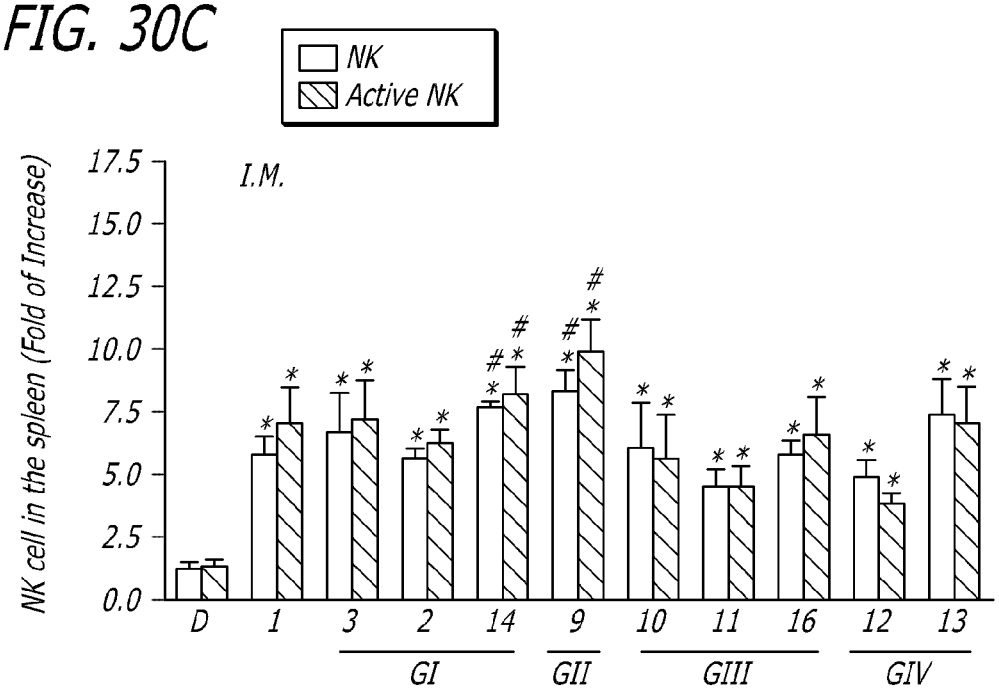
Figure 30D:
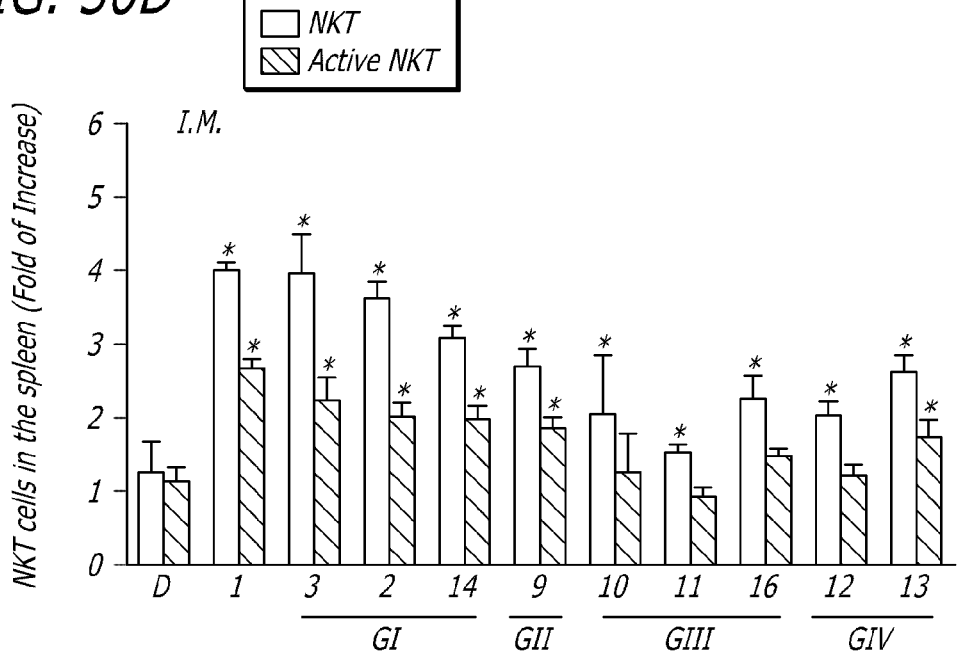
Figure 30G:
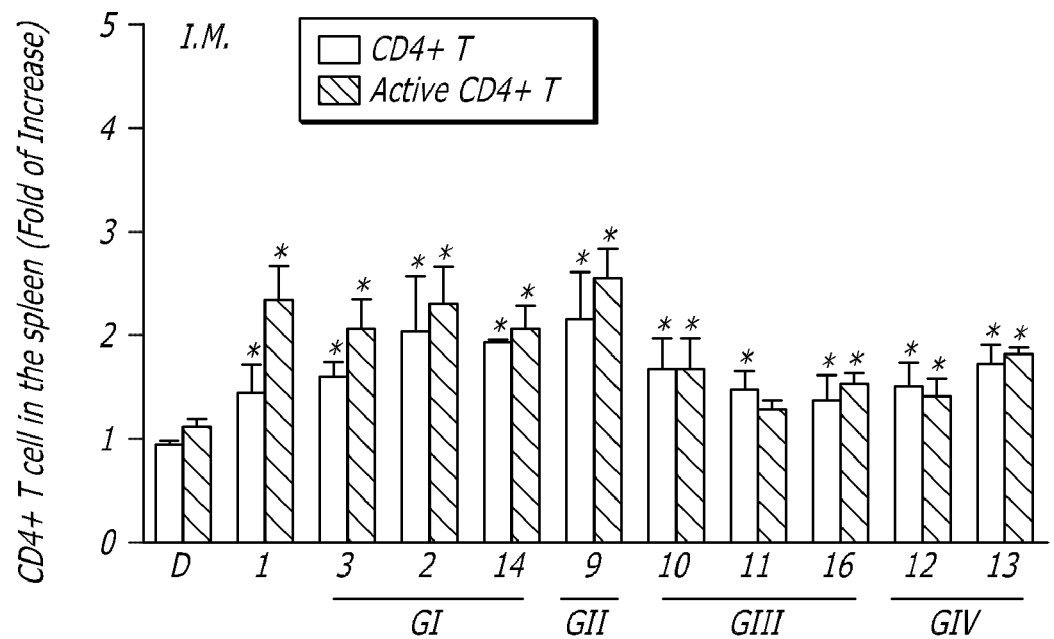
Figure 30H:
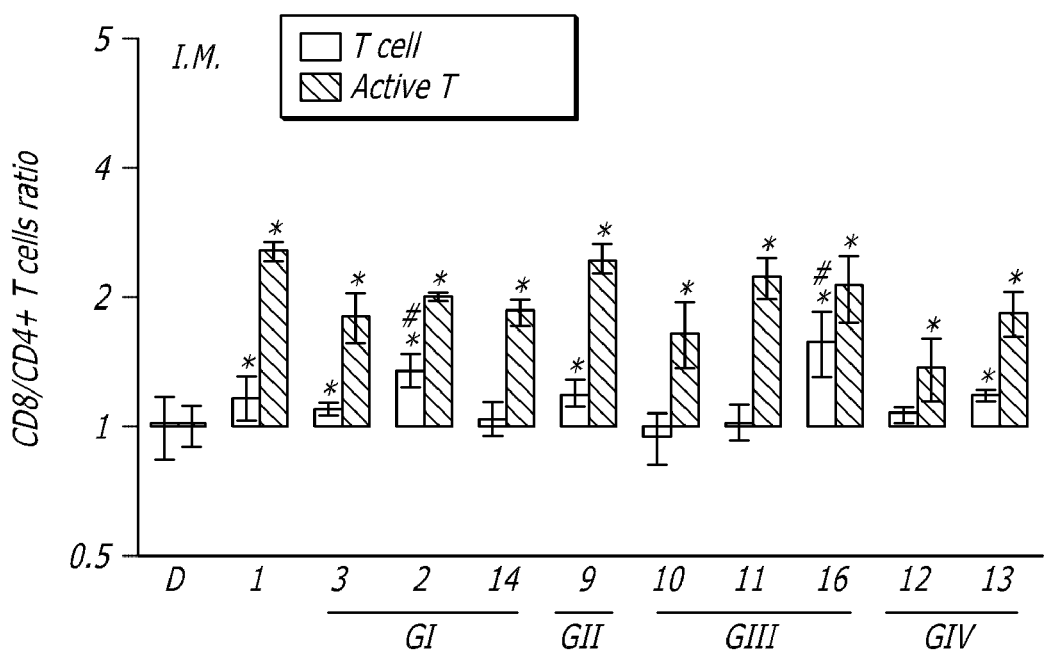
Figure 31A:
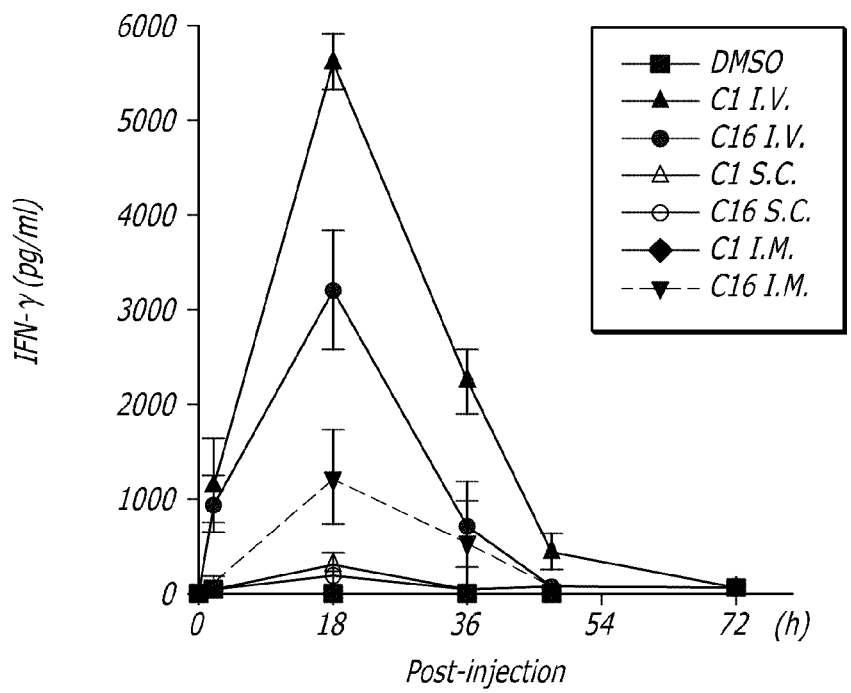
FIG. 31(A-K) show the effects of route of administration (IV, SubQ or IM) of vehicle, α-GalCer or the indicated α-GalCer analogs of the present disclosure on cytokine kinetics and splenocytes expansion/activation. (A) shows mouse serum levels (pg/ml) of IFN-γ. (B) shows mouse serum levels (pg/ml) of IL-4. (C) shows the ratio of IFN-γ/IL-4 (log 10). (D) shows the total number of mouse nucleated cells (splenocytes). (E) shows the population of innate immune cells, including mature dendritic cells in the spleen. (F) shows the population of activated NKs in the spleen. (G) shows the population of activated NKTs in the spleen. (H) shows the population of active B cells in the spleen. (I) shows the population of active CD8$^+$ T cells in the spleen. (J) shows the population of active CD4$^+$ T cells in the spleen. (K) shows the ratio of CD8$^+$/CD4$^+$ T cells. All analysis was performed by normalizing to vehicle.
Figure 31B:
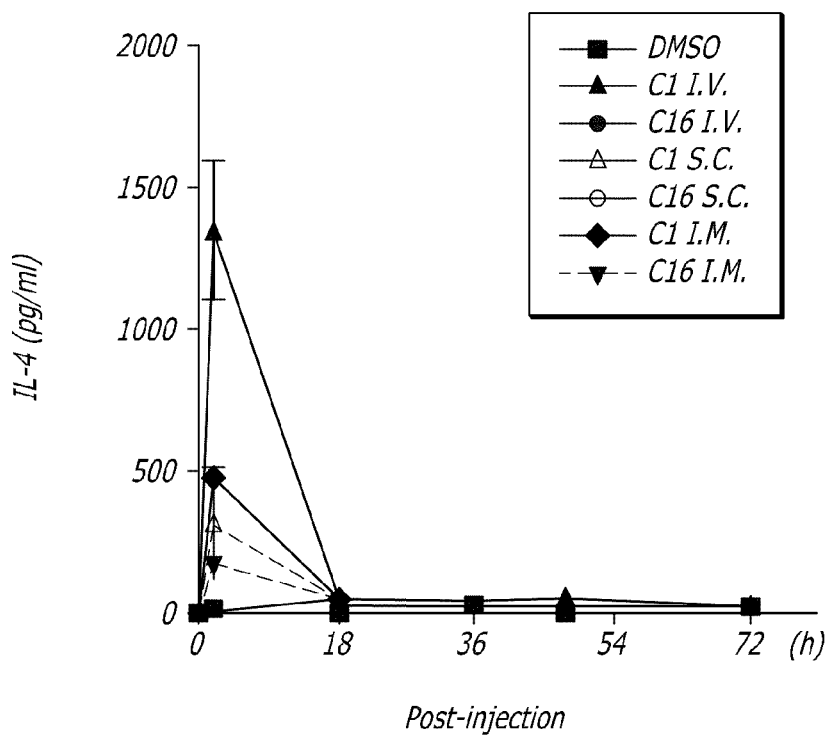
Figure 31C:
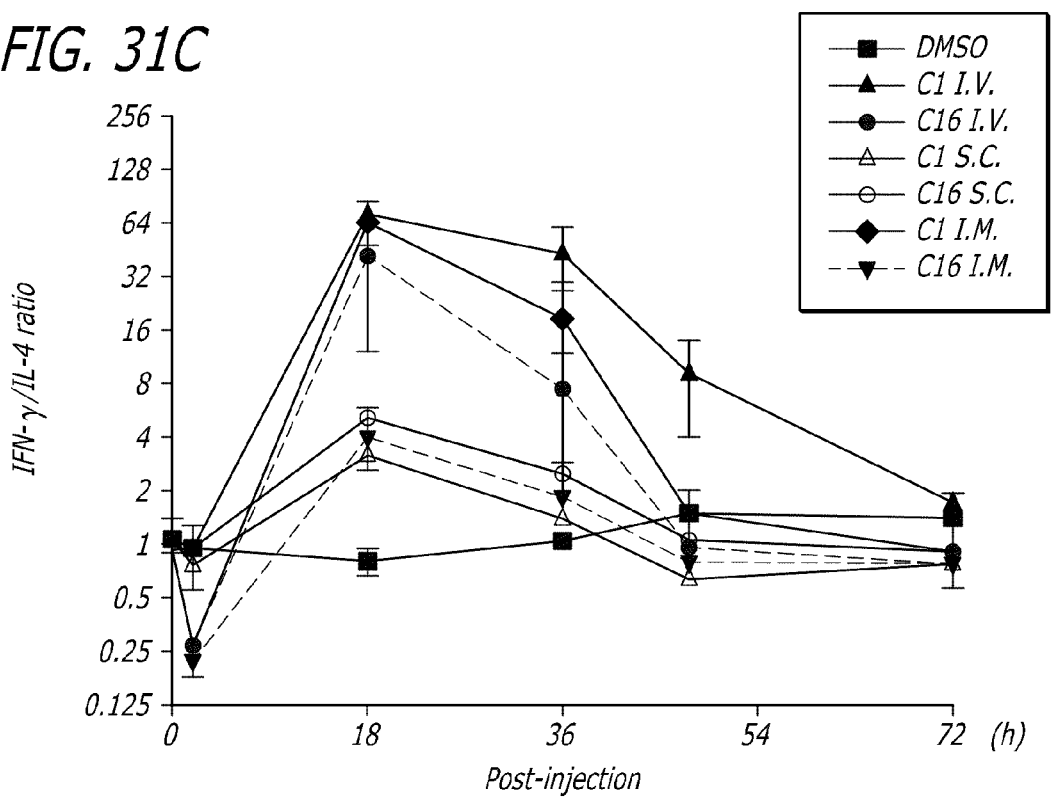
Figure 31D:
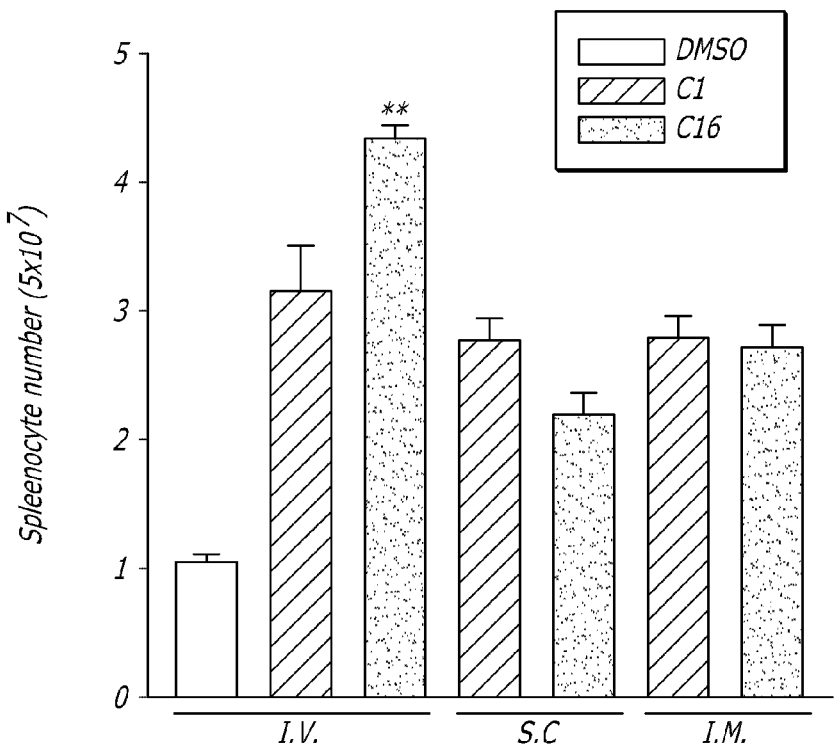
Figure 31E:
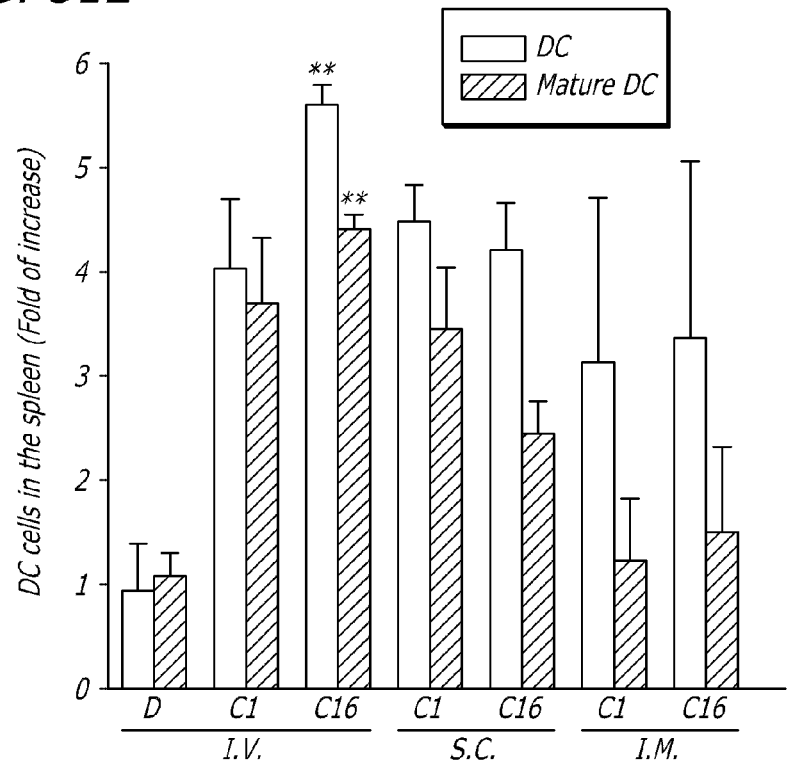
Figure 31F:
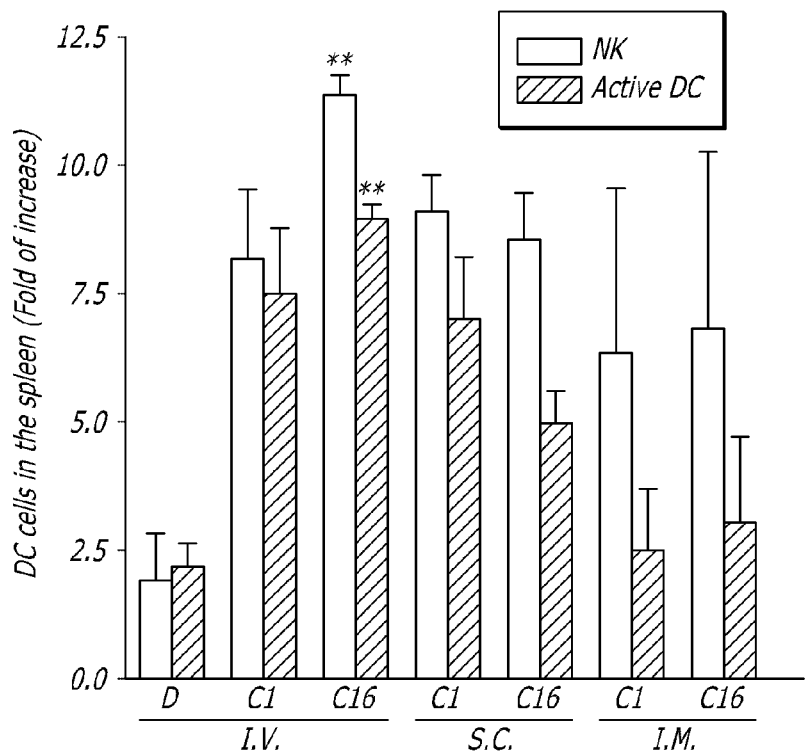
Figure 31G:
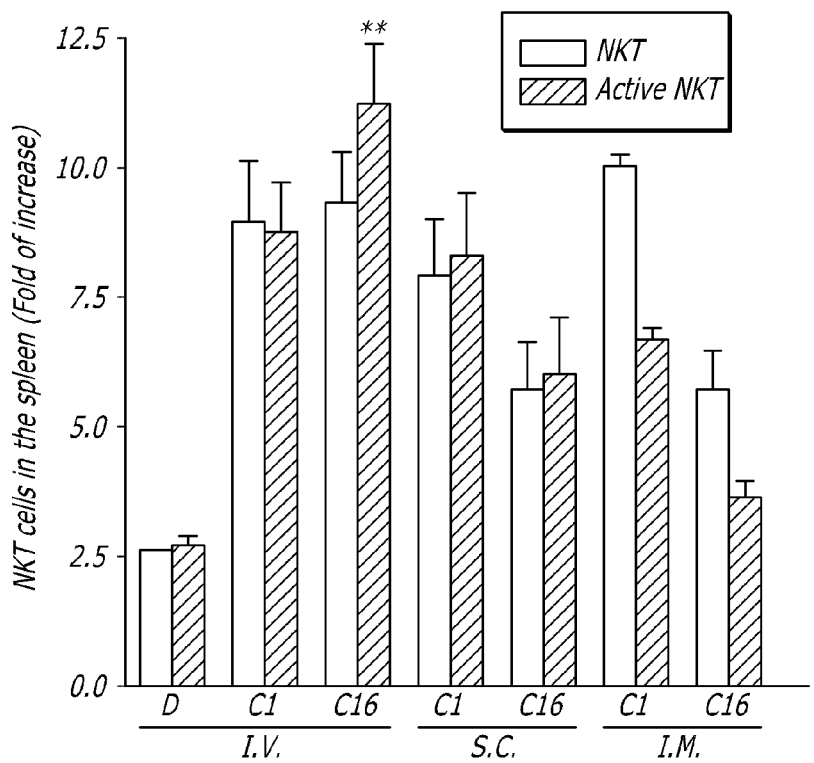
Figure 31H:
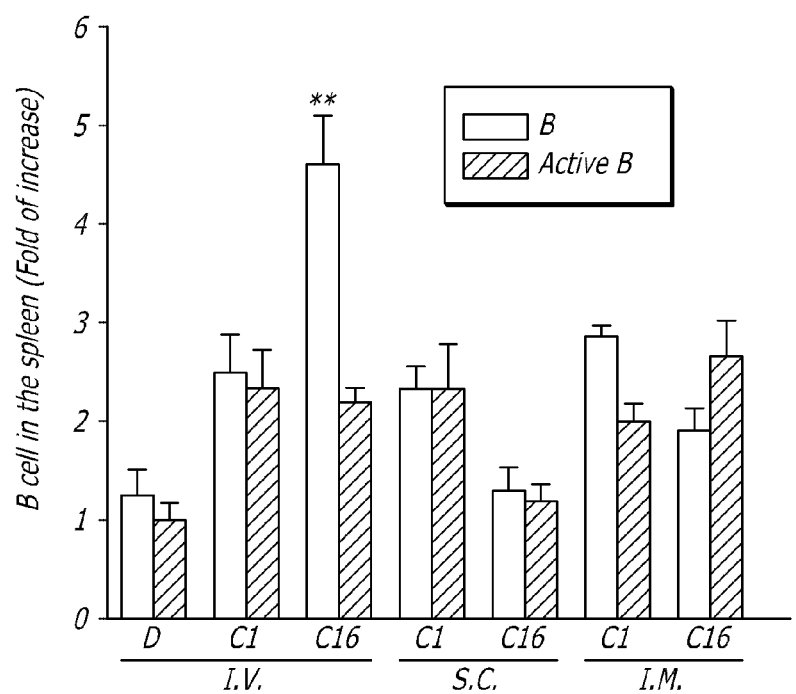
Figure 31I:
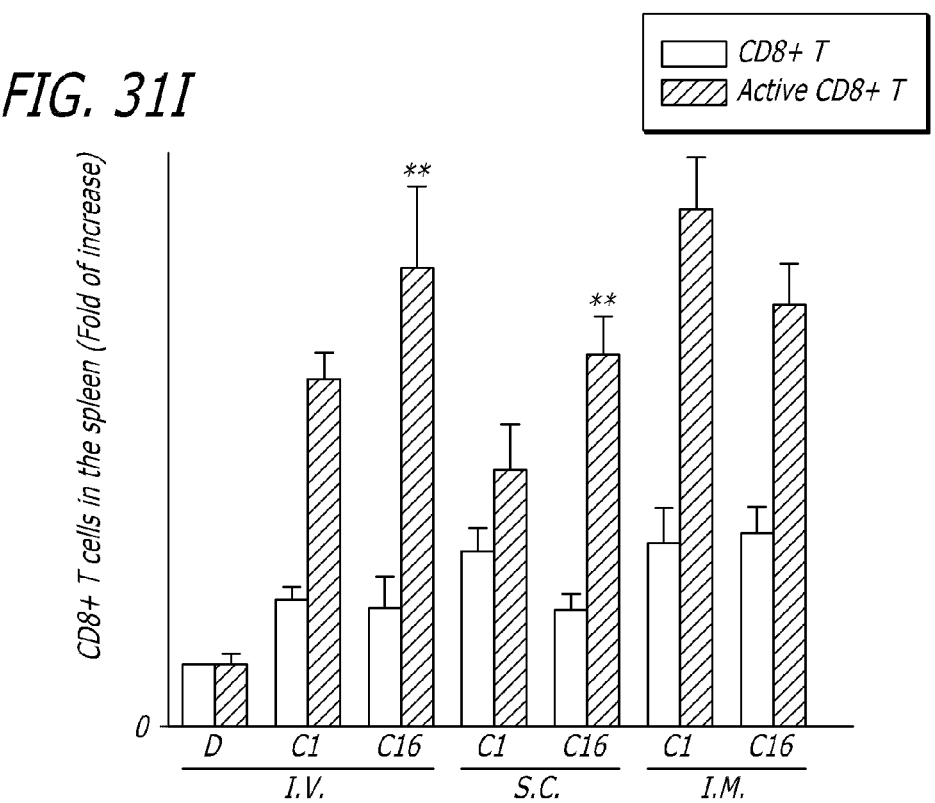
Figure 31J:
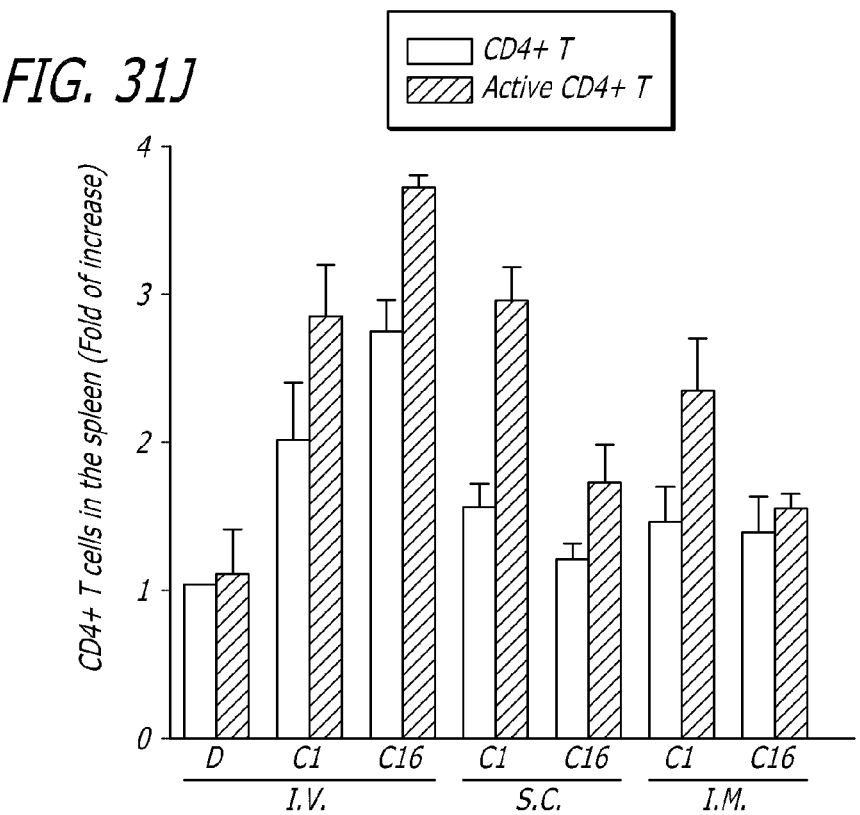
Figure 31K:
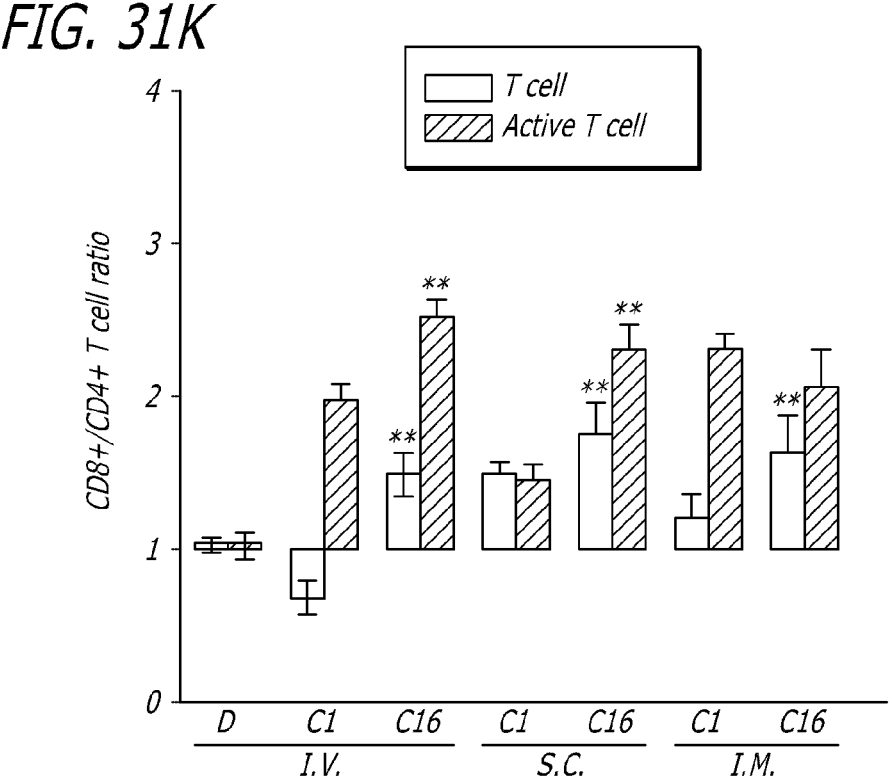
Figure 32A:
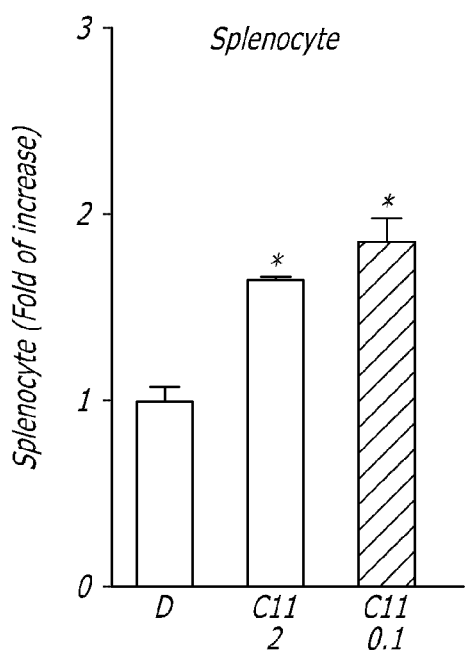
FIG. 32(A-H) show the dose-response of splenocytes expansion/activation in response to the IV administration of the α-GalCer analog C11 or vehicle. (A) shows the total number of mouse nucleated cells (splenocytes). (B) shows the population of innate immune cells, including mature dendritic cells, in the spleen. (C) shows the population of activated NKs in the spleen. (D) shows the population of activated NKTs in the spleen. (E) shows the population of monocyte granulocyte cells in the spleen. (F) shows the population of active CD4$^+$ T cells in the spleen. (G) shows the population of active CD8$^+$ T cells in the spleen. (H) shows the population of active B cells in the spleen. All analysis was performed by normalizing to vehicle.
Figure 32B:
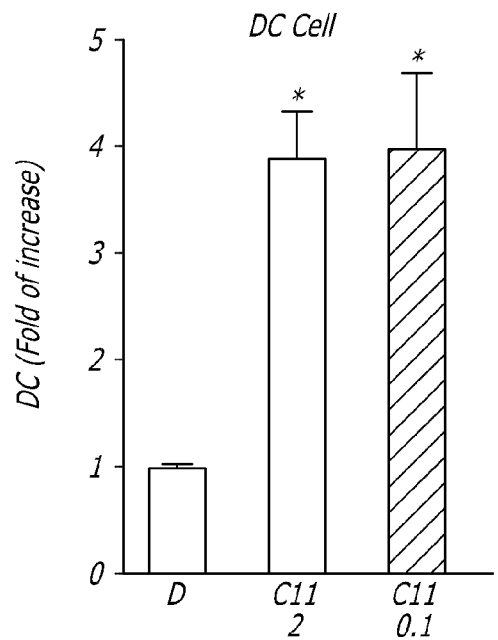
Figure 32C:
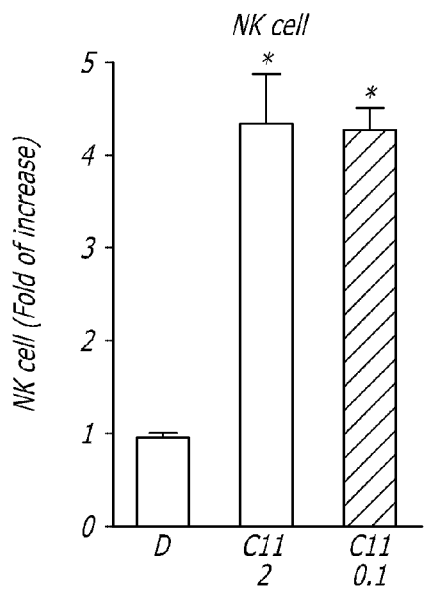
Figure 32D:
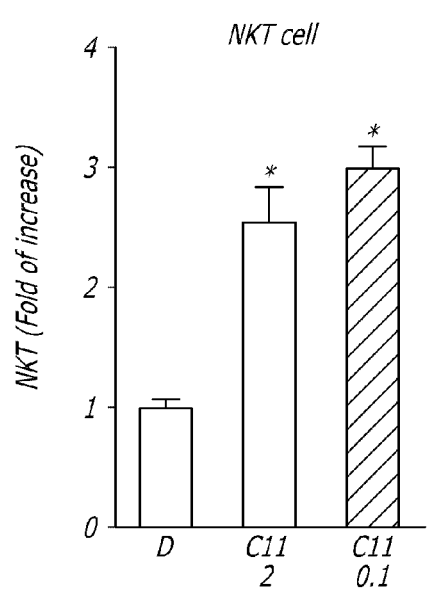
Figure 32E:
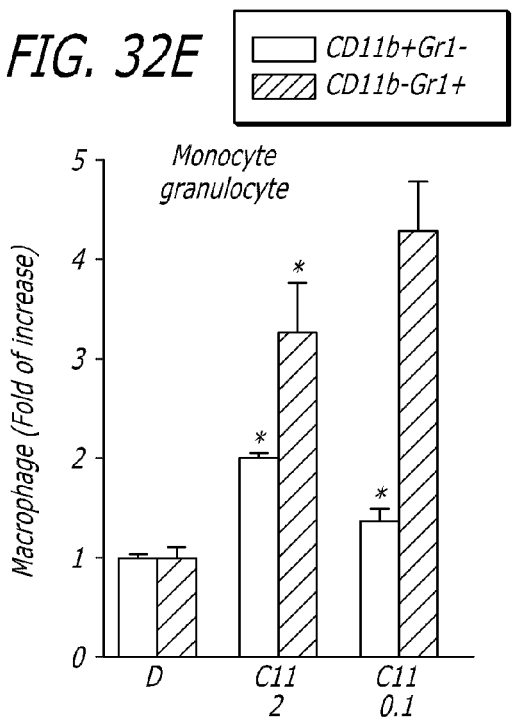
Figure 32F:
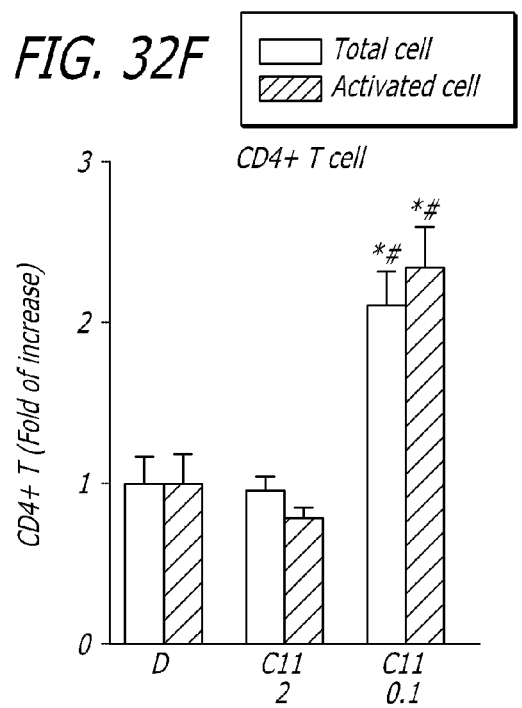
Figure 33A:
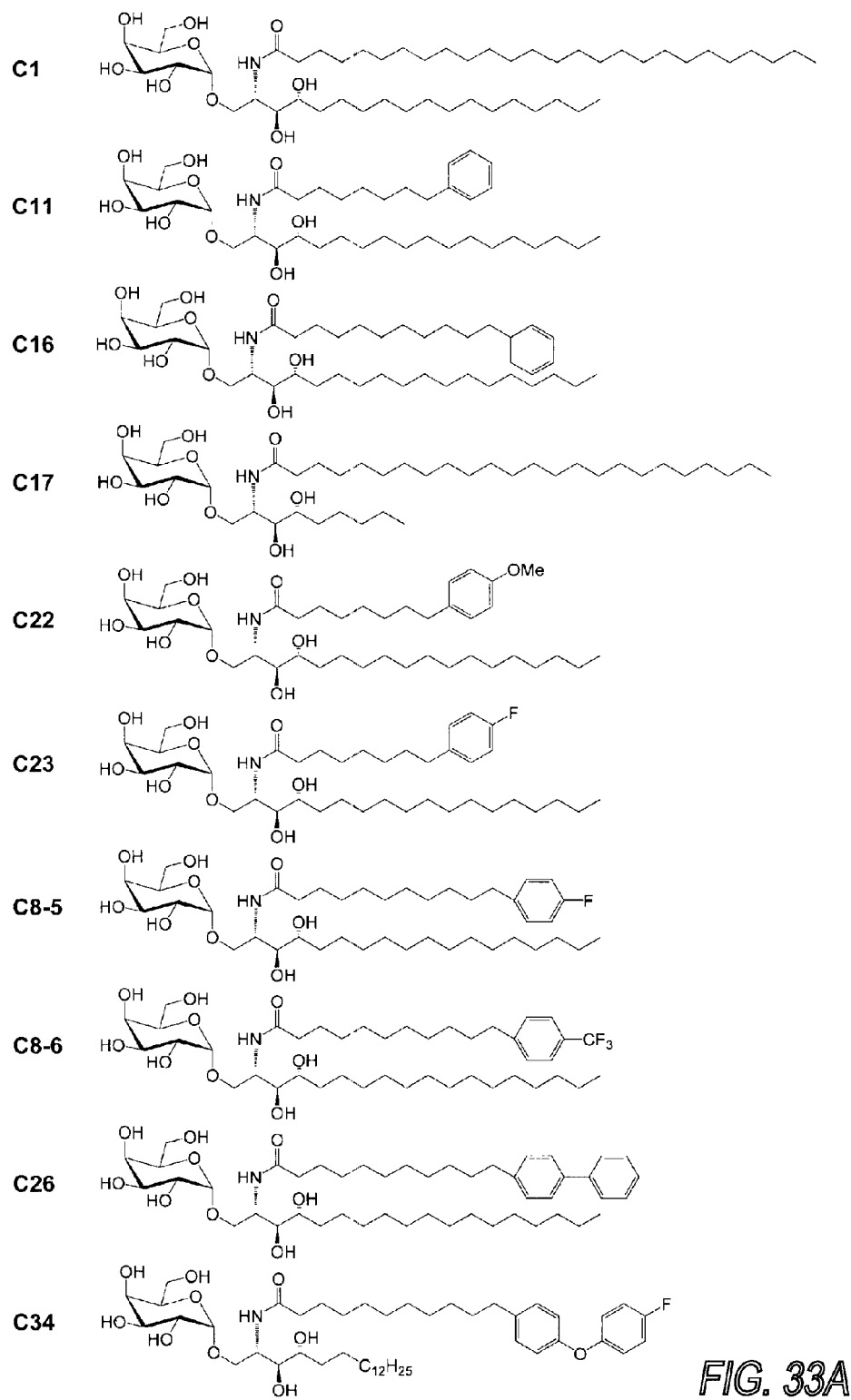
FIG. 33(A-D) shows mouse serum levels of various cytokines (B) IFN-γ, (C) IL-4, and (D) the ratio of IFN-γ/IL-4 after IV injection with (A) vehicle, α-GalCer or various α-GalCer analogs of the present disclosure at 0, 12, 24, 36, 48, 72 h post-injection and normalized to vehicle control.
Figure 33B:
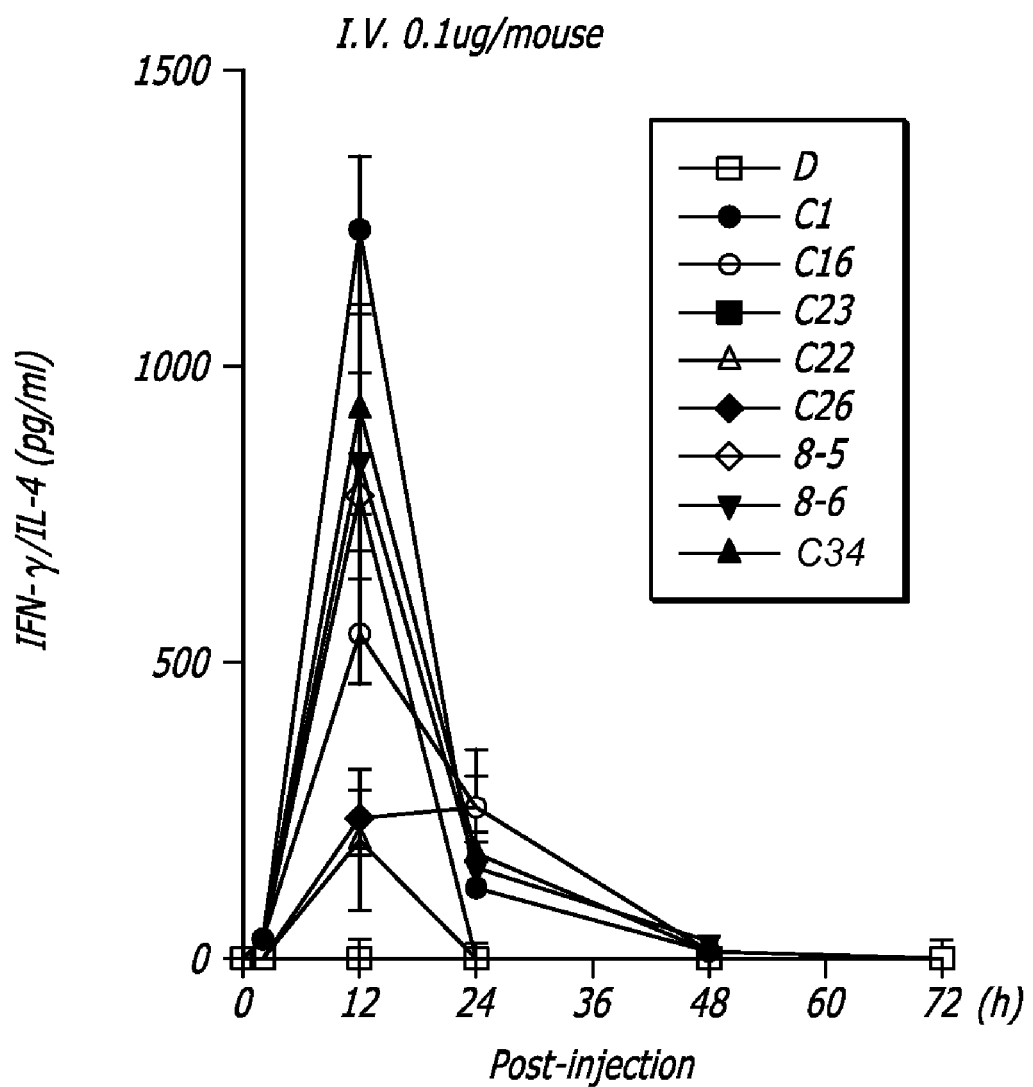
Figure 33C:
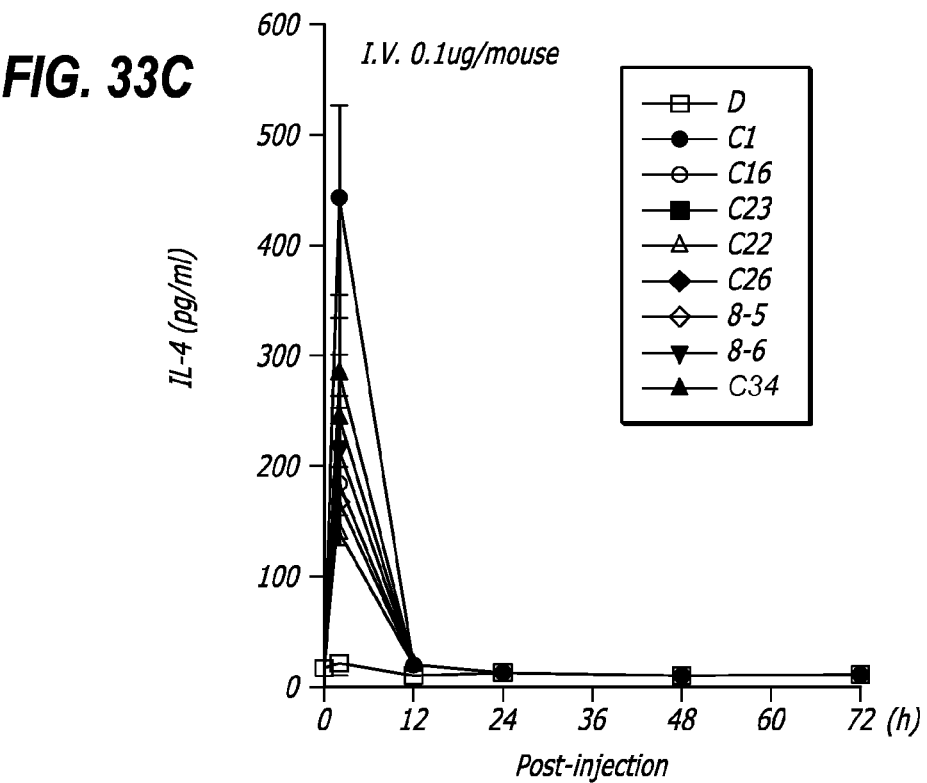
Figure 33D:
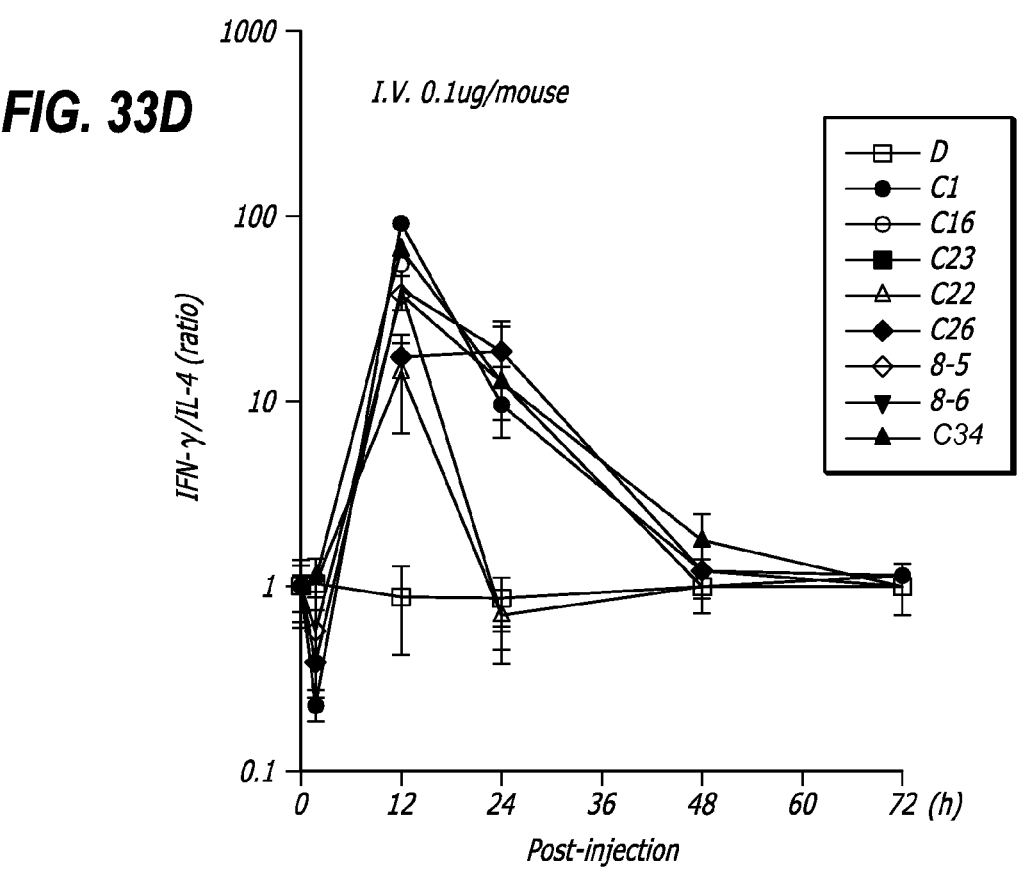
Figure 35B:
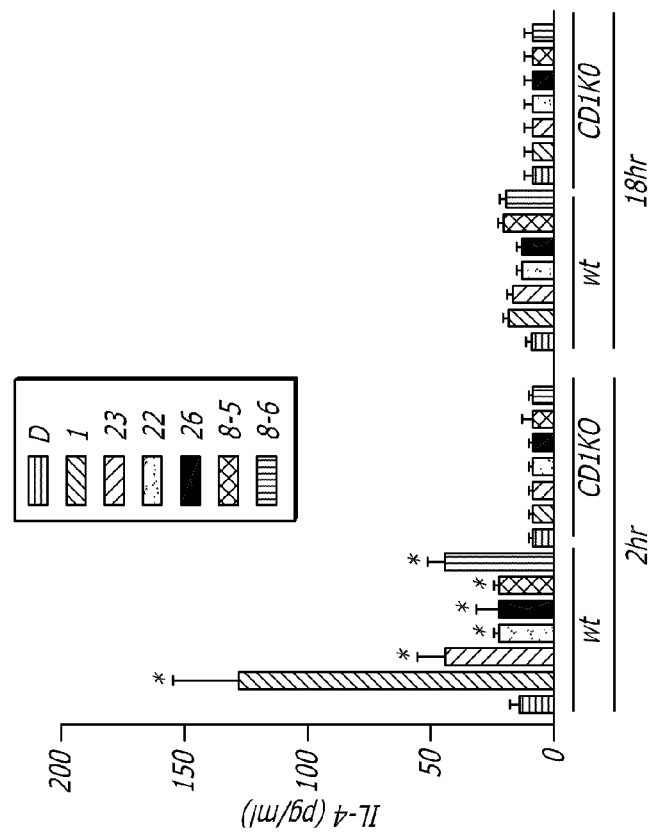
FIG. 35 (A-G) show serum levels (pg/ml) of various cytokines/chemokines at 2 and 18 h after IV injection of vehicle, α-GalCer or the indicated α-GalCer analogs of the present disclosure to wild type BALB/c (wt) and CD1d KO BALB/c (CD1KO) mice. (A) IFN-γ. (B) IL-4. (C) IFN-γ/IL-4 ratio (log 10). (D) IL-10. (E) IL-12p70. (F) KC. (G) MCP-1.
Figure 35A:
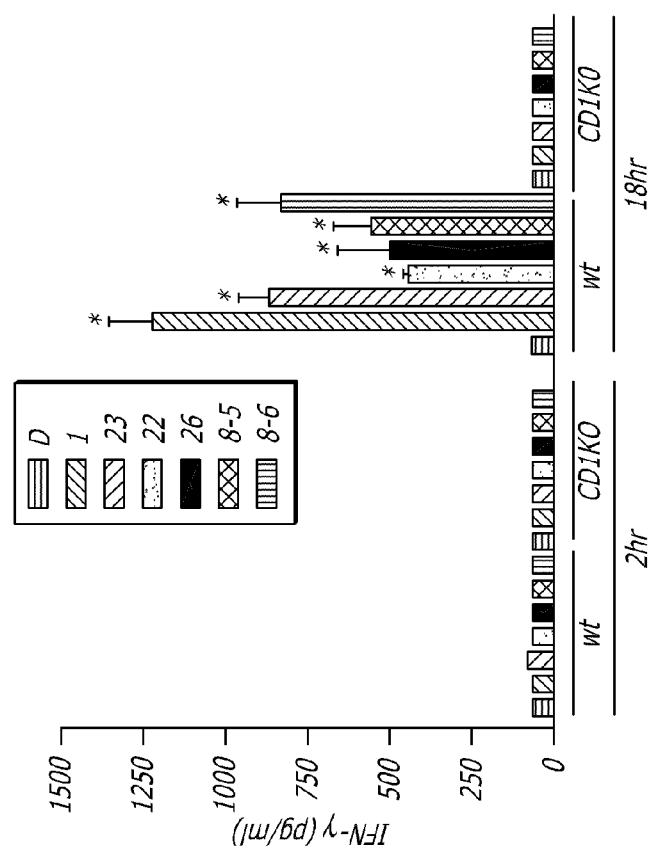
Figure 35C:
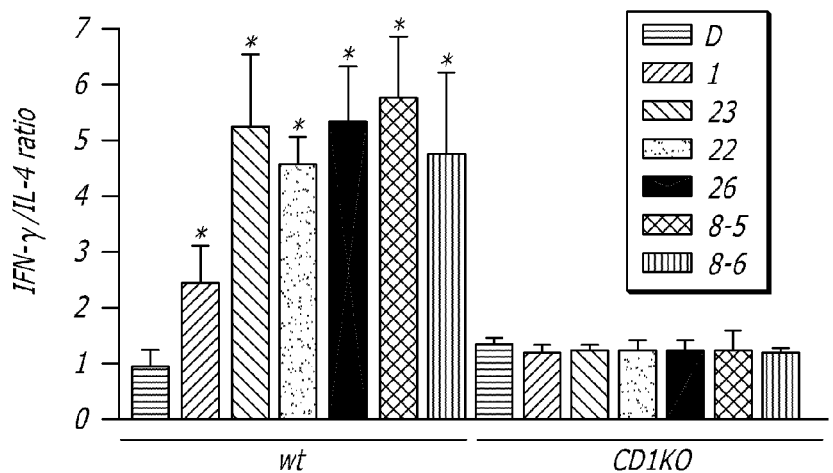
Figure 35D:
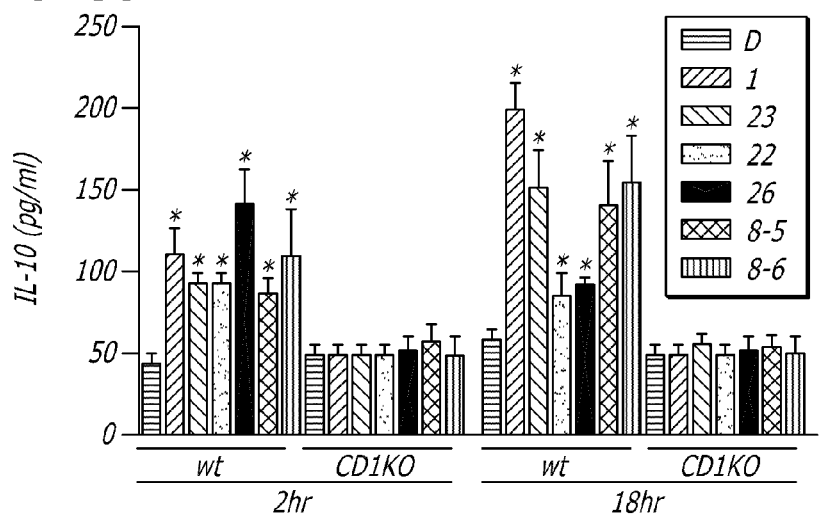
Figure 35E:
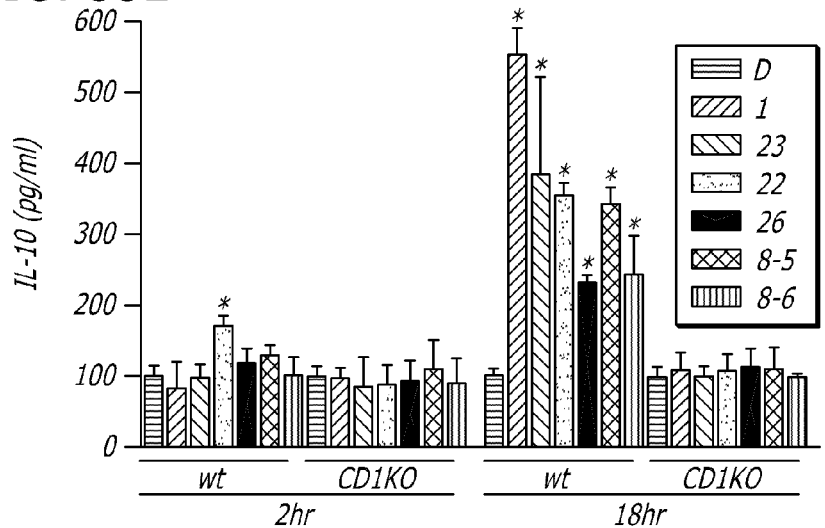
Figure 35F:
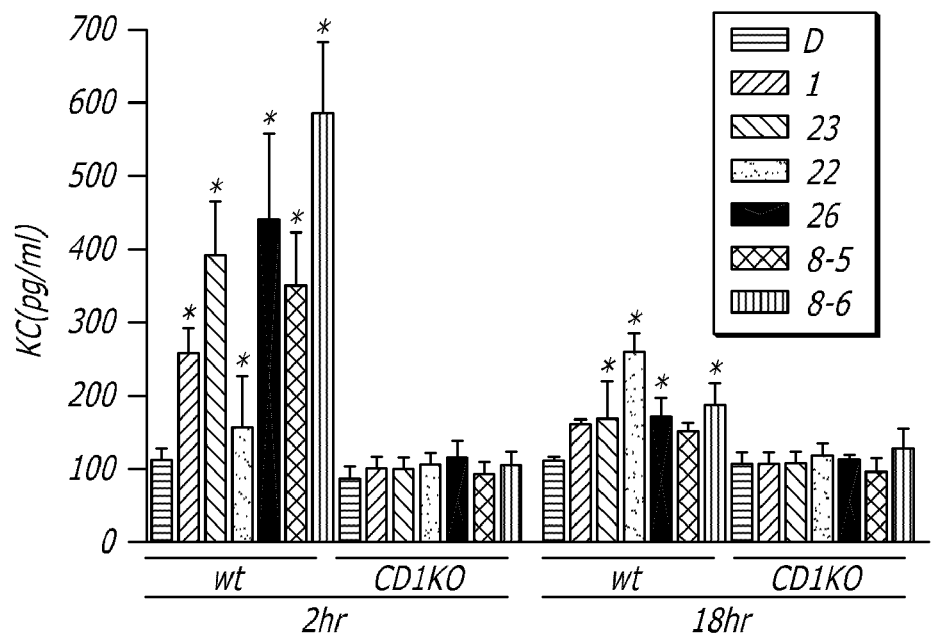
Figure 35G:
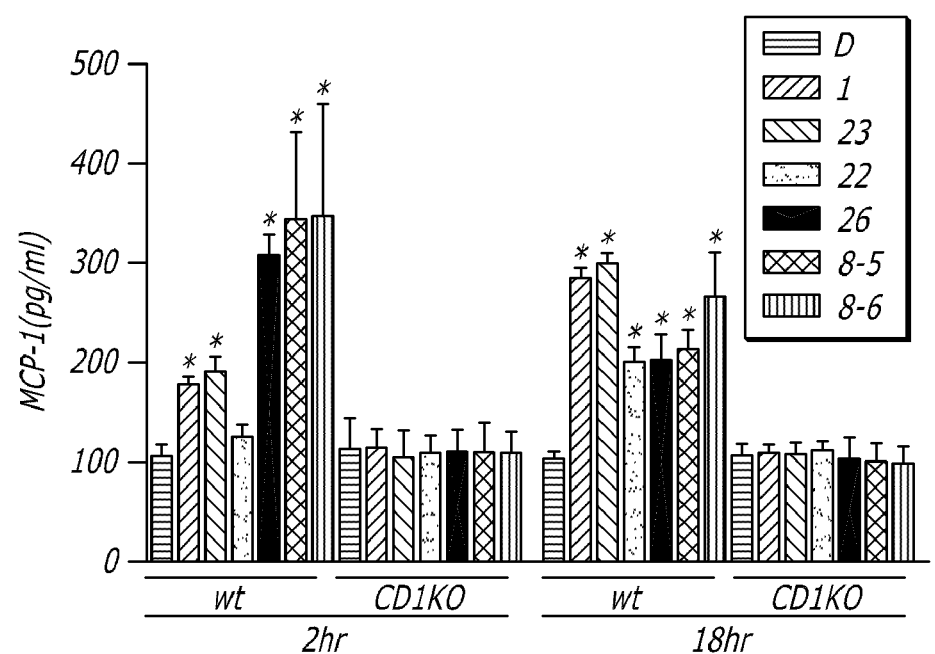
Figure 36C:
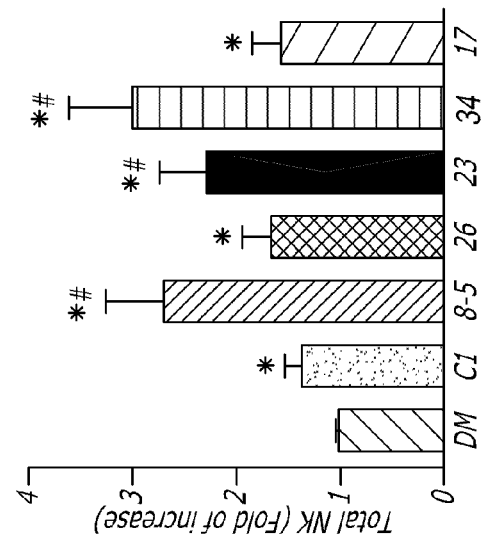
FIG. 36(A-I) shows the expansion/activation of splenocytes in C57BL/6 mice after IV injection of vehicle, α-GalCer or the indicated α-GalCer analogs of the present disclosure, and (G-I) shows the CD1d-dependent activation of two NKTs subsets (C57BL/6 wild type (Wt) and CD1 KO mice and after IV injection of vehicle, α-GalCer or the indicated α-GalCer analogs of the present disclosure. (A) shows the total number of C57BL/6 mouse nucleated cells (splenocytes). (B) shows the population of mature dendritic cells. (C) shows the population of activated NKs. (D) shows the population of active CD4+ T cells. (E) shows the population of active CD8+ T cells. (F) shows the ratio of CD8+/CD4+ T cells normalized with DMSO. (G) shows determination of NKT cells in Wt mice by flow cytometry (lower-left panel), total number of NKTs (upper-left panel), and its two subtypes including Type II NKT (upper-right panel) and Type I NKT (lower-right panel). (H) shows the total number of NKTs in CD1 KO mice. (I) shows the total number of Treg cells in Wt mice. All analysis was performed by normalizing to vehicle.
Figure 36B:
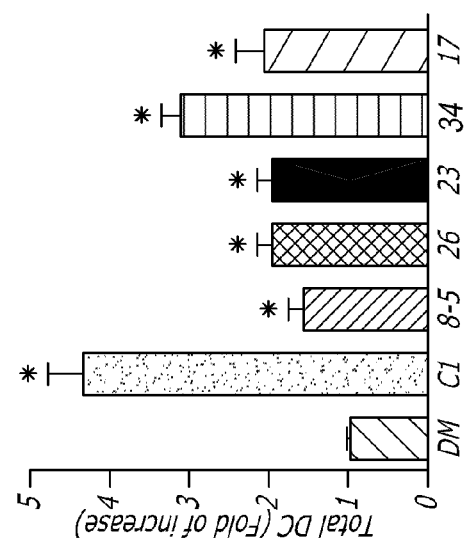
Figure 36A:
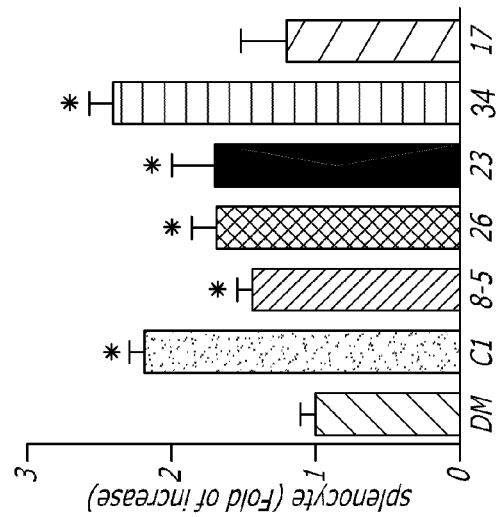
Figures 36D, 36E, 36F:
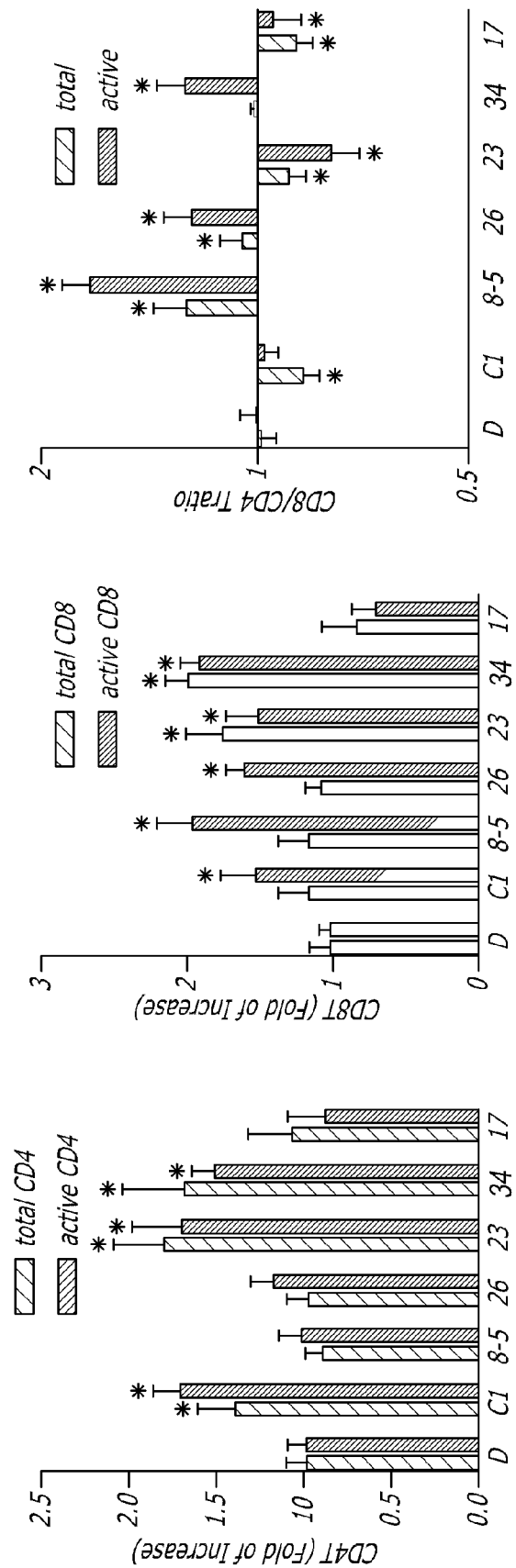
Figure 36G:
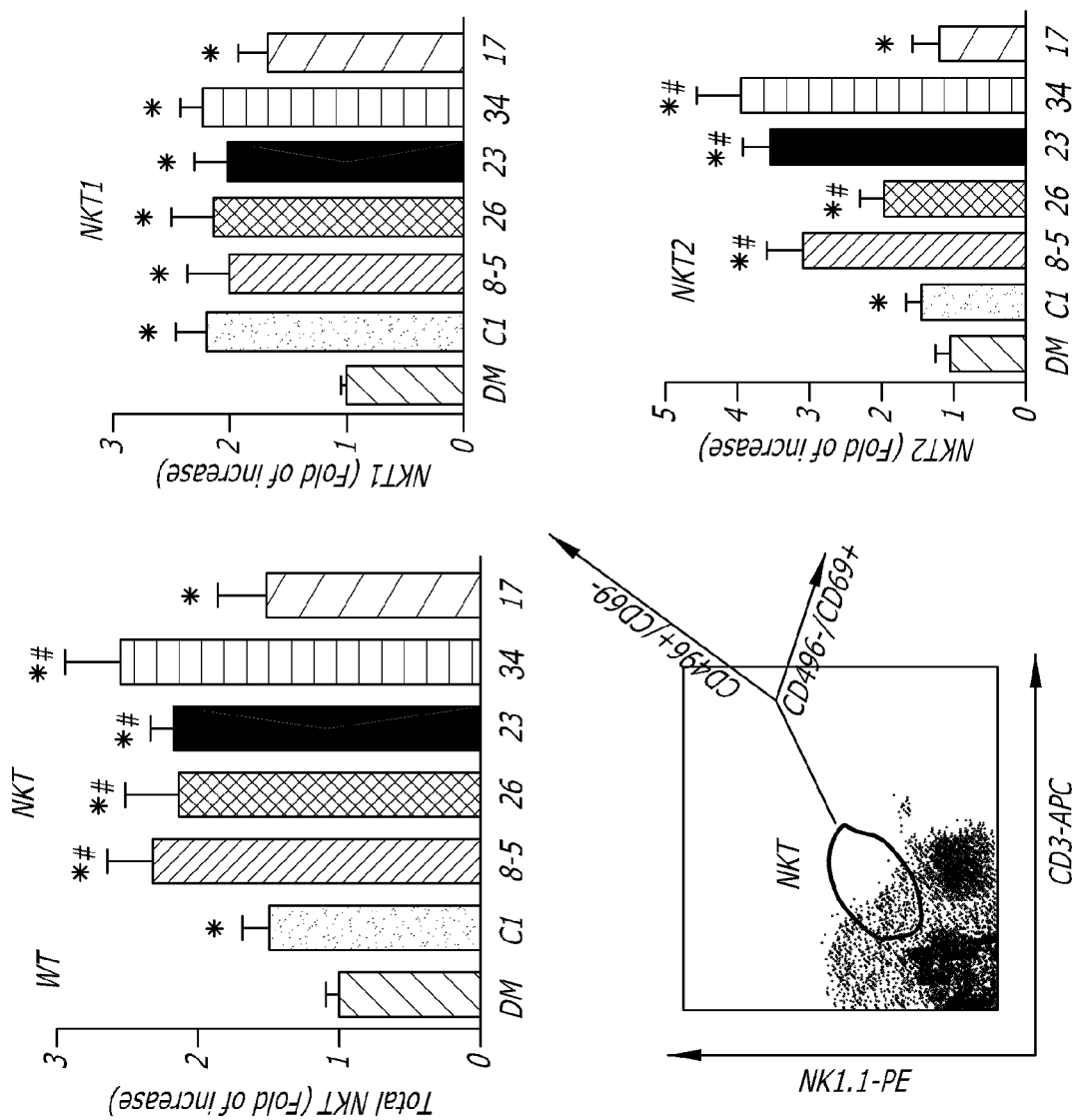
Figure 36H:
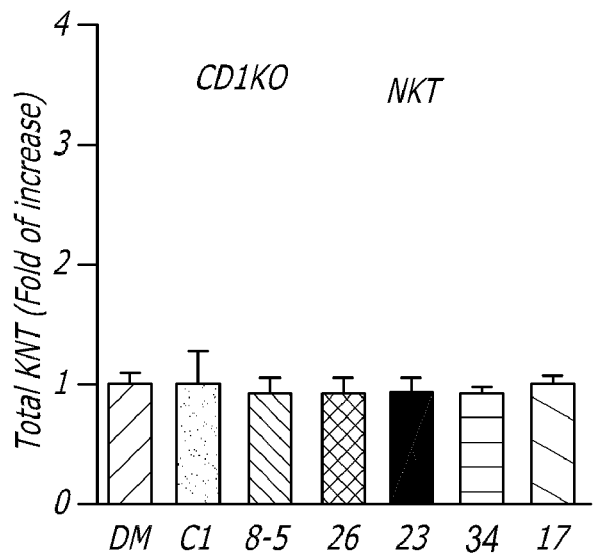
Figure 36I:
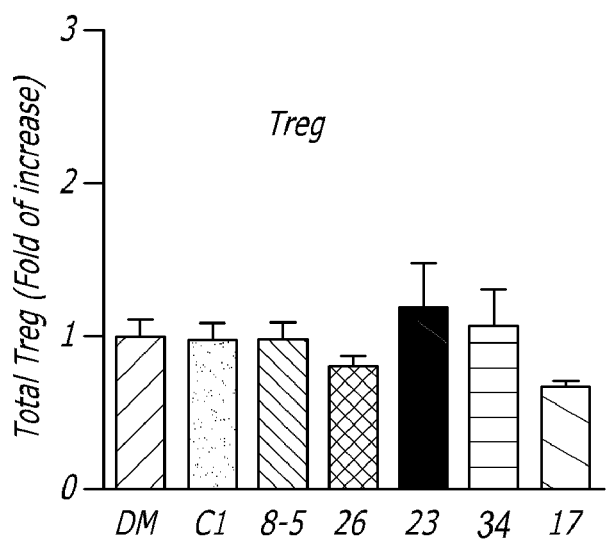

To determine the populations of immune cells in the spleens of BALB/c mice injected with α-GalCer or the indicated α-GalCer analogs of the present disclosure, BALB/c mice were injected and then examined 72 hours after injection. As shown in FIG. 26, after IV administration all of the α-GalCer analogs tested induced significant expansion in (A) splenocytes, with C9, C13 and C16 showing greater potency than C1, (B) DCs, (C) NKs, (D) NKTs, (E) B cells, (F) CD8+ T cells, (G) CD4+ T cells and (H) activated CD8+/CD4+ ratios. As shown in FIG. 28 after SubQ administration, none of the α-GalCer analogs tested showed a significant effect on the expansion of (A) splenocytes, as compared with that of C1. As shown in FIG. 30, after IM administration all of the α-GalCer analogs tested induced (A) splenocyte expansion, with C9, C13 and C14 having greater effects than C1. Aromatic α-GalCer analogs C12, C13 and C16 induced significantly greater rises in total and mature DCs than C1 (FIGS. 26B, 28B and 30B). α-GalCer analogs C9, C12, C13 and C16 displayed the best capacity for expansion/activation of NKs and NKTs (FIGS. 26C-D, 28C-D and 30C-D). α-GalCer analog C16 was most effective in B cell expansion, and α-GalCer analogs C2, C9, C10, and C11 were also more active than C1 (FIGS. 26E, 28E and 30E). For CD8+ T cells, α-GalCer analog C14 was most effective in cell expansion/ activation, although α-GalCer analogs C9, C11, C16, C12 and C13 were also more active than C1 (FIGS. 26F, 28F and 30F). α-GalCer analog C9 was most effective in CD4+ T cell expansion/activation than C1 (FIGS. 26G, 28G and 30G). Among the T cell subpopulations, all of the α-GalCer analogs tested induced a rise in CD8+/CD4+ ratio, with α-GalCer analogs C1, C13, C14 and C16 being more potent than C1 (FIGS. 26H, 28H and 30H). In mice treated with the α-GalCer analogs by the SubQ route, α-GalCer analog C9 induced significantly greater expansion of total and mature DCs than C1, while the remaining α-GalCer analogs were comparable to C1 (FIG. 28B). For NK and NKT expansion/activation, α-GalCer analogs C9, C11, C13, C14 and C16 showed comparable activities as C1, and the remaining α-GalCer analogs seemed less active (FIG. 28C-D). For B cell expansion/activation, α-GalCer analogs C1, C9, C11 and C13 showed significant activities (FIG. 28E). For CD8+ T cells, α-GalCer analogs C9, C1, C13, C14 and C16 showed more activity than C1, and the remaining α-GalCer analogs appeared to be comparable activities as C1 (FIG. 28F). For CD4+ T cells, C1 was most effective, although α-GalCer analogs C9, C11, C13, C14 and C16 were also more active over control (FIG. 28G). For T cells, most α-GalCer analogs tested elicited a greater increase in CD8+/CD4+ ratio than C1 (FIG. 28H). When the α-GalCer analogs were introduced through the IM route, all induced significant increases in DCs, NK, NKT, B cells and CD8+/CD4+ ratio. The majority of novel α-GalCer analogs elicited greater expansion of DCs than C1 (FIG. 30B). α-GalCer analogs C9 and C14 displayed stronger induction of NK cells (FIG. 30C) than C1, but comparable or less effects on NKT cells (FIG. 30D). α-GalCer analogs C2, C11, C12 and C16 showed stronger activations of B cells than C1 (FIG. 30E). For CD8+ T cells, α-GalCer analogs C9 and C16 showed comparable activities as C1 in cell expansion/activation, and the remaining α-GalCer analogs induced significant increases over the control (FIG. 30F). For CD4+ T cells, α-GalCer analogs C2 and C9 showed comparable activities as C1 in cell expansion/activation, and the remaining α-GalCer analogs induced significant increases over the control (FIG. 30G). α-GalCer analogs C9, C11 and C16 showed similar activities as C1 in raising CD8+/CD4+ ratio (FIG. 30H).

FIG. 31 shows another exemplary implementation of the effects of route of administration of α-GalCer analogs on cytokine kinetics and splenocytes expansion/activation. FIG. 31(A-C) shows the kinetics of cytokines in response to DMSO vehicle, α-GalCer or α-GalCer analog C16 given by different routes. BALB/c mice were injected with vehicle, C1 or C16 (2 μg per mouse) IV, SubQ or IM. Serum samples collected at 0, 2, 18, 36, 48, 72 h were analyzed for cytokines: (A) IFN-γ, (B) IL-4 and (C) the ratio of IFN-γ over IL-4, normalized to DMSO vehicle. FIG. 31(D-K) shows the expansion/activation of splenocytes in response to vehicle, C1 and C16 given by different routes. Spleens from BALB/c mice were harvested 72 h after injection of C1, C16 (2 μg per mouse) or vehicle IV, SubQ or IM. (D) shows the total number of nucleated cells, (E-G) shows the population of innate immune cells including mature dendritic cells (CD11C+/CD80+/CD86+), activated NKs (U5A2⁻13Ag+/CD3⁻/CD69+), activated NKTs (U5A2⁻13Ag+/CD3+/CD69+), (H-J) shows adaptive immune cells including activated B cells (CD45R+/CD23+/CD69+), activated CD8 T cells (CD3+/CD4⁻/CD8+/CD69+), and activated CD4 T cells (CD3+/CD4+/CD8⁻/CD69+), (K) shows the ratio of CD8/CD4, normalized to DMSO. **, p<0.05, compared with C1.

In another exemplary implementation, the α-GalCer analogs of the present disclosure were administered to mice at various doses to determine whether a dose-response is noticeable for the expansion/activation of splenocytes. As shown in FIG. 32A-H, spleens from BALB/c mice were harvested 72 h after IV injection of vehicle or α-GalCer analog C11 (2 or 0.1 μg per mouse). (A) shows the total number of nucleated cells, (B-H) shows the population of innate immune cells including mature DCS (CD11C+/CD80+/CD86+), activated NKs (U5A2⁻13Ag+/CD3⁻/CD69+), activated NKTs (U5A2⁻13Ag+/CD3+/CD69+), monocyte (CD11b+Gr1⁻), granulocyte (CD11b⁻Gr1+); (F-H) shows adaptive immune cells including activated CD4 T cells (CD3+/CD4+/CD8⁻/CD69+), activated CD8 T cells (CD3+/CD4⁻/CD8+/CD69+), and activated B cells (CD45R+/CD23+/CD69+). *, p<0.05, compared with DMSO, #, p<0.05, compared with C11 (2 μg per mouse).

In yet another in vivo exemplary implementation, the kinetics of $T_H1/T_H2$ cytokines induced by various α-GalCer analogs of the present disclosure was assessed (FIG. 33). BALB/c mice were injected IV with vehicle, C1 or the indicated α-GalCer analogs (see A, 0.1 μg per mouse). Serum samples were collected at 0, 2, 12, 24, 48, and 72 h, and then assessed for the secretions of (B) IFN-γ, (C) IL-4 and (D) the ratio of IFN-γ over IL-4, normalized to DMSO control. These potent α-GalCer analogs elicited cytokines/chemokines as can be seen from the Table in FIG. 34 which shows serum samples collected at 2 and 18 h. α-GalCer analogs of the present disclosure were administered IV to wild type (WT) and CD1d knockout (CD1KO) BALB/c mice (at 0.1 μg per mouse), see FIG. 35. Serum samples were collected at 2 and 18 hour, and then analyzed for cytokines/chemokines, including (A) IFN-γ, (B) IL-4, (C) IFN-γ/IL-4 ratio, (D) IL-10, (E) IL-12p70, (F) KC) and (G) MCP-1. *, p<0.05, compared with DMSO. The results indicate that the α-GalCer analogs of the present disclosure elicit CD1-dependent cytokines/chemokines secretion in mice.

FIG. 36 shows another exemplary implementation of the expansion/activation of splenocytes and CD1d-dependent activation of two NKT subsets after injection with various α-GalCer analogs of the present disclosure. (A-F) shows the expansion/activation of splenocytes in response to the α-GalCer analogs tested. Spleens from C57BL/6 mice were harvested 72 h after IV injection of vehicle, α-GalCer or the indicated α-GalCer analogs (0.1 μg per mouse). (A) shows the total number of nucleated cells, (B-F) show the population of mature dendritic cells (CD11C+/CD80+/CD86+), activated NKs (NK1.1+/CD3⁻/CD69+), activated CD4 T cells (CD3+/CD4+/CD8⁻/CD69+), activated CD8 T cells (CD3+/CD4⁻/CD8+/CD69+), and CD8/CD4 ratio, normalized to DMSO. *, p<0.05, compared with DMSO. (G-H) shows the CD1-dependent expansion of two NKT subsets. Spleens from C57BL/6 wild type (Wt) or CD1 knockout (CD1KO) mice were harvested 72 h post IV injection of vehicle, C1, 7DW8-5, C22, C23, C26, C34 and C17, 0.1 µg per mouse. (G) shows the determination of mouse NKTs by flow cytometry (lower-left panel). An increase of total number of NKTs (upper-left panel) and its two subtypes including Type II NKT (CD3$^+$/NK1.1$^+$/CD49$^+$/CD69$^-$) (upper-right panel) and Type I NKT (CD3$^+$/NK1.1$^+$/CD49$^-$/CD69$^+$) (lower-right panel) in Wt was noted by FACS. (H) shows the total number of NKTs in CD1KO mice and (I) shows the total number of Treg cells (CD4$^+$/CD25$^+$/FoxP3$^+$) in Wt C57BL/6 mice in response to the α-GalCer analogs. *, $p<0.05$, compared with DMSO; #, $p<0.05$, compared with C1.

Immunotherapy

The immune system effectively prevents our body's from being overtaken by scavenging germs. Without an effective immune system, people are subject to developing all sorts of infections from bacteria, viruses, protozoa, parasites and fungi. They are also more likely to develop cancer. Because NKTs play a regulatory role in the immune system, they are attractive targets for immunotherapy. The activation of NKTs paradoxically can lead either to suppression or stimulation of immune responses. For example, the production of $T_H1$ cytokines are thought to correlate with antitumor, antiviral/antibacterial, and adjuvant activities, whereas $T_H2$ cytokine production is thought to subdue autoimmune diseases.

Anti-Tumor Immunotherapy

It is now understand that there is a firm link between the immune system and cancer, and that by properly stimulating the immune system, there is the possibility of impacting many cancers. Treatment of mice with α-GalCer has been shown to suppress tumor metastasis to liver, lung and lymph nodes. In two phase I clinical trials in patients with advanced cancers who were injected with α-GalCer or α-GalCer-loaded iDCs, a distinct activation of the immune system was observed in those patients who had a detectable Vα24$^+$Vβ11$^+$ NKT number prior to treatment. Although there was no durable tumor regression, stable disease was noted in several patients, without any toxicity, and some patients even showed a transient reduction of serum tumor markers or tumor size. The lack of significant anti-cancer activity of α-GalCer in several clinical trials may be due to the effect of IFN-γ (a $T_H1$ cytokine) counteracted by IL-4 (a $T_H2$ cytokine), resulting in no net benefit.

In one aspect, the synthetic α-GalCer analogs of the present disclosure have use as anti-tumor immunotherapy active agents. The α-GalCer analogs of the present disclosure may be designed such that they are $T_H1$-biased. These $T_H1$-biased α-GalCer analogs are capable of eliciting a $T_H1$ cytokine response, increasing survival time of animals afflicted with cancer, slowing down tumor growth in animals afflicted with cancer and increasing the tumor-infiltrating lymphocytes, including T, CD8T, NK and NKT cells.

In an exemplary implementation, the α-GalCer analogs of the present disclosure act as therapeutic drugs in anti-tumor immunotherapy. The α-GalCer analogs may be administered as cancer vaccines. In another exemplary implementation, the α-GalCer analogs of the present disclosure may be used in combined immunotherapy, where the α-GalCer analogs are combined with an already existing cancer vaccine. A subject treated with any of the α-GalCer analogs of the present disclosure may be afflicted with cancer, may be at an elevated risk for cancer or may have precancerous precursors.

In some exemplary implementations the disclosure provides an anti-tumor immunotherapy comprising administering an effective amount of a compound or a salt or a mixture thereof to a subject, the compound selected from the group consisting of C3, C10-C17, C19-C28, C34 and C8-5.

Figure 37A:
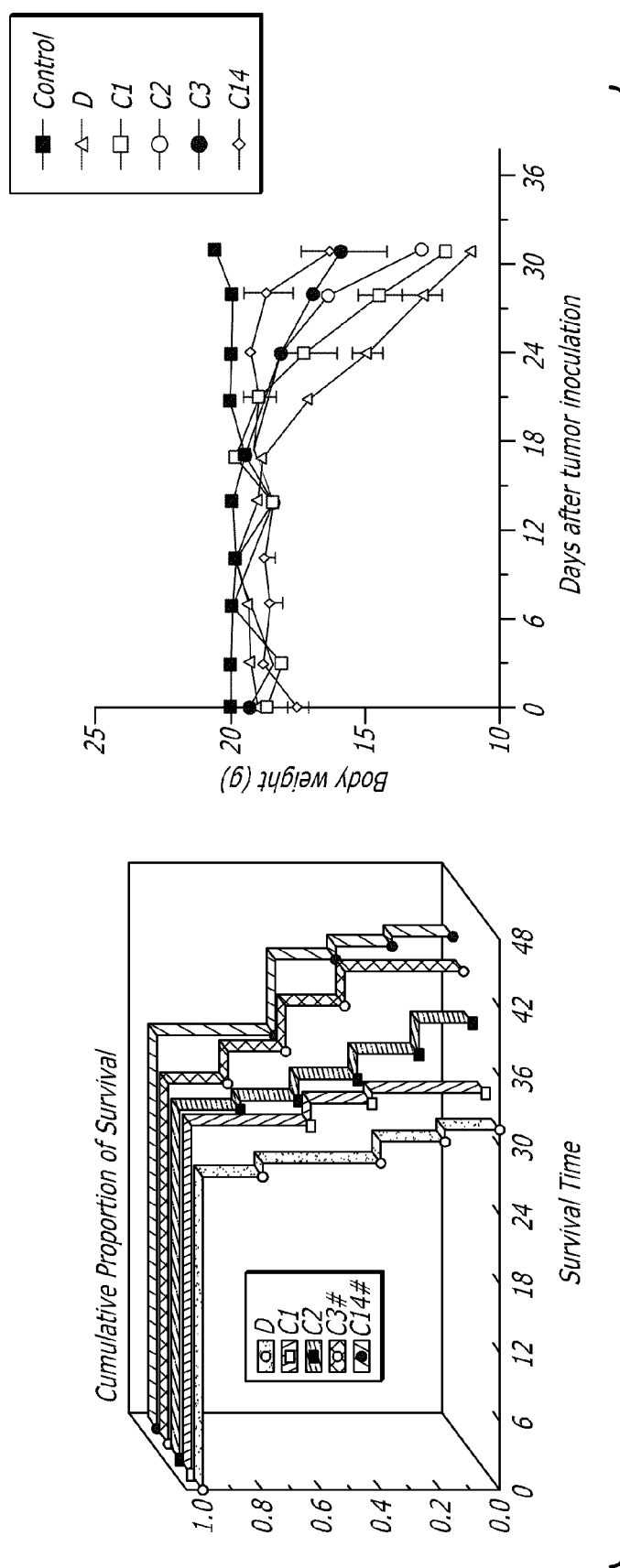
FIG. 37(A-B) show how α-GalCer analogs of the present disclosure can prolong survival of mice bearing lung cancer. C57BL/6 mice were inoculated IV with mouse lung cancer cells (TC-1), and then treated with control, α-GalCer or the indicated α-GalCer analog of the present disclosure twice per week for four weeks. (A) shows the results from the testing of Group I α-GalCer analogs. (B) shows the results from the testing of Group II α-GalCer analogs. (C) shows the results from the testing of Group III α-GalCer analogs. (D) shows the results from the testing of Group IV α-GalCer analogs. Shown are the Kaplan Meier survival curves (left panels) and changes in body weight (right panels) of mice bearing lung cancer. The control is the mouse without tumor inoculation.
Figure 37C:
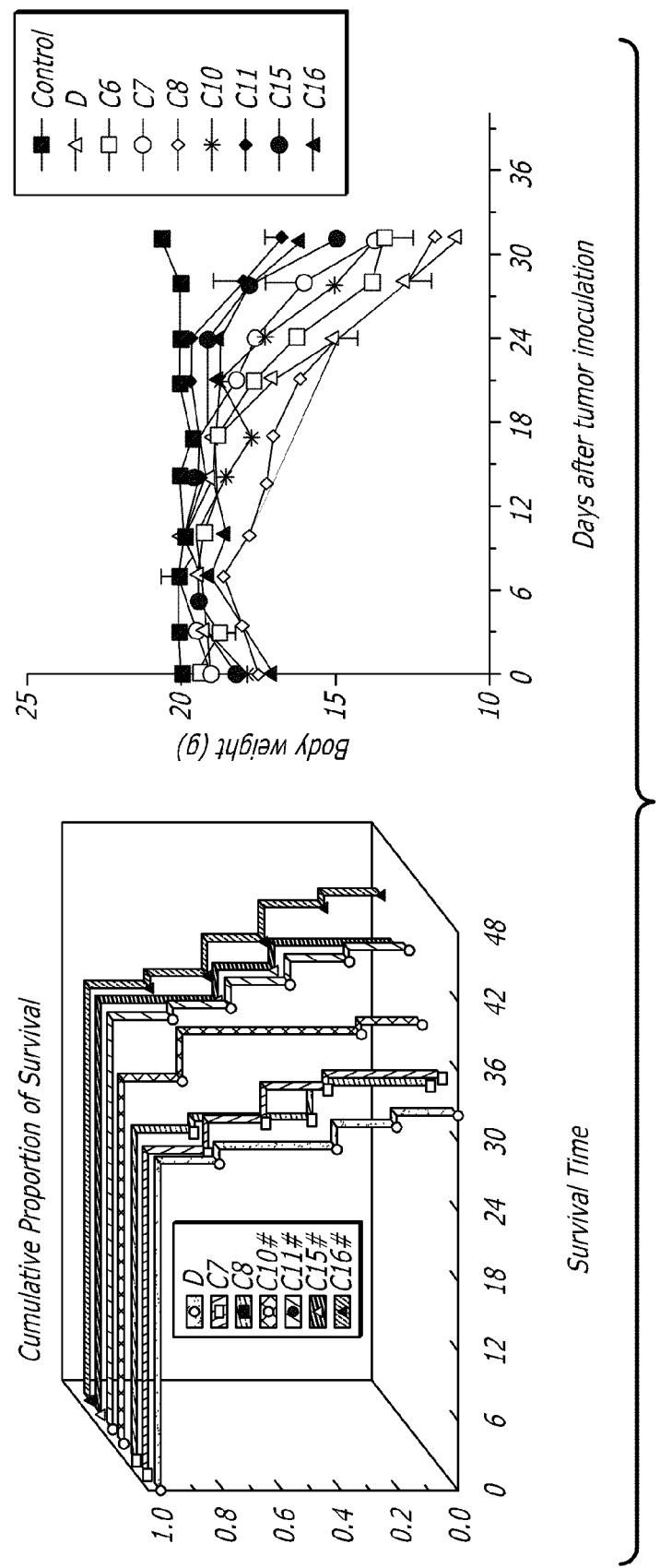
Figure 37D:
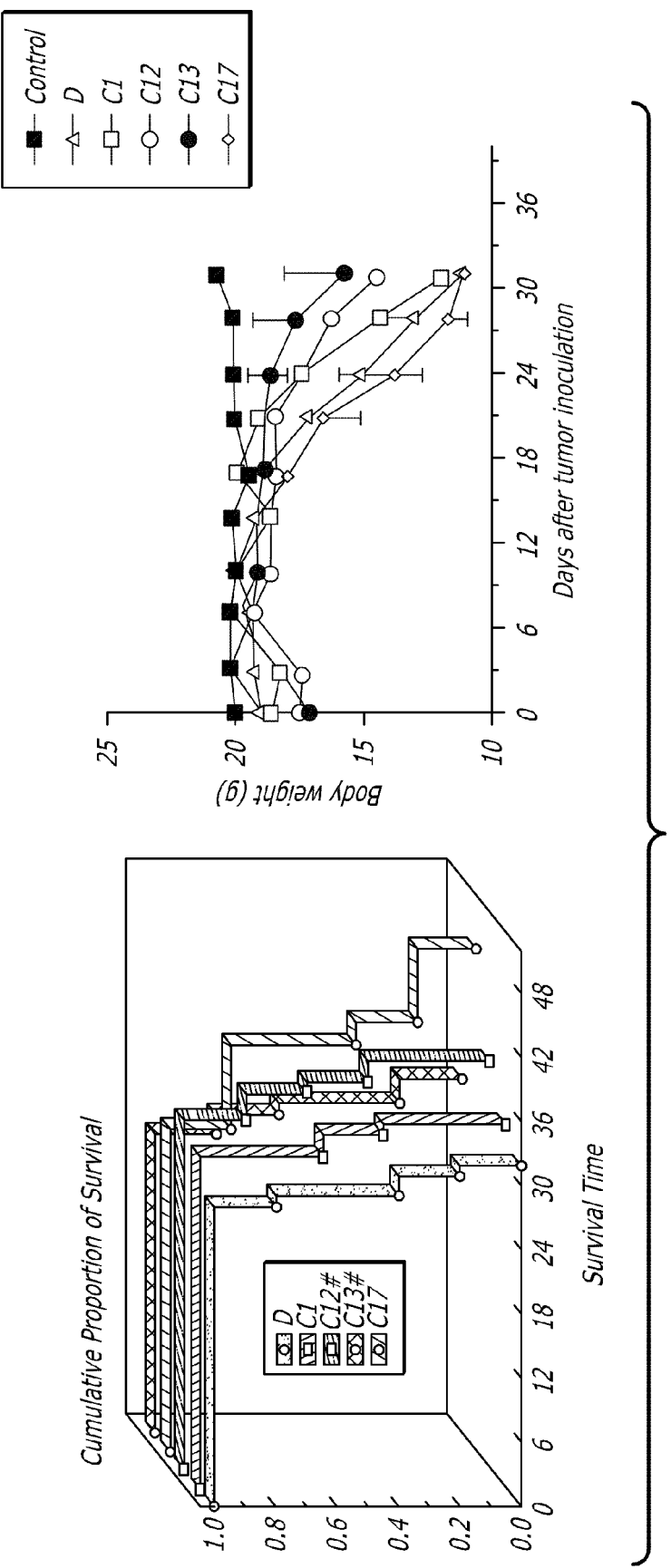
Figure 38A:
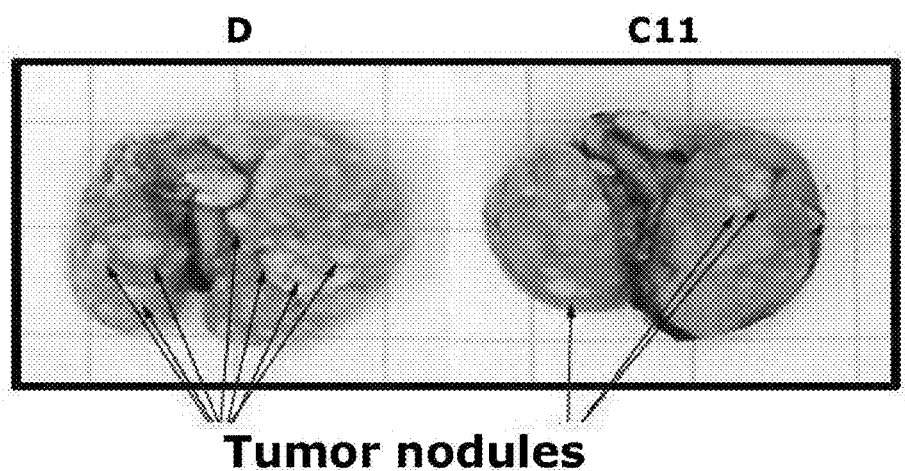
FIG. 38(A-B) show tumor nodules and sizes (A) on a surface of lungs of mice treated with α-GalCer analog C11 or control, and sacrificed on day 16 after tumor inoculation with TC-1 cells and (B) in subcutaneous tumors of mice treated with α-GalCer analog C11 or control, and sacrificed on day 16 after SubQ tumor inoculation with mouse breast cancer cells (4T-1).
Figure 38B:
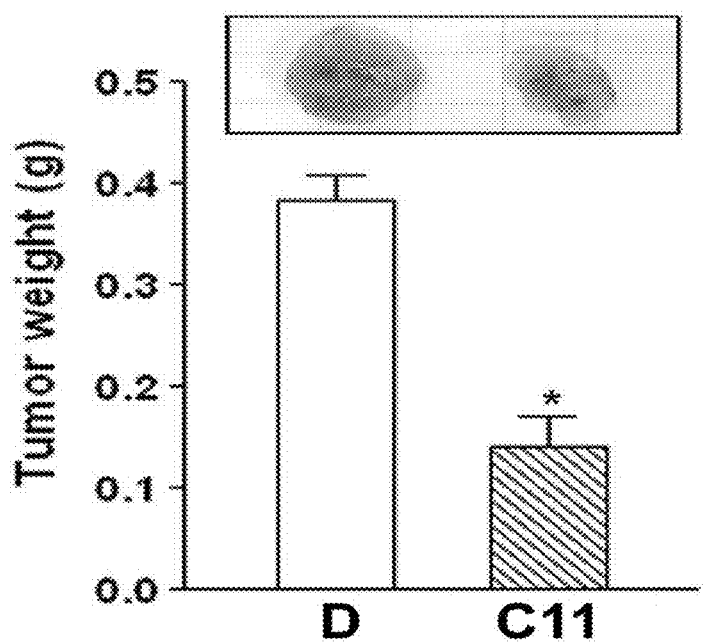
Figure 39A:
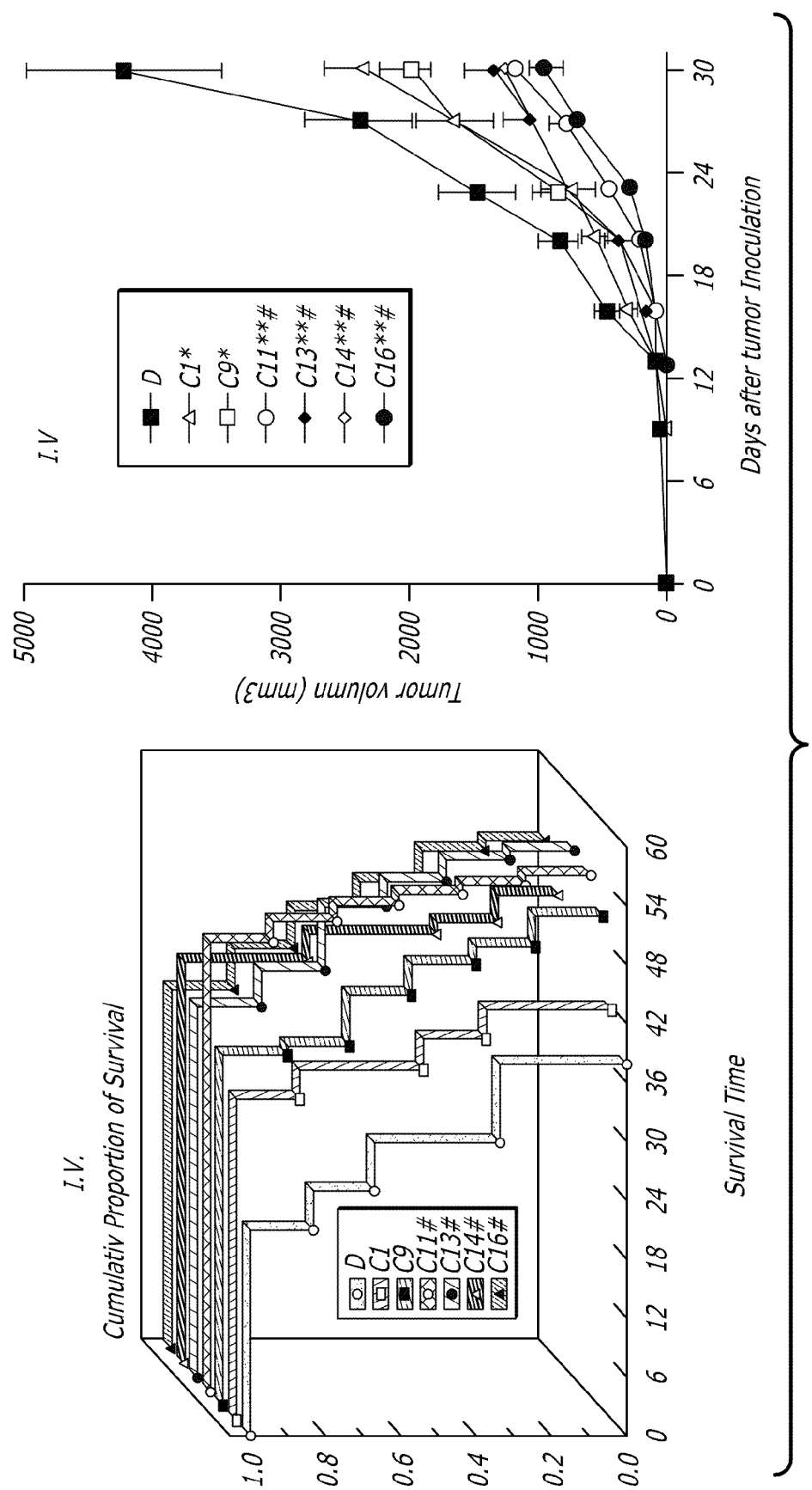
FIG. 39(A-B) shows Kaplan Meier survival curves (left panel) and tumor growth (right panel) of mice subcutaneously inoculated with mouse breast cancer cells 4T-1, and treated with control, α-GalCer or the indicated α-GalCer analog of the present disclosure three days after inoculation, and twice per week for four weeks by (A) IV injection or (B) SubQ injection.
Figure 39B:
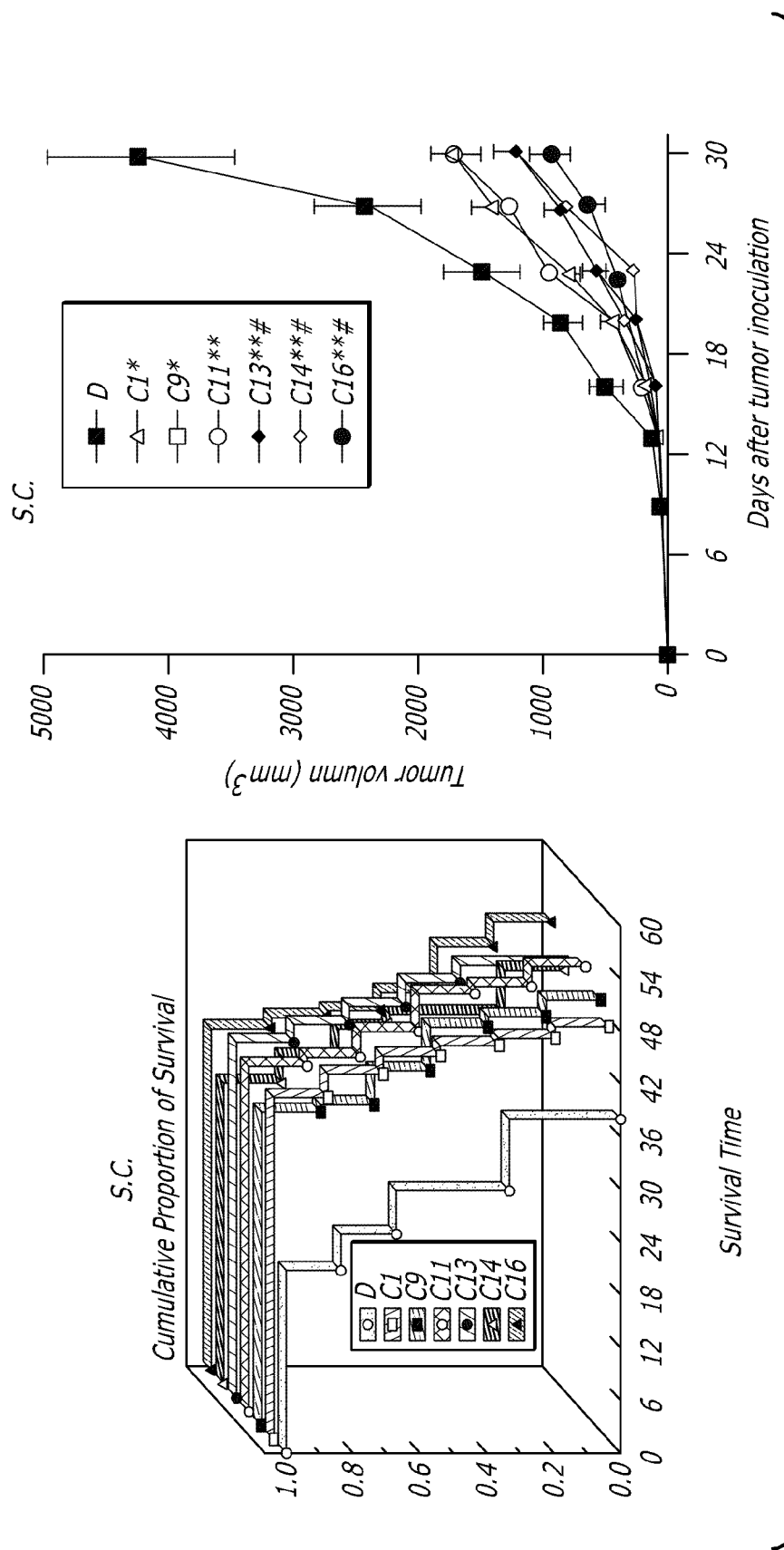
Figure 40:
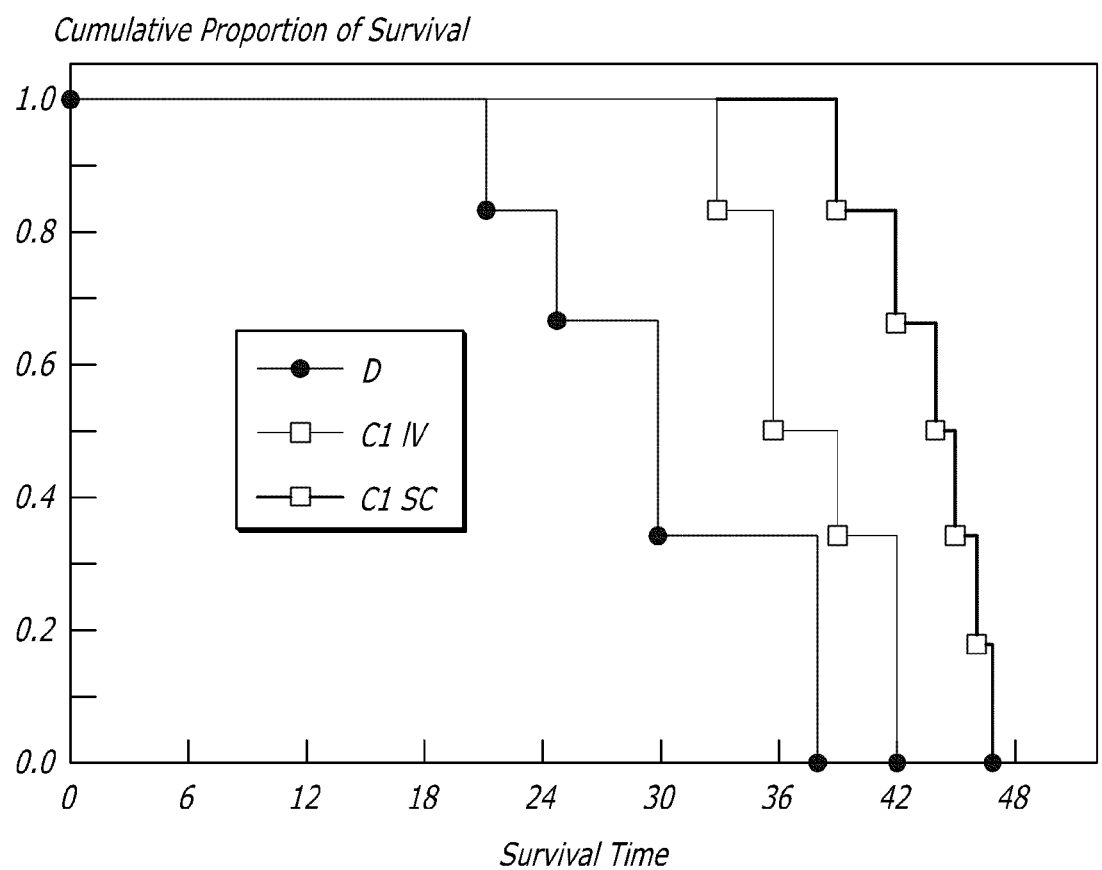
FIG. 40 shows Kaplan Meier survival curves of mice bearing breast cancer and treated by either IV or SubQ injection with α-GalCer (C1). SubQ delivery of C1 is more effective than IV delivery in prolonging the survival of mice bearing breast cancer.
Figure 41A:
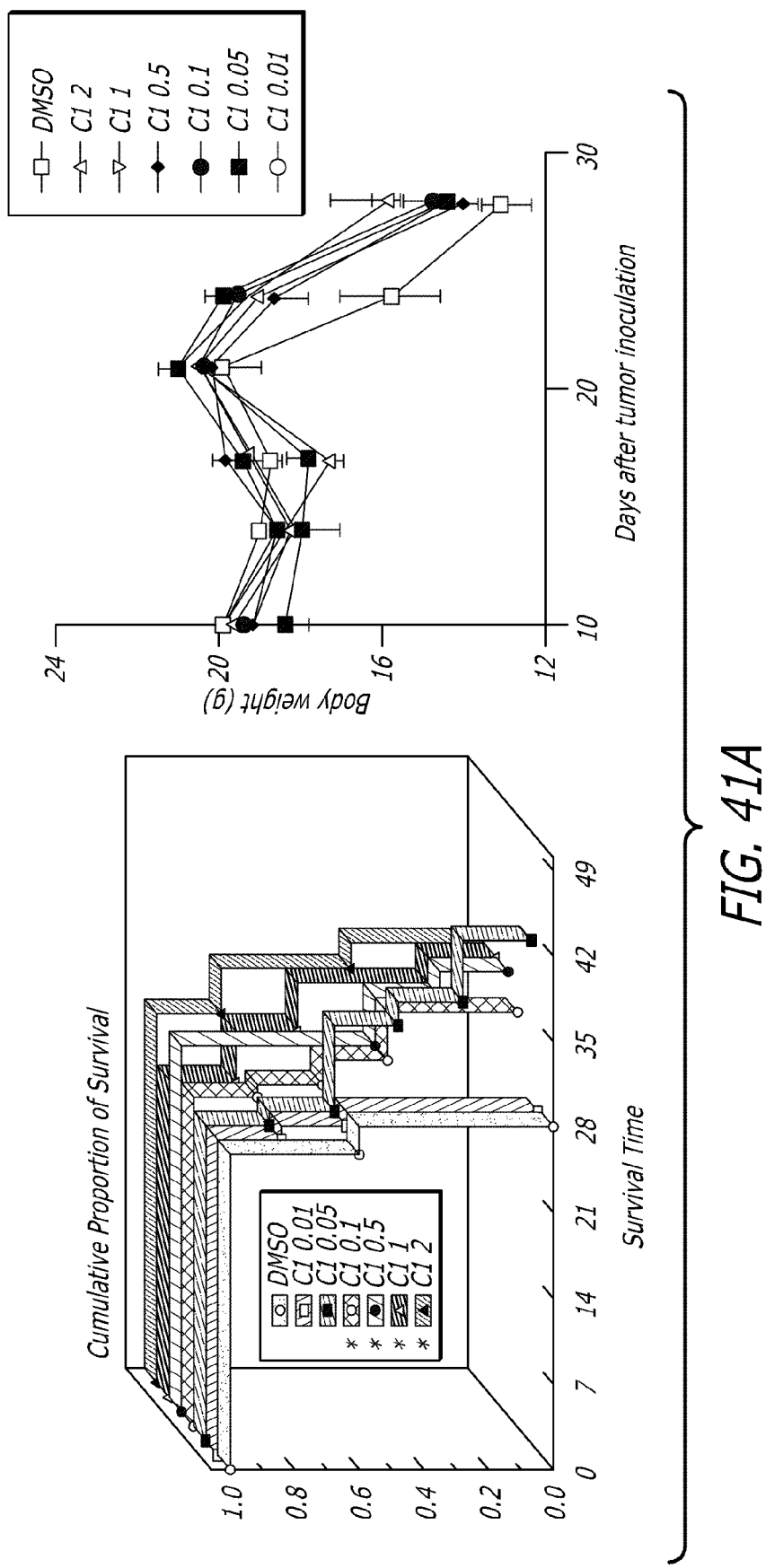
FIG. 41(A-C) show optimization of therapeutic anticancer protocols of α-GalCer analogs of the present disclosure by dosage of administration. Changes in body weight (right panel) and Kaplan Meier survival curves (Left panel) of C57BL/6 mice after IV inoculation with mouse lung cancer cells (TC-1), and then treated with α-GalCer or α-GalCer analogs 7DW8-5 or C26 at various dosages twice per week or once per week for four weeks. (A) α-GalCer. (B) α-GalCer analog 7DW8-5. (C) α-GalCer analogs C26.
Figure 41B:
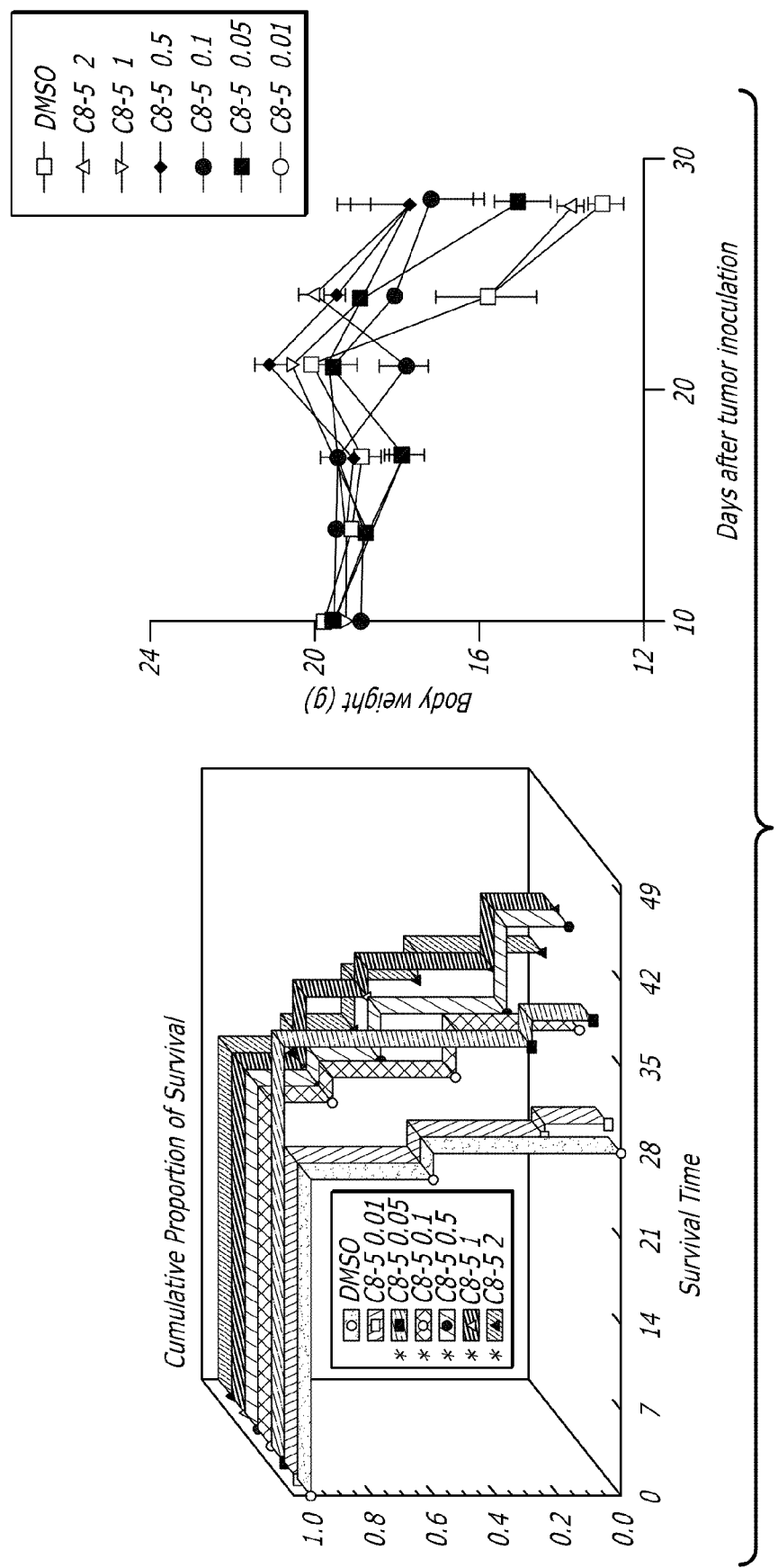
Figure 41C:
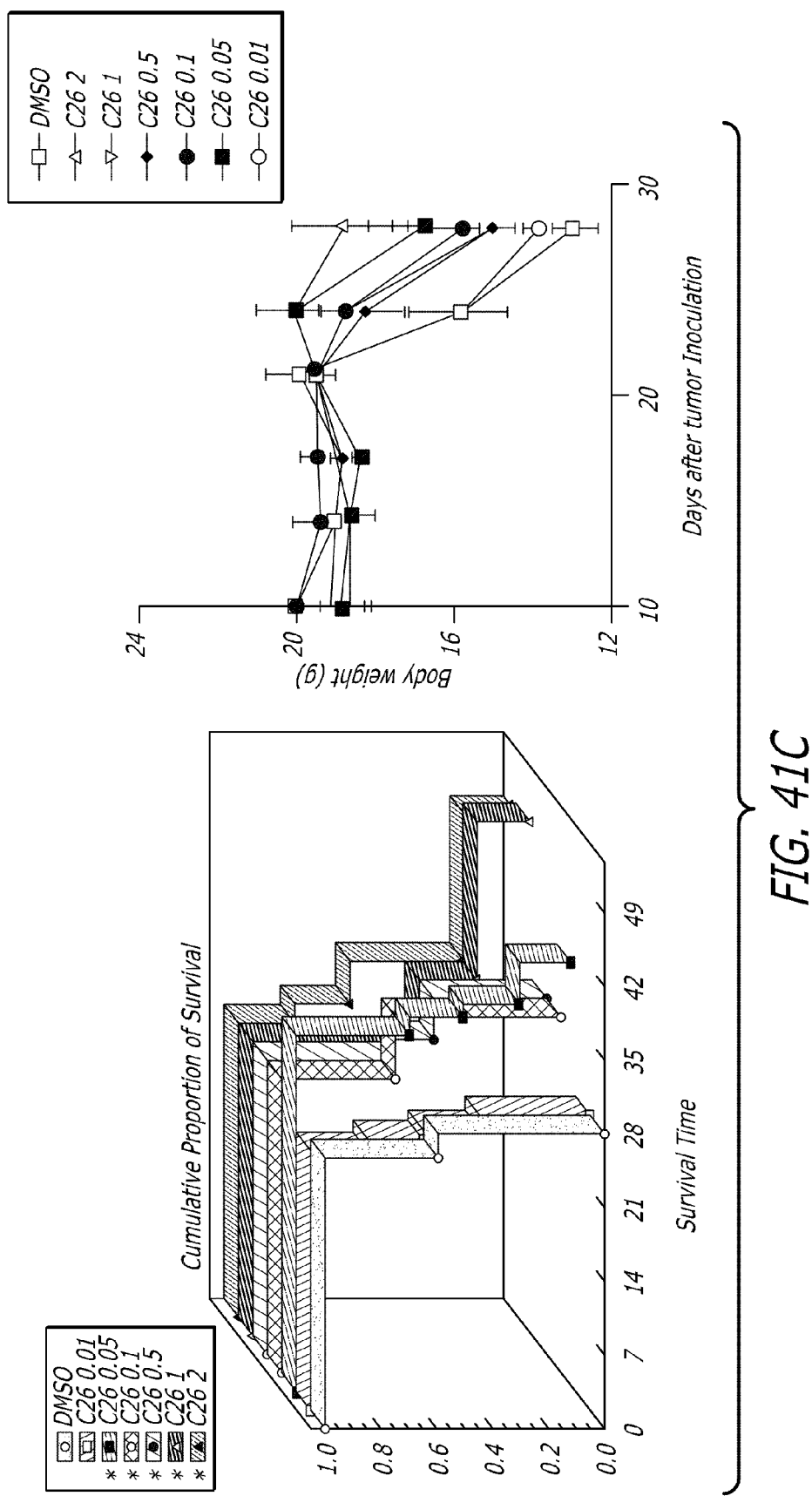
Figure 42A:
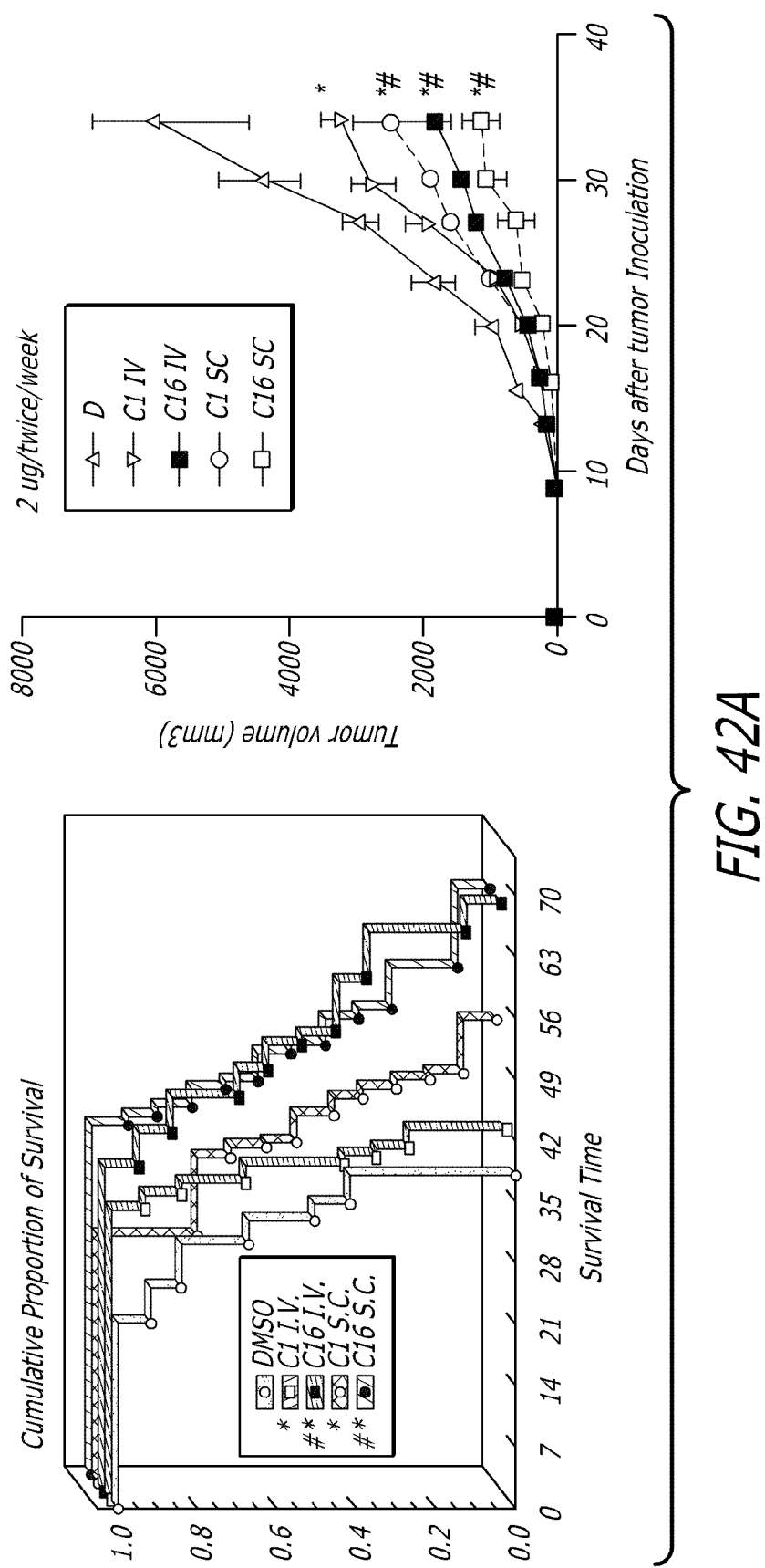
FIG. 42(A-C) show optimization of therapeutic anticancer protocols of α-GalCer analogs of the present disclosure by varying routes and frequency. (A) shows the tumor volume (mm³) (right panel) and Kaplan Meier survival curves (left panel) of BALB/c mice after SubQ inoculation with mouse breast cancer cells, 4T-1, and then treated three days after inoculation with vehicle, α-GalCer or the indicated α-GalCer analogs of the present disclosure twice per week for four weeks by the IV or SubQ route. (B) shows changes in body weight (right panel) and Kaplan Meier survival curves (left panel) of C57BL/6 mice after IV inoculation with mouse lung cancer cells, TC-1, and then treated three days after inoculation with vehicle, α-GalCer or the indicated α-GalCer analogs of the present disclosure twice per week for four weeks by the IV or SubQ route. (C) shows the impacts of frequency of administration on body weight (right panel) and Kaplan Meier survival curves (left panel) of C57BL/6 mice after IV inoculation with mouse lung cancer cells, TC-1, and then treated with vehicle or α-GalCer analog C16 twice per week or once per week for four weeks by the IV route.
Figure 42B:
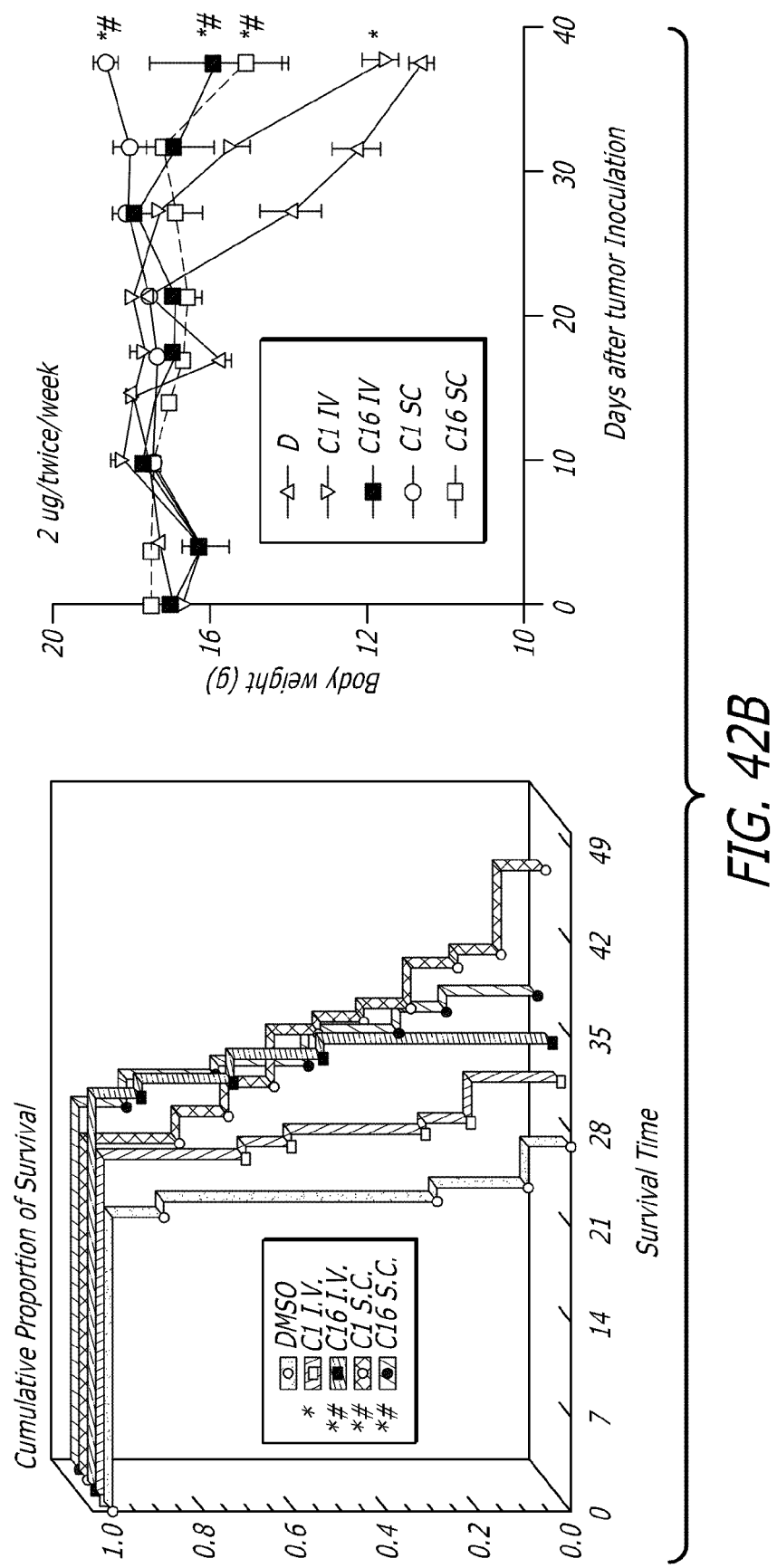
Figure 42C:
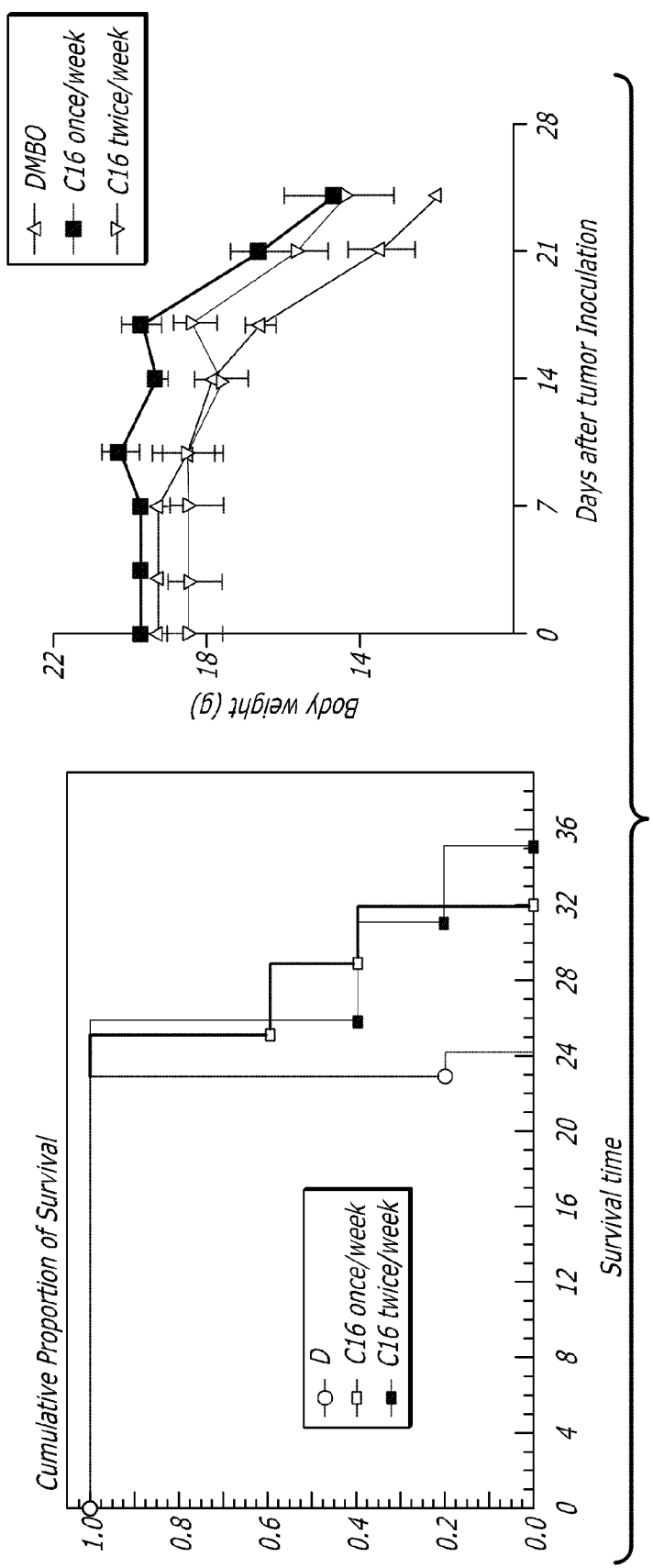

In order to determine the anticancer efficacy of the α-GalCer analogs of the present disclosure, in an exemplary implementation, mouse models of metastatic lung cancer with TC1 cell line, and SubQ tumor model of breast cancer with 4T1 cell line in syngeneic immunocompetent mice (C57BL/6 and BALB/c, respectively) were studied. FIG. 38A shows the result of a representative experiment with reduced number of tumor nodules on the lung surface of mice treated with α-GalCer analog C11. The effects of IV administration of various α-GalCer analogs of the present disclosure from groups l-IV and C1 on the survival of TC1 tumor-bearing mice are shown in FIG. 37. Significant prolongation of survival and reduced weight loss were observed with many of the α-GalCer analogs tested, except for C4, C6, C7, C8 and C17. Moreover, eight of the α-GalCer analogs tested, C3, C10, C11, C12, C13, C14, C15 and C16, have significantly greater anti-cancer efficacy than C1. Next, the anti-tumor efficacy of eight α-GalCer analogs and C1 administered IV on mice bearing 4T1 breast cancer was assessed. The reduced tumor size of mice 16 days after treatment with α-GalCer analog C11 is shown in FIG. 38B as an example. All of the α-GalCer analogs tested were able to suppress tumor growth and prolong survival as compared to the control, and all were more effective than C1, FIG. 39A. Based on these findings, the effect of the SubQ delivery of some of the most active α-GalCer analogs of the present disclosure (C9, C11, C13, C14, C16) and C1 were tested. SubQ delivery of the α-GalCer analogs tested were able to suppress tumor growth and prolong survival as compared to control. α-GalCer analogs C13, C14 and C16 achieved significantly greater suppression of tumor size than C1, although their effects on survival did not differ significantly from that of C1 (FIG. 39B). C1 showed a statistically better efficacy with SubQ delivery over IV route (FIG. 40), whereas the route of administration did not significantly affect the anti-tumor effects of the remaining α-GalCer analogs tested (FIG. 39A-B). Mice receiving a SubQ injection of α-GalCer analogs appeared to be less morbid than those treated IV, which is consistent with lower serum levels of cytokines/chemokines following SubQ administration.

In order to optimize the therapeutic protocol of these novel α-GalCer analogs, we assessed the anticancer efficacy in tumor-bearing mice, with special focus on the routes, frequency, and dosage of administration (see FIG. 41-44). The results showed optimal dose schedule to be IV administration of 0.1 µg α-GalCer per mice, once per week. This is applicable to the treatment of mice bearing breast and lung cancer, as well as melanoma (see, FIGS. 43 and 44). Treatment with new α-GalCer analogs led to an increase in the tumor-infiltrating lymphocytes, including T, CD8T, NK, and NKT (see, FIG. 45). FIG. 41A-B, show the impacts of different routes of administration. (A) BALB/c mice were SubQ inoculated with mouse breast cancer cells, 4T-1. Three days after tumor inoculation, the mice were treated (IV or SubQ) with vehicle, α-GalCer or the indicated α-GalCer analogs (2 µg per mouse) twice per week for four weeks. The tumor volume was recorded every 3 days for 33 days and survival was monitored for up to 70 days. Left panel, Kaplan Meier survival curve of mice bearing breast cancer; right panel, tumor growth curve. (B) C57BL/6 mice were IV inoculated with mouse lung cancer cells, TC-1, and then treated (IV or SubQ) with vehicle, α-GalCer or the indicated α-GalCer analogs (2 µg per mouse) twice per week for four weeks. Left panel, Kaplan Meier survival curve of mice bearing lung cancer; right panel, changes of body weight.

(C) shows the impacts of frequency of administration. C57BL/6 mice were IV inoculated with mouse lung cancer cells, TC-1, and then treated (IV or SubQ) with vehicle, α-GalCer or the indicated α-GalCer analogs (2 µg per mouse) twice per week or once per week for four weeks. Left panel, Kaplan Meier survival curve of mice bearing lung cancer; right panel, changes of body weight.

Figure 43B:
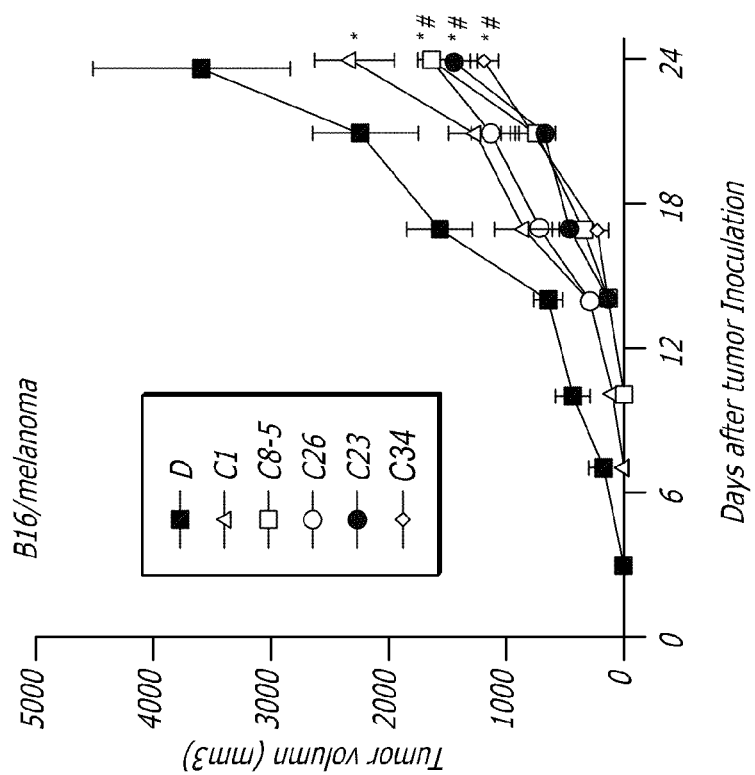
FIG. 43(A-B) show the evaluation of the anticancer efficacy of various α-GalCer analogs of the present disclosure. C57BL/6 mice were IV inoculated with mouse lung cancer cells, TC-1, or SubQ inoculated with mouse melanoma, B16 cells, and then treated with vehicle, α-GalCer or the indicated α-GalCer analogs of the present disclosure once per week for four weeks. (A) shows the Kaplan Meier survival curves. (B) shows the tumor volume (mm³) growth curves.
Figure 43A:
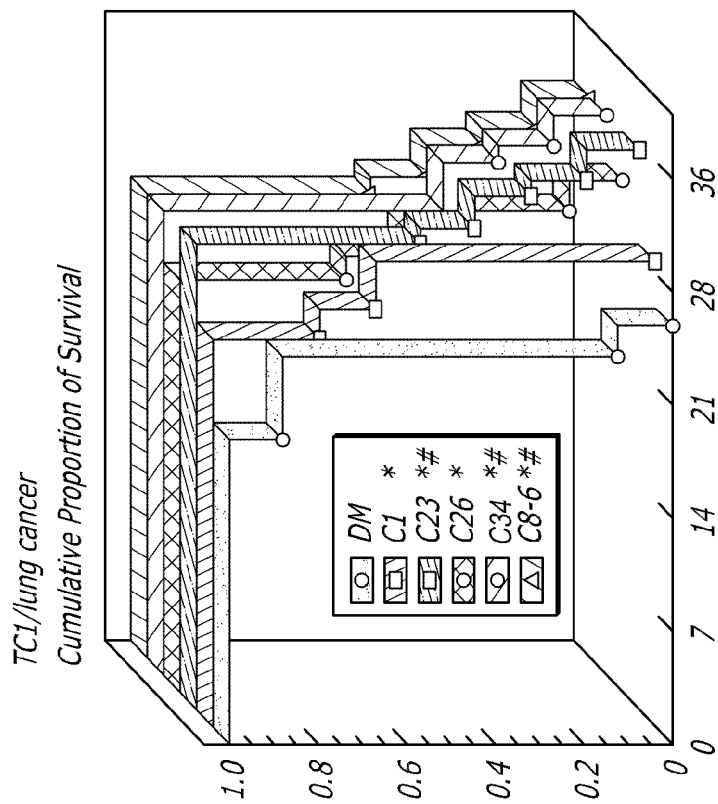
Figure 44:
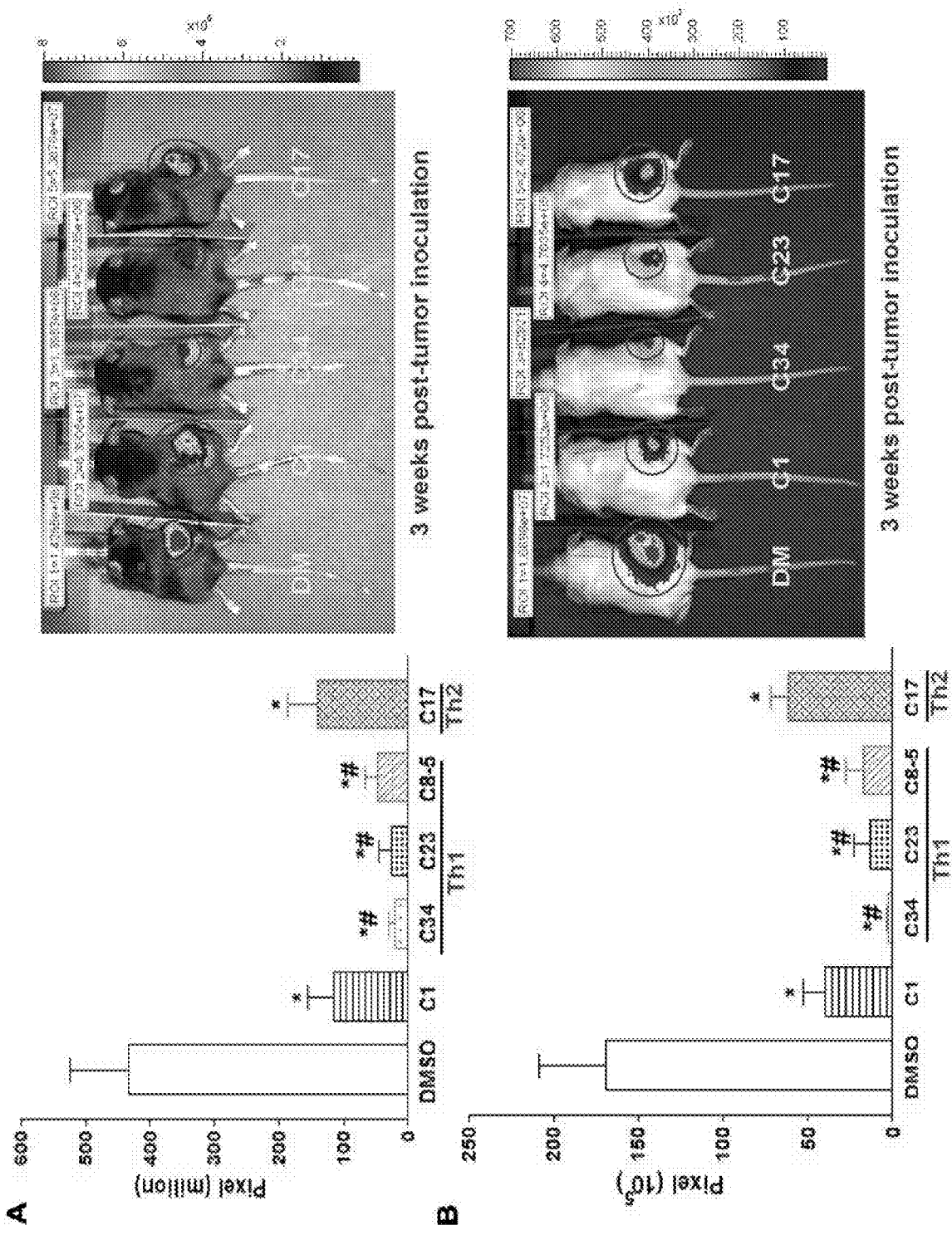
FIG. 44(A-B) show the real time assessment of tumor growth in (A) C57BL/6 mice after SQ inoculation with lung cancer cells (TC-1-GRP-Luciferase) or (B) breast cancer cells (4T-1-GFP-Luciferase), and then treated with vehicle, α-GalCer or the indicated α-GalCer analogs of the present disclosure once per week for four weeks.

FIGS. 43 and 44 show the evaluation of the anticancer efficacy of α-GalCer analogs of the present disclosure with the optimized protocol. FIG. 43 shows C57BL/6 mice were inoculated with lung cancer (TC1) IV or with melanoma (B16) cells SubQ, and then treated IV (0.1 µg per mouse) with vehicle, α-GalCer or the indicated x-GalCer analogs (C23, C26, C34, 7DW8-5) once per week for four weeks. (A) shows the Kaplan Meier survival curve of mice bearing TC1, (B) shows growth curves of B16 tumor. All of the α-GalCer analogs tested showed a significant increase in the survival time of mice bearing TC1. Also, when mice bearing B16 were treated with the α-GalCer analogs of the present disclosure, there was a significant decrease in the size of the tumors. FIG. 44(A-B) show the real time assessment of tumor growth in mice. C57BL/6 mice were SubQ inoculated with (A) lung cancer (TC1-GFP-Luciferase) or (B) breast cancer (4T1-GFP-Luciferase) cells, and then treated IV (0.1 µg per mouse) with vehicle, α-GalCer or the indicated α-GalCer analogs (C23, C34, 7DW8-5 and C17) once per week for four weeks. The pixel of the bioluminescence of the tumor in vivo was assessed and calculated by IVIS system. Left panel, the quantitative data of bioluminescence; Right panel, the representative images of mice bearing tumor. *, p<0.05, compared with DMSO; #, p<0.05, compared with C1. In mice inoculated with lung cancer, the α-GalCer analogs C34, C23 and C8-5 showed a significant decrease in tumor growth compared with both control and α-GalCer. Interestingly, these α-GalCer analogs, C34, C23 and C8-5, all have been shown to produce a $T_H1$-biased response, as shown in the results above. In mice inoculated with breast cancer, the α-GalCer analog C8-5 showed a significant decrease in tumor growth compared with both control and α-GalCer. The α-GalCer analog C17 showed a significant decrease in tumor growth compared with control, but had a similar result to α-GalCer. Interestingly, the α-GalCer analog C17, has been shown to produce a $T_H2$-biased response, as shown in the results above. These results confirm the idea that the production of $T_H1$ cytokines are thought to correlate with antitumor activities.

FIG. 45 shows in an exemplary implementation, how the α-GalCer analogs of the present disclosure elicit $T_H1$-biased tumor infiltrating lymphocytes in lung and melanoma tumors. (A-D) show tumor infiltrating lymphocytes in lung cancer. Single cell suspensions of tumors removed on day 21 from the C57BL/6 mice bearing TC1 tumor treated with vehicle, α-GalCer or the indicated α-GalCer analogs (C23, C34, C8-5; 0.1 µg/mouse, once/week) were stained for (A) CD3$^+$ T cell, (B) CD8 T cells (CD3$^+$/CD4$^-$/CD8$^+$), (C) NKs (NK1.1$^+$/CD3$^-$) and (D) NKTs (NK1.1$^+$/CD3$^+$), normalized to DMSO. The α-GalCer analog C34, showed a significantly significant increase in the number of $T_H1$-biased tumor infiltrating lymphocytes in lung cancer, as compared with both control and α-GalCer. The α-GalCer analogs C23 and C8-5 also showed a significantly significant increase in the number of tumor infiltrating lymphocytes in lung cancer, as compared with control (for CD3$^+$ T cells) and as compared with both control and α-GalCer (for CD8 T cells, NKs and NKTs). (E-H) show tumor infiltrating lymphocytes in melanoma. Single cell suspensions of tumors removed on day 21 from C57BL/6 mice bearing B16 melanoma treated with the vehicle, α-GalCer or the indicated α-GalCer analogs (C23, C34, C8-5; 0.1 µg/mouse, once/week), were stained for (E) CD3$^+$ T cell, (F) CD8 T cells (CD3$^+$/CD4$^-$/CD8$^+$), (G) NKs (NK1.1$^+$/CD3$^-$) and (H) NKTs (NK1.1$^+$/CD3$^+$) and normalized to DMSO. The α-GalCer analogs C23, C8-5 and C34, all showed a significantly significant increase in the number of $T_H1$-biased tumor infiltrating lymphocytes in melanoma, as compared with both control and α-GalCer. *, p<0.05, compared with DMSO; #, p<0.05, compared with C1.

Adjuvant Immunotherapy

Adjuvant Effects on Peptide, Protein, Polysaccharide and DNA Immunogens

Adjuvants are compounds that, when combined with an antigen, potentiate an immune response in an immunized species. For over eighty years, adjuvants have been used to boost the effectiveness of vaccines. Live vaccines, containing weakened forms of an infectious organism, generally work fine by themselves. But vaccines containing dead organisms (inactivated vaccines) or pieces of the infectious organisms or their toxins (acellular or recombinant vaccines) generally need adjuvants to boost their effectiveness. In most situations, the type of response induced (type 1 or type 2) has a significant impact on the protective efficacy of the vaccine. Alternative adjuvants tend to favor specific types of responses. However, adjuvant selection is complicated by functional unpredictabilities and also by commercial constraints and availability.

Aluminum salts, known as alum, are the only adjuvant approved for use in the United States for routine preventive vaccines. However, aluminum salts have been shown to increase in humans, as well as in animals, exclusively a shift to $T_H2$-type responses (e.g., IL-4 production). The inability of aluminum salts to elicit a $T_H1$ cell-mediated immune responses (e.g., IFN-y production) is a major limitation of its use as adjuvant. Particularly for vaccines against intracellular viral and bacterial infections, the lack of cytotoxic T cell responses is fatal.

The α-GalCer analogs of the present disclosure may be synthesized such that a $T_H1$ biased immunogenic response is initiated. Therefore, improved vaccines which show a $T_H1$-type directed immune response or vaccines which allow-in addition to a $T_H2$-type response-also a $T_H1$-type shift of the immune reaction may be achieved using the α-GalCer analogs of the present disclosure as adjuvants. As such, one or more α-GalCer analogs are administered as an adjuvant in conjunction with administration of a vaccine. Moreover, vaccines already available can be provided in an improved form, when the α-GalCer analogs of the present disclosure are added to them, which allows the induction of a $T_H1$-type response.

In some exemplary implementations the disclosure provides a vaccine comprising an effective amount of a compound or a salt or a mixture thereof selected from the group consisting of C3, C11, C13-C14, C16-C18, C20, C22-C24, C26, C8-5 and C8-6; and a vaccine agent. In some instances the vaccine agent is selected from the group consisting of a killed microorganism, a live attenuated virus microorganism, a toxoid and a fragment of an inactivated or attenuated microorganism. In some instances the microorganism is a bacteria or a fungi. In some instances the toxoid is a tetanus or a diphtheria. In some instances the vaccine agent is capable of eliciting an immune response in a subject that is administered the vaccine. In some instances the compound acts as an immunologic adjuvant and is capable of modifying or augmenting the immune response elicited by the vaccine agent by stimulating the immune system which results in the subject responding to the vaccine more vigorously than without the compound.

In one aspect, appropriate vaccines may comprise peptide, protein, polysaccharide or DNA immunogens. In another aspect, the vaccine may be selected from one or more commercially available vaccines, such as, but not limited to, vaccines for Hepatitis A, Hepatitis B, Rotavirus, Diptheria, Tetanus, Pertussis, *Haemophilus influenza* type b, Pneumococcal, Poliovirus, Influenza, Measles, Mumps, Rubella, Varicella, Meningiococcal, Human Papillomavirus, Herpes Zoster, *Borrelia burgdorferi, Typhoid, Japanese encephalitis, Rabies, Tick Borne encephalitis, Cholera, Yellow Fever, H5N1, West Nile, Parvovirus, Feline Rhinotracheitis, Calicivirus, Panleukopenia virus, Chlamydia psittaci, Feline leukemia, Canine Distemper, Canine Adenovirus, Canine Parainfluenza, Bordetella Bronchiseptica*, Canine Coronavirus, *Giardia lamblia, Leptospira* bacterin, Infectious Bovine Rhinotracheitis virus, Parainfluenza 3 virus, Bovine Repiratory Syncytial virus, Bovine Viral Diarrhea virus, *Clostridium Chauvoei, Septicum Haemolyticum, Septicum Novyi, Tetani, Sordellii Perfringens, Moraxella bovis, Mannheimia haemolytica, Pateurella multocida, Leptospira pomona, Leptospira hardjo, Leptospira grippotyphosa, Leptospira canicola,* and *Leptospira icterohaemorrhagiae*.

A method is provided for enhancing immunogenicity of a compound, composition, or vaccine in a subject, the method including: administering to the subject a compound, composition or vaccine further comprising an adjuvant according to the present disclosure, wherein the adjuvant enhances the immunogenicity of the compound, composition or vaccine.

Figure 46A:
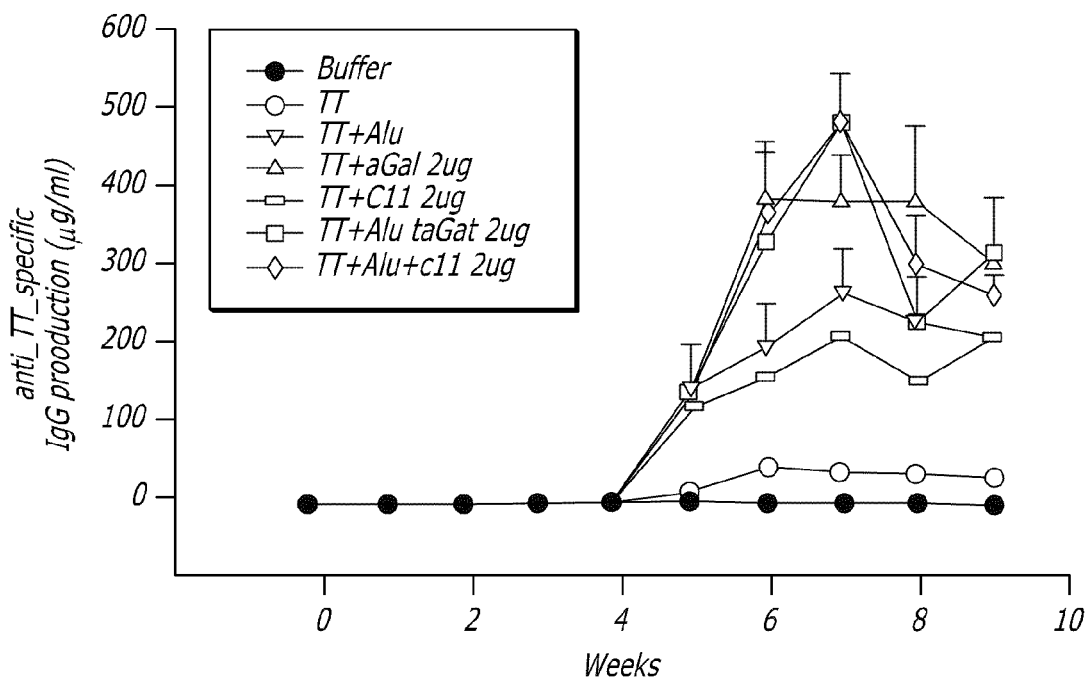
FIG. 46(A-B) show adjuvant effects of alum, α-GalCer and α-GalCer analog C11 on antibody response to tetanus toxoid (TT)—protein vaccine. (A) mice were vaccinated TT without or with conventional adjuvant alum, α-GalCer or α-GalCer analog C11 on day 0 (first vaccination) and day 28 (4 weeks-second vaccination). Serum was harvested weekly for determination of anti-TT-specific antibodies. (B) shows the effects of conventional adjuvant alum, α-GalCer and α-GalCer analog C11 on delayed antigen boost 20 weeks after the second vaccination.
Figure 46B:
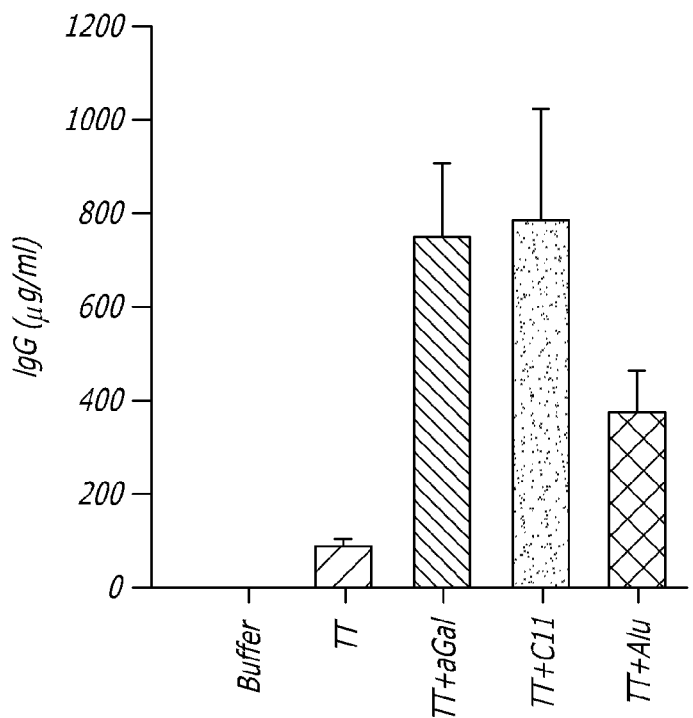

Adjuvant Effect on Protein Vaccines

α-GalCer and the α-GalCer analogs of the present disclosure were tested for the ability to enhance immune responses to existing protein based vaccine such as tetanus toxoid (TT) inactivated toxin. Mice were vaccinated TT without or with α-GalCer analogs of the present disclosure on day 0 and day 28. Serum was harvested weekly for determination of anti-TT-specific antibodies. FIG. 46A shows adjuvant effects of α-GalCer analogs of the present disclosure on antibody response to TT. As shown in FIG. 46A, production of anti-TT-specific IgG antibody was enhanced by α-GalCer (C1) and the α-GalCer analog C11. Although the kinetics of anti-TT production was similar to that induced by conventional adjuvant alum ("Alum"), C1 elicited significantly greater antibody production than Alum. When the conventional TT+Alum was combined with C1 or C11, the antibody response was further augmented to ~2 fold of conventional vaccine. These findings indicate that C1 and C11 had adjuvant effects which are synergistic with Alum to further augment immune responses. The adjuvant effects of the α-GalCer analog C11 were remarkably durable. Twenty weeks after the second immunization, a booster dose of TT alone (without Alum or α-GalCer analog C11) in mice led to a rapid rise of anti-TT antibody 1 week later. FIG. 46B shows the effects of α-GalCer analog C11 on delayed antigen boost twenty weeks after the second vaccination. The level of antibody in mice treated with C1 or C11 was twice as high as those given TT+Alum, and more than 25 fold higher than those injected with TT only as shown in FIG. 46B. These findings suggested that C1 or the α-GalCer analog C11 have effects on the memory T and B cells leading to an augmented booster immune response.

Adjuvant Effect on Peptide Vaccines

Figure 47:
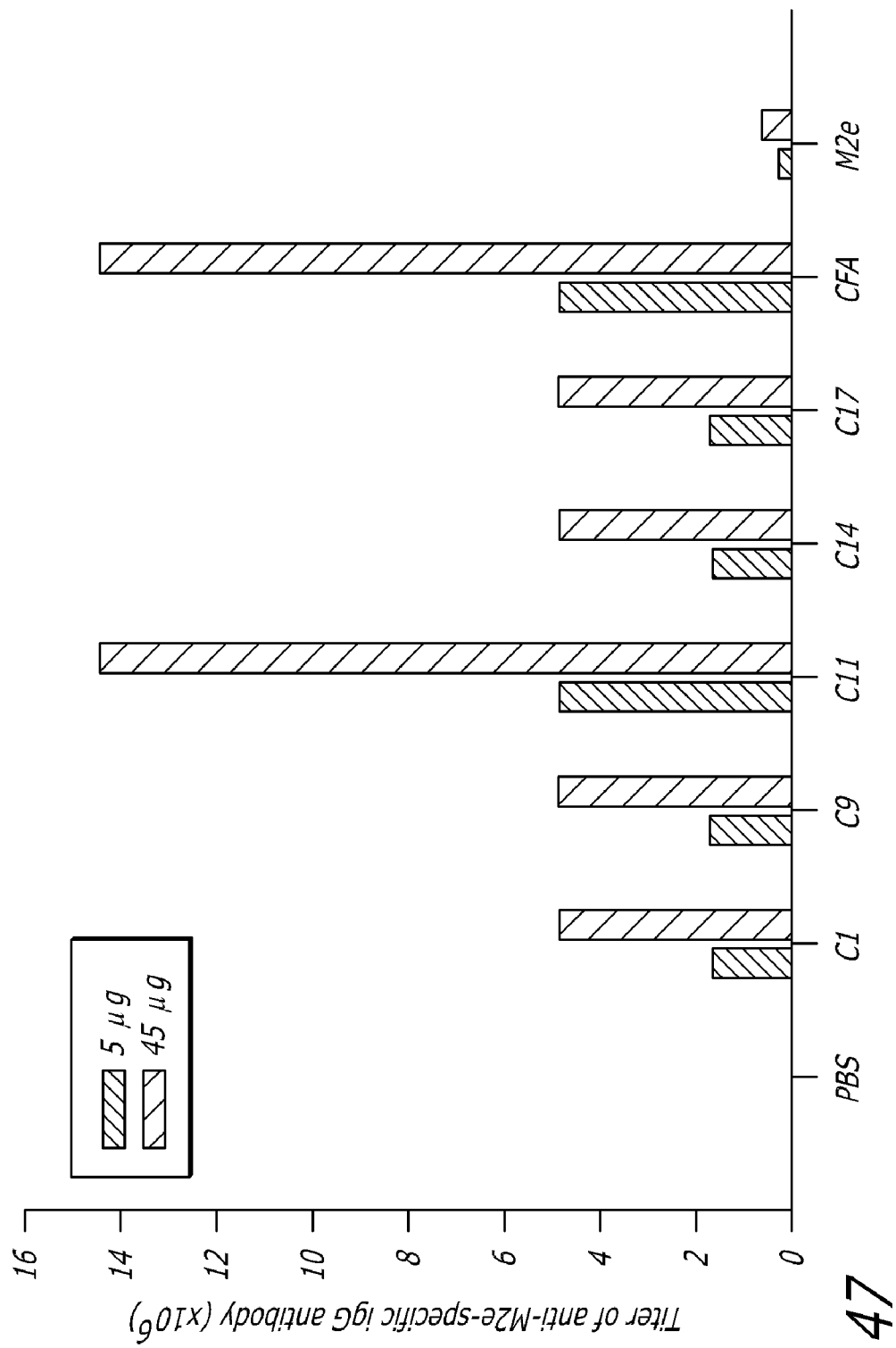
FIG. 47 shows adjuvant effects of conventional adjuvant alum, α-GalCer and various α-GalCer analogs of the present disclosure on peptide containing extracellular domain of M2 (M2e) protein of H1N1 virus strain, two weeks after a third immunization. BALB/c mice were vaccinated with 5 or 45 μg of M2e peptide with or without α-GalCer and various α-GalCer analogs on week 0, 3 and 6.

The adjuvant effects were evaluated with peptide vaccine containing the extracellular domain of the M2 protein of the H1N1 subtype of the Influenza A virus. The amino acid sequence of the peptide vaccine was MSLLTEVET-PIRNEWGCRCN. Female BALB/c mice were vaccinated with 5 or 45 μg of M2e peptide without or with various α-GalCer analogs of the present disclosure (C9, C11, C14, C17) on week 0, 3, and 6. FIG. 47 shows adjuvant effects of various α-GalCer analogs on M2e peptide vaccine. As shown in FIG. 47, two weeks after the third immunization, the M2e peptide alone induced anti-M2e-specific IgG titer of $1.8 \times 10^5$ and $5.4 \times 10^5$ for 5 and 45 μg antigen dosage, respectively. When combined with α-GalCer analogs of the present disclosure, 10–30 fold higher anti-M2 antibody titers were obtained. Among the α-GalCer analogs tested, C11 had the best adjuvant effect which was equivalent to complete Freund's adjuvant (CFA) but 3 fold higher titer than C1. The remaining α-GalCer analogs (C9, C14 and C17) were equivalent to C1. These findings suggest that α-GalCer and its analogs have strong adjuvant activities for peptide antigens with those containing aromatic ring in the acyl tail such as C11 being most potent.

Adjuvant Effect on DNA Vaccines

Figure 48A:
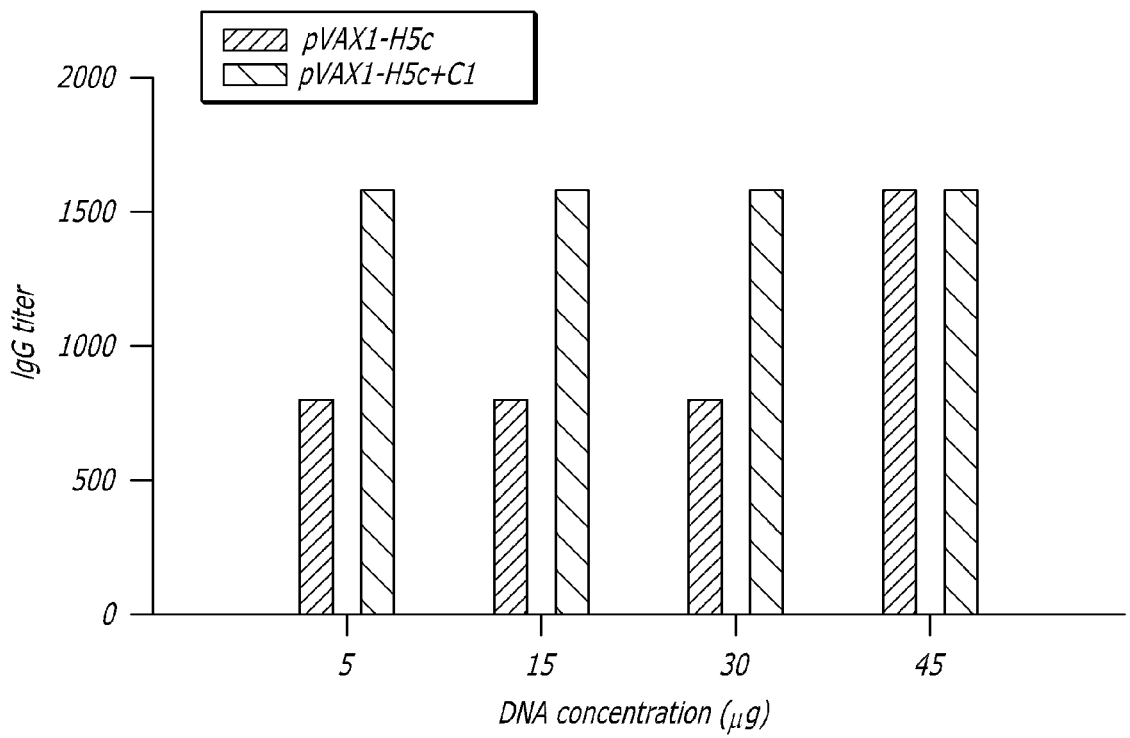
FIG. 48(A-C) shows adjuvant effects of α-GalCer (C1) on mice immunized with pHA, a DNA plasmid containing consensus sequence of full length H5 of avian influenza viruses. (A) mice were immunized with between 5 and 45 μg of pHA without or with C1 on week 0 and 3. (B) mice were immunized with low doses of pHA vaccine without or with C1. (C) shows protection against viral challenge with 20 $LD_{50}$ of Vietnam reassortant influenza strain NIBRG-14 two weeks after H5 DNA vaccine without or with C1.
Figure 48B:
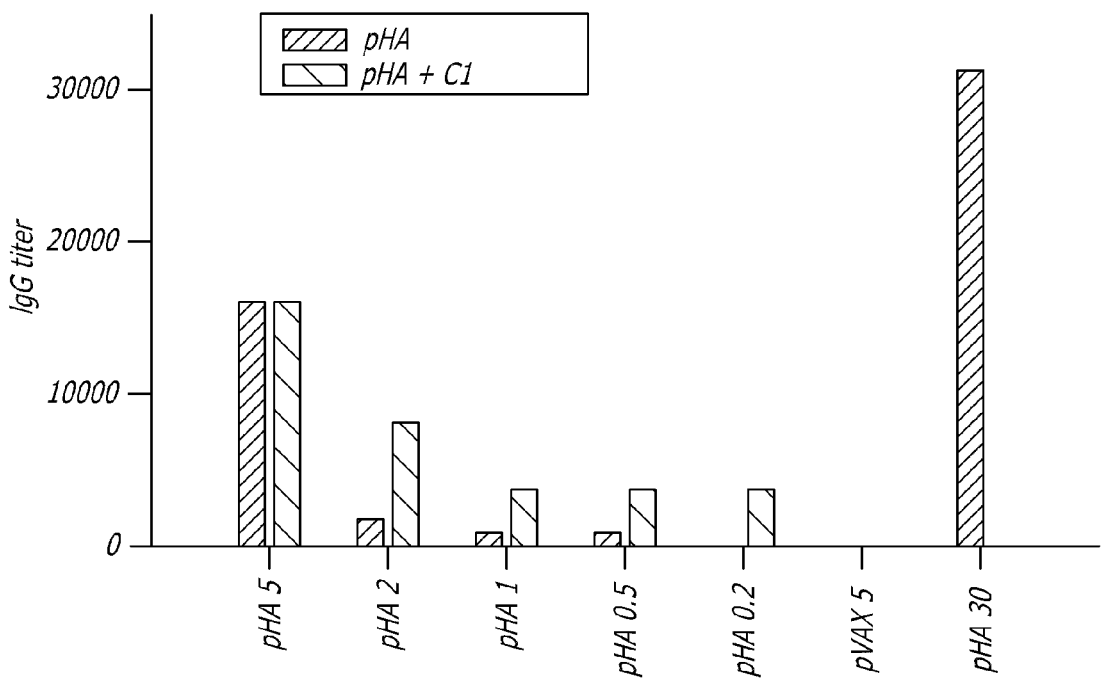
Figure 48C:
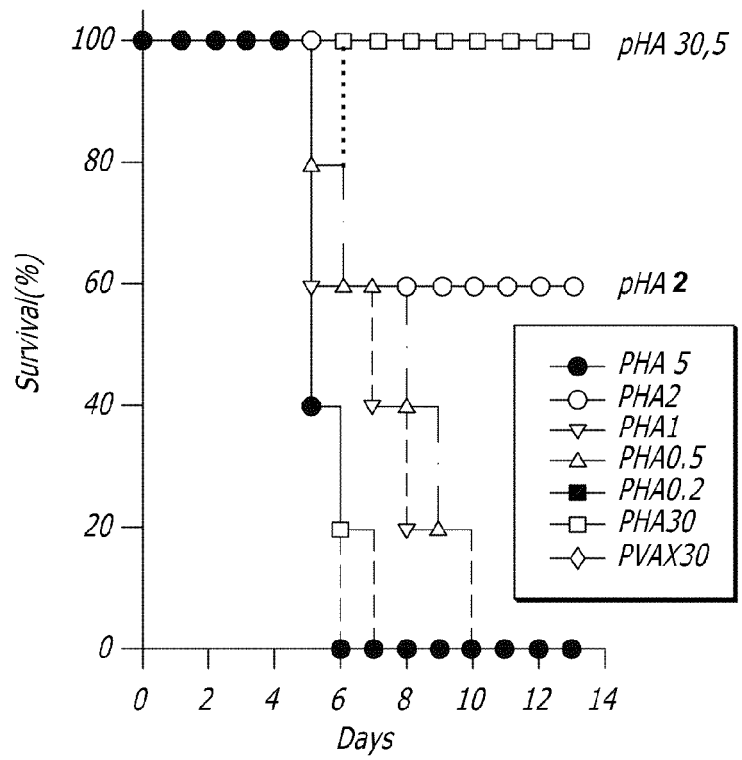
Figure 48D:
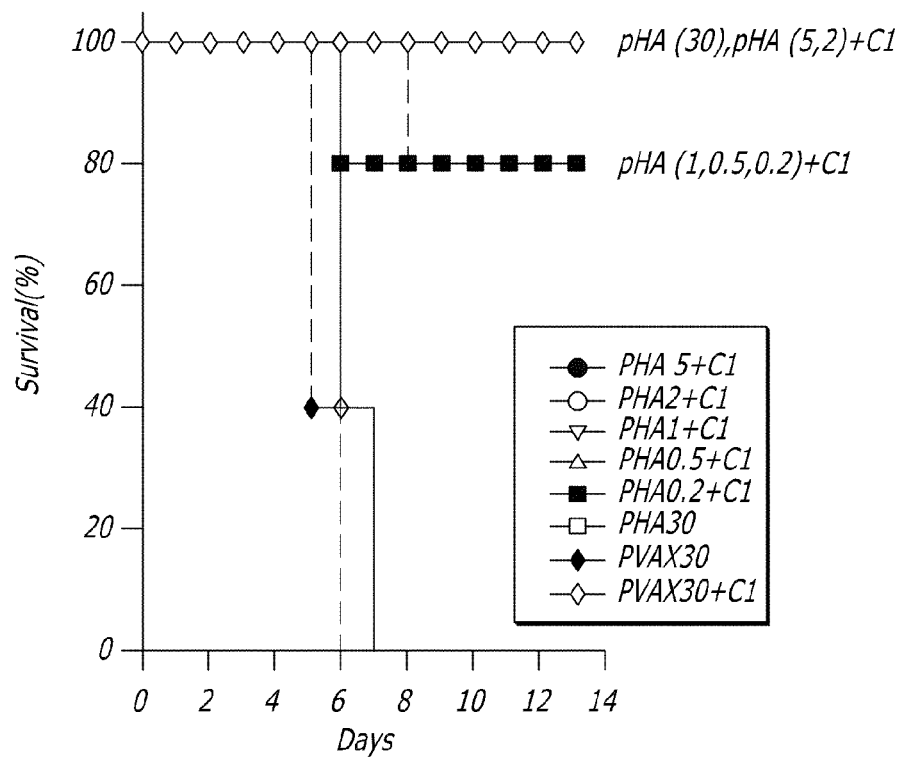

An H5 DNA construct (pHA) was prepared as a plasmid containing full length H5 consensus sequence of avian influenza viruses. Briefly, in order to cover the genetic variability and thus induce cross-protection across different H5N1 strains, a consensus HA sequence was deduced from HA gene of 500 H5N1 virus strains and used for a vaccine development effort. The consensus sequences of HA were constructed into a pVAX vector as DNA vaccine candidates, based on a similar strategy for ADVAX, a DNA vaccine for HIV, developed by Ho et al. (Jin et al., (2002) J. Virol. 76 (5):2306-2216). The effects of H5 DNA vaccine (pHA) dosage without and with α-GalCer (C1) on anti-H5 titers in mice at three weeks after first immunization are shown in FIG. 48A. Immunization of mice with 5-45 μg H5 DNA vaccine without or with x-GalCer showed that the anti-H5 responses were enhanced by α-GalCer at 5-30 μg H5 DNA, but reached a plateau at 45 μg. FIG. 48B shows the effects of low dose H5 DNA vaccine and α-GalCer (C1) on anti-H5 titers two weeks after second immunization. When H5 DNA dose was reduced to 0.2-5 μg, the adjuvant effect of v-GalCer was evident for all low dosages tested. FIG. 48C shows protection against viral challenge by Vietnam reassortant influenza strain NIBRG-14 two weeks after low dose H5 DNA vaccine without or with C1. None of the animals treated with <2 μg survived viral challenges with 20 $LD_{50}$ of NIBRG-14 without α-GalCer, while 80% protection was noted among those treated with 0.2 to 1 μg pHA with α-GalCer (FIG. 48C). These findings confirm the adjuvant effects of α-GalCer when used with low dose pHA vaccine on induction of protective immunity against NIBRG-14.

Figure 49A:
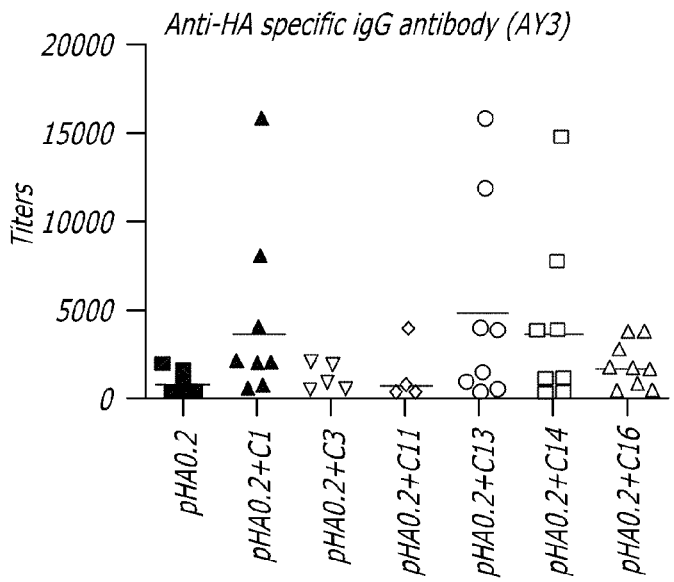
FIG. 49(A-C) show induction of anti-HA-specific IgG antibody after mice were immunized with pHA with or without C1 or the indicated α-GalCer analogs of the present disclosure. (A) shows titers of anti-HA specific IgG antibody (AY3) in mice following immunization with 0.2 µg pHA. (B) shows titers of anti-HA specific IgG antibody (AY4) in mice following immunization with 0.2 µg pHA. (C) shows percent mouse survival following viral challenge.
Figure 49B:
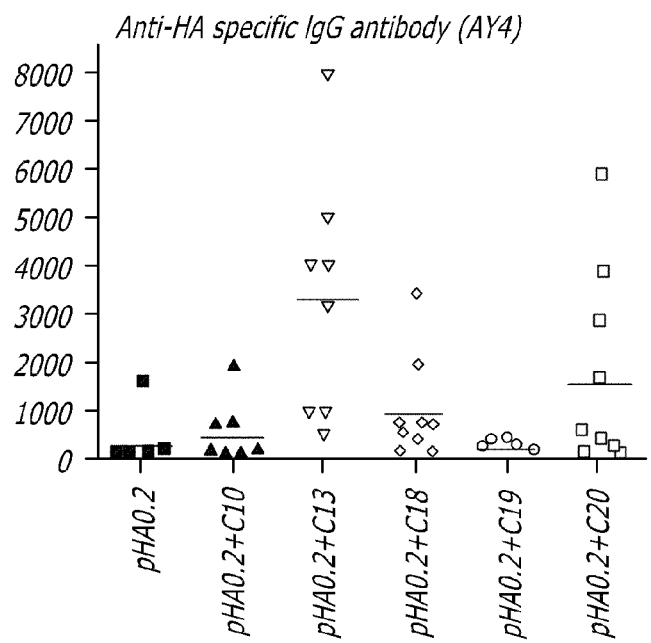
Figure 49C:
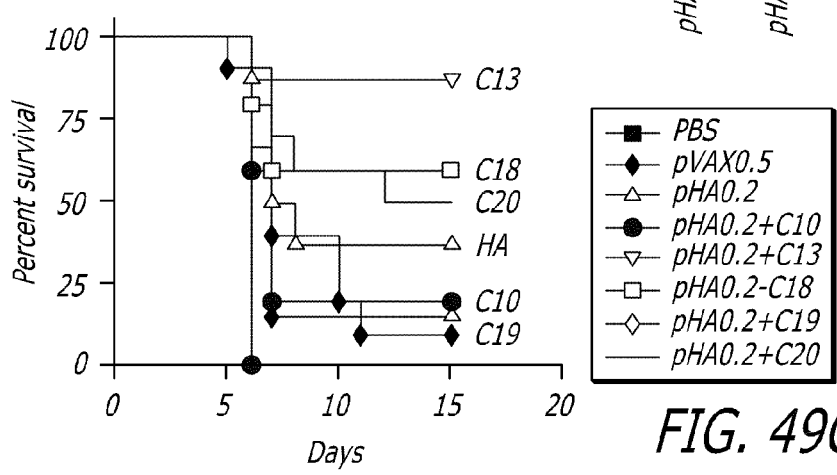
Figure 50A:
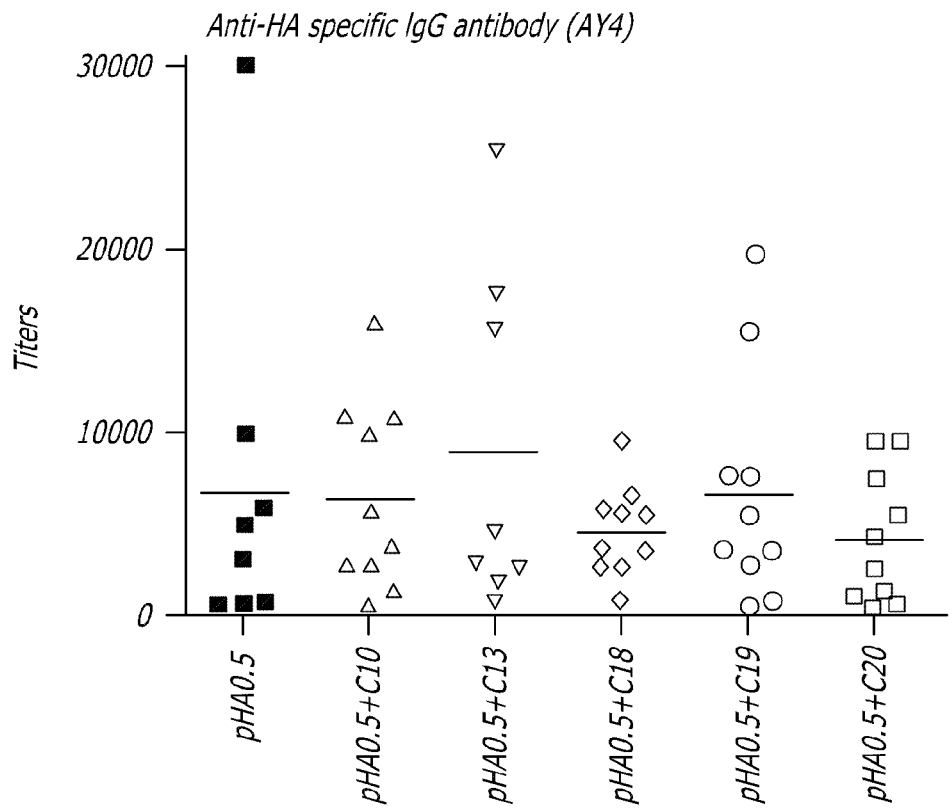
FIG. 50(A-B) show induction of anti-HA-specific IgG antibody after mice were immunized with pHA with or without C1 or the indicated α-GalCer analogs of the present disclosure. (A) shows titers of anti-HA specific IgG antibody (AY4) following immunization with 0.5 µg pHA and the indicated α-GalCer analogs of the present disclosure. (B) shows percent survival following viral challenge.
Figure 50B:
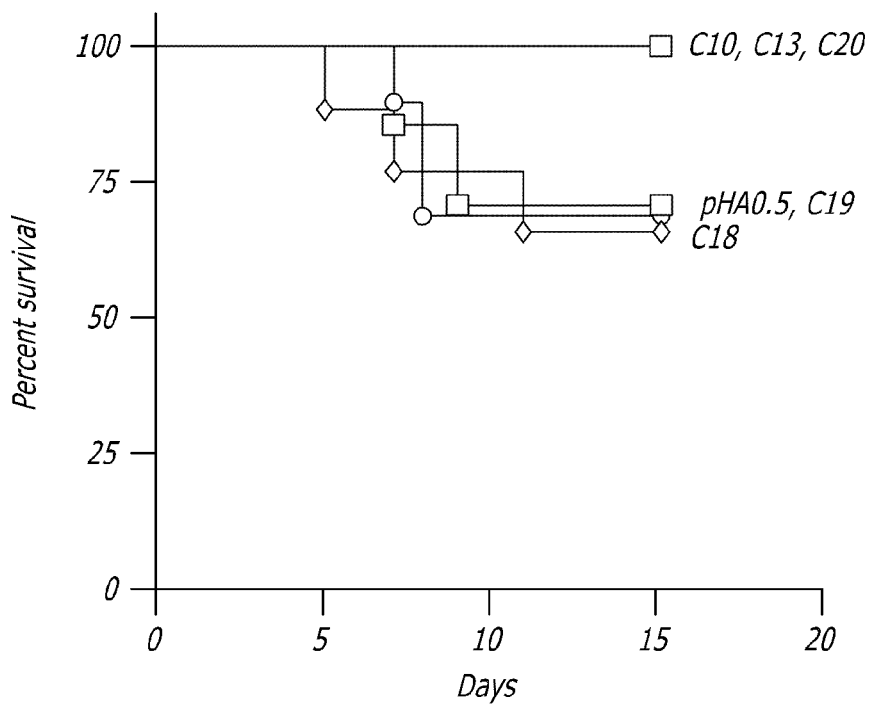
Figure 51A:
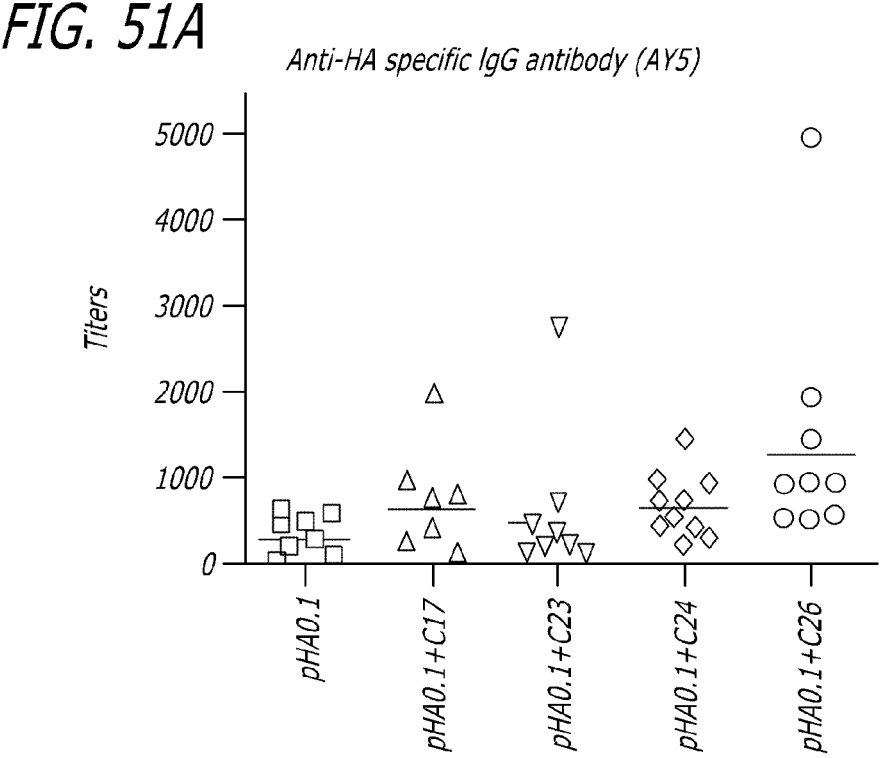
FIG. 51(A-B) show mouse titer of anti-HA specific IgG antibody (AY5) following immunization with either (A) 0.1 µg pHA or (B) 0.2 µg pHA and the indicated α-GalCer analogs of the present disclosure.
Figure 51B:
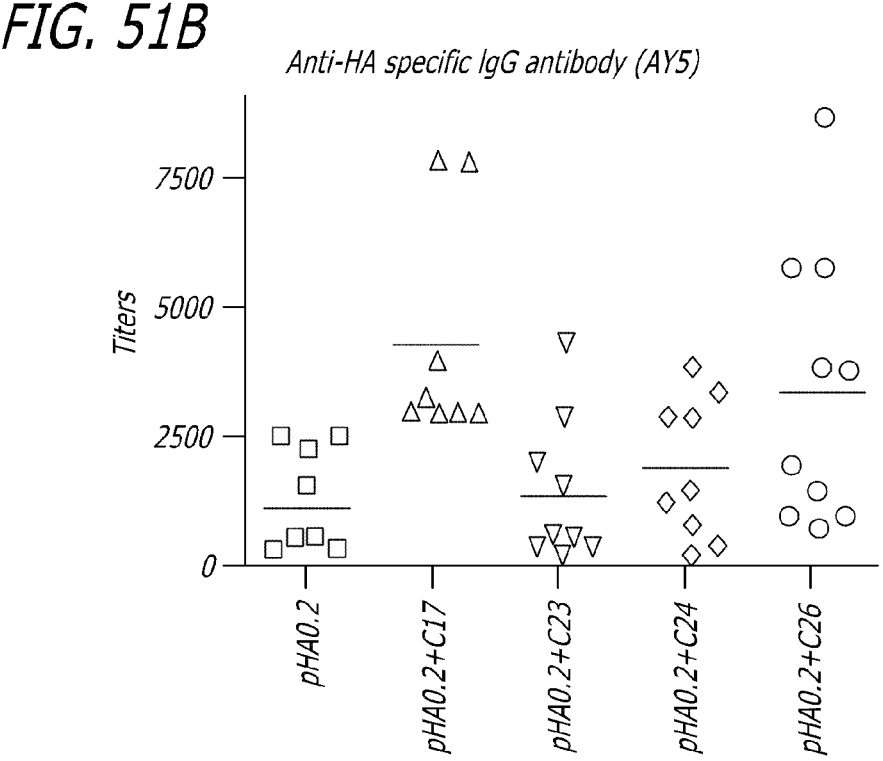
Figure 52A:
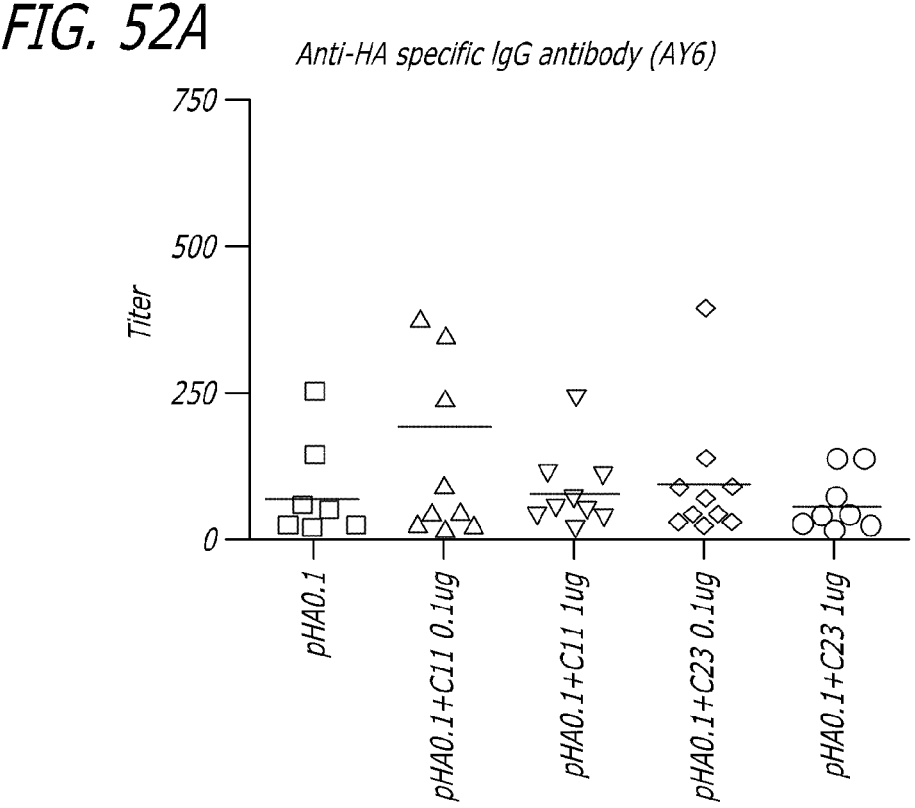
FIG. 52(A-B) show mouse titer of anti-HA specific IgG antibody (AY6) following immunization with either (A) 0.1 µg pHA or (B) 0.2 µg pHA and the indicated α-GalCer analogs of the present disclosure at 0.1 µg or 1 µg.
Figure 52B:
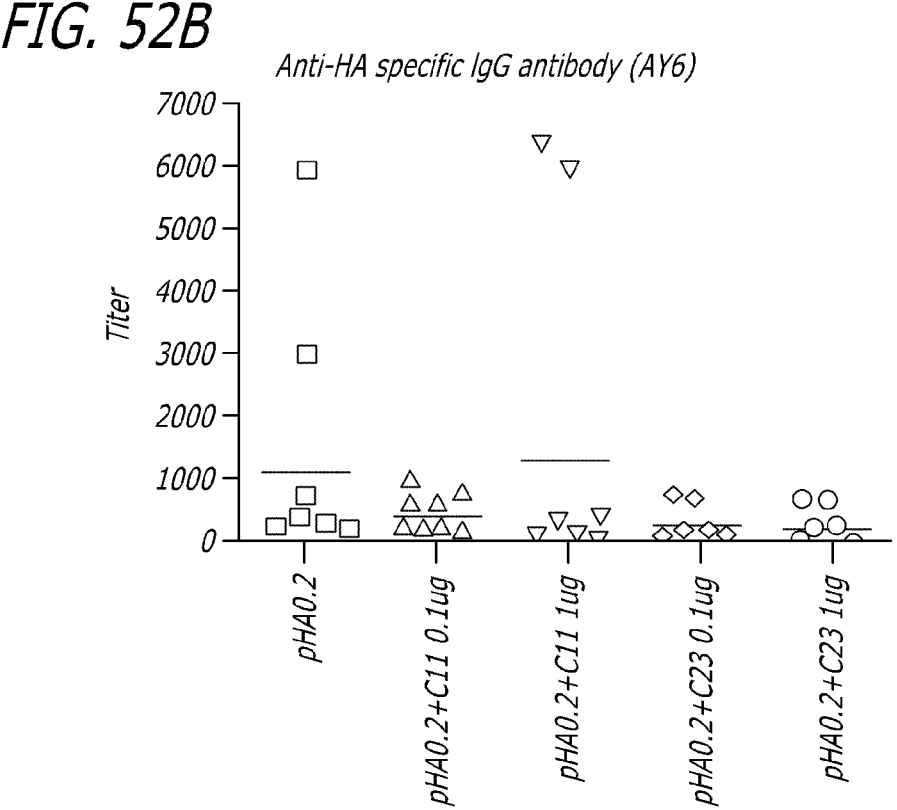

Other α-GalCer analogs of the present disclosure were also tested as adjuvants with the pHA vaccine in mice with a similar protocol and schedule as used above, differences are noted. 6-7 week old female BALB/C mice were vaccinated by electrotransfer in muscle with α-GalCer or the indicated α-GalCer analogs with pHAc and boosted once with the same formulation four weeks later. Blood samples were collected at 2 weeks after the second vaccination and tested for anti-HAc-specific IgG antibody titers by ELISA. FIG. 49A shows titers of anti-HA specific IgG antibody (AY3) in mice following immunization with 0.2 μg pHA without or with α-GalCer or α-GalCer analog C3, C11, C13, C14 and C16. FIG. 49B shows titers of anti-HA specific IgG antibody (AY4) in mice following immunization with 0.2 μg pHA without or with α-GalCer or α-GalCer analog C10 C13, C18, C19 and C20. FIG. 49C shows percent mouse survival following viral challenge as above for some of the α-GalCer analogs tested. FIG. 50A shows anti-HA specific IgG antibody (AY4) following immunization with 0.5 μg pHA and indicated α-GalCer analogs. FIG. 50B shows percent survival following viral challenge as described above. FIG. 51 shows mouse titer of anti-HA specific IgG antibody (AY5) following immunization with either (A) 0.1 μg pHA (pHA$_{0.1}$ vs pHA$_{0.1}$+C26: p<0.01 in one-way ANOVA Kruskal-Walis test) or (B) 0.2 μg pHA (pHA$_{0.2}$ vs pHA$_{0.2}$+C17: p<0.01, pHA$_{02}$ vs pHA$_{0.2}$+C26: p<0.05 in one-way ANOVA Kruskal-Walis test) and the indicated α-GalCer analog. FIG. 52 shows mouse titers of anti-HA specific IgG antibody (AY6) following immunization with either (A) 0.1 μg pHA or (B) 0.2 μg pHA and the indicated α-GalCer analog at 0.1 μg or 1 μg. α-GalCer analog of the present disclosure particularly effective as adjuvants at 0.2 μg-pHA dose were C13, C17, C20 and C26.

Figure 54A:
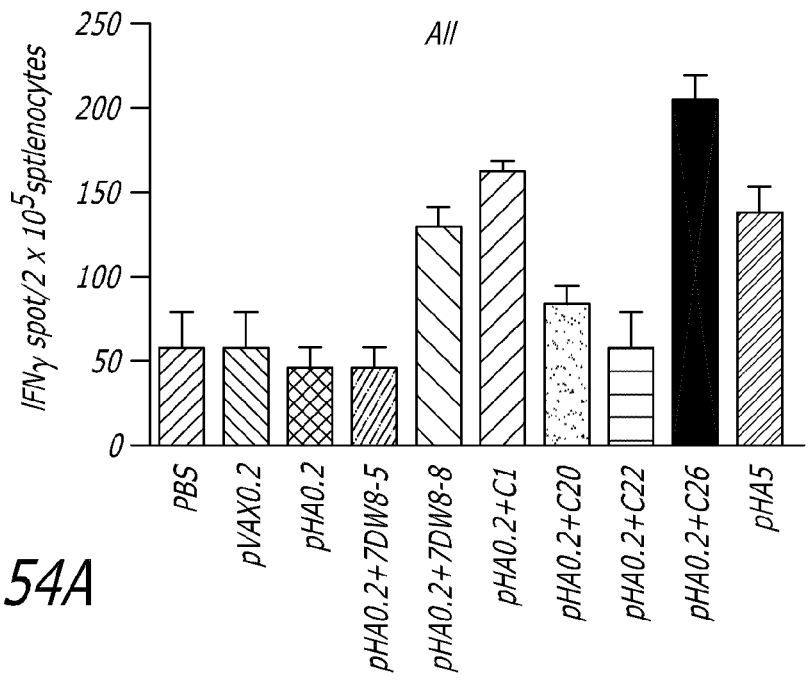
FIG. 54(A-B) show (A) HA-specific IFN-γ producing cells and (B) HA-specific peptide response cells. BALB/c mice were vaccinated by electrotransfer in muscle with pHAc and α-GalCer or the indicated α-GalCer analogs of the present disclosure and boosted once with the same formulation three weeks later. Splenocytes were cultured with HA-specific peptide (9-mer) and spots were determined after 1 day.
Figure 54B:
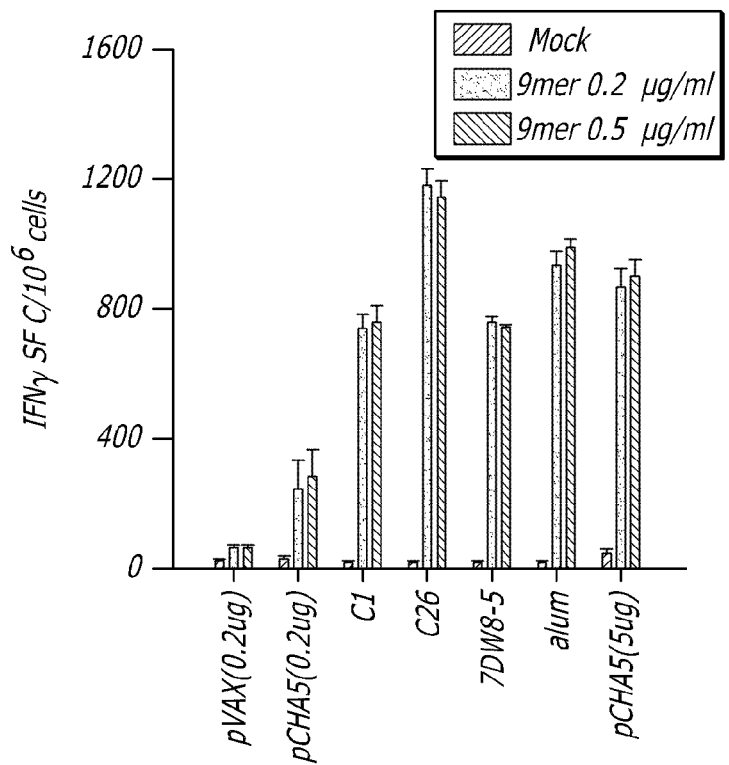
Figure 55:
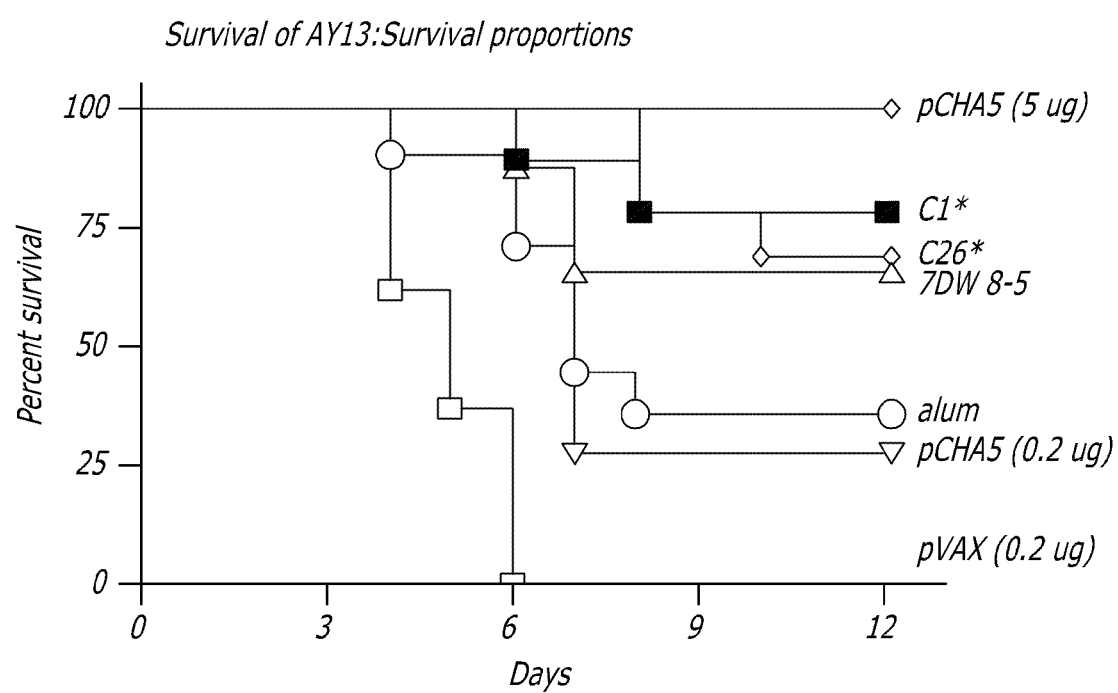
FIG. 55 shows protection against viral challenge. BALB/c mice were vaccinated by electrotransfer in muscle with pHAc and α-GalCer or the indicated α-GalCer analogs of the present disclosure and boosted once with the same formulation three weeks later. Mice were challenged with 200 LD$_{50}$ NIBRG-14 viruses at two weeks after the second vaccination and mice survival was monitored.

FIG. 53 shows mouse titers of anti-HAc specific IgG antibody (A) AY3, (B) AY4, (C) AY5 and (D) AY15 following immunization with 0.2 μg pHAc and α-GalCer or the indicated α-GalCer analog C3, C10, C11, C13, C14, C16, C17, C18, C19, C20, C23, C24, C26, 7DW8-5, and alum. The results indicate that C1, C13, C14, C17, C26 and 7DW8-5 had the better adjuvant activities than the others in enhancing the antibody titer. To investigate whether the HA specific CD8 T cell response would be enhanced by the use of an α-GalCer analog of the present disclosure as an adjuvant, C1, C26 and 7DW8-5 were assessed further. As shown in FIG. 54, the IFN-γ secreting cells increased in α-GalCer analog-adjuvanted groups. Furthermore, after NIBRG-14 virus challenge, the survival percentage of C1, C26 and 7DW8-5 adjuvanted groups were higher than alum-adjuvanted or pHA only groups (FIG. 55).

Figure 56A:
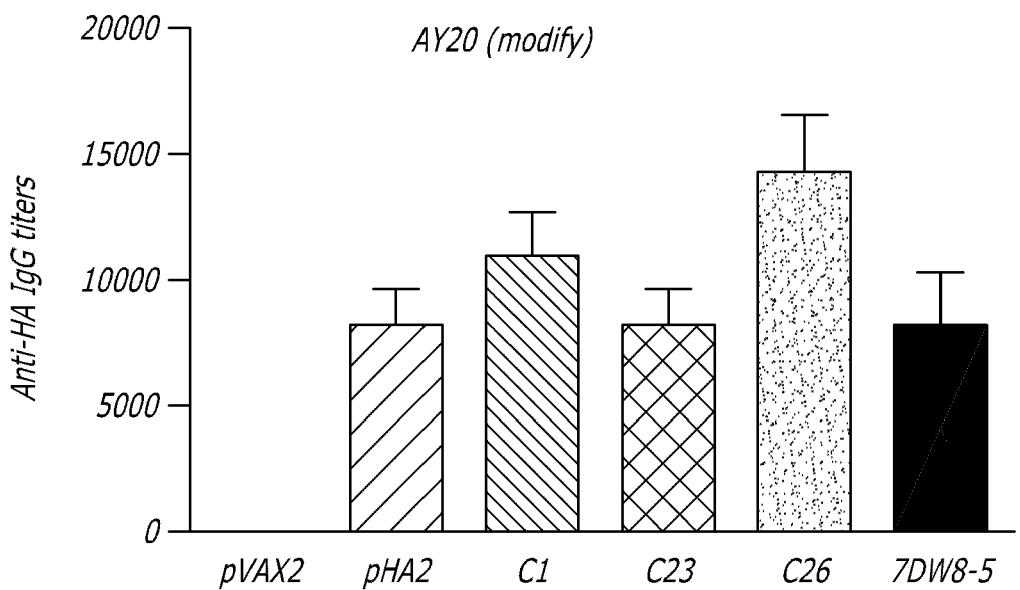
FIG. 56 (A-B) show the effect of single dose vaccination. BALB/c mice were vaccinated by electrotransfer in muscle with pHAc (2 µg) and α-GalCer or the indicated α-GalCer analogs of the present disclosure (2 µg). (A) Blood samples were collected three weeks later and tested for anti-HAc-specific IgG antibody titers. (B) Mice were challenged with 200 LD$_{50}$ NIBRG-14 viruses at three weeks after prime and survival was monitored.
Figure 56B:
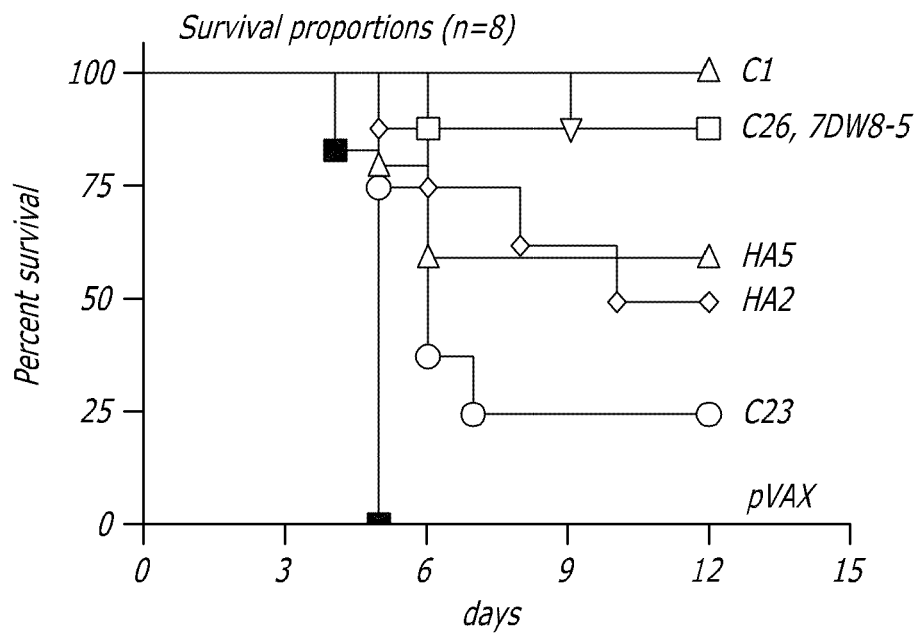

The adjuvant effects of α-GalCer analogs of the present disclosure was also evident after single dose of pHA vaccination. At three weeks after one dose immunization, anti-HA-specific IgG antibody was enhanced in mice treated with C26 and C1 as adjuvant (FIG. 56). Mice treated with C1, C26 or 7DW8-5 were protected effectively from lethal challenge by NIBRG-14 virus challenge, with the survival rates ranged from 87.5% to 100% These findings indicate that C1, C26 and 7DW8-5 have good adjuvant activities in the setting of single vaccination procedure.

Adjuvant Effect on Polysaccharide Immunogens

Globo H, a hexasaccharide (Fucα1→2Galβ1→3GalNAcβ1→3Galα1→4Galβ1→4Glcβ1) had been shown to be overexpressed on a variety of epithelial cell tumors such as colon, ovarian, gastric, pancreatic, endometrial, lung, prostate and breast cancers, with the use of monoclonal antibodies MBr1 (IgM) and VK-9 (IgG3). In normal tissues, globo H is limited to the apical surface of epithelial cells at the lumen border, a site that appears not to be accessible to the immune system. Therefore, globo H is an ideal target antigen for immunotherapy of breast cancer and other epithelial cancers.

Figure 57A:
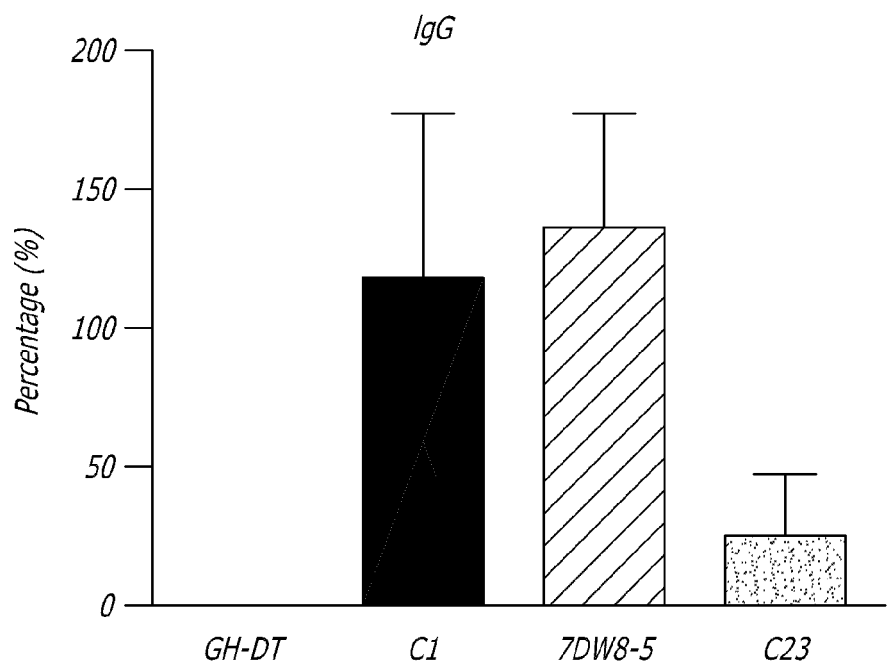
FIG. 57 (A-B) show adjuvant effects of α-GalCer or the indicated α-GalCer analogs of the present disclosure on carbohydrate antigens. BALB/c mice were vaccinated by IM injection with α-GalCer or the indicated α-GalCer analogs and mixed with globo H-DT and boosted twice within a two week interval. Blood samples were collected two weeks after a third vaccination and tested for (A) anti-globo H-specific IgG antibody and (B) anti-globo H-specific IgM antibody production.
Figure 57B:
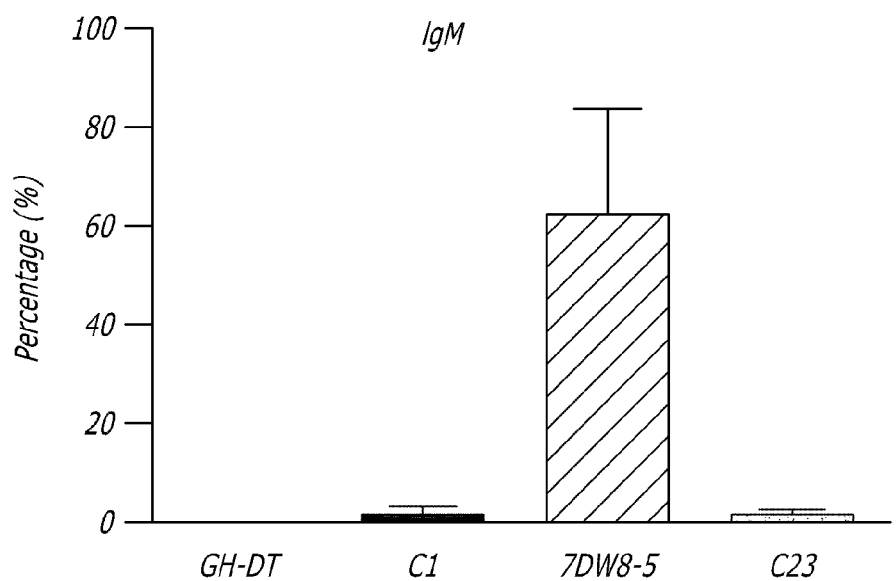

The adjuvant effects of α-GalCer and the α-GalCer analogs of the present disclosure C23 and 7DW8-5, were evaluated for globo H conjugated to diphtheria toxoid (GH-DT) vaccine. BALB/c mice were injected IM with globo H-DT/α-GalCer or globo H-DT/α-GalCer analogs three times at two weeks interval. Sera was collected two weeks after the third vaccination and tested for IgG and IgM anti-globo H-specific antibody at 1:480 and 1:240 dilution, respectively, using a glycan microarray. As shown in FIG. 57A, GH-DT alone did not induce any anti-globo H antibody, but the addition of C1 or 7DW8-5 elicited significant IgG antibody production. On the other hand, the production of IgM was observed only in 7DW8-5-adjuvanted groups but not in C1 treated group (FIG. 57B). In conclusion, adding C1 or 7DW8-5 into GH-DT vaccine could enhance specific antibody production against carbohydrate antigen.

Antimicrobial Immunotherapy

In still another aspect, an α-GalCer analog of the present disclosure has use, for example, in treatment methods for infectious diseases resulting, for example, from the presence of pathogenic microbial agents, including viruses, bacteria, fungi, protozoa, multicellular parasites, and aberrant proteins (prions).

In some exemplary implementations the method provides an anti-microbial immunotherapy for a subject comprising: administering an effective amount of a compound or a salt or a mixture thereof to a subject, the compound selected from the group consisting of C9, C11, C13-C16, C23 and C34.

Antiviral Effects:

Antiviral drugs are a class of medication used specifically for treating viral infections. Like antibiotics, specific antivirals are used for specific viruses. They are relatively harmless to the host, and therefore can be used to treat infections. Antiviral drugs are available to treat only a few viral diseases. Two useful antivirals are: the nucleoside analogues and the interferons. There are three classes of interferons: alpha- beta- and gamma-interferons. The alpha and beta interferons are cytokines which are secreted by virus infected cells. They bind to specific receptors on adjacent cells and protect them from infection by viruses. They form part of the immediate protective host response to invasion by viruses. In addition to these direct antiviral effects, alpha and beta interferon also enhance the expression of class I and class II MHC molecules on the surface of infected cells, in this way, enhancing the presentation of viral antigens to specific immune cells. Their presence can be demonstrated in body fluids during the acute phase of virus infection. Recombinant alpha and beta interferons are now available and have been used for the treatment of Chronic hepatitis B and C virus infections. However, side effects such as fever, malaise and weight loss have limited the use. Gamma Interferon (immune interferon) is a cytokine secreted by T$_H$1 CD4 cells. Its function is to enhance specific T cell mediated immune responses.

The mechanism of action of the interferons include: 1) enhancement of the specific immune response. By increasing the expression of MHC class 1 molecules on the surface of infected cells, the interferons increase the opportunity for specific cytotoxic T cells to recognise and kill infected cells; and 2) Direct antiviral effect: a) degradation of viral mRNA and b) inhibition of protein synthesis, which prevents the infection of new cells.

In one aspect, the synthetic α-GalCer analogs of the present disclosure have use for antiviral treatment of and prophylaxis for various infectious viruses. Examples of infectious virus to which stimulation of a protective immune response is desirable, which may be accomplished via the methods of this disclosure, or utilizing the NKTs, vaccines or compositions of the present disclosure include, but are not limited to, Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g. influenza viruses); Bungaviridae (e.g., Hantaan viruses, bunga viruses, phleboviruses and Nairo viruses); Arena viridae (hemorrhagic fever viruses); Reoviridae (erg., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes viruses'); Poxyiridae (variola viruses, vaccinia viruses, pox viruses); and Iridoviridae (e.g. African swine fever virus); and unclassified viruses (e.g., the etiological agents of Spongiform encephalopathies, the agent of delta hepatities (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Viral Challenge—Influenza Virus H1N1 Infection

Treatment Via IP Injection of α-GalCer Analogs

Figure 58A:
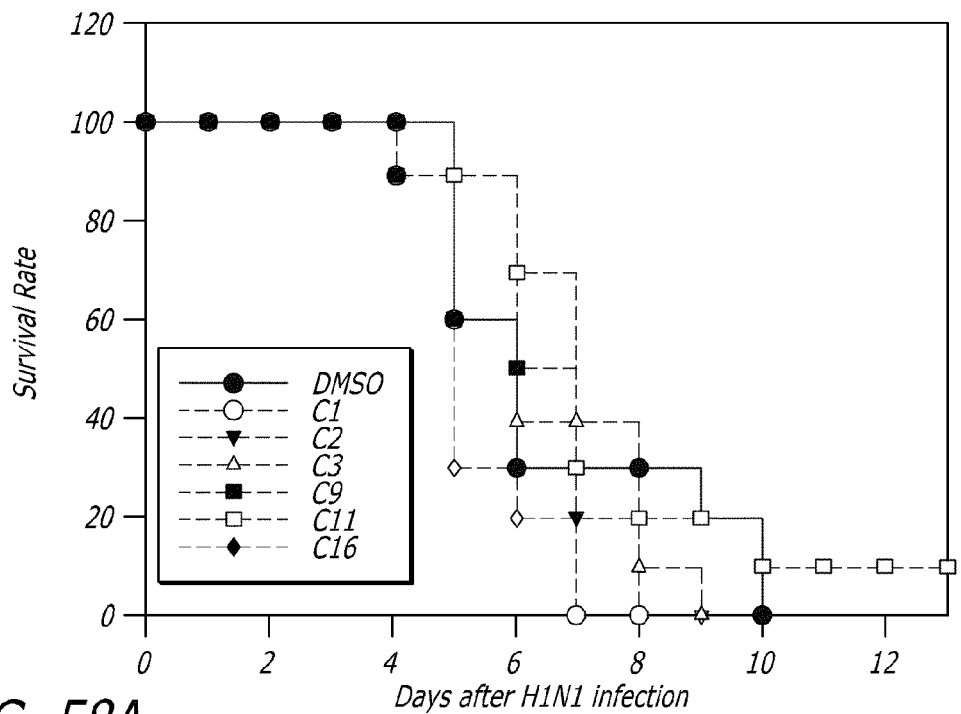
FIG. 58(A-B) shows survival rate when BALB/c mice were treated with α-GalCer or the indicated α-GalCer analogs of the present disclosure via intraperitoneal (IP) route (A) starting at 30 min after FLU-A virus serotype H1N1 (WSN) virus challenge and (B) starting 2 weeks prior to H1N1 virus challenge.
Figure 58B:
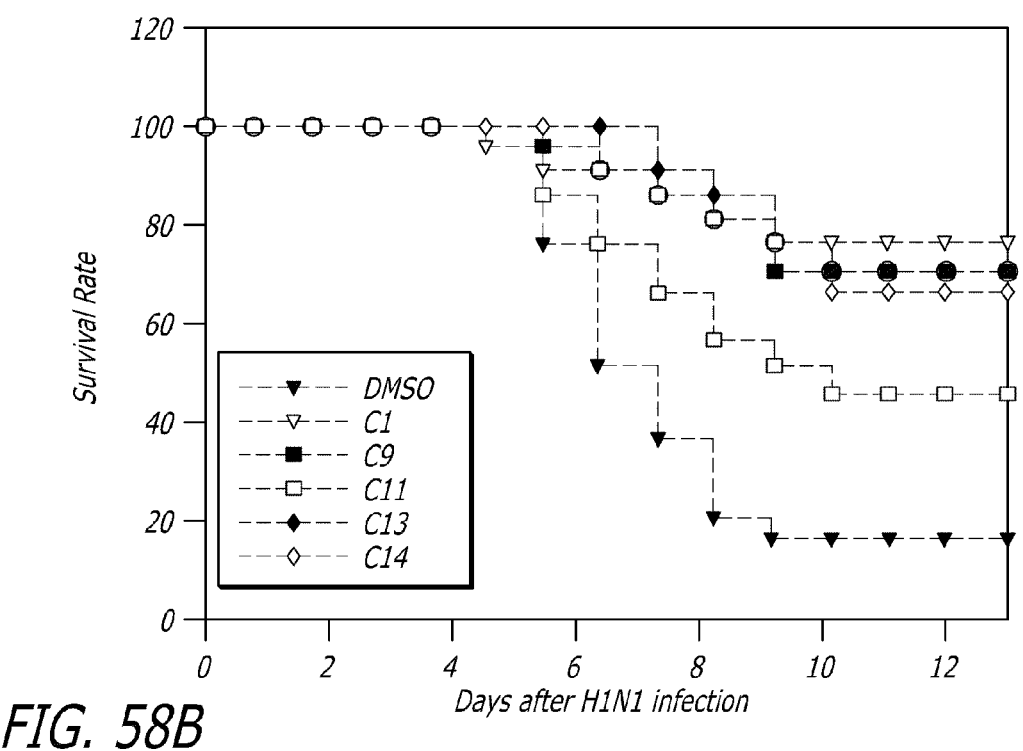
Figure 59A:
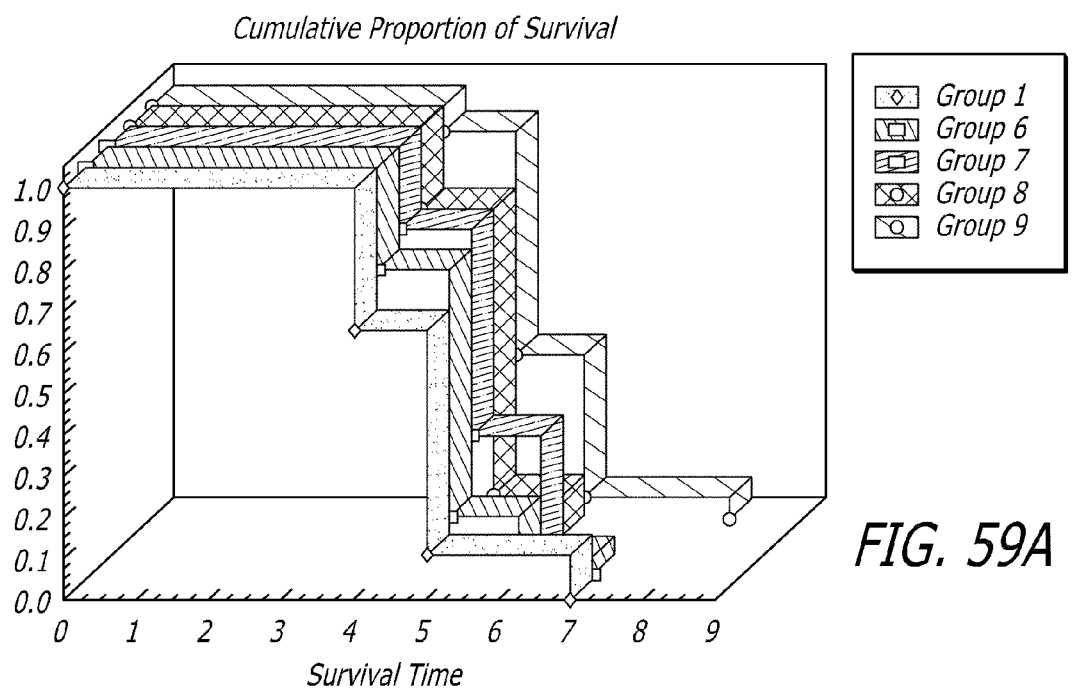
FIG. 59 (A-B) shows cumulative proportion of survival of BALB/c mice infected with H1N1 (WSN) and treated with α-GalCer or the indicated α-GalCer analogs of the present disclosure (A) starting at 2 weeks prior to virus challenge with a high dose of H1N1 (WSN) virus and (B) via intranasal route.

FIG. 58 shows mouse survival at 0 to 12 days post influenza virus H1N1 infection. Mice were treated (IP injection) with 2 μg of α-GalCer (C1) or the α-GalCer analogs C2, C3, C9, C11, C13, C14 and C16, and compared to control DMSO. Three different treatment schedules were tested. FIG. 58A shows survival rate when BALB/c mice were treated starting at 30 minutes post-H1N1 virus challenge. P values compared to control were C1: 0.4554, C2: 0.5149, C3: 0.5764, C9: 0.5466, C11 0.2031, C16: 0.0359. FIG. 58B shows survival rate when BALB/c mice were treated starting at two weeks prior to virus challenge with H1N1 (WSN). Mice were treated at −14 days, −10 days, −3 days, 0.5 hour, 2 days, 4 days, 6 days 8 days 10 days and 12 days with 2 μg (IP injection) of control, α-GalCer (C1) or the α-GalCer analogs. When treatment started two weeks before virus challenge and was given two times per week, mice exhibited significantly enhanced survival with α-GalCer analog treatment with all analogs tested (C9, C11, C13 and C14). P values compared to control were C1: 0.000116, C9: 0.000126, C11: 0.02627, C13: 0.000027, and C14: 0.000147. FIG. 59 shows cumulative proportion of survival with mice that were infected with a higher dose of influenza virus H1N1. In FIG. 59A, BALB/c mice were treated starting at two weeks prior to virus challenge with H1N1 (WSN). Mice were treated at −14 days, −10 days, −3 days, 0.5 h, 2 days, 4 days, and 6 days with 2 μg (IP injection) of control, α-GalCer (C1) or the α-GalCer analogs. Group 1 is the control group. Group 6 were treated with αGalCer (C1). Group 7 were treated with α-GalCer analog C13. Group 8 were treated with α-GalCer analog C14. Group 9 were treated with α-GalCer analog C16. α-GalCer analog C16 showed prolonged survival, indicative of C16 having a direct anti-viral effect.

Treatment Via Intranasal Administration of α-GalCer Analogs

Figure 59B:
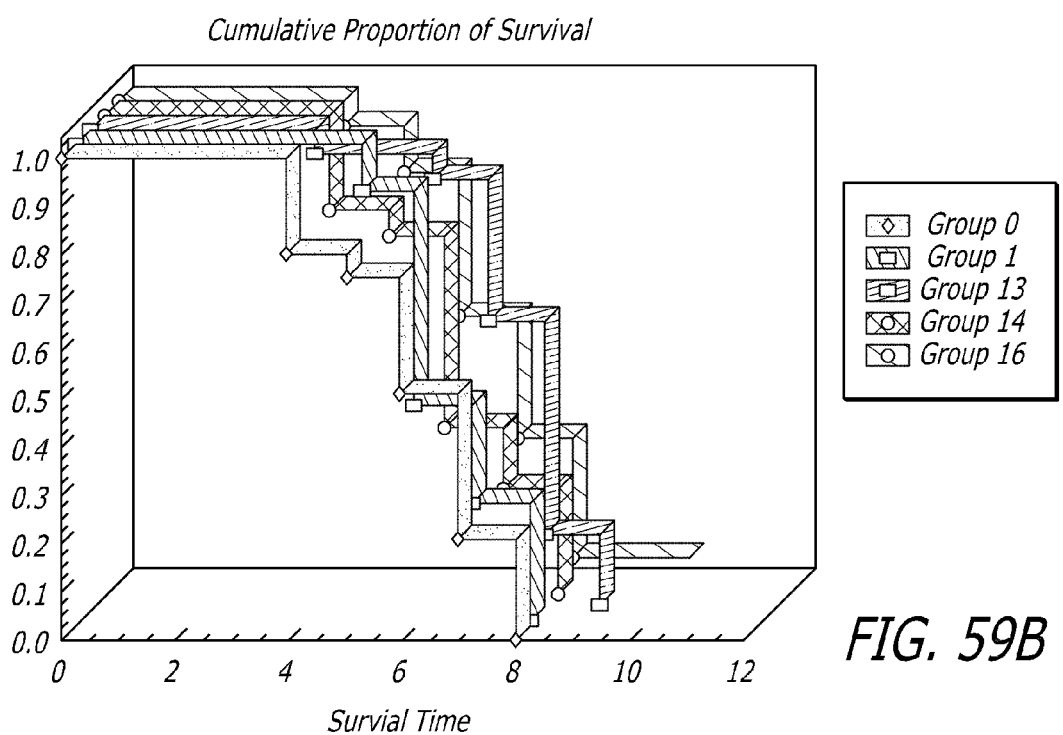

FIG. 59B shows cumulative proportion of survival with mice infected with H1N1. BALB/c mice were treated via intranasal route with control, α-GalCer (C1) or the α-GalCer analogs C13, C14 or C16 at one hour prior to virus challenge with H1N1 (WSN). C13 showed prolonged survival, suggestive of direct anti-viral effects. In general, certain α-GalCer analogs may exert direct anti-viral effects, or act indirectly via immune stimulation. FIG. 60 shows the cytopathetic effect (CPE) of Madin-Darby canine kidney (MDCK) cells in vitro. MDCK cells were pretreated with vehicle, α-GalCer or one of the α-GalCer analogs C13, C14 or C16 at 10 μg/ml for four hours, followed by infection with FLU-A virus serotype H1N1 (WSN) at 10TCID50. The virus titer in MDCK cells was determined at 48 hours post-infection (right panel). α-GalCer, as well as the three α-GalCer analogs tested showed slight inhibition of the entry/replication of H1N1 virus in vitro.

Antibacterial Effects:

Since the introduction of penicillin into clinical use in the 1940s, antibacterials have saved millions of lives. However, the lengthening shadow of antimicrobial resistance threatens a return to the pre-antibiotic era. Synthetic glycolipids such as α-GalCer and natural bacterial glycolipids were demonstrated as CD1-d ligands that activated NKT cells and contributed the antibacterial functions of the hosts. The antibacterial activities of α-GalCer were documented in the amelioration of *mycobacterium tuberculosis* infections, clearance of lung infection by *Pseudomonas aeruginosa*. Infections by *Spingomonas capsulate* and *Ehrlichia muris* were also attenuated in mice by the activation of NKT cells via glycolipids.

Examples of infectious bacteria to which stimulation of a protective immune response is desirable, which may be accomplished via the methods of this disclosure, or utilizing the NKTs, vaccines or compositions of the present disclosure include, but are not limited to, *Helicobacter pylori, Borellia burgdorferi, Legionella pneumophilia, Klebsiella Pneumoniae, Mycobacteria* sps (e.g. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Chlamidia* sp., *Haemophilus influenzae, Bacillus* antracis, *corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Actinomyces israelli, Sphingomonas capsulata* and *Francisella tularensis*.

Enhanced Bacterial Clearance—Sphingomonas Capsulate Infected Mice

Figure 61A:
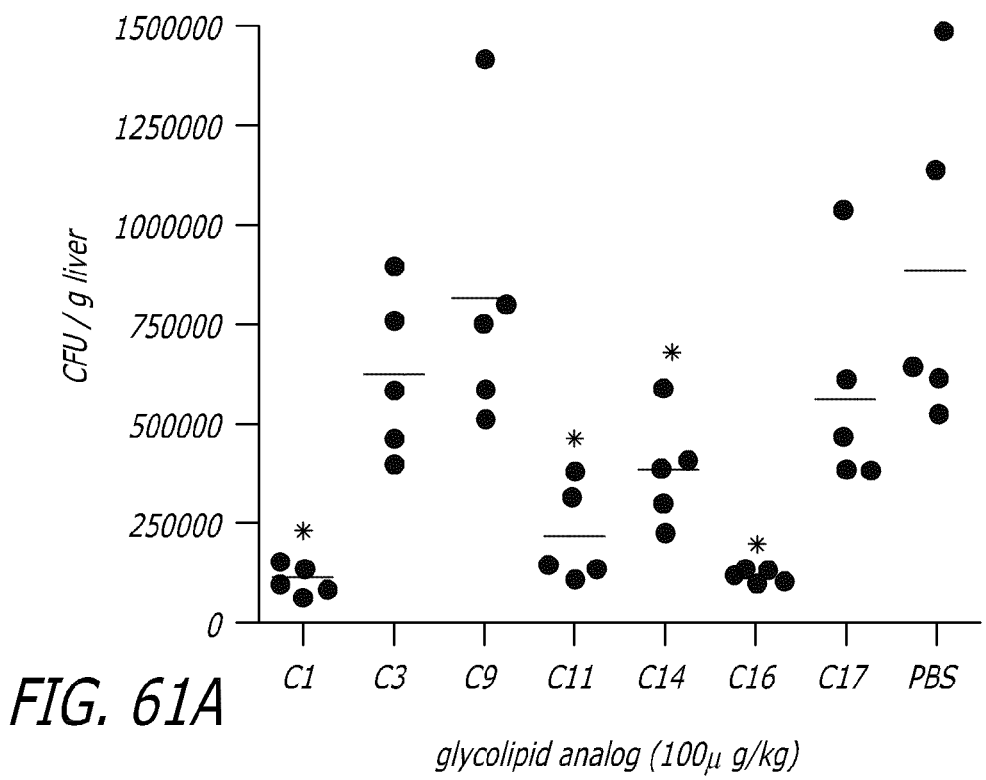
FIG. 61(A-B) show antibacterial efficacies of α-GalCer or the indicated α-GalCer analogs of the present disclosure treated at (A) 100 µg/kg or (B) 50 µg/kg in mice infected with *Sphingomonas capsulata*.
Figure 61B:
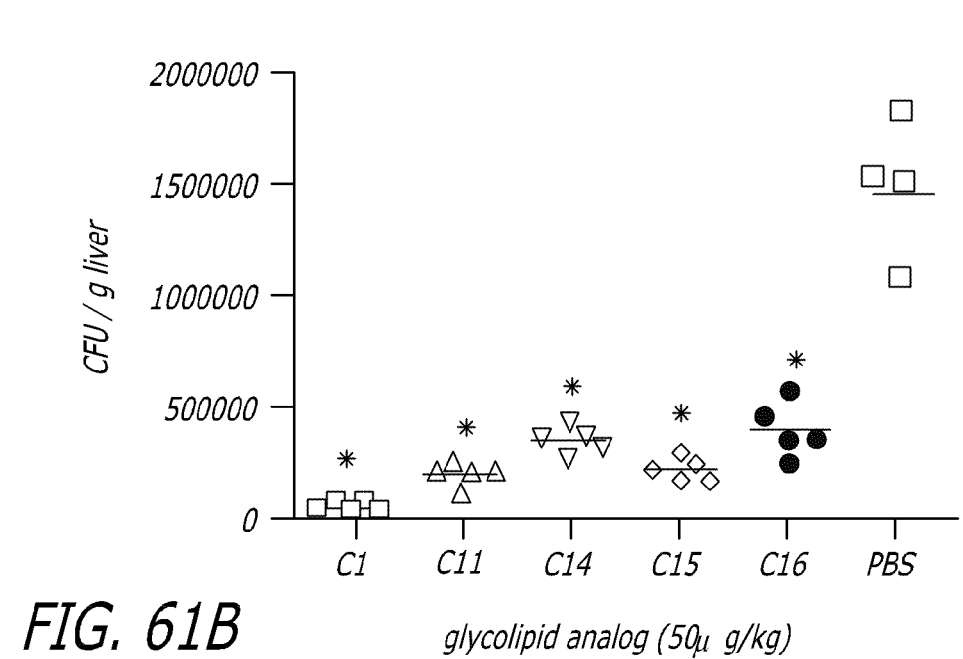
Figure 63:
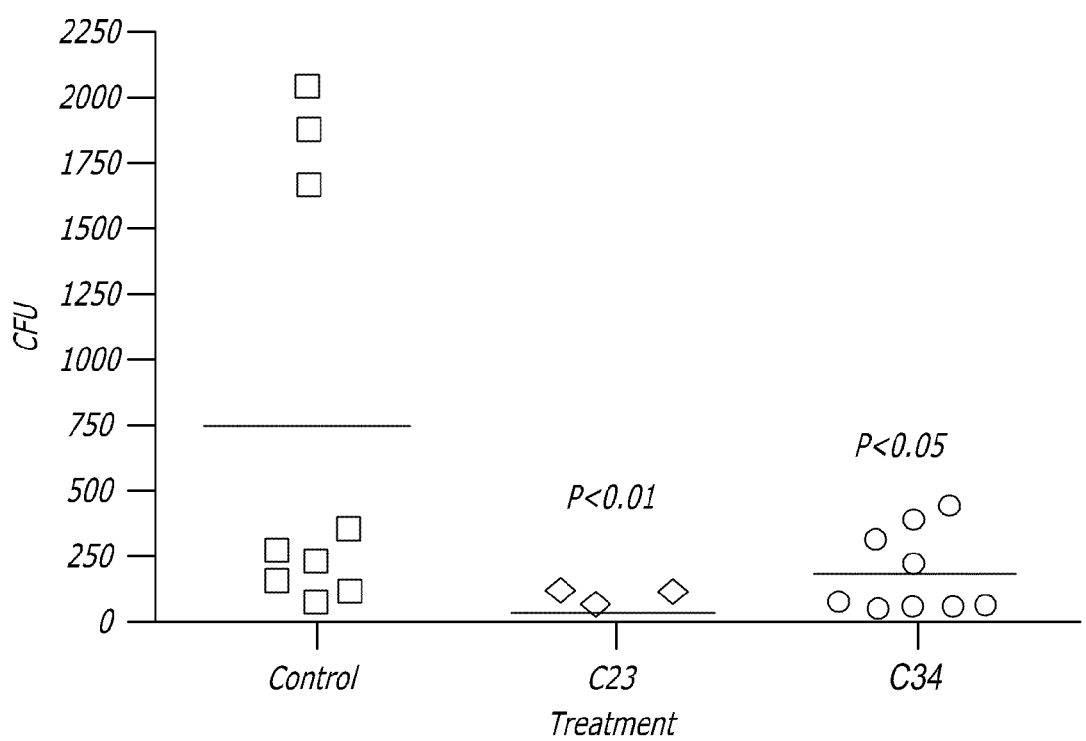
FIG. 63 shows that the CFU numbers (in lungs) of the groups treated with C23 and C34 at 50 µg/kg, are significant in comparison to the untreated group.

Sphingomonas capsulata is a common environmental bacterial strain that is found in many places such as the air and water. It can be easily identified on nutrient agar plates because of its yellow colony color. Unlike most Gram negative bacteria, Sphingomonas capsulata does not contain lipopolysaccharide (LPS) that is used by animals for the activation of the host antibacterial activities. Since the antibacterial activities of glycolipid antigens are mediated through the activation of NKT cells by glycolipid bound-CD1-d molecules, evaluation of the antibacterial efficacies using the disease model of Sphingomonas capsulata infection will focus on the impact of the NKT mediated pathway that is activated by glycolipid bindings. Six to eight week old female C57BL/6 mice were injected IP with Sphingomonas capsulate cells. Four hours after the infection, mice were injected IP with control, α-GalCer (C1) or the α-GalCer analogs (C3, C9, C11, C14, C16 or C17) at 50 or 100 μg/kg. Twenty-four hours after bacterial infection, livers were removed from mice and homogenized. Colony formation units (CFU) of Sphingomonas capsulate in liver homogenates were determined by plating diluted samples on nutrient plates. Colonies were counted after incubation for 48 hours at 37° C. FIG. 61A shows that the CFU numbers of the groups treated with α-GalCer and C11, C14, and C16 at 100 μg/kg, 24 hour after bacterial infections, are significantly lower than the control group. To confirm the antibacterial efficacies of these α-GalCer analogs, another study was conducted to repeat the study by treating infected mice with 50 μg/kg in the same disease model. FIG. 61B shows that the antibacterial efficacies of mice treated with C11, C14, C16, and also C15 are significant in comparison to the untreated group. Among the three efficacious groups, C1, C11, and C15, the difference in the values of the CFU per gram liver is not statistically significant. FIG. 63 shows that the CFU numbers (in lungs) of the groups treated with C23 and C34 at 50 μg/kg, are significant in comparison to the untreated group. Similar results were found in the CFU numbers in livers after mice were treated with C23 and C34.

Enhanced Bacterial Clearance—*Klebsiella Pneumoniae* Infected Mice

Figure 62A:
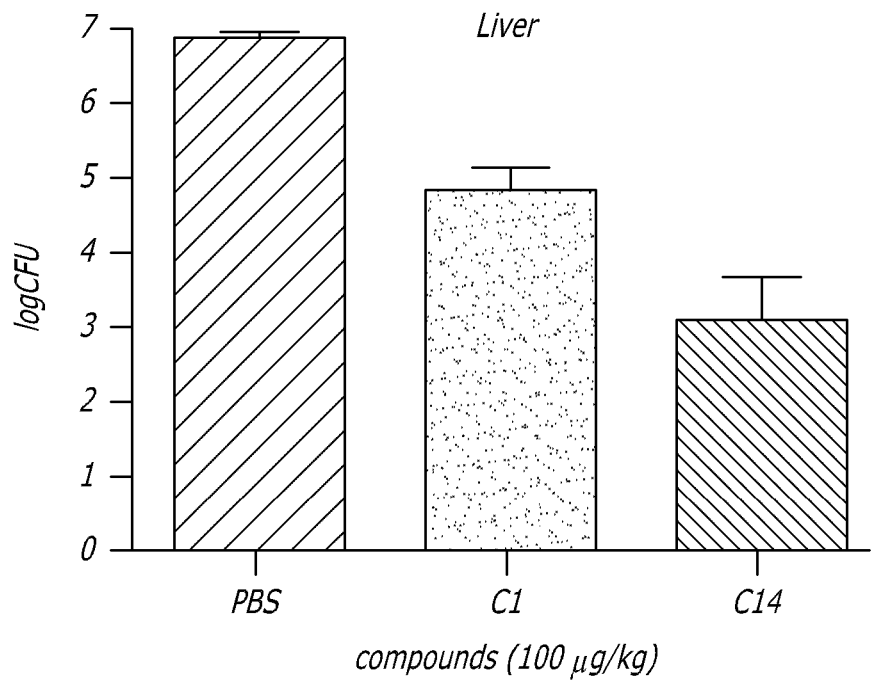
FIG. 62 (A-B) show the antibacterial efficacy of α-GalCer or the indicated α-GalCer analogs of the present disclosure in mice infected with *Klebsiella pneumoniae*. C1 and C14 can significantly reduce the bacterial loads in (A) mouse lung and (B) liver after injection.
Figure 62B:
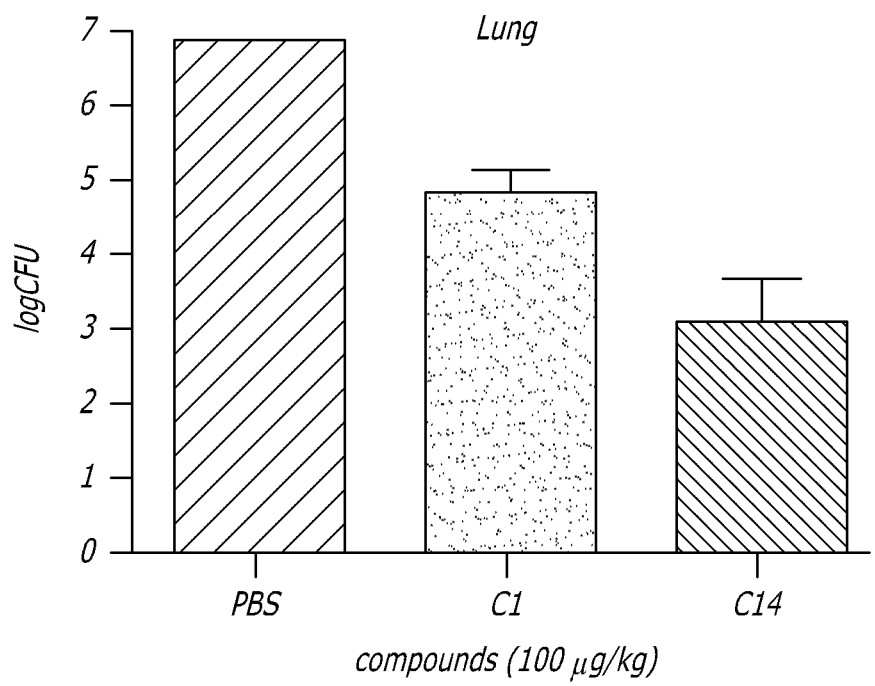

*K. pneumoniae* is a Gram negative bacterium that causes liver abscess and is becoming a serious disease in Taiwan among diabetic patients. FIG. 62 shows that both C1 and C14 can significantly reduce the bacterial loads in mouse lung and liver after injection. BALB/cByl female mice were administered a single dose of live *K. pneumoniae* by oral gavage. Mice were injected with control, α-GalCer or the α-GalCer analog C14 at 100 μg/kg twice at 4-hour and 8-hour after bacterial infection. Twenty four hours after infection, both the liver and lungs were collected from each mouse, and homogenized. Bacterial counts were determined similarly as described above.

The extent of bacterial clearance by C14 is found to be greater than the clearance by C1 as shown in FIG. 62.

Antifungal Effects:

T helper cell type 1 ($T_H1$) cell-mediated immunity plays a critical role in protection against various infectious fungi. In still another aspect, the α-GalCer analogs of the present disclosure may be used in antifungal therapies. Antifungal drugs are used to treat infections caused by fungus and to prevent the development of fungal infections in patients with weakened immune systems. Fungal infections have become one of the leading factors contributing to morbidity and mortality in immunosuppressed patients.

The innate host defense against fungal diseases is based on the action of phagocytic cells (PMNLs and macrophages); both the number and the function of these cells can be regulated by the colony-stimulating factors (CSFs). On the other hand, acquired defense involves cellular and humoral immunity that requires interactions between antigen-presenting cells, T lymphocytes, B lymphocytes, and NKs that are driven and regulated by cytokines such as IL-2 and IFN-γ. The potential importance of immune activation via cytokines in the host defense against opportunistic fungi has been the subject of several studies and has raised some intriguing questions about novel antifungal strategies for candida and *aspergillus* infections. Different potential roles for cytokines have been described. First, exposure to fungi and their antigens may induce release of IL-2, IFN-γ, tumor necrosis factor-α (TNF-α), granulocyte colony-stimulating factor (G-CSF), and granulocyte macrophage colony-stimulating factor (GM-CSF). These cytokines may in turn activate or enhance the antifungal function of phagocytes against *Candida* and *Aspergillus* species.

Examples of infectious fungi to which stimulation of a protective immune response is desirable, which may be accomplished by administering an α-GalCer analog of the present disclosure alone or in combination with an antifungal drug include, but are not limited to, *Cryptococcus neoformans, Histoplasma capsulatum, Coccidioides immitis, Blastomyces dermatitidis, Chlamydia trachomatis, Candida albicans*. Other infectious organisms (i.e., protists) include: *Plasmodium* sp., *Leishmania* sp., *Schistosoma* sp. and *Toxoplasma* sp.

Immunotherapy for Autoimmune Diseases

Autoimmunity results from a breakdown in the regulation in the immune system resulting in an inflammatory response directed at self-antigens and tissues. Autoimmune diseases are the third most common category of disease in the United States after cancer and heart disease; they affect approximately 5%-8% of the population or 14-22 million persons. Autoimmune diseases involving the destruction of self-antigen by T lymphocytes includes, but are not limited to, multiple sclerosis, insulin-dependent diabetes mellitus, and rheumatoid arthritis.

According to the current dogma, inflammatory autoimmune diseases such as myocarditis are primarily attributable to $T_H1$ responses, with IFN-γ as the prototypic cytokine; $T_H2$ responses where IL-4 dominates are believed to reduce autoimmunity. Because the α-GalCer analogs of the present disclosure can be designed such that a $T_H2$-biased immunogenic response is initiated, these α-GalCer analogs can be used as immunotherapies for autoimmune diseases.

EXAMPLES

Glycolipid Analogs of α-GalCer, Reagents and Mice

α-GalCer (C1) and synthetic α-GalCer analogs of the present disclosure were synthesized and purified by column chromatography by techniques previously described in Fujio et al. (2006) J. Am. Chem. Soc. 128:9022-9023; Xing et al. (2005) Bioorg. Med. Chem. 13:2907-2916; Kinjo et al. (2005) Nature 434:520-525; Wu et al. (2006) Natl. Acad. Sci. U.S.A 103:3972-3977; and Wu et al. (2005) Proc. Natl. Acad. Sci. U.S.A 102:1351-1356; each of which is hereby incorporated herein by reference.

The synthetic α-GalCer analogs of the present disclosure, as shown in FIG. 2, were separated into four groups based on their chemical structures. Group I: C2, C3 and C14 are of bacterial origin, Group II: C4, C5 and C9 contain sulfur modification of O-linkage to ceramide (C4) or a sulfate group at 3"-OH of the galactose moiety (C5, C9), Group III: C6-C8, C8-5, C8-6, C10-C11, C15-C16 and C18-C34 are modified with an aromatic ring in their acyl tail and Group IV: C12, C13 and C17 contain truncated phytosphingosine. Among these new analogs, C10, C11, C16, C27, C28, C29 are modified with a phenyl group in various length of fatty amide chain (Ph); C18, C22 are modified with methoxy group (—OMe) at the phenyl ring; C19, C23, 7DW8-5 are modified with fluoride group (—F) at the phenyl ring; C20, C24, 7DW8-6 are modified with trifluoromethyl group (—CF3) at the phenyl ring; C21, C25, C26 are modified with phenyl group (-Ph) at the phenyl ring; C30 is modified with 4'-fluorophenyl group (-Ph-F) at the phenyl ring; C34 is modified 1'-oxy-4'-fluorophenyl (O-Ph-F)

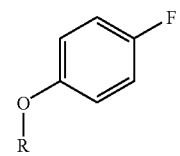

at the phenyl ring. However, substitution of the para-oxy-fluorophenyl (1'-oxy-4'-fluorophenyl) at the phenyl ring with an oxy-fluorophenyl with the F group at a non-para position or one of a difluoro, trifluoro, tetrafluoro and pentafluoro phenyl may also yield useful properties; and C17 contains a truncated phytosphingosine.

Synthesis of glycosphingolipid compounds C12 and C13 are summarized in Scheme 1 (FIG. 3). Characterization data for these compounds are described below.

Compound C13 (lot. MFJ3-017-1): $^1$H NMR (500 MHz, CDCl$_3$-MeOH 4:1) δ: 7.26 (m, 2H), 7.23-7.19 (m, 2H), 7.18-7.14 (m, 1H), 4.90 (d, J=3.9 Hz, 1H), 4.24-4.19 (m, 1H), 3.86 (dd, J=10.8, 5.2 Hz, 1H), 3.82-3.62 (m, 7H), 3.58-3.53 (m, 2H), 2.92-2.84 (m, 1H), 2.67 (ddd, J=13.7, 9.3, 7.5 Hz, 1H), 2.16 (m, 2H), 2.06-1.98 (m, 1H), 1.74-1.65 (m, 1H), 1.62-1.53 (m, 2H), 1.33-1.19 (m, 44H), 0.88 (t, J=7.0 Hz, 3H). $^{13}$C NMR (125 MHz, CDCl$_3$-MeOH 4:1) δ: 174.06, 141.93, 128.25, 128.01, 125.43, 99.48, 74.60, 70.75, 70.44, 69.99, 69.52, 68.66, 67.03, 61.69, 50.15, 50.06, 36.27, 34.13, 31.67, 31.59, 29.43, 29.31, 29.15, 29.09, 25.55, 22.41, 17.60, 13.76. HRMS (ESI-TOF) for C$_{44}$H$_{80}$NO$_9^+$ [M+H]$^+$ calcd 766.5827, found 766.5813.

Compound C12 (lot. MFJ3-018-1): $^1$H NMR (400 MHz, CDCl$_3$-MeOH 4:1) δ: 7.26 (m, 2H), 7.19-7.13 (m, 3H), 4.91 (d, J=3.8 Hz, 1H), 4.20 (q, J=4.4 Hz, 1H), 3.95-3.85 (m, 2H), 3.83-3.61 (m, 6H), 3.59-3.50 (m, 2H), 2.63 (t, J=7.5 Hz, 2H), 2.20 (t, J=7.5 Hz, 2H), 1.78-1.54 (m, 6H), 1.47-1.17 (m, 46H), 0.89 (t, J=6.9 Hz, 3H). $^{13}$C NMR (100 MHz, CDCl$_3$-MeOH 4:1) δ: 174.16, 142.27, 127.91, 127.77, 125.14, 99.33, 74.28, 71.38, 70.42, 69.86, 69.33, 68.51, 66.84, 61.40, 50.02, 36.04, 35.52, 31.93, 31.51, 31.21, 29.26, 29.14, 28.99, 28.94, 25.47, 25.08, 22.25, 13.51. HRMS (ESI-TOF) for C$_{46}$H$_{84}$NO$_9^+$ [M+H]$^+$ calcd 794.6140, found 794.6129.

All the synthetic α-GalCer analogs were originally dissolved in 100% DMSO at a concentration of 1-2 mg/ml. For in vivo experiments, synthetic α-GalCer analogs were diluted to 20 or 1 μg/ml in saline just before injection into mice. Pathogen-free BALB/c (wild type or CD1d knockout) and C57BL/6 female mice aged 6-10 weeks were obtained from the National Laboratory Animal Center (Taipei, Taiwan). CD1d-deficient BALB/c and C57BL/6 were obtained from the Jackson laboratory (C.129S2-CD1tm1Gru/J, U.S) and provided by Dr. Steve R. Roffler (Academia Sinica, Taiwan), respectively. All the mice were maintained in pathogen free animal facility.

Isolation and Generation of Human NK Cell Lines, Immature Monocyte-Derived Dendritic Cells and NK/NKTs The naïve Vα24i NKT cells were separated using indirectly conjugated anti-Vα24iTCR microbeads (Miltenyi Biotec, USA). The isolated cells were incubated in the presence of 50 U/ml IL-2 (R&D system) and replenished with fresh media every 3 days. The generation of α-Galcer-pulsed or phenyl glycolipid-pulsed Vα24i NKT were done as follows. Anti-Vα24i TCR mAbs, and anti-CD14 mAbs, each coupled to magnetic beads (Miltenyi Biotec, Auburn, Calif.), were used sequentially to isolate Vα24i NKT cells and CD14 cells from leukopaks. Immature dendritic cells were generated from the CD14 cells after a 2-day incubation in the presence of 300 U/ml GM-CSF (R & D Systems) and 100 U/ml IL-4 (R& D Systems). After irradiation with 2,000 rad, the immature dendritic cells were cocultured with syngeneic CD161 cells in the presence of 100 ng/ml α-GalCer or C1 and 50 U/ml IL-2 (Invitrogen) for 10-14 days. After stimulating the Vα24i NKT cells a second time with 100 ng/ml α-GalCer or C11-pulsed irradiated immature dendritic cells to generate α-GalCer pulsed or phenyl-glycolipid pulsed iNKT cells, respectively. All iNKT cell lines (naïve, α-GalCer pulsed or phenyl-glycolipid pulsed) were shown flow cytometrically to express Vα24i T cell antigen receptor (95% purity). NK and NKT cells were isolated from human leukopaks using anti-CD56 microbeads (Miltenyi Biotec, USA).

The generation of α-GalCer analog-pulsed human NKT cell lines was done according to the methods of Fujio et al., and these cells were used to assess cytokine response to the studied α-GalCer analogs (see FIGS. 5 and 6). Immature DCs were derived from CD14$^+$ cells in leukopaks after a two-day incubation with 300 U/ml GM-CSF and 100 U/ml IL-4. After irradiation (3,000 rad), the iDCs were cultured together with autologous CD161$^+$ cells in the presence of 100 ng/ml α-GalCer and 10 U/ml IL-2 for 10 days. After repeating this stimulation, NK cell lines were generated and shown to express CD161$^+$/CD3$_+$/Vα24iTCR$^+$ (99% purity). To generate immature human monocyte-derived DCs, CD14$^+$ cells in leukopaks were cultured in the presence of 300 U/ml GM-CSF and 100 U/ml IL-4 for 6 days. These DCs had an immature phenotype (CD14$^-$CD80$^+$CD86$^+$CD83$^{weak}$ HLA$^-$DR$^+$) and exhibited higher CD1d expression than mature DCs. The iDCs were pulsed with various α-GalCer analogs at 3 μg/ml and their phenotype and morphology were examined 48 hours later.

The naïve NKTs (CD161$^+$/CD3$^+$) used for TCR activation experiments (see FIG. 19) were isolated by using indirectly conjugated anti-CD161 multi-sort microbeads and were further separated by anti-CD3 microbeads. The isolated cells were incubated in the presence of 100 U/ml IL-2 and replenished with fresh media every 3 days.

In vitro Human NKT Cell Cytokine Secretion Assay

Vα24i human NKT cells (1×10$^5$) were cocultured with 5×10$^4$ irradiated immature CD14$^+$ DCs in the presence of the α-GalCer analogs of the present disclosure at 10 μg/ml in a 96-well flat-bottom plate. Cytokines/chemokines in the supernatant collected at 18 h were quantified with the Beadlyte® Human 22-plex Multi-Cytokine Detection System and determined by Luminex® 100™ system.

In Vitro Expansion of iNKTs.

Human CD56$^+$ cells (NK/NKT mixtures) used for iNKT cell expansion experiments (see FIGS. 13 and 14) were isolated from human leukopaks by using anti-CD56 microbeads. Human CD56$^+$ cells (NK/NKT mixtures) were cultured with 4×10$^5$ autologous immature CD14$^+$ DCs pulsed with the indicated α-GalCer analogs at 3 μg/ml or 0.3% DMSO on day 2 for 18 hours (see FIGS. 13 and 14) or at 10 or 100 ng/ml on day 2 for 18 hours (see FIG. 15). On day 3, the suspension cells were transferred to a new dish, cultured in the presence of 100 U/ml IL-2, and replenished with fresh medium every 3 days. The population of CD161$^+$/Vα24TCR$^+$ cells in the NK/NKT mixtures were gated by flow cytometry on day 9, and the total number of Vα24i NKT were counted.

Human NKT TCR Activation

In an exemplary implementation, HeLa, HeLa-CD1d or autologous iDCs were incubated on 24 well-plate with C1, C11, C13 or C17 at 10 μg/ml or with DMSO for 2 h, and then 3×10$^5$ naïve CD161$^+$/CD3$^+$ NKTs were added (see FIG. 19). In another exemplary implementation, HeLa or HeLa-CD1d cells were loaded with C1, C16, C23, C8-5, C8-6 or C26 at 100 ng/ml or with DMSO for 2 hours, and then 3×10$^5$ naïve CD161$^+$/CD3$^+$ NKTs were added (see FIG. 20). After 5-10 min stimulation, cells in suspension were transferred to tubes, washed with PBS, and lysed with Beadlyte® Cell Signaling Universal Lysis Buffer at 4° C. The concentrations of phospho-CD3ε (Phospho-tyrosine), phospho-ERK1/2 (Thr185/Tyr187), phospho-CREB (Ser133), phospho-Syk (Phospho-tyrosine), phospho-p38 (THr180/Tyr 182), phospho-IκBα (Ser32), phospho-Lck, phospho-Lat, phospho-STAT3 (Ser727), phospho-STAT5 A/B (Tyr 694/699) and phospho-Dap-70 (Phospho-tyrosine) in lysates were assessed by Beadlyte® Phosphoprotein Detection System according to the assay protocol, and determined by a Luminex100 system. The value was normalized with the amount of total input protein.

In Vitro CD1d-Tetramer Assay

1 µg of soluble divalent mouse CD1d-IgG1 fusion protein (mouse CD1d-IgG1 tetramers, BD Pharmingen) was incubated overnight with 10 mole of each α-GalCer analog at 37° C. and at neutral pH according to the manufacturer's protocol. The glycolipid-loaded CD1d-IgG1 tetramers were incubated with mouse NKTs at 4° C. for 60 min, followed by incubation with FITC-coupled anti-mouse IgG1 mAb (A85-1). The cells were also surface-stained with a PE coupled anti-NK and APC coupled anti-CD3 mAb (BD Pharmingen).

Preparation of Mouse Splenocytes

BALB/c mice treated with the indicated α-GalCer analogs of the present disclosure or vehicle were sacrificed at 72 h after injection. The spleens were harvested. In brief, after pressing the spleen through 70 µm strainer and lysis of erythrocytes, the nucleated cells were resuspended in Hank's Balanced Salt Solution and centrifuged at 300 g for 5 min at 4° C., then subjected to FACS analysis.

Determination of Mouse Splenocyte Subpopulations

BALB/c mice treated with the indicated α-GalCer analogs of the present disclosure (2 ug/mouse) or vehicle (1% DMSO in PBS) and were sacrificed at 72 h and the spleen was harvested. In brief, after pressing the spleen through 70 µm strainer and lysis of erythrocytes, the nucleated cells were resuspended in Hank's Balanced Salt Solution and centrifuged at 300 g for 5 min at 4° C., then subjected to FACS analysis. The anti-CD3e-allophycocyanin, anti-CD4-PE, anti-CD8α-allophycocyanin-cyanide-dye7, anti-CD11c-allophycocyanin, anti-CD23-PE, anti-45R-allophycocyanin, anti-CD69-FITC, anti-CD80-FITC, anti-CD86-PE, anti-Ly6G-PE, and U5A2-13Ag+-PE were obtained from BD Bioscience-Pharmingen.

Determination of Mouse Splenocyte NKT and NK Subpopulations

BALB/c mice treated with indicated α-GalCer analogs of the present disclosure (0.1 ug/mouse) or vehicle (0.1% DMSO in PBS) and were sacrificed at 72 h and the spleen was harvested. In brief, after pressing the spleen through 70 um strainer and lysis of erythrocytes, the nucleated cells were resuspended in Hank's Balanced Salt Solution and centrifuged at 300 g for 5 min at 4° C., then subjected to FACS analysis. The anti-CD3e-allophycocyanin and NK marker U5A2-13Ag+-PE were obtained from BD Bioscience-Pharmingen.

Serum Cytokines/Chemokines

Mouse serum samples were collected at 0, 2, 18, 36, 48, and 72 h after administration of vehicle or synthetic α-GalCer analogs of the present disclosure. The serum concentrations of various cytokines/chemokines were measured by Beadlyte® Mouse 21-plex Cytokine Detection System and read by a Luminex® 100™ system.

Lung Cancer Model in Mice

C57BL/6 mice (6-8 weeks, female) were injected IV with $2\times10^5$ syngeneic lung cancer (TC1) cells suspended in 0.1 ml of PBS. At 1 hr, groups of C57BL/6 mice (n=5) were treated with the indicated α-GalCer analogs of the present disclosure IV (2 µg per mouse) or vehicle twice per week for four weeks. The body weight was recorded for one month and survival was monitored for 50 days.

Breast Cancer Model in Mice

BALB/C mice (6-8 weeks, female) were inoculated with $2\times10^5$ syngeneic breast cancer (4T1) SubQ on the right lower back. Groups of BALB/c mice (n=6) were treated IV or SubQ with the indicated α-GalCer analogs of the present disclosure or vehicle twice per week for four weeks 3 days after tumor inoculation. The α-GalCer analogs were injected at a site distal to the tumor inoculation site. The tumor volume was recorded every 3 days for one month by measuring with a caliper along the long axis (a), the short axis (b) and the height (c). Tumor volumes ($mm^3$) were calculated by the formula: a×b×c, and survival was monitored for 70 days.

Real Time Assessment of Tumor Growth in Mice

Mouse images were obtained and analyzed by Xenogen's IVIS® 200 Series and Living Image® Software (Xenogen, U.S.). In melanoma model, C57BL/6 mice (6-8 weeks, female) were injected intravenously with $2\times10^5$ syngeneic melanoma (B16) cells suspended in 0.1 ml of PBS. After 3 days, groups of C57BL/6 mice (n=5) were treated intravenously with indicated glycolipids under the indicated therapeutic protocol. The tumor volume was recorded every three days for 24 days.

Infiltration of Lymphocytes by Flow Cytometric Analysis

Tumors from control and glyclolipids treated mice were aseptically removed on days 21 after tumor implantation and manually cut into 2-3-mm pieces in a culture Petri dish. The small tissue fragments were then digested with 0.01% DNase, 0.01% hyaluranidase, and 0.1% collagenase (all from Sigma Chemical Co.) in RPMI 1640 for 2-3 h at 37° C. with continuous stirring. The resulting single cell suspensions were then washed twice with 0.1% FCS in PBS and stained by standard flow cytometry methods. To detect subpopulations of lymphocytes infiltrating these tissues, the following conjugated antibodies were used for FACS: FITC-anti-CD3, PE-anti-NK, APCCy7-anti-CD8, (BD Biosciences PharMingen, San Diego, Calif.).

Immunohistochemistry Staining

The lung nodules were taken from B6 mice i.v injected with $2\times10^5$ TC1 tumor cells for 3 weeks then sacrificed to do paraffin-embedded sections. 3 µm thick sections were treated at 56° C. oven overnight followed by deparaffinization & heat-mediated antigen retrieval (in pH 9 Tris-EDTA buffer at 121° C. for 7.5 mins) and incubated with anti-CD45RA antibody (clone RA3-6B2; BD Biosciences PharMingen, San Diego, Calif.) as an indicative of common lymphocyte antigens at a titration of 1:100 at 4° C. overnight. The bound primary antibody is detected by the addiction of secondary antibody conjugated with horseradish peroxidase and DAB substrate. All sections were counterstained with haematoxylin prior to mounting.

Statistical Analysis

Unpaired two-tailed Student's t test was used for data analysis with PRISM software. Graphs show mean values of triplicate experiments, and error bars represent the SD. Differences in tumor protection of each group were analyzed by using the log-rank test. $P<0.05$ was considered statistically significant.

Antibacterial Efficacy Studies

Glycolipid Analogs of α-GalCer

The structures of the α-GalCer analogs used in the antibacterial studies are shown in FIG. 2, C3, C9, C11 and C14-C17. α-GalCer analogs stock solutions were prepared as 1 mg/ml DMSO solutions. α-GalCer analogs were diluted with phosphate buffered saline (PBS) to 10 µg/ml before use.

Animals and Bacteria

Female C57L/6 and BALB/c-Byl mice at 6-8 week old were used for studies. Mice were housed in plastic cages with free access to food and water and allowed to acclimate at least one week prior to the start of the experiments. The bacterial strain *Spingomonas capsulate* (ATCC 14666) was obtained from BCRC, Taiwan. The bacterial strain *Klebsiella pneumoniae* (NTUH-KP2044) was a gift from Dr. J. T. Wang, National Taiwan University Hospital, Taiwan.

Antibacterial Efficacy Study Using Sphingomonas Capsulate Infected Mice

Six to eight week old female C57BL/6 mice were injected IP with $5\times10^8$ Sphingomonas capsulate cells. Mice were grouped into treatment and control groups with 4-6 mice per group. Four hours after the infection, mice in the treatment group were injected IP with testing α-GalCer analogs at 50 or 100 μg/kg, and the control group mice were injected with same volumes of PBS. Twenty-four hours after bacterial infection, mice from all groups were sacrificed. Livers were removed from mice and homogenized in 0.9% NaCl, 0.02% Tween 80 using tissue homogenizers. Colony formation units (CFU) of Sphingomonas capsulate in liver homogenates were determined by plating diluted samples on nutrient plates. Colonies were counted after incubation for 48 hours at 37° C.

Antibacterial Efficacy Study Using *K. Pneumoniae* Infected Mice

BALB/c-Byl female mice (ten mice per group) were administered a single dose ($10^6$ CFU) of live *K. pneumoniae* by oral gavage. Mice in the treatment groups were injected with testing α-GalCer analogs at 100 μg/kg twice at 4-hour and 8-hour after bacterial infection. Mice in the control group were injected with PBS at 4- and 8-hour. Twenty four hours after infection, all mice were sacrificed. Both livers and lungs were collected from each mouse, and homogenized. Bacterial counts were determined similarly as described above.

Statistical Analysis

Comparative efficacies of testing α-GalCer analogs were illustrated by comparison of the organ CFU values of treatment groups with those in control groups, and the significance of the efficacy was indicated in p-values of <0.05 or <0.01, respectively.

The invention claimed is:

1. A method of activating a cytokine response in a subject comprising:
   administering an effective amount of a compound to a subject,
      wherein the subject has an adaptive immune system that includes a population of cells, the population including at least one lymphocyte and at least one antigen-presenting cell, and
      wherein the compound is represented by the structure of formula 1:

(1)

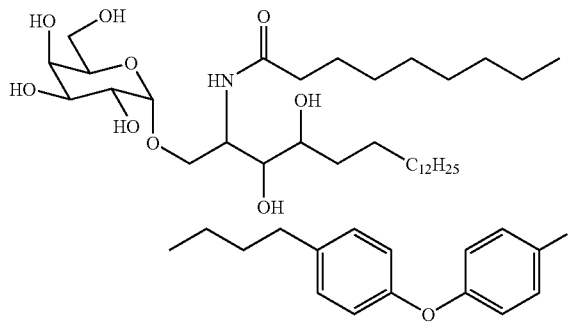

or a pharmaceutically acceptable salt thereof;
      forming a complex between the compound and the antigen-presenting cell, wherein the formation of the complex results in the activation of a receptor on the lymphocyte; and
      activating the lymphocyte to produce the cytokine response.

2. The method of claim 1 wherein the cytokine response is a $T_H1$-type cytokine response which produces $T_H1$ cytokines.

3. The method of claim 2 wherein the $T_H1$ cytokines are selected from the group consisting of IFN-γ, IL-1β, IL-2, IL-3, IL-8, IL-12, IL-15, TNF-α, GM-CSF, RANTES, MIP-1α and MCP-1.

4. The method of claim 1 wherein the cytokine response is a $T_H2$-type cytokine response which produces $T_H2$ cytokines.

5. The method of claim 4 wherein the $T_H2$ cytokines are selected from the group consisting of IL-4, IL-6, IL-8, IL-10, IL-13, RANTES, MIP-1α and MCP-1.

6. The method of claim 1 wherein administering the compound is accomplished by subcutaneous administration, intravenous administration, intranasal administration or intramuscular administration.

7. The method of claim 1 wherein the at least one lymphocyte is a T lymphocyte.

8. The method of claim 7 wherein the T lymphocyte is a Natural Killer T cell.

9. The method of claim 8 wherein the Natural Killer T cell is an invariant Natural Killer T cell.

10. The method of claim 1 wherein the at least one antigen-presenting cell is a dendritic cell.

11. The method of claim 10 wherein the dendritic cell is an immature or a mature dendritic cell.

12. The method of claim 1 wherein the compound forms a complex with a CD1 molecule on the antigen-presenting cell.

13. The method of claim 12 where the CD1 molecule is a CD1d molecule.

14. The method of claim 7 wherein the receptor on the T lymphocyte is a T cell receptor.

15. The method of claim 1 further comprising:
   stimulating at least one other lymphocyte to produce the cytokine response.

16. The method of claim 15 wherein the at least one other lymphocyte is a T helper cell.

17. The method of claim 1 wherein the administration of the compound results in an expansion of the population of cells in the adaptive immune system of the subject.

18. The method of claim 2 wherein the subject suffers from a cancer or an infectious disease.

19. The method of claim 4 wherein the subject suffers from an autoimmune disease.

20. A vaccine comprising:
   an effective amount of a compound represented by the structure of formula 1:

(1)

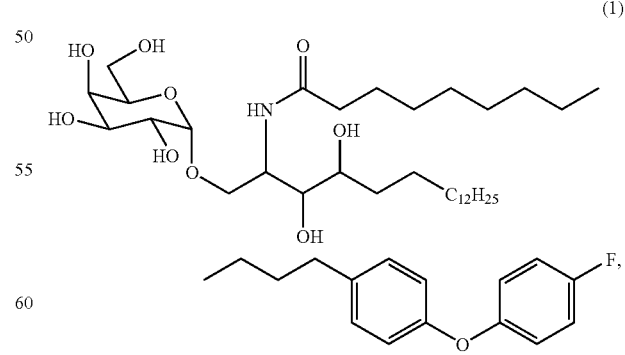

or a pharmaceutically acceptable salt thereof; and
   a vaccine agent.

21. The vaccine of claim 20 wherein the vaccine agent is selected from the group consisting of a killed microorganism, a live attenuated virus microorganism, a toxoid and a fragment of an inactivated or attenuated microorganism.

22. The vaccine of claim 21 wherein the microorganism is a bacteria or a fungi.

23. The vaccine of claim 21 wherein the toxoid is a tetanus or a diphtheria.

24. The vaccine of claim 20 wherein the vaccine agent is capable of eliciting an immune response in a subject that is administered the vaccine.

25. The vaccine of claim 24 wherein the compound acts as an immunologic adjuvant and is capable of modifying or augmenting the immune response elicited by the vaccine agent by stimulating the immune system which results in the subject responding to the vaccine more vigorously than without the compound.

26. The vaccine of claim 24 wherein the subject is administered the vaccine by subcutaneous administration, intravenous administration, intranasal administration or intramuscular administration.

27. A method of anti-tumor immunotherapy comprising: administering an effective amount of a compound represented by the structure of formula 1:

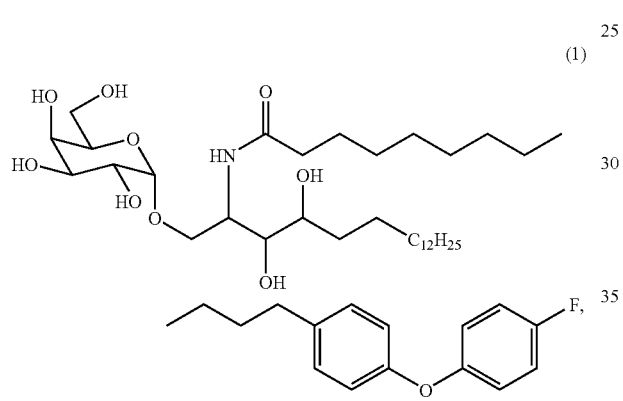

(1)

or a pharmaceutically acceptable salt thereof.

28. The method of claim 27 wherein the administration is based on at least one of cancer, an elevated risk for cancer and precancerous precursors.

29. The method of claim 28 wherein the administration of the compound elicits a response in at least one of tumor and cancer cells.

30. The method of claim 29 wherein the response elicited is a slowing down in a growth of the tumor.

31. The method of claim 29 wherein the response elicited is a reduction in a size of the tumor.

32. The method of claim 27 wherein the administration of the compound is to effect an adaptive immune system that includes a population of cells, the population including at least one lymphocyte and wherein the response elicited is an expansion of the population of cells in the adaptive immune system.

33. The method of claim 32 wherein the expansion of the population of cells in the adaptive immune system includes an expansion in a number of T cells, CD8 T cells, NK cells or NKT cells.

34. The method of claim 27 further comprising providing a cancer vaccine to which the compound is added.

35. The method of claim 28 wherein the cancer is selected from the group consisting of lung cancer, breast cancer, hepatoma, leukemia, solid tumor and carcinoma.

36. A compound represented by the structure of formula 1:

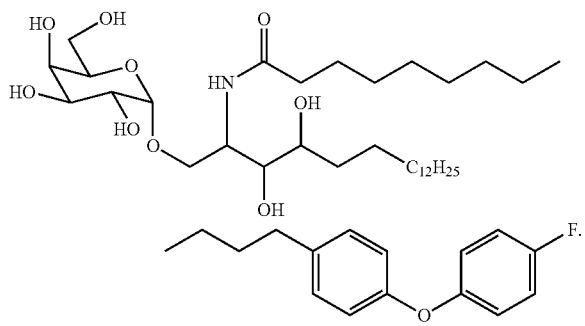

(1)

37. A method of anti-microbial immunotherapy for a subject comprising: administering an effective amount of a compound represented by the structure of formula 1:

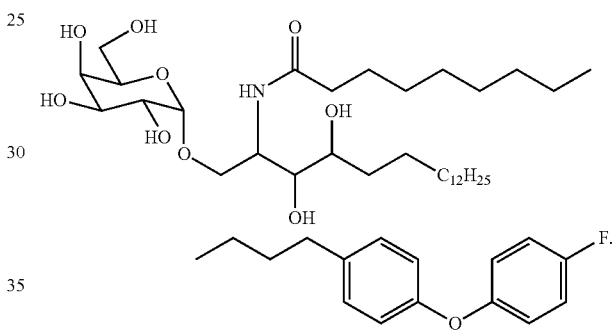

(1)

or a salt or a mixture thereof to a subject.

38. The method of claim 37 wherein the administration is based on an infectious disease resulting from the presence of pathogenic microbial agents.

39. The method of claim 38 wherein the pathogenic microbial agents are selected from the group consisting of viruses, bacteria, fungi, protozoa, multicellular parasites and aberrant proteins.

40. The method of claim 38 wherein the pathogenic microbial agent is a virus.

41. The method of claim 40 wherein the virus is selected from the group consisting of Retroviridae, Picornaviridae, Calciviridae, Togaviridae, Flaviridae, Coronaviridae, Rhabdoviridae, Filoviridae, Paramyxoviridae, Orthomyxoviridae, Bungaviridae, Arena viridae, Reoviridae, Birnaviridae, Hepadnaviridae, Parvoviridae, Papovaviridae, Adenoviridae, Herpesviridae, Poxviridae and Iridoviridae.

42. The method of claim 38 wherein the pathogenic microbial agent is a bacteria.

43. The method of claim 41 wherein the bacteria is selected from the group consisting of *Helicobacter pylori, Borellia burgdorfeni, Legionella pneumophilia, Kiebsiella pneumoniae, Mycobacteria* spp., *Staphylococcus aureus, Neisseria gonorrhoeae, Neisseria meningitidis, Listeria monocytogenes, Streptococcus pyogenes, Streptococcus agalactiae, Streptococcus, Streptococcus faecalis, Streptococcus bovis, Streptococcus pneumoniae*, pathogenic *Campylobacter* sp., *Enterococcus* sp., *Chlamidia* sp., *Haemophilus influenzae, Bacillus antracis, Corynebacterium diphtheniae, Corynebacterium* sp., *Erysipelothrix rhusiopathiae, Clostridium* peifringers, Clostridium tetani, Enterobacter aerogenes, Klebsiella pneumoniae, Pasturella multocida, Bacteroides sp., Fusobacterium nucleatum, Streptobacillus moniliformis, Treponema pallidium, Treponema pertenue, Leptospira, Actinomyces israeli, Sphingomonas capsulata and Francisella tularensis.

44. The method of claim 41 wherein the administration of the compound to a subject results in an enhanced bacterial clearance as compared to a subject not administered the compound.

45. The method of claim 27 wherein the administration of the compound results in the killing of the microbial agent.

46. The method of claim 37 wherein the administration of the compound results in the microbial agent not being able to grow.

47. A compound C34 represented by the structure:

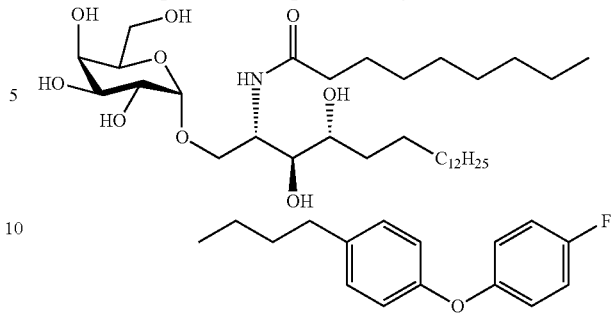

or, a pharmaceutically acceptable salt thereof.

* * * * *

UNITED STATES PATENT AND TRADEMARK OFFICE
CERTIFICATE OF CORRECTION

PATENT NO. : 7,928,077 B2  
APPLICATION NO. : 12/218082  
DATED : April 19, 2011  
INVENTOR(S) : Chi-Huey Wong et al.

Page 1 of 6

It is certified that error appears in the above-identified patent and that said Letters Patent is hereby corrected as shown below:

Title Page, item (57)

In the Abstract, please delete

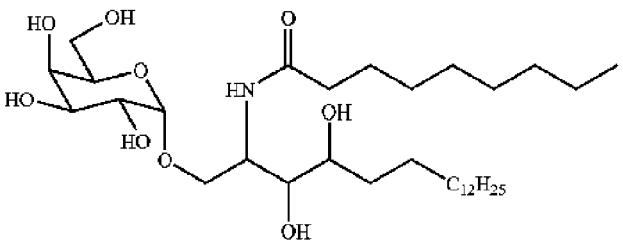

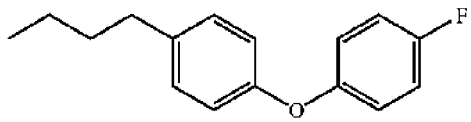 " and insert

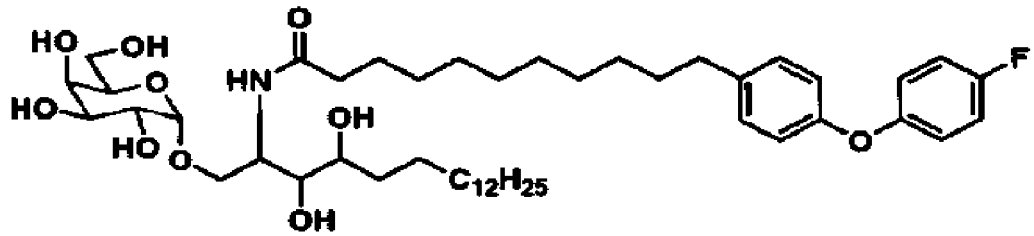

-- --

Signed and Sealed this
Twenty-sixth Day of January, 2016

Michelle K. Lee
*Director of the United States Patent and Trademark Office*

CERTIFICATE OF CORRECTION (continued)
U.S. Pat. No. 7,928,077 B2

In the Specification

At column 3, line 50, please delete

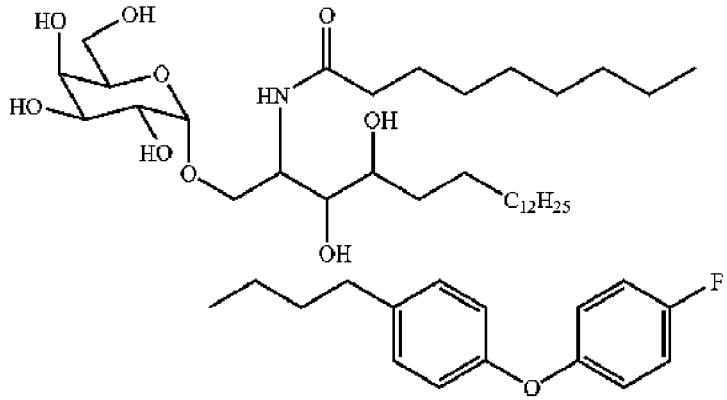

" and insert

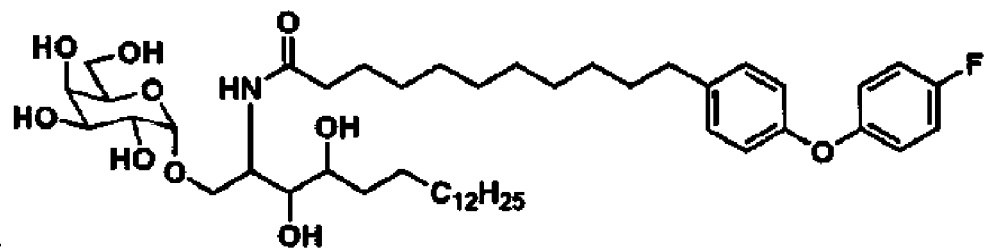

-- --

At column 4, line 50, please delete

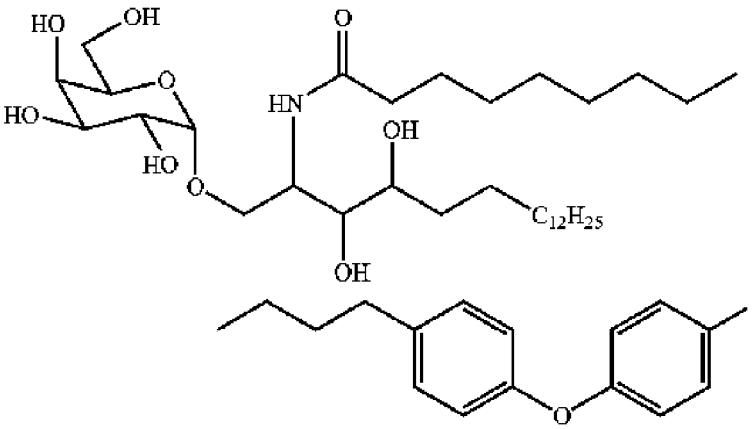

" and insert

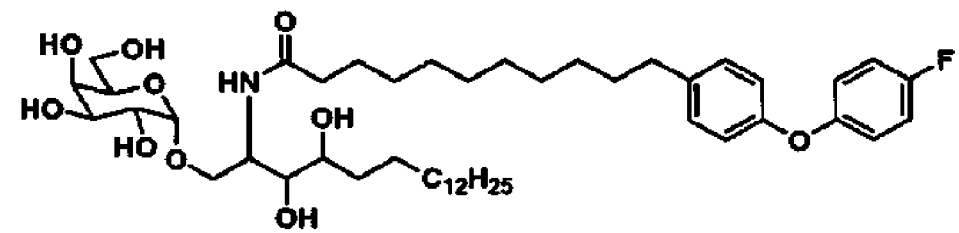

-- --

At column 5, line 40, please delete
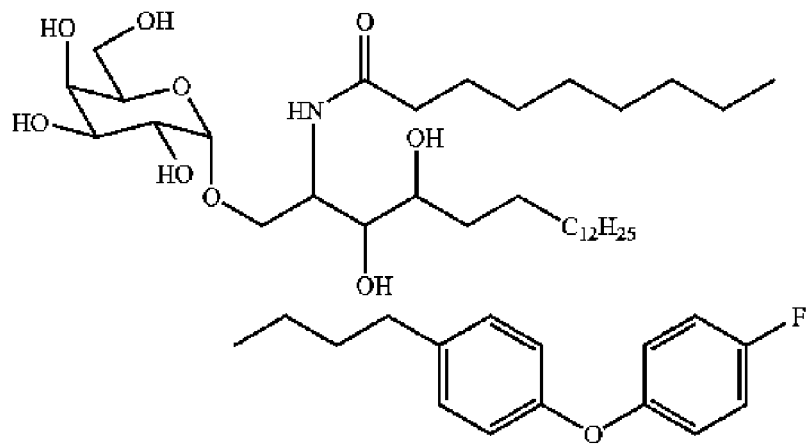
" " and insert
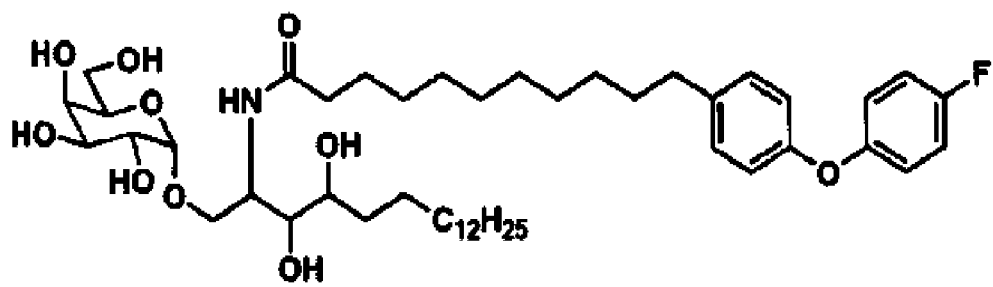
" --
At column 6, line 8, please delete
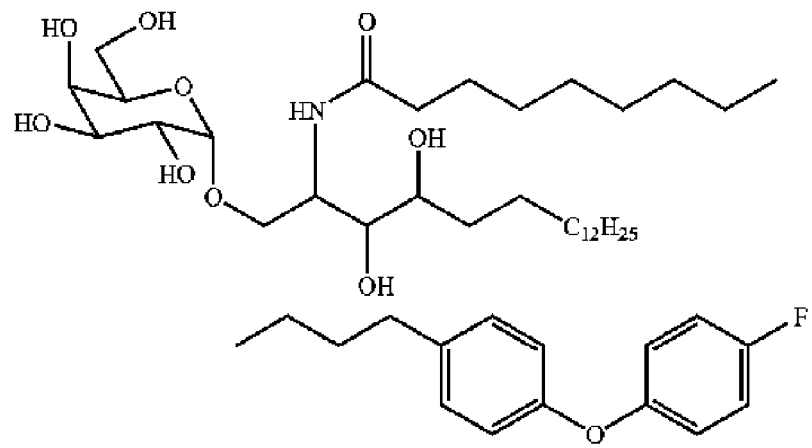
" " and insert
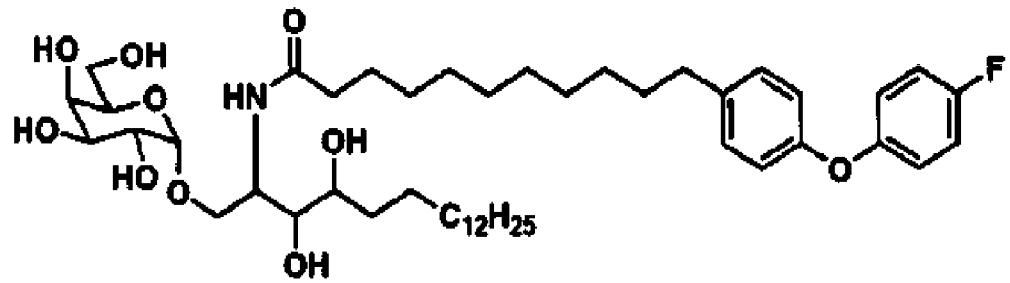
" --

CERTIFICATE OF CORRECTION (continued)
U.S. Pat. No. 7,928,077 B2

In the Claims

At column 43, Claim 1, line 47, please delete

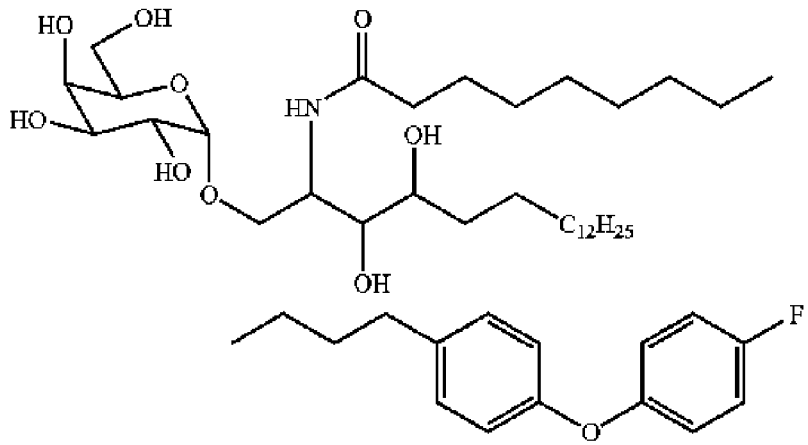

" and insert

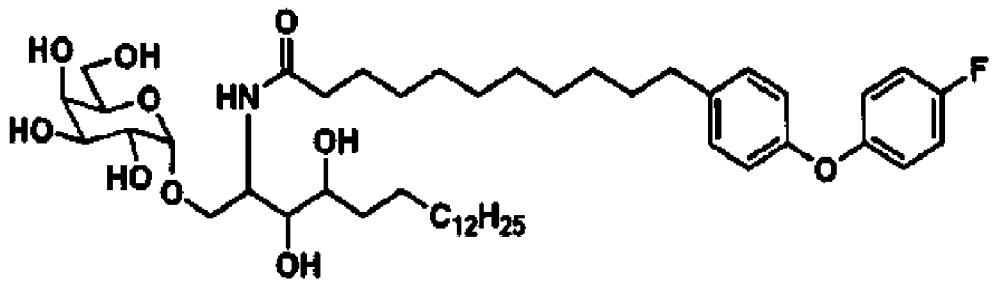

--

At column 44, Claim 20, line 50, please delete

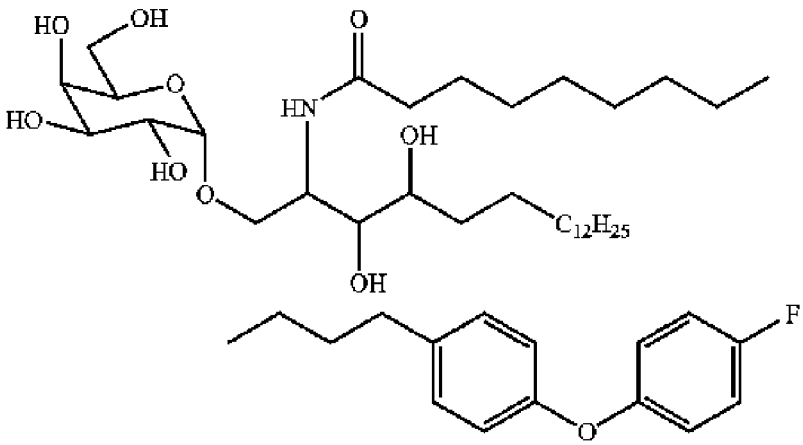

" and insert

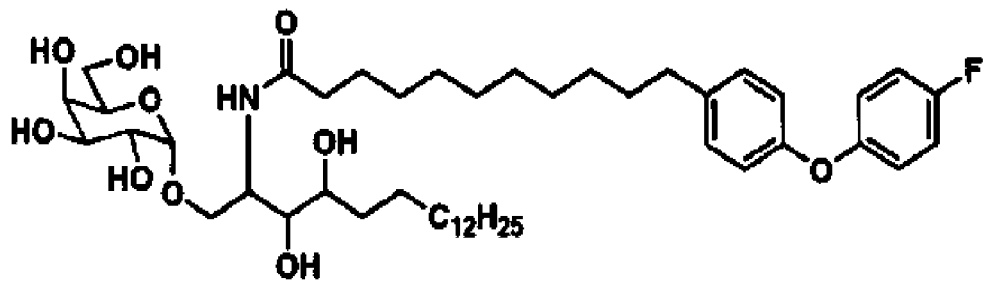

--

At column 45, Claim 27, line 29, please delete
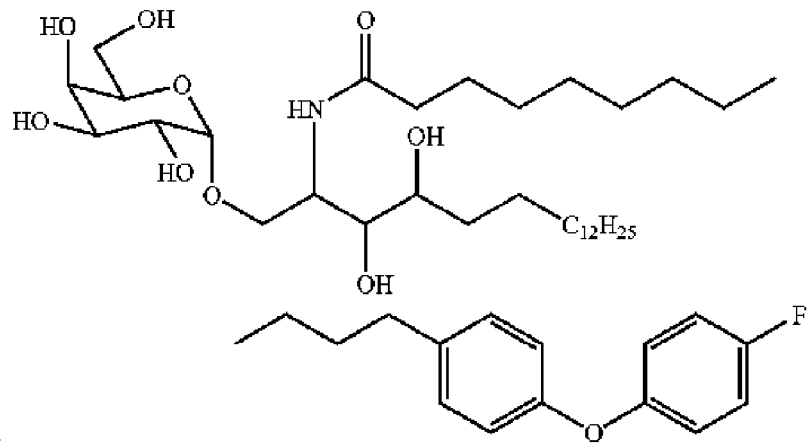
" " and insert
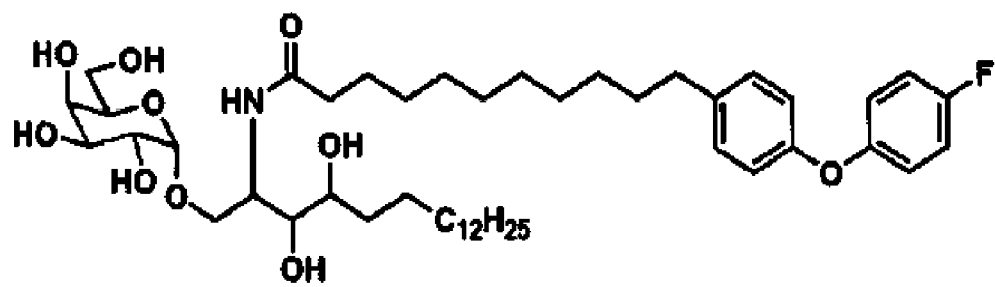
-- --
At column 46, Claim 36, line 5, please delete
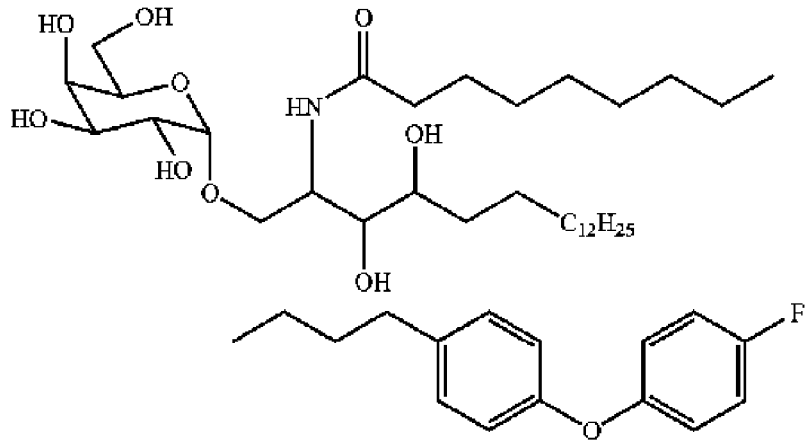
" " and insert
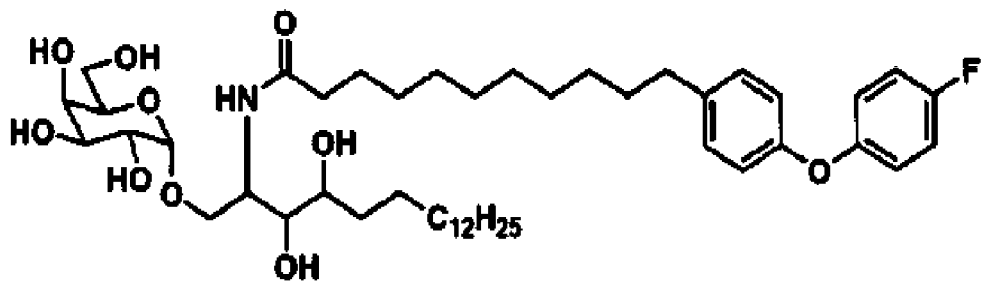
-- --

At column 46, Claim 37, line 25, please delete
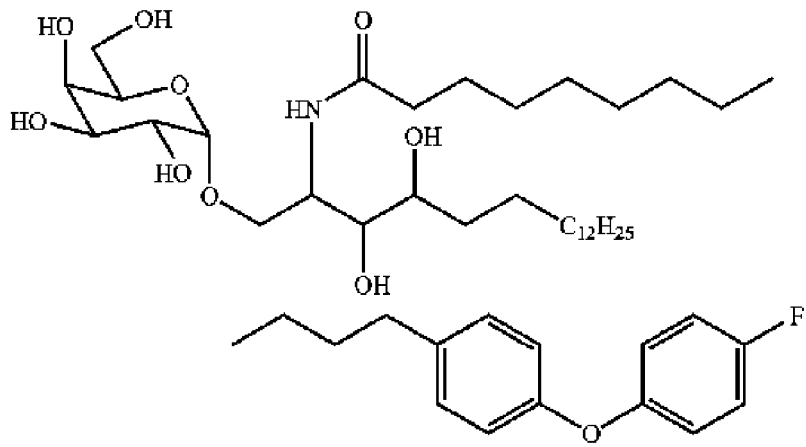
" " and insert
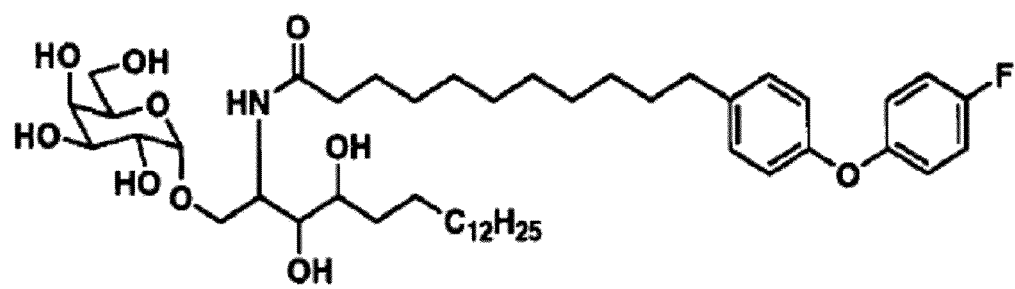
-- --
At column 48, Claim 47, line 2, please delete
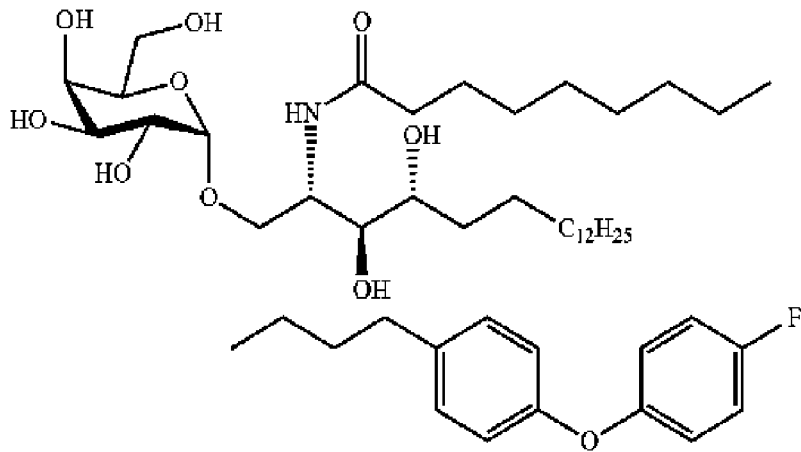
" " and insert
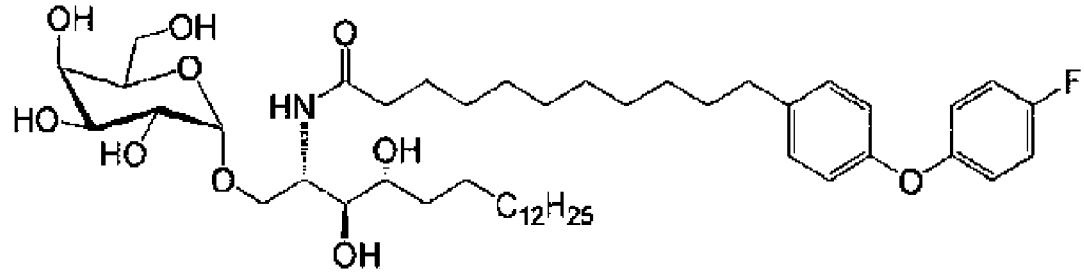
-- --